US010517958B2

(12) United States Patent
Babcook et al.

(10) Patent No.: US 10,517,958 B2
(45) Date of Patent: Dec. 31, 2019

(54) COMPOSITIONS AND METHODS FOR THE TREATMENT OF PLATINUM-DRUG RESISTANT CANCER

(71) Applicants: ZYMEWORKS INC., Vancouver (CA); VAR2 PHARMACEUTICALS APS, Copenhagen N (DK)

(72) Inventors: John Babcook, Vancouver (CA); James R. Rich, Vancouver (CA); Mads Daugaard, Vancouver (CA); Ali El-Salanti, Farum (DK)

(73) Assignees: ZYMEWORKS INC., Vancouver (CA); VAR2 PHARMACEUTICALS APS, København (DK)

( * ) Notice: Subject to any disclaimer, the term of this patent is extended or adjusted under 35 U.S.C. 154(b) by 0 days.

(21) Appl. No.: 15/724,763

(22) Filed: Oct. 4, 2017

(65) Prior Publication Data

US 2018/0193473 A1    Jul. 12, 2018

Related U.S. Application Data

(60) Provisional application No. 62/404,096, filed on Oct. 4, 2016.

(51) Int. Cl.
*A61K 47/64* (2017.01)
*A61K 47/65* (2017.01)
(Continued)

(52) U.S. Cl.
CPC .......... *A61K 47/6425* (2017.08); *A61K 38/06* (2013.01); *A61K 47/64* (2017.08); *A61K 47/65* (2017.08); *A61P 35/00* (2018.01)

(58) Field of Classification Search
None
See application file for complete search history.

(56) References Cited

U.S. PATENT DOCUMENTS 5,349,066 A    9/1994   Kaneko et al.
5,502,032 A    3/1996   Haupt et al.
(Continued)

FOREIGN PATENT DOCUMENTS

WO    WO 1996/14856 A1    5/1996
WO    WO 1996/33211 A1    10/1996
(Continued)

OTHER PUBLICATIONS

Ohmichi et al., Trends Pharmacol Sci. Mar. 2005;26(3):113-6 (Year: 2005).*

(Continued)

*Primary Examiner* — Karl J Puttlitz
(74) *Attorney, Agent, or Firm* — Todd A. Lorenz; David Goetz

(57) ABSTRACT

VAR2CSA-drug conjugates for targeting and inhibiting the growth of cancer cells that have developed resistance to a platinum drug and the use of the conjugates in the treatment of platinum drug-resistant cancers. VAR2CSA-drug conjugates (VDCs) comprise a VAR2CSA polypeptide that is capable of binding to oncofetal chondroitin sulfate (ofCS) and one or more toxins having anti-cancer activity conjugated to the VAR2CSA polypeptide, either directly or via a linker.

50 Claims, 12 Drawing Sheets
(11 of 12 Drawing Sheet(s) Filed in Color)
Specification includes a Sequence Listing.

(51) Int. Cl.
*A61P 35/00* (2006.01)
*A61K 38/06* (2006.01)

(56) References Cited

U.S. PATENT DOCUMENTS

| | | | |
|---|---|---|---|
| 5,635,483 | A | 6/1997 | Pettit et al. |
| 5,663,149 | A | 9/1997 | Pettit et al. |
| 5,780,588 | A | 7/1998 | Pettit et al. |
| 6,124,431 | A | 9/2000 | Sakakibara et al. |
| 6,153,590 | A | 11/2000 | Anderson et al. |
| 6,323,315 | B1 | 11/2001 | Pettit et al. |
| 6,569,834 | B1 | 5/2003 | Pettit et al. |
| 6,870,028 | B1 | 3/2005 | Andersen et al. |
| 6,884,869 | B2 | 4/2005 | Pettit et al. |
| 7,064,211 | B2 | 6/2006 | Kowalczyk et al. |
| 7,078,572 | B2 | 7/2006 | Kendall |
| 7,098,308 | B2 | 8/2006 | Senter et al. |
| 7,192,972 | B2 | 3/2007 | Kowalczyk et al. |
| 7,256,257 | B2 | 8/2007 | Doronina et al. |
| 7,390,910 | B2 | 6/2008 | Zask et al. |
| 7,410,951 | B2 | 8/2008 | Andersen et al. |
| 7,423,116 | B2 | 9/2008 | Doronina et al. |
| 7,498,298 | B2 | 3/2009 | Doronina et al. |
| 7,528,152 | B2 | 5/2009 | Kowalczyk et al. |
| 7,579,323 | B1 | 8/2009 | Andersen et al. |
| 7,585,976 | B2 | 9/2009 | Campagna et al. |
| 7,626,023 | B2 | 12/2009 | Zask et al. |
| 7,659,241 | B2 | 2/2010 | Senter et al. |
| 7,745,394 | B2 | 6/2010 | Doronina et al. |
| 7,772,397 | B2 | 8/2010 | Andersen et al. |
| 7,851,437 | B2 | 12/2010 | Senter et al. |
| 8,129,407 | B2 | 3/2012 | Kowalczyk et al. |
| 8,394,922 | B2 | 3/2013 | Cheng et al. |
| 8,609,105 | B2 | 12/2013 | Senter et al. |
| 8,633,224 | B2 | 1/2014 | Kowalczyk et al. |
| 8,992,932 | B2 | 3/2015 | Lerchen et al. |
| 9,522,876 | B2 | 12/2016 | Winters et al. |
| 9,801,951 | B2 | 10/2017 | Miao et al. |
| 9,879,086 | B2 | 1/2018 | Winters et al. |
| 2004/0121965 | A1 | 6/2004 | Greenberger et al. |
| 2008/0108820 | A1 | 5/2008 | Campagna et al. |
| 2008/0300192 | A1 | 12/2008 | Doronina et al. |
| 2009/0264487 | A1 | 10/2009 | Anderson et al. |
| 2011/0020343 | A1 | 1/2011 | Senter et al. |
| 2011/0027274 | A1 | 2/2011 | Cheng et al. |
| 2011/0293704 | A1 | 12/2011 | Holst et al. |
| 2013/0095123 | A1 | 4/2013 | Lerchen et al. |
| 2013/0129753 | A1 | 5/2013 | Doroski et al. |
| 2013/0190248 | A1 | 7/2013 | Mendelsohn et al. |
| 2015/0250896 | A1 | 9/2015 | Zhao |
| 2015/0284416 | A1 | 10/2015 | Zhao |
| 2016/0038606 | A1 | 2/2016 | Winters et al. |
| 2016/0130299 | A1 | 5/2016 | Perez et al. |
| 2016/0311853 | A1 | 10/2016 | Geirstanger et al. |
| 2017/0029490 | A1 | 2/2017 | Winters et al. |
| 2017/0246310 | A1 | 8/2017 | Rich et al. |
| 2017/0247408 | A1 | 8/2017 | Winters et al. |
| 2018/0117163 | A9 | 5/2018 | Rich et al. |

FOREIGN PATENT DOCUMENTS

| | | |
|---|---|---|
| WO | WO 1999/32509 A2 | 7/1999 |
| WO | WO 2001/18032 A2 | 3/2001 |
| WO | WO 2002/088172 A2 | 11/2002 |
| WO | WO 2003/082268 A2 | 10/2003 |
| WO | WO 2004/010957 A2 | 2/2004 |
| WO | WO 2004/026293 A2 | 4/2004 |
| WO | WO 2005/030794 A2 | 4/2005 |
| WO | WO 2006/027711 A2 | 3/2006 |
| WO | WO 2006/039652 A2 | 4/2006 |
| WO | WO 2007/008603 A1 | 1/2007 |
| WO | WO 2007/008848 A2 | 1/2007 |
| WO | WO 2011/154359 A1 | 12/2011 |
| WO | WO 2012/014073 A2 | 2/2012 |
| WO | WO 2012/135440 A1 | 10/2012 |
| WO | WO 2013/071035 A1 | 5/2013 |
| WO | WO 2013/117705 A1 | 8/2013 |
| WO | WO 2013/173391 A1 | 11/2013 |
| WO | WO 2013/173392 A1 | 11/2013 |
| WO | WO 2013/173393 A1 | 11/2013 |
| WO | WO 2014/004376 A2 | 1/2014 |
| WO | WO 2014/136836 A1 | 9/2014 |
| WO | WO 2014/144871 A1 | 9/2014 |
| WO | 2015095952 * | 7/2015 |
| WO | WO 2015/095952 A1 | 7/2015 |
| WO | WO 2015/095953 A1 | 7/2015 |
| WO | WO 2016/041082 A1 | 3/2016 |
| WO | WO 2016/123412 A1 | 8/2016 |
| WO | WO 2017/054080 A1 | 6/2017 |

OTHER PUBLICATIONS

Goodman & Gilman's Manual of Pharmacology and Therapeutics, 2008, McGraw Hill Medical (Year: 2008).*
Seiler et al., European Urology 72 (2017) 142-150 (Year: 2017).*
Alexander-Bryant et al., "Bioengineering Strategies for Designing Targeted Cancer Therapies," Adv Cancer Res, vol. 118, pp. 1-59 (2013).
Alkhalil A, et al. "Structural requirements for the adherence of Plasmodium falciparum-infected erythrocytes to chondroitin sulfate proteoglycans of human placenta." J. Biol. Chem., vol. 275 (51), pp. 40357-40364 (2000).
Amsberry, et al. "The lactonization of 2'-hydroxyhydrocinnamic acid amides: a potential prodrug for amines," J. Org. Chem., vol. 55 (23), pp. 5867-5877 (1990).
Axup et al., "Synthesis of site-specific antibody-drug conjugates using unnatural amino acids," PNAS vol. 109 (40), pp. 16101-16106 (2012).
Bai et al., "Interactions of the Sponge-Derived Antimitotic Tripeptide Hemiasterlin with Tubulin: Comparison with Dolastatin 10 and Cyrpotphycin 1," Biochemistry, vol. 38, pp. 14302-14310 (1999).
CAS RN 1350253-85-8, STN Entry Date: Dec. 7, 2011.
Chan et al., "Mitosis-targeted anti-cancer therapies: where they stand," Cell Death and Disease, vol. 3, pp. 1-11 (2012).
Chen, X. et al., "Fusion protein linkers: property, design and funtionality,", Adv Drug Deliv Rev., vol. 65(10), pp. 1357-1369 (2013).
Choi, K.Y., "Protease-Activated Drug Development," Theranostics, 2(2), pp. 156-178, (2012).
Clausen TM et al., "Structural and Functional Insight into How the Plasmodium falciparum VAR2CSA Protein Mediates Binding to Chondroitin Sulfate A in Placental Malaria," J. Biol. Chem., vol. 287, No. 28, pp. 23332-23345 (2012).
Coleman et al., "Cytotoxic Peptides from the Marine Sponge *Cymbastella sp.*," Tetrahedron vol. 51, No. 39, pp. 10653-10662 (1995).
Dahlback M et al., "The Chondroitin Sulfate A-binding Site of the VAR2CSA Protein Involves Multiple N-terminal Domains," J. Biol. Chem., vol. 286, No. 18, pp. 15908-15917 (2011).
De Graaf et al., "Beta-glucuronidase-mediated drug release," Curr Pharm Des., vol. 8(15), pp. 1391-1403 (2002).
De Klerk P., "The glycosaminoglycans of human bladder cancers of varying grade and stage," J Urol, vol. 134, pp. 978-981 (1985).
Doronina et al., "Development of potent monoclonal antibody auristatin conjugates for cancer therapy," Nature Biotechnology, vol. 21, No. 7, pp. 778-784 (2003).
Doronina et al., "Enhanced Activity of Monomethylauristatin F through Monoclonal Antibody Delivery: Effects of Linker Technology on Efficacy and Toxicity," Bioconjugate Chem., vol. 17, pp. 114-124 (2006).
Doronina et al., "Novel Peptide Linkers for Highly Potent Antibody—Auristatin Conjugate," Bioconjugate Chem., vol. 19, pp. 1960-1963 (2008).
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity," Bioconjugate Chem., vol. 13, pp. 855-869 (2002).

(56) References Cited

OTHER PUBLICATIONS

Ferreira, et al. "Mechanisms of cisplatin resistance and targeting of cancer stem cells: Adding glycosylation to the equation," Drug Resistance Updates 24, pp. 34-54 (2015).
Fried and Duffy, "Adherence of Plasmodium falciparum to chondroitin sulfate A in the human placenta," Science, vol. 272(5267), pp. 1502-1504 (1996).
Gajula et al., "A Synthetic Dolastatin 10 Analgoue Supresses Mictrotubule Dynamics, Inhibits Cell Proliferation, and Induces Apoptotic Cell Death," J. Med. Chem, vol. 56, pp. 2235-2245 (2013).
Gao et al. "Up-regulation of CD44 in the development of metastasis, recurrence and drug resistance of ovarian cancer," Oncotarget. vol. 6, pp. 9313-9326 (2015).
Gura, T.,"Cancer Models: Systems for Identifiying New Drugs Are Often Faulty," Science 7, vol. 278, No. 5340, pp. 1041-1042 (1997).
Haba, K., "Single-Triggered Trimeric Prodrugs," Angew. Chem. Int. Ed., vol. 44, pp. 716-720 (2005).
Hadaschik, B.A. et al., "Intravesical Chemotherapy of High-Grade Bladder Cancer with HTI-286, A Synthetic Analogue of the Marine Sponge Product Hemiasterlin," Clin Cancer Res., vol. 14, pp. 1510-1518 (2008).
Hamada et al., caplus an 2008:324765.
Hennessy BT et al., "Urinary Glycosaminoglycan Excretion as a Biochemical Marker in Patients with Bladder Carcinoma," Cancer Res. vol. 41, pp. 3868-3873.
Hofer et al., "Molecularly definded antibody conjugation through a selenocysteine interface," Biochemistry, vol. 48, pp. 12047-12057 (2009).
Huang, S. et al., "Synthesis and evaluation of N-acyl sulfonamides as potential prodrugs of cyclin-dependent kinase inhibitor JNJ-7706621," Bioorganic & Medicinal Chemistry Letters, vol. 16, pp. 3639-3641 (2006).
Ishikawa et al, "Preparation of endothelin antagonistic peptide derivatives," caplus an Eur. Pat. Appl., p. 121, 1992:256053.
Kamb, A., "What's wrong with our cancer models?," Nature Reviews Drug Discovery 4, vol. 4, pp. 161-165 (2005).
Kulsum et al., "Cancer stem cell mediated acquired chemoresistance in head and neck cancer can be abrogated by aldehyde dehydrogenase 1 A1 inhibition," Mol Carcinog. vol. 56(2), pp. 694-711 (2016).
Kuznetsov et al., "Tubulin-based antimitotic mechanism of E7974, a novel analogue of the marine sponge natural product hemiasterlin," Mol Cancer Ther, vol. 8(10), pp. 2852-2860 (2009).
Lesma et al., "Hemiasterlin Analogues Incorporating an Aromatic, and Heterocyclic Type C-terminus: Design, Synthesis and Biological Evaluation," Mol Divers.,18(2), pp. 357-373 (2004).
Leung et al., "Non-small cell lung cancer cells expressing CD44 are enriched for stem cell-like properties," PLoS One., vol. 5(11), p. e14062 (2010).
Li et al., "Immunotoxins and Cancer Therapy," Cellular & Molecular Immunology, vol. 6, No. 2, pp. 106-112 (2005).
Loganzo et al., "HTI-286 , a Synthetic Analogue of the Tripeptide Hemiasterlin, is a Potent Antimicrotubule Agent that Circumvents P-Glycoprotein-mediated Resistance in Vitro and in Vivo," Cancer Res, 63, pp. 1838-1845 (2003).
Mader, M.M. et al., "Acyl sulfonamide anti-proliferatives. Part 2: Activity of heterocyclic sulfonamide derivatives," Bioorganic & Medicinal Chemistry Letters, 15, pp. 617-620 (2005).
Marzo et al., "Antimitotic drugs in cancer chemotherapy: Promises and pitfalls," Biochemical Pharmacology, Vo. 86, pp. 703-710 (2013).
Merkx et al., "Resin-bound sulfonyl-azides: Efficient loading and activation strategy for the preparation of the N-acyl sulfonamide linker," J. Org. Chem., vol. 72, pp. 4574-4577 (2007).
Mitra, A. and Sept D., "Localization of the Antimitotic Peptide and Depsipeptide Binding Site on B-tubulin," Biochemistry, 43, pp. 13955-13962 (2004).
Neidle, S., "Failure Modes in Clinical Development," Cancer Drug Design and Discovery, ed. (Elsevier/Academic Press) pp. 427-431 (2008).

Neiman et al., "Synthesis and Antimitotic/Cytotoxic Activity of Hemiasterlin Analogues," J. Nat. Prod. vol. 66, pp. 183-199 (2003).
Niu et al., "Absolute configurations of tubulin inhibitors taltobulin (HTI-286) and HTI-042 characterized by X-ray diffraction analysis and NMR studies," Bioorganic & Medicinal Chmistry Letters, 20, pp. 1535-1538 (2010).
Nolting, B., "Linker Technolgoies for Antibody-Drug Conjugates," Chapter 5, Antibody-Drug Conjugates: Methods in Molecular Biology, vol. 1045, Ducry (Ed.), pp. 71-100 (2013).
Ohmichi M et al., Mechanisms of platinum drug resistance. Trends Pharmacol Sci. 2005;26:113-116.
Ohyama C., "Glycosylation in Bladder Cancer," Int. J. Clin. Oncol., vol. 13, pp. 308-312 (2008).
Olsen et al., caplus an 2010:213501.
Otani et al., "TZT-1027, an antimicrotubule agent, attacks tumor vasculature and induces tumor cell death," Jpn. J. Cancer Res., vol. 91, pp. 837-844 (2000).
Pettit et al., "Antineoplastic agents 337. Synthesis of dolastatin 10 structural modifications," Anti-Cancer Drug Des., vol. 10, pp. 529-544 (1995).
Pettit et al., "Specific activities of dolastatin 10 and peptide derivatives against *Cryptococcus neoformans*," Antimicrob. Agents Chemother., vol. 42, pp. 2961-2965 (1998).
Pettit et al., "Antineoplastic agents 365. Dolastatin 10 SAR probes," Anti-Cancer Drug Des., vol. 13, pp. 243-277 (1998).
Pettit et al., "Antineoplastic agents. 592. Highly effective cancer cell growth inhibitory structural modifications of dolastatin 10," J. Nat. Prod., vol. 74, pp. 962-968 (2011).
Pylvas-Eerola et al., "Cancer Stem Cell Properties as Factors Predictive of Chemoresistance in Neoadjuvantly-treated Patients with Ovarian Cancer," Anticancer Res., vol. 36(7), pp. 3425-3431 (2016).
Ratain et al., "Phase I and pharmacological study of HTI-286, a novel antimicrotubule agent: correlation of neutropenia with time above a threshold serum concentration," Proc. Am. Soc. Clin. Oncol., vol. 22, p. 129 (2003).
Ravi M. et al., "Structure-Based Identification of the Binding Site for the Hemiasterlin Analogue HTI-286 on Tubulin," Biochemistry, 44, pp. 15871-15879 (2005).
Rich, J.R., et al., CAPLUS AN 2015:1087487.
Rocha-Lima et al., "A Phase 1 Trial of E7974 Administrated on Day 1 of a 21 Day Cycle in Patients with Advanced Solid Tumors," Cancer, pp. 4262-4270, Sep. 1 (2012).
Rodrigues et al., "Synthesis and beta-lactamase-mediated activation of a cephalosporin-taxol prodrug." Chem Biol., vol. 2(4), pp. 223-227 (1995).
Rogerson et al., "Chondroitin sulfate A is a cell surface receptor for Plasmodium falciparum-infected erythrocytes.", J Exp Med., vol. 182(1), pp. 15-20 (1995).
Salanti et al. "Evidence for the involvement of VAR2CSA in pregnancy-associated malaria," J Exp Med., vol. 200(9), pp. 1197-1203 (2004).
Salanti et al., "Targeting Human Cancer by a Glycosaminoglycan Binding Malaria Protein," Cancer Cell., vol. 28(4), pp. 500-514 (2015).
Shen et al. ZIP4 in homologous chromosome synapsis and cross-over formation in rice meiosis. J Cell Sci, vol. 125(Pt 11), pp. 2581-2591 (2012).
Shnyder et al., "Auristatin PYE, a novel synthetic derivative of dolastatin 10, is highly effective in human colon tumour models," Int. J. Oncol., vol. 31, pp. 353-360 (2007).
Talpir et al., "Hemiasterlin and Geodiamolide TA; Two New Cytotoxic Peptides from the Marine Sponge Hemiasterella Minor (Kirkpatrick)," Tetrahedron Letters, vol. 35, No. 25, pp. 4453-4456 (1994).
Temming et al., "Improved Efficacy of αvβ3-Targeted Albumin Conjugates by Conjugation of a Novel Auristatin Derivative," Molecular Pharmaceutics, vol. 4, No. 5, pp. 686-694 (2007).
Vedejs, et al., "A Total Synthesis of (-)-Hemiasterlin Using N-Bts Methodology," J. Org. Chem., vol. 66, pp. 7355-7364 (2001).
Wu, et al., "Site-specific chemical modification of recombinant proteins produced in mammalian cells by using the genetically encoded aldehyde tag." PNAS, vol. 106(9) 3000-3005 (2009).

(56) References Cited

OTHER PUBLICATIONS

Yamashita et al., "Synthesis and Activity of Novel Analogs of Hemiasterlin as Inhibitors of Tubulin Polymerization: Modification of the A Segment," Bioorganic and Medicinal Chemistry Letters, vol. 14, pp. 5317-5322 (2004).

Zask et al., "D-piece Modifications of the Hemiasterlin Analog HTI-286 Produce Potent Tubulin Inhibitors," Bioorganic & Medicinal Chemistry Letters, vol. 14, pp. 4353-4358 (2004).

Zask et al., "Synthesis and Biological Activity of Analogues of the Antimicrotubule Agent N,β,β-Trimethyl-I-phenylalanyl-N1-[(1S,2E)-3-carboxy-1-isopropylbut-2-enyl]-N1,3-dimethyl-I-valinamide (HTI-286)," J. Med. Chem., vol. 47, pp. 4774-4786 (2004).

Zimmerman et al., "Production of site-specific antibody-drug conjugates using optimized non-natural amino acids in a cell-free expression system," Bioconjug Chem., vol. 25(2), pp. 351-361 (2014).

Restriction Requirement dated Oct. 5, 2017 in U.S. Appl. No. 15/108,258.

Non-final Office Action dated May 18, 2018 in U.S. Appl. No. 15/108,258.

Non-final Office Action dated Mar. 19, 2019 in U.S. Appl. No. 15/108,258.

\* cited by examiner

A

Compound 1

B

MTvc886

C

VDC886

COMPOSITIONS AND METHODS FOR THE TREATMENT OF PLATINUM-DRUG RESISTANT CANCER

CROSS-REFERENCE

This application claims the benefit under 35 U.S.C. § 119(e) of U.S. Provisional Patent Application No. 62/404,096, filed Oct. 10, 2016, the application for which is incorporated herein by reference in its entirety.

SEQUENCE LISTING

This application contains a Sequence Listing which has been submitted in ASCII format via EFS-Web and is hereby incorporated by reference in its entirety. Said ASCII copy was created on Mar. 15, 2018, is named KV2-005US2_SL.txt and is 268,465 bytes in size.

FIELD

The present disclosure relates to the field of cancer therapeutics, in particular to methods of treating platinum-drug resistant cancer using targeted drug-conjugates.

BACKGROUND

Platinum-based drugs find widespread use in the treatment of cancer. Cisplatin, carboplatin and oxaliplatin, for example, are used extensively in the treatment of a range of solid tumors including bladder cancer, breast cancer, colon cancer, head and neck cancer, small cell and non-small cell lung cancer, ovarian cancer, melanoma and non-Hodgkin lymphoma. The efficacy and applicability of platinum drugs, however, are limited by systemic toxicity and drug resistance with significant relapse and progression rates being observed amongst patients.

Resistance to platinum drugs is believed to be multifaceted (Shen, et al., 2012, *Pharmacological Reviews*, 64:706-721). Upregulation of CD44 and/or the presence of cancer stem cells has been observed in a number of platinum drug-resistant cancers, including for example, ovarian cancer (see, for example, Pylväs-Eerola, et al., 2016, *Anticancer Res.*, 36:3425-3432; Gao, et al., 2015, *Oncotarget*, 6:9313-9326), head and neck cancer (see, for example, Kulsum, et al., 2016, *Mol. Carcinog*. doi: 10.1002/mc.22526) and lung cancer (see, for example, Leung, et al., 2010, *PLoS One*, 5: e14062-10). Alterations in glycosylation patterns have also been reported (Ferreira, et al., 2015, *Drug Resistance Updates*, 24:34-54).

Glycosaminoglycans (GAGs) are carbohydrate modifications attached to cellular and extra-cellular proteins. Changes in expression and composition of GAGs have been sporadically reported in bladder cancer over the past three decades (De Klerk, 1985, *J Urol.*, 134:978-81; Hennessey, et al., 1981, *Cancer Res.*, 41:3868-73; Ohyama, 2008, *International Journal of Clinical Oncology*, 13:308-13). Chondroitin sulfate (CS) is a major cancer-associated GAG, which also plays a key role in malaria pathogenesis (Rogerson, et al., 1995, *J Exp. Med.*, 182:15-20). The malaria parasite *Plasmodium falciparum* has evolved a protein VAR2CSA that mediates attachment of infected erythrocytes to a distinct type of chondroitin sulfate (CS) chain in the placental syncytium (Salanti, et al., 2004, *J Exp. Med.*, 200:1197-203). CS chains are comprised of alternating glucoronic acid and N-acetylgalactosamine (GalNAc) residues that vary in chain length and sulfation pattern. Although not fully resolved, placental-type CS is likely comprised of dense patches of carbon-4 GalNAc sulfations (Alkhalil, et al., 2000, *J Biol Chem.*, 275:40357-64; Beeson, et al., 2007, *J Biol Chem.*, 282:22426-36). This particular CS signature is required for exclusive sequestration of VAR2CSA$^+$ erythrocytes to placenta giving rise to pregnancy-associated malaria in endemic regions of the world (Salanti, et al., 2004, ibid.; Fried and Duffy, 1996, *Science*, 272:1502-4). Many tumors express placental-type CS as a secondary oncofetal CS (ofCS) modification, which can be specifically recognized by recombinant malarial VAR2CSA (rVAR2) proteins (International Patent Publication No. WO 2013/117705; Salanti, et al., 2015, *Cancer Cell*, 28:500-14).

Functional binding fragments of VAR2CSA and their use in the treatment of conditions associated with the expression of chondroitin sulfate A (CSA) have been described (International Patent Publication No. WO 2013/117705). VAR2CSA-drug conjugates and their use in the treatment of cancer and other diseases have also been described (International Patent Publication No. WO 2015/095952).

This background information is provided for the purpose of making known information believed by the applicant to be of possible relevance to the present disclosure. No admission is necessarily intended, nor should be construed, that any of the preceding information constitutes prior art against the claimed invention.

SUMMARY

Described herein are compositions and methods for the treatment of platinum-drug resistant cancer.

In one aspect, the present disclosure relates to a method of treating a platinum drug-resistant cancer in a subject comprising administering to the subject an effective amount of a VAR2CSA-drug conjugate (VDC), the VDC comprising: a) a VAR2CSA polypeptide that specifically binds to oncofetal chondroitin sulfate (ofCS), and b) one or more toxins having anti-cancer activity conjugated to the VAR2CSA polypeptide.

In one aspect, the present disclosure relates to a method of treating cancer in a subject who has received a prior treatment regimen comprising a platinum drug, the method comprising administering to the subject an effective amount of a VAR2CSA-drug conjugate (VDC), the VDC comprising: a) a VAR2CSA polypeptide that specifically binds to oncofetal chondroitin sulfate (ofCS), and b) one or more toxins having anti-cancer activity conjugated to the VAR2CSA polypeptide. In certain embodiments, the subject has relapsed or progressed following the prior treatment regimen.

In one aspect, the present disclosure relates to a method of inhibiting growth of a platinum drug-resistant tumor in a subject comprising administering to the subject an effective amount of a VAR2CSA-drug conjugate (VDC), the VDC comprising: a) a VAR2CSA polypeptide that specifically binds to oncofetal chondroitin sulfate (ofCS), and b) one or more toxins having anti-cancer activity conjugated to the VAR2CSA polypeptide.

In one aspect, the present disclosure relates to a method of inhibiting the proliferation of platinum drug-resistant cancer cells comprising contacting the cells with an effective amount of a VAR2CSA-drug conjugate (VDC), the VDC comprising: a) a VAR2CSA polypeptide that specifically binds to oncofetal chondroitin sulfate (ofCS), and b) one or more toxins having anti-cancer activity conjugated to the VAR2CSA polypeptide.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
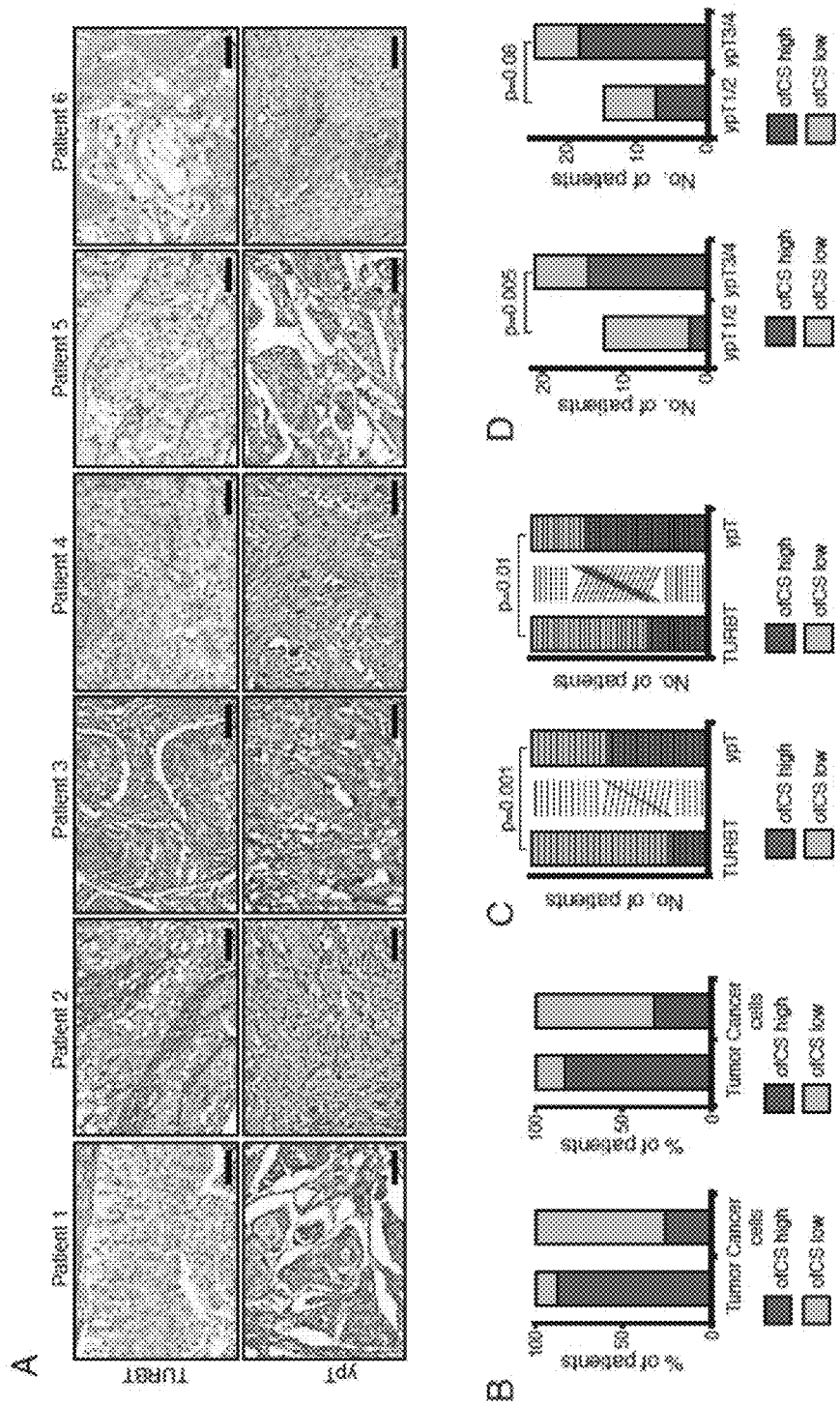
FIG. 1 shows oncofetal chondroitin sulfate (ofCS) expression in chemotherapy naïve and cisplatin-resistant bladder cancer: (A) Representative immunohistochemistry (IHC) images of ofCS expression in matched bladder cancer cases showing cellular ofCS expression in paired transurethral resection of primary tumor (TURBT) samples (upper panel) and cisplatin resistant tumor (ypT) samples (lower panel). Scale bar represents 50 μm. (B) ofCS expression was examined in chemotherapy naïve bladder cancers (TURBT) of two independent cohorts (discovery: left, validation: right). "Tumor" represents overall ofCS expression in bladder tumor including the microenvironment; "Cancer Cells" represents ofCS expression in cancer cellular compartment only. (C) Plots indicating paired analysis of chemotherapy naïve (TURBT) and cisplatin-resistant (ypT) tumors in discovery (left) and validation (right) cohorts. Each box indicates the tumor of a given patient and the lines indicates the pairs between TURBT to ypT. (D) Bar plots indicating the relation of cellular ofCS expression in ypT compared to tumor stage in discovery (left) and validation (right) cohorts. (E) Representative IHC images of ofCS expression in different ypT stages of muscle invasive bladder cancer (MIBC). Scale bar represents 50 μm. (F) Kaplan-Meier plots for overall survival (OS) stratified according to high and low cellular ofCS expression in ypT (discovery: upper, validation: lower).
Figure 1:
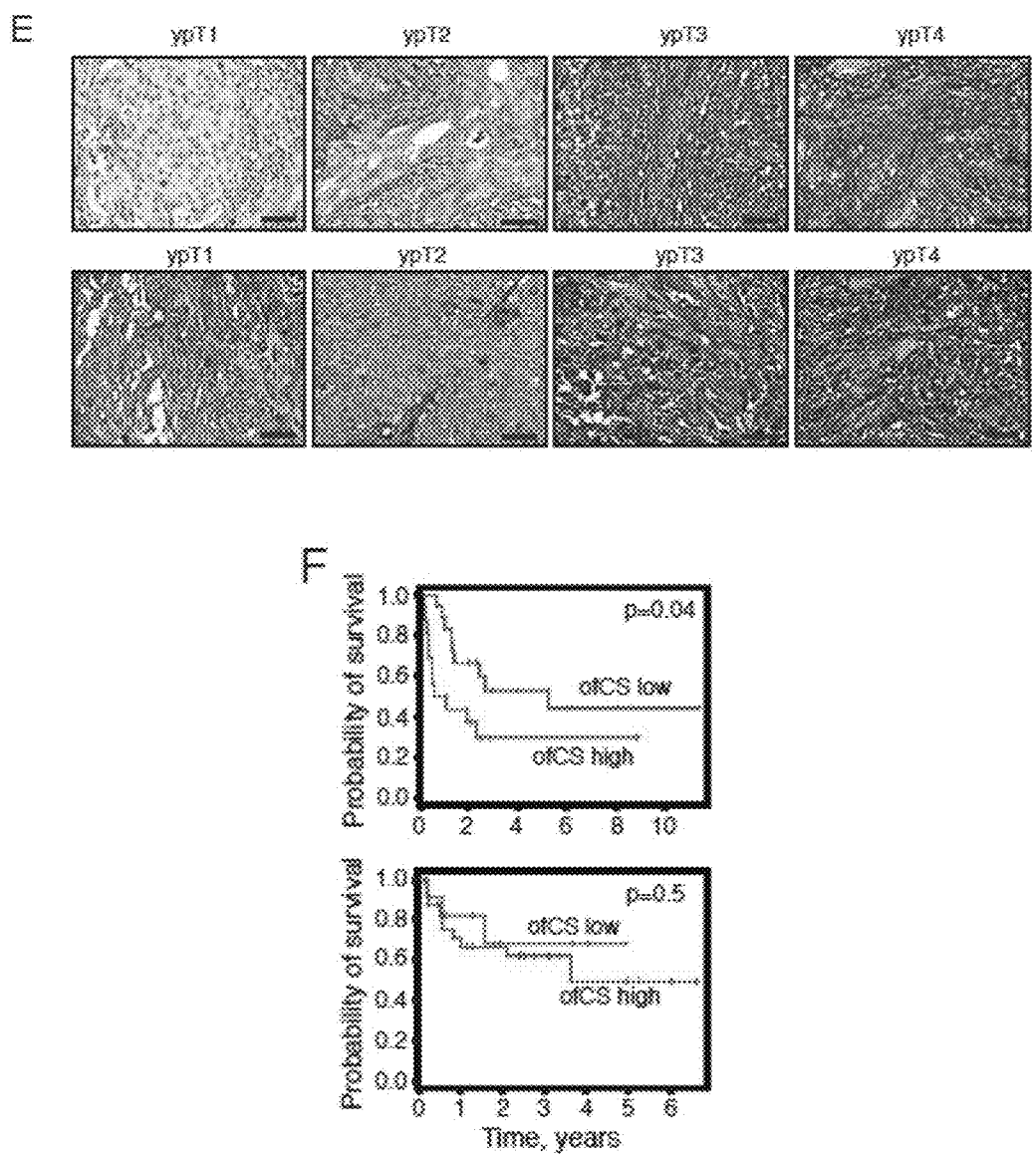

The present disclosure relates to the ability of VAR2CSA-drug conjugates to effectively target and inhibit the growth of cancer cells that have developed resistance to a platinum drug. VAR2CSA-drug conjugates (VDCs) comprise a VAR2CSA polypeptide that is capable of binding to oncofetal chondroitin sulfate (ofCS) and one or more toxins having anti-cancer activity conjugated to the VAR2CSA polypeptide.

As demonstrated herein, elevated ofCS expression levels are associated with platinum drug-resistance in bladder cancer. The increased expression of ofCS correlates with an increased expression of the proteoglycan CD44, which is a known cancer stem cell marker. Upregulation of CD44 and/or the presence of cancer stem cells has been observed in a number of different platinum drug-resistant cancers, including for example, ovarian cancer (see, for example, Pylväs-Eerola, et al., 2016, *Anticancer Res.*, 36:3425-3432; Gao, et al., 2015, *Oncotarget*, 6:9313-9326), head and neck cancer (see, for example, Kulsum, et al., 2016, Mol. Carcinog. doi: 10.1002/mc.22526) and lung cancer (see, for example, Leung, et al., 2010, *PLoS One*, 5: e14062-10).

Certain embodiments of the present disclosure relate to the use of VDCs in the treatment of a platinum drug-resistant cancer. In certain embodiments, the platinum drug-resistant cancer shows a higher expression of ofCS compared to a corresponding cancer that is not resistant to the platinum drug. In some embodiments, the VDC is administered as a second-line therapy after a prior treatment regimen that included the platinum drug. Certain embodiments relate to the use of VDCs in the treatment of a platinum drug-resistant cancer in which expression of CD44 is upregulated.

Definitions

Unless defined otherwise, all technical and scientific terms used herein have the same meaning as commonly understood by one of ordinary skill in the art.

As used herein, the term "about" refers to an approximately +/−10% variation from a given value. It is to be understood that such a variation is always included in any given value provided herein, whether or not it is specifically referred to.

Similarly, ranges may be expressed herein as from about one particular value, and/or to about another particular value. When such a range is expressed, it is to be understood that another embodiment is from the one particular value and/or to the other particular value, along with all combinations within said range.

The use of the word "a" or "an" when used herein in conjunction with the term "comprising" may mean "one," but it is also consistent with the meaning of "one or more," "at least one" and "one or more than one."

As used herein, the terms "comprising," "having," "including" and "containing," and grammatical variations thereof, are inclusive or open-ended and do not exclude additional, unrecited elements and/or method steps. The term "consisting essentially of" when used herein in connection with a composition, use or method, denotes that additional elements and/or method steps may be present, but that these additions do not materially affect the manner in which the recited composition, method or use functions. The term "consisting of" when used herein in connection with a composition, use or method, excludes the presence of additional elements and/or method steps. A composition, use or method described herein as comprising certain elements and/or steps may also, in certain embodiments consist essentially of those elements and/or steps, and in other embodiments consist of those elements and/or steps, whether or not these embodiments are specifically referred to.

The term "DBL2Xb" as used herein refers to a domain of VAR2CSA characterized by having an amino acid sequence substantially identical to an amino acid sequence identified by amino acids 153-577 of SEQ ID NO:1.

The term "ID1" as used herein refers to a domain of VAR2CSA characterized by having an amino acid sequence substantially identical to an amino acid sequence identified by amino acids 1-152 of SEQ ID NO:1.

The term "ID2a" as used herein refers to a domain of VAR2CSA characterized by having an amino acid sequence substantially identical to an amino acid sequence identified by amino acids 578-640 of SEQ ID NO: 1.

The term "substantially identical" as used herein in relation to a nucleic acid or amino acid sequence indicates that, when optimally aligned, for example using the methods described below, the nucleic acid or amino acid sequence shares at least 70% sequence identity with a defined second nucleic acid or amino acid sequence (or "reference sequence"). In certain embodiments, the nucleic acid or amino acid sequence shares at least 75%, at least 80%, at least 85%, at least 90%, at least 95%, at least 96%, at least 97%, at least 98% or at least 99% sequence identity with the reference sequence. "Substantial identity" may be used to refer to various types and lengths of sequence, such as full-length sequence, functional domains, coding and/or regulatory sequences, promoters, and genomic sequences. Percent identity between two amino acid or nucleic acid sequences can be determined in various ways that are within the skill of a worker in the art, for example, using publicly available computer software such as Smith Waterman Alignment (Smith, T. F. and M. S. Waterman, 1981, *J Mol Biol*, 147:195-7); "BestFit" (Smith and Waterman, 1981, *Advances in Applied Mathematics*, 2:482-489) as incorporated into GeneMatcher Plus™, Schwarz and Dayhof (1979) *Atlas of Protein Sequence and Structure*, Dayhof, M. O., Ed pp 353-358; BLAST program (Basic Local Alignment Search Tool) (Altschul, S. F., W. Gish, et al., 1990, *J Mol Biol*, 215:403-10), and variations thereof including BLAST-2, BLAST-P, BLAST-N, BLAST-X, WU-BLAST-2, ALIGN, ALIGN-2, CLUSTAL, and Megalign (DNASTAR) software. In addition, those skilled in the art can determine appropriate parameters for measuring alignment, including algorithms needed to achieve maximal alignment over the length of the sequences being compared. One skilled in the art will understand that the actual length will depend on the overall length of the sequences being compared. In certain embodiments, for amino acid sequences, the length of comparison sequences may be at least 100 amino acids, for example, at least 150, at least 200, or at least 250 amino acids, or it may be the full-length of the amino acid sequence.

A polypeptide that is "derived from" a native protein sequence means that the polypeptide has an amino acid sequence that is substantially identical to the referenced sequence of the native protein.

The term "anti-cancer activity" as used herein with reference to a toxin means that the toxin is able to inhibit the proliferation of cancer cells and/or tumor growth.

The term "inhibit" and grammatical variations thereof, as used herein, refers to a measurable decrease in a given parameter or event. Inhibition may be complete or partial and may be of short or long term duration.

It is contemplated that any embodiment discussed herein can be implemented with respect to any method, use or composition disclosed herein, and vice versa.

VAR2CSA-Drug Conjugates (VDCs)

The VAR2CSA-drug conjugates (VDCs) of the present disclosure comprise a VAR2CSA polypeptide and one or more toxins having anti-cancer activity conjugated to the VAR2CSA polypeptide. In certain aspects, the VAR2CSA polypeptide included in the VDC is capable of specifically binding to oncofetal chondroitin sulfate (ofCS).

In certain aspects, the VDCs comprise a VAR2CSA polypeptide that is a functional fragment of a full-length VAR2CSA protein conjugated to a toxin either directly or via a linker. In certain embodiments, the VDC is a compound of general formula (I):

$$V-[(L)_n-(T)_m]_p \quad (I)$$

wherein
V is a VAR2CSA polypeptide;
L is a linker;
T is a toxin;
n is 0 or 1;
m is an integer from 1 to 8, and
p is an integer from 1 to 12.

In some embodiments, in compounds of general formula (I), when n is 0, then m is 1.

In some embodiments, in compounds of general formula (I): n is 1.

In some embodiments, in compounds of general formula (I): n is 1, and m is an integer from 1 to 4.

In some embodiments, in compounds of general formula (I): n is 1, and m is 1.

In some embodiments, in compounds of general formula (I): m+p is less than or equal to 12, for example, m+p may be less than or equal to 10, less than or equal to 8, less than or equal to 6, or less than or equal to 4.

In some embodiments, in compounds of general formula (I): p is an integer from 1 to 10.

In some embodiments, in compounds of general formula (I): p is an integer from 1 to 4.

In some embodiments, in compounds of general formula (I): n is 1; m is 1, and p is an integer from 1 to 4.

In certain embodiments, the VDC is a compound of general formula (II):

$$V-[L-T]_q \quad (II)$$

wherein:
V, L and T are as defined above for general formula (I), and
q is an integer from 1 to 12.

In some embodiments, in compounds of general formula (II): q is an integer from 1 to 10, for example, from 1 to 8, or from 1 to 4.

VAR2CSA Polypeptides

In certain embodiments, the VAR2CSA polypeptide for inclusion in the VDCs described herein is capable of specifically binding to oncofetal chondroitin sulfate (ofCS).

The term "oncofetal chondroitin sulfate" (ofCS) is used herein to refer to a distinct CSA subtype that is predominantly expressed in the placenta and is specifically bound by native VAR2CSA. ofCS has also been shown to be present on cancer cells and in the extracellular matrix of tumors. In the placenta, ofCS has been characterized as a long polymer larger than a DP12 (degree of polymerization) and having a high level of C4 sulfation.

Figure 7:
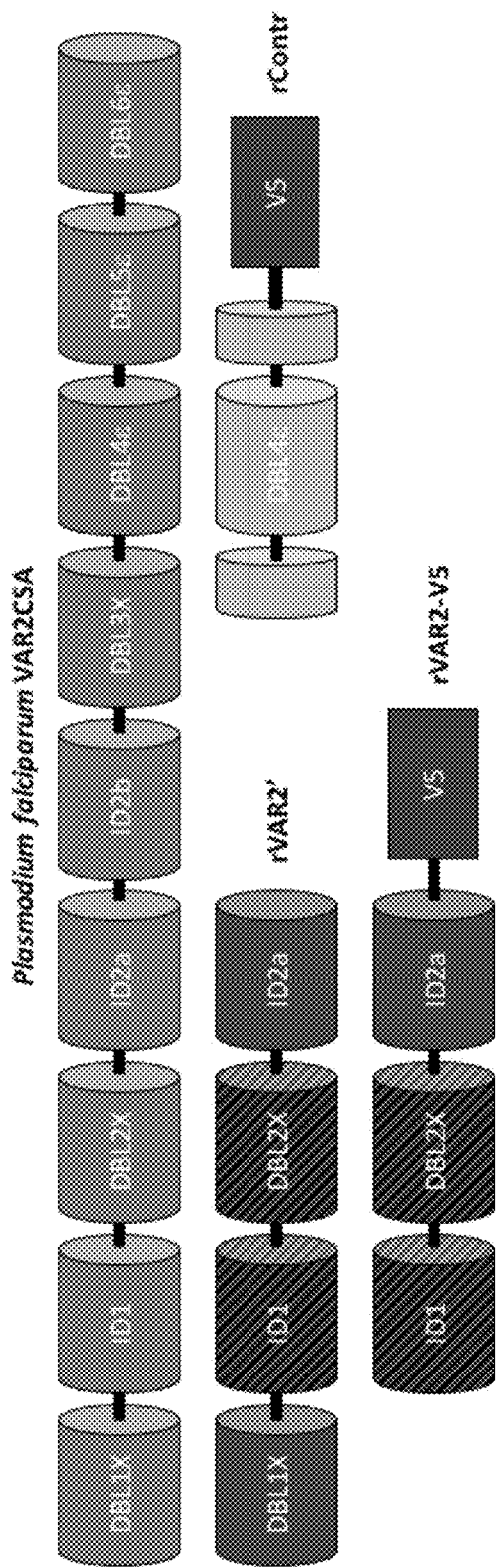
FIG. 7 shows a schematic representation of the full-length *Plasmodiun falciparum* VAR2CSA protein and the rVAR2-v5, rVAR2' and rContr polypeptides. The minimal chondroitin sulfate binding region (ID1-DBL2X) is denoted with cross hatching.

VAR2CSA is a large multi-domain protein of approximately 350 kDa (see FIG. 7). In certain aspects, the VAR2CSA polypeptides for inclusion in the VDCs are functional fragments of a full-length VAR2CSA protein. The term "functional fragment" as used herein with reference to VAR2CSA refers to a fragment of a native full-length VAR2CSA protein that comprises at least the minimal binding sequences from the VAR2CSA protein and possesses the ability to specifically bind ofCS. Typically, the functional fragment will be a fragment of an extracellular portion of the VAR2CSA.

Representative sequences of the extracellular portion of native VAR2CSA from *P. falciparum* strains 3D7 and FCR3 are provided herein as SEQ ID NOs:55 and 56, respectively.

Minimal structural elements of the VAR2CSA protein required for retention of binding to ofCS with high affinity and specificity have been identified. The minimal binding region is the region spanning the ID1 to DBL2Xb domains (see International Patent Publication No. WO 2013/117705). The ID1-DBL2Xb minimal binding region has a molecular weight of approximately 62 kDa. A number of other VAR2CSA polypeptides smaller than full length VAR2CSA that are capable of binding ofCS with high affinity (typically nM affinity) and high specificity have been identified (see International Patent Publication No. WO 2013/117705) and are suitable for inclusion in the VDCs described herein.

In some embodiments, the VAR2CSA polypeptide for inclusion in the VDCs described herein comprises a sequential amino acid sequence of ID1 and DBL2Xb domains. A representative sequence for the ID1 and DBL2Xb domains of *P. falciparum* strain FCR3 VAR2CSA is provided herein as SEQ ID NO:57.

In some embodiments, the VAR2CSA polypeptide for inclusion in the VDCs described herein comprises an amino acid sequence having at least 70% sequence identity with the amino acid sequence as set forth in SEQ ID NO:57. In some embodiments, the VAR2CSA polypeptide for inclusion in the VDCs described herein comprises an amino acid sequence having at least 80% sequence identity, for example at least 85%, at least 90%, at least 95%, or at least 98% sequence identity, with the amino acid sequence as set forth in SEQ ID NO:57. In some embodiments, the VAR2CSA polypeptide for inclusion in the VDCs described herein comprises the amino acid sequence as set forth in SEQ ID NO:57.

In some embodiments, the VAR2CSA polypeptide for inclusion in the VDCs described herein comprises a sequential amino acid sequence of ID1, DBL2Xb and ID2a domains. A representative sequence for the ID1, DBL2Xb and ID2a domains of *P. falciparum* strain FCR3 VAR2CSA is provided herein as SEQ ID NO:1. In some embodiments, the VAR2CSA polypeptide for inclusion in the VDCs described herein comprises a sequential amino acid sequence of ID1 and DBL2Xb domains and all or a N-terminal portion of an ID2a domain. The N-terminal portion of the ID2a domain may be, for example, at least 5, at least 10, at least 15, at least 20, at least 25, at least 30, at least 35, at least 40, at least 45 or at least 50 amino acids in length, or any amount therebetween.

In some embodiments, the VAR2CSA polypeptide for inclusion in the VDCs described herein further comprises an additional amino acid sequence at the N-terminus, at the C-terminus, or within, the sequence of the VAR2CSA polypeptide of not more than 100 amino acids, such as not more than 90, not more than 80, not more than 70, not more than 60, not more than 50, not more than 40, not more than 30, not more than 20, not more than 15, not more than 10, or not more than 5 amino acids. For example, from about 2 to about 100, from about 2 to about 50, from about 2 to about 20, from about 2 to about 10, from 2 to about 10 amino acids, or from 2 to 10 amino acids. The additional amino acid sequence may be derived from another part of the VAR2CSA protein, or it may be a heterologous sequence that is not derived from any part of a VAR2CSA protein.

In some embodiments, the VAR2CSA polypeptide for inclusion in the VDCs described herein competes with the parental full-length VAR2CSA for binding to ofCS. In some embodiments, the VAR2CSA polypeptide for inclusion in the VDCs described herein competes with the parental full-length VAR2CSA for binding to cancer cells.

In some embodiments, the VAR2CSA polypeptide for inclusion in the VDCs described herein binds plCSA on proteoglycans (CSPG) with an affinity as measured by a $K_D$ lower than 100 nM, such as lower than 80 nM, lower than 70 nM, lower than 60 nM, lower than 50 nM, lower than 40 nM, lower than 30 nM, lower than 26 nM, lower than 24 nM, lower than 22 nM, lower than 20 nM, lower than 18 nM, lower than 16 nM, lower than 14 nM, lower than 12 nM, lower than 10 nM, lower than 9 nM, lower than 8 nM, lower than 7 nM, lower than 6 nM, or lower than 4 nM. For example, with an affinity as measured by $K_D$ of from about 1 nM to about 100 nM, from about 1 nM to about 50 nM, or from about 1 nM to about 25 nM.

In some embodiments, the VAR2CSA polypeptide for inclusion in the VDCs described herein comprises an amino acid sequence having at least 70% sequence identity, for example, at least 80%, at least 85%, at least 90%, at least 95%, or at least 98% sequence identity, with the amino acid sequence as set forth in any one of: amino acids 1-577 of SEQ ID NO:1, amino acids 1-592 of SEQ ID NO:3, amino acids 1-579 of SEQ ID NO:4, amino acids 1-576 of SEQ ID NO:5, amino acids 1-586 of SEQ ID NO:10, amino acids 1-579 of SEQ ID NO: 11, amino acids 1-565 of SEQ ID NO:29, amino acids 1-584 of SEQ ID NO:34, amino acids 1-569 of SEQ ID NO:36, amino acids 1-575 of SEQ ID NO:37, amino acids 1-592 of SEQ ID NO:38, amino acids 1-603 of SEQ ID NO:41, amino acids 1-588 of SEQ ID NO:43, amino acids 1-565 of SEQ ID NO:44, amino acids 1-589 of SEQ ID NO:45, amino acids 1-573 of SEQ ID NO:48, amino acids 1-583 of SEQ ID NO:53, or amino acids 1-569 of SEQ ID NO:54.

In some embodiments, the VAR2CSA polypeptide for inclusion in the VDCs described herein comprises the amino acid sequence as set forth in any one of: amino acids 1-577 of SEQ ID NO:1, amino acids 1-592 of SEQ ID NO:3, amino acids 1-579 of SEQ ID NO:4, amino acids 1-576 of SEQ ID NO:5, amino acids 1-586 of SEQ ID NO:10, amino acids 1-579 of SEQ ID NO:11, amino acids 1-565 of SEQ ID NO:29, amino acids 1-584 of SEQ ID NO:34, amino acids 1-569 of SEQ ID NO:36, amino acids 1-575 of SEQ ID NO:37, amino acids 1-592 of SEQ ID NO:38, amino acids 1-603 of SEQ ID NO:41, amino acids 1-588 of SEQ ID NO:43, amino acids 1-565 of SEQ ID NO:44, amino acids 1-589 of SEQ ID NO:45, amino acids 1-573 of SEQ ID NO:48, amino acids 1-583 of SEQ ID NO:53, or amino acids 1-569 of SEQ ID NO:54.

In some embodiments, the VAR2CSA polypeptide for inclusion in the VDCs described herein comprises an amino acid sequence having at least 70% sequence identity, for example, at least 80%, at least 85%, at least 90%, at least 95%, or at least 98% sequence identity, with the amino acid sequence as set forth in any one of SEQ ID NO: 1, SEQ ID NO:3, SEQ ID NO:4, SEQ ID NO:5, SEQ ID NO:10, SEQ ID NO:11, SEQ ID NO:29, SEQ ID NO:34, SEQ ID NO:36, SEQ ID NO:37, SEQ ID NO:38, SEQ ID NO:41, SEQ ID NO:43, SEQ ID NO:44, SEQ ID NO:45, SEQ ID NO:48, SEQ ID NO:53, or SEQ ID NO:54.

In some embodiments, the VAR2CSA polypeptide for inclusion in the VDCs described herein comprises the amino acid sequence as set forth in any one of SEQ ID NO:1, SEQ ID NO:3, SEQ ID NO:4, SEQ ID NO:5, SEQ ID NO:10, SEQ ID NO:11, SEQ ID NO:29, SEQ ID NO:34, SEQ ID NO:36, SEQ ID NO:37, SEQ ID NO:38, SEQ ID NO:41, SEQ ID NO:43, SEQ ID NO:44, SEQ ID NO:45, SEQ ID NO:48, SEQ ID NO:53, or SEQ ID NO:54.

In some embodiments, the VAR2CSA polypeptide for inclusion in the VDCs described herein comprises the amino acid sequence as set forth in amino acids 1-969 of SEQ ID NO:58.

In some embodiments, the VAR2CSA polypeptide for inclusion in the VDCs described herein comprises a sequence derived from a portion of a full-length VAR2CSA that comprises at least the ID1 and DBL2Xb domains and that is 1100 amino acids or less in length, for example, about 1000 amino acids or less, about 950 amino acids or less, about 900 amino acids or less, about 850 amino acids or less, about 800 amino acids or less, about 750 amino acids or less, about 700 amino acids or less, about 650 amino acids or less, or about 600 amino acids or less, in length.

In some embodiments, the VAR2CSA polypeptide for inclusion in the VDCs described herein comprises a sequence derived from a portion of a full-length VAR2CSA that is from about 550 amino acids to 1100 amino acids in length and comprises at least the ID1 and DBL2Xb domains. For example, the VAR2CSA polypeptide may comprise a sequence derived from a portion of a full-length VAR2CSA that is from about 570 and 1100, from about 570 to about 1000, from about 570 to about 950, from about 570 to about 900, from about 570 to about 850, from about 570 to about 800, from about 570 to about 750, from about 570 to about 700, or from about 570 to about 650 amino acids in length.

In some embodiments, the VAR2CSA polypeptide for inclusion in the VDCs described herein is a recombinant protein. In some embodiments, the VAR2CSA polypeptide is non-glycosylated. In some embodiments, the VAR2CSA polypeptide is glycosylated.

VAR2CSA Polypeptide Modifications

Certain embodiments contemplate conservative modifications to the amino acid sequence of the native VAR2CSA polypeptide (and the corresponding modifications to the encoding nucleotides) that result in variant VAR2CSA polypeptides having functional and chemical characteristics similar to those of native VAR2CSA polypeptide. A non-limiting example of a "conservative amino acid substitution" would be a substitution of a native amino acid residue with a different residue such that there is little or no effect on the polarity or charge of the amino acid residue at that position.

Naturally occurring residues may be divided into classes based on common side chain properties: 1) hydrophobic: norleucine, Met, Ala, Val, Leu, Ile; 2) neutral hydrophilic: Cys, Ser, Thr, Asn, Gln; 3) acidic: Asp, Glu; 4) basic: His, Lys, Arg; 5) residues that influence chain orientation: Gly, Pro; and 6) aromatic: Trp, Tyr, Phe. Non-conservative substitutions may involve, for example, the exchange of a member of one of these classes for a member from another class. Conservative substitutions may involve, for example, the exchange of one member within one of these classes for another member in the same class.

Conservative substitutions may also be made on the basis of the hydropathic index of amino acids. Each amino acid has been assigned a hydropathic index on the basis of its hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is understood in the art (see, for example, Kyte et al., 1982, *J Mol. Biol.*, 157:105-131). It is known that certain amino acids may be substituted for other amino acids having a similar hydropathic index or score and still retain a similar biological activity. In some embodiments, when making changes based upon the hydropathic index, substitution involves amino acids whose hydropathic indexes are within ±2. In some embodiments, when making changes based upon the hydropathic index, substitution involves amino acids whose hydropathic indexes are within ±1 or within ±0.5.

It is also understood in the art that conservative substitutions of amino acids can be made effectively on the basis of hydrophilicity. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In some embodiments, when making changes based upon similar hydrophilicity values, substitution involves amino acids whose hydrophilicity values are within ±2. In some embodiments, when making changes based upon similar hydrophilicity values, substitution involves amino acids whose hydrophilicity values are within ±1 or within ±0.5.

A skilled artisan will be able to determine suitable variants of native VAR2CSA polypeptides using well known techniques. For identifying suitable areas of the molecule that may be changed, for example, one skilled in the art may target areas believed not to be important for activity. For example, when similar polypeptides with similar activities from the same species or from other species are known, one skilled in the art may compare the amino acid sequence of a VAR2CSA polypeptide to such similar polypeptides. With such a comparison, the skilled person can identify residues and portions of the molecules that are conserved among similar polypeptides. It will be appreciated that changes in areas of a VAR2CSA polypeptide that are not conserved relative to such similar polypeptides would be less likely to adversely affect the biological activity and/or structure of the VAR2CSA polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a VAR2CSA polypeptide that correspond to amino acid residues that are important for activity or structure in similar polypeptides. One skilled in the art may opt for chemically similar amino acid substitutions for such predicted important amino acid residues of VAR2CSA polypeptides described herein. One skilled in the art can also analyze the three-dimensional structure and amino acid sequence in relation to that structure in similar polypeptides. In view of that information, one skilled in the art may predict the alignment of amino acid residues of a VAR2CSA polypeptide with respect to its three-dimensional structure.

One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays as described herein. Such variants could be used to gather information about suitable variants. For example, if one discovered that a change to a particular amino acid residue resulted in abolished, unacceptably reduced, or unsuitable activity, variants with such a change would be avoided. In other words, based on information gathered from such routine experiments, one skilled in the art can readily determine the amino acids where further substitutions should be avoided either alone or in combination with other mutations.

A number of methods for predicting secondary structure of proteins and polypeptides have been described (see, for example, Moult, 1996, *Curr. Op. Biotech.*, 7(4):422-427; Chou et al., 1974, *Biochemistry*, 13(2):222-245; Chou et al., 1974, *Biochemistry*, 13(2):211-222; Chou et al., 1978, *Adv. Enzymol. Relat. Areas Mol. Biol*, 47:45-148; Chou et al., 1978, *Ann. Rev. Biochem.*, 47:251-276, and Chou et al., 1979, *Biophys. J.*, 26:367-384). Other methods are well known to those of skill in the art. In addition, a variety of computer programs are currently available to assist with predicting secondary structure, such as JPred (University of Dundee), PredictProtein (Technical University of Munich), SPIDER[2] (Griffith University), YASPIN (Lin et al., 2005, *Bioinformatics*, 21:152-9), and others available through the ExPASy Bioinformatics Resource Portal. The recent growth of the RCSB Protein Data Bank (PDB) has provided enhanced predictability of secondary structure using such methods.

Identity and similarity of related polypeptides can be readily calculated by known methods. Such methods include, but are not limited to, those described in *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part 1, Griffin, A. M., and Griffin, H. G., eds., Humana Press, New Jersey, 1994; *Sequence Analysis in Molecular Biology*, von Heinje, G., Academic Press, 1987; *Sequence Analysis Primer*, Gribskov, M. and Devereux, J., eds., M. Stockton Press, New York, 1991; and Carillo et al., 1988, *SIAM J. Applied Math.*, 48:1073.

Various computer program methods are also available to determine identity and similarity between two sequences and include, but are not limited to, the GCG program package, including GAP (Devereux et al., 1984, *Nucl. Acid. Res.*, 12:387; Genetics Computer Group, University of Wisconsin, Madison, Wis.); and BLASTP, BLASTN, BLASTX and FASTA (Altschul et al., 1990, *J Mol. Biol.*, 215:403-410, publicly available from the National Center for Biotechnology Information (NCBI)). The well-known Smith Waterman algorithm may also be used to determine identity.

The amino acid sequence alterations may be accomplished by a variety of techniques. For example, modification of the nucleic acid sequence may be by standard site-specific mutagenesis techniques such as those described in, for example, Ausubel et al. (1994 & updates), *Current Protocols in Molecular Biology*, John Wiley & Sons, New York). Likewise, procedures for preparing a DNA construct encoding the VAR2CSA polypeptide are well known to persons skilled in the art. For example, a DNA construct may be prepared using the polymerase chain reaction (PCR) with specific primers (*PCR Protocols*, 1990, Academic Press, San Diego, Calif., USA; Ausubel et al. (1994 & updates), *Current Protocols in Molecular Biology*, John Wiley & Sons, New York).

In certain embodiments, the VAR2CSA polypeptides for inclusion in the VDCs described herein may comprise one or more non-naturally occurring amino acid residues. Non-naturally occurring amino acids include, but are not limited to, beta-alanine, desaminohistidine, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, nor-valine, 2-azaphenylalanine, 3-azaphenylalanine, 4-azaphenylalanine, and 4-fluorophenylalanine. Several methods are known in the art for incorporating non-naturally occurring amino acid residues into polypeptides. For example, an in vitro system can be employed in which nonsense mutations are suppressed using chemically aminoacylated suppressor tRNAs. Methods for synthesizing amino acids and aminoacylating tRNA are known in the art. For example, transcription and translation of plasmids containing nonsense mutations may be carried out in a cell-free system comprising an *E. coli* S30 extract and commercially available enzymes and other reagents, with the polypeptides being purified by chromatography (see, for example, Robertson et al., 1991, *J. Am. Chem. Soc.* 113:2722; Ellman et al., 1991, *Methods Enzymol.* 202:301; Chung et al., 1993, *Science*, 259:806-9, and Chung et al., 1993, *Proc. Natl. Acad. Sci. USA*, 90:10145-9). Alternatively, translation may be carried out in *Xenopus oocytes* by microinjection of mutated mRNA and chemically aminoacylated suppressor tRNAs (Turcatti et al., 1996, *J. Biol. Chem.* 271:19991-8). Another method involves culturing *E. coli* cells in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine) with the non-naturally occurring amino acid being incorporated into the polypeptide in place of its natural counterpart (Koide et al., 1994, *Biochem.* 33:7470-6). Naturally occurring amino acid residues may also be converted to non-naturally occurring species by in vitro chemical modification. Chemical modification may optionally be combined with site-directed mutagenesis to further expand the range of substitutions (Wynn and Richards, 1993, *Protein Sci.* 2:395-403).

Preparation of VAR2CSA Polypeptides

The VAR2CSA polypeptides for inclusion in the VDCs described herein may be produced recombinantly using standard molecular biology techniques. Nucleic acid sequences encoding VAR2CSA proteins are known in the art and many are available from the GenBank database maintained by the National Center for Biotechnology Information (NCBI). For example, the VAR2CSA nucleic acid sequence from *Plasmodium falciparum*: strain FCR3 is deposited under Accession No. GU249598, and the VAR2CSA nucleic acid sequence from *Plasmodium falciparum* strain 3D7 is deposited under Accession No. JQ247428.

The nucleic acid construct encoding the VAR2CSA polypeptide may be of genomic or cDNA origin, for instance obtained by preparing a genomic or cDNA library and screening for DNA sequences coding for all or part of the polypeptide by hybridization using synthetic oligonucleotide probes in accordance with standard techniques (see, for example, Sambrook et al., *Molecular Cloning: A Laboratory Manual*, 2nd. Ed. Cold Spring Harbor Laboratory, Cold Spring Harbor, N.Y., 1989). Alternatively, the DNA sequences encoding the VAR2CSA polypeptide may be prepared using the polymerase chain reaction (PCR) using specific primers, for instance as described in U.S. Pat. No. 4,683,202; Saiki et al., 1988, *Science*, 239:487-491, or Ausubel et al. (1994 & updates), *Current Protocols in Molecular Biology*, John Wiley & Sons, New York.

The nucleic acid construct encoding the VAR2CSA polypeptide may also be prepared synthetically by established standard methods, for example, the phosphoamidite method described by Beaucage and Caruthers (1981, *Tetrahedron Letters*, 22:1859-1869) or the method described by Matthes et al. (1984, *EMBO J*, 3:801-805).

The nucleic acid construct is typically a DNA construct. In certain embodiments, DNA sequences for use in producing VAR2CSA polypeptides encode a pre-pro polypeptide at the amino-terminus of VAR2CSA to help in obtaining proper posttranslational processing and secretion from the host cell.

The DNA sequences encoding the VAR2CSA polypeptides may be inserted into a recombinant vector which may conveniently be subjected to recombinant DNA procedures. The choice of vector will often depend on the host cell into which it is to be introduced and can be readily made by the skilled artisan. The vector may be an autonomously replicating vector that exists as an extrachromosomal entity, the replication of which is independent of chromosomal replication, such as a plasmid. Alternatively, the vector may be one which, when introduced into a host cell, is integrated into the host cell genome and replicated together with the chromosome(s) into which it has been integrated.

The nucleic acid construct encoding the desired VAR2CSA polypeptide is typically inserted into an expression vector, which is in turn transformed or transfected into host cells. The host cell selected for expression of the VAR2CSA polypeptide may be one of a variety of cells that are capable of producing posttranslationally modified polypeptides, such as yeast, fungi and eukaryotic cells (for example, mammalian or insect cells). VAR2CSA polypeptides may also be produced recombinantly in prokaryotic cells provided that the cells allow for the formation of disulfide bonds and correct folding of the polypeptide (for example, *E. coli* SHuffle® cells available from New England Biolabs, Ipswich, Mass., or *E. coli* Origami™ cells available from EMD Millipore, Billirica, Mass.).

The DNA sequence encoding the VAR2CSA polypeptide may be inserted directly into the expression vector or they may be subcloned, directly or after undergoing additional recombinant DNA procedures, from a cloning vector into the expression vector. In the expression vector, the DNA sequence encoding the VAR2CSA polypeptide is operably linked to additional segments required for transcription of the DNA. Expression vectors for use in expressing VAR2CSA polypeptides will comprise a promoter capable of directing the transcription of a cloned gene or cDNA. The promoter may be one of a variety of known promoters that show transcriptional activity in the host cell of choice and may be derived from genes encoding proteins that are either homologous or heterologous to the host cell.

Examples of suitable promoters for use in mammalian cells include, but are not limited to, the SV40 promoter (Subramani et al., 1981, *Mol. Cell Biol.*, 1:854-864), the MT-1 (metallothionein gene) promoter (Palmiter et al., 1983, *Science*, 222:809-814), the CMV promoter (Boshart et al., 1985, *Cell*, 41:521-530) and the adenovirus 2 major late promoter (Kaufman and Sharp, 1982, *Mol. Cell. Biol*, 2:1304-1319).

Examples of suitable promoters for use in insect cells include, but are not limited to, the polyhedrin promoter (U.S. Pat. No. 4,745,051; Vasuvedan et al., 1992, *FEBS Lett.*, 311:7-11), the P10 promoter (Vlak et al., 1988, *J. Gen. Virol.*, 69:765-776), the *Autographa californica* polyhedrosis virus basic protein promoter (European Patent Application No. EP 397 485), the baculovirus immediate early gene 1 promoter (U.S. Pat. Nos. 5,155,037 and 5,162,222), and the baculovirus 39K delayed-early gene promoter (U.S. Pat. Nos. 5,155,037 and 5,162,222).

Examples of suitable promoters for use in yeast host cells include, but are not limited to, promoters from yeast glycolytic genes (Hitzeman et al., 1980, *J. Biol. Chem.*, 255: 12073-12080; Alber and Kawasaki, 1982, *J. Mol. Appl. Gen.*, 1:419-434) and alcohol dehydrogenase genes (Young et al., in *Genetic Engineering of Microorganisms for Chemicals* (Hollaender et al, eds.), Plenum Press, New York, 1982), and the TPI1 (U.S. Pat. No. 4,599,311) and ADH2-4c (Russell et al., 1983, *Nature*, 304:652-654) promoters.

Examples of suitable promoters for use in filamentous fungus host cells include, but are not limited to, the ADH3 promoter (McKnight et al., 1985, *EMBO J.*, 4:2093-2099) and the tpiA promoter. Examples of other useful promoters include those derived from the gene encoding *A. oryzae* TAKA amylase, alkaline protease or triose phosphate isomerase; *Rhizomucor miehei* aspartic proteinase or lipase; *A. niger* neutral alpha-amylase or acid stable alpha-amylase; *A. niger* or *A. awamori* glucoamylase (gluA), or *A. nidulans* acetamidase, such as the TAKA-amylase and gluA promoters.

The DNA sequences encoding the VAR2CSA polypeptides may also, if necessary, be operably connected to a suitable terminator, such as the human growth hormone terminator (Palmiter et al., 1983, *Science*, 222:809-814) or the TPI1 (Alber and Kawasaki, 1982, ibid.) or ADH3 (McKnight et al., 1985, ibid.) terminators. Expression vectors may also contain a set of RNA splice sites located downstream from the promoter and upstream from the insertion site for the VAR2CSA sequence itself. Examples of suitable RNA splice sites include those obtained from adenovirus and/or immunoglobulin genes. Also contained in the expression vectors may be a polyadenylation signal located downstream of the insertion site. Examples of polyadenylation signals include the early or late polyadenylation signal from SV40 (Kaufman and Sharp, ibid.), the polyadenylation signal from the adenovirus E1b region, the human growth hormone gene terminator (DeNoto et al., 1981, *Nucl. Acids Res.*, 9:3719-3730) and the polyadenylation signal from *Plasmodium falciparum*, human or bovine genes. The expression vectors may also include a noncoding viral leader sequence (such as the adenovirus 2 tripartite leader) located between the promoter and the RNA splice sites, and enhancer sequences (such as the SV40 enhancer).

To direct the expressed VAR2CSA polypeptides into the secretory pathway of the host cells, a secretory signal sequence, a leader sequence, pre-pro sequence or pre sequence may be provided in the recombinant vector and joined to the DNA sequence encoding the VAR2CSA polypeptide in the correct reading frame. Secretory signal sequences are commonly positioned 5' to the DNA sequence encoding the polypeptide. The secretory signal sequence may be that normally associated with the parent protein, or may be a heterologous sequence, for example, from a gene encoding another secreted protein.

For secretion from yeast cells, suitable signal peptides include, for example, the alpha-factor signal peptide (U.S. Pat. No. 4,870,008), the signal peptide of mouse salivary amylase (Hagenbuchle et al., 1981, *Nature*, 289:643-646), a modified carboxypeptidase signal peptide (Valls et al., 1987, *Cell*, 48:887-897), the yeast BAR1 signal peptide (International Patent Publication No. WO 87/02670), or the yeast aspartic protease 3 (YAP3) signal peptide (Egel-Mitani et al., 1990, *Yeast*, 6:127-137).

For efficient secretion in yeast, a sequence encoding a leader peptide may also be inserted downstream of the signal sequence and upstream of the DNA sequence encoding the VAR2CSA polypeptide. The function of the leader peptide is to allow the expressed polypeptide to be directed from the endoplasmic reticulum to the Golgi apparatus and further to a secretory vesicle for secretion into the culture medium. The leader peptide may be the yeast alpha-factor leader (the use of which is described in, for example, U.S. Pat. Nos. 4,546,082 and 4,870,008, and European Patent Application Nos. EP 123 294, EP 123 544 and EP 163 529). Alternatively, the leader peptide may be a synthetic leader peptide, for instance, constructed as described in International Patent Publication Nos. WO 89/02463 or WO 92/11378.

For use in filamentous fungi, the signal peptide may conveniently be derived from a gene encoding an *Aspergillus* sp. amylase or glucoamylase, a gene encoding a *Rhizomucor miehei* lipase or protease, or a gene encoding a *Humicola lanuginosa* lipase. For example, the signal peptide may be derived from a gene encoding *A. oryzae* TAKA amylase; or *A. niger* neutral alpha-amylase, acid-stable amylase, or glucoamylase. Exemplary suitable signal peptides are described in European Patent Application Nos. EP 238 023 and EP 215 594.

For use in insect cells, the signal peptide may conveniently be derived from an insect gene (International Patent Publication No. WO 90/05783), such as the lepidopteran *Manduca sexta* adipokinetic hormone precursor signal peptide (U.S. Pat. No. 5,023,328).

The procedures used to ligate the DNA sequence encoding the VAR2CSA polypeptide, the promoter and optionally the terminator and/or secretory signal sequence, and insert them into a suitable vector containing the information necessary for replication, are well known to persons skilled in the art (see for example, Sambrook et al., ibid.).

Methods of transforming or transfecting various types of host cells and expressing DNA sequences introduced into the cells are well-known in the art (see, for example, Ausubel et al. (1994 & updates), *Current Protocols in Molecular Biology*, John Wiley & Sons, New York).

For example, cloned DNA sequences may be introduced into cultured mammalian cells by calcium phosphate-mediated transfection (Wigler et al., 1978, *Cell*, 14:725-732; Corsaro and Pearson, 1981, *Somatic Cell Genetics*, 7:603-616; Graham and Van der Eb, 1973, *Virology*, 52d:456-467) or electroporation (Neumann et al., 1982, *EMBO J.*, 1:841-845). To identify and select cells that express the exogenous DNA, a gene that confers a selectable phenotype (a selectable marker) is generally introduced into cells along with the DNA sequence encoding the VAR2CSA polypeptide. Typically, the selectable marker will be included on the same plasmid as the DNA sequence encoding the VAR2CSA polypeptide, although a separate plasmid may be used in some embodiments. Examples of selectable markers include genes that confer resistance to drugs such as neomycin, hygromycin, and methotrexate. The selectable marker may optionally be an amplifiable selectable marker, such as a dihydrofolate reductase (DHFR) sequence. The use of selectable markers is well-known in the art (see review by Thilly, in *Mammalian Cell Technology*, Butterworth Publishers, Stoneham, Mass.).

After the host cells have taken up the DNA, they are grown in an appropriate growth medium, typically for 1-2 days, to begin expressing the VAR2CSA polypeptide. In this context, "appropriate growth medium" means a medium containing nutrients and other components required for the growth of cells and the expression of the VAR2CSA polypeptide. Various media suitable for growing a given host cell are well-known in the art. Drug selection may be applied to select for the growth of cells that are expressing the selectable marker in a stable fashion. For cells that have been transfected with an amplifiable selectable marker the drug concentration may be increased to select for an increased copy number of the cloned sequences, thereby increasing expression levels. Clones of stably transfected cells are then screened for expression of the VAR2CSA polypeptide.

Examples of mammalian cell lines that may be used to express the VAR2CSA polypeptides in some embodiments include the COS-1 (ATCC CRL 1650), baby hamster kidney (BHK) and 293 (ATCC CRL 1573; Graham et al., 1977, *J. Gen. Virol.*, 36:59-72) cell lines. An example of a BHK cell line is the tk-ts13 BHK cell line ("BHK 570 cells") (Waechter and Baserga, 1982, *Proc. Natl. Acad. Sci. USA*, 79:1106-1110), which has been deposited under ATCC accession number CRL 10314. A tk-ts13 BHK cell line is also available from the ATCC under accession number CRL 1632. Other examples of mammalian cell lines include Rat Hep I (rat hepatoma; ATCC CRL 1600), Rat Hep II (rat hepatoma; ATCC CRL 1548), TCMK (ATCC CCL 139), human lung (ATCC HB 8065), NCTC 1469 (ATCC CCL 9.1), CHO (ATCC CCL 61) and DUKX cells (Urlaub and Chasin, 1980, *Proc. Natl. Acad. Sci. USA*, 77:4216-4220).

Examples of suitable yeasts cells include cells of *Saccharomyces* spp. or *Schizosaccharomyces* spp., in particular strains of *Saccharomyces cerevisiae* or *Saccharomyces kluyveri*. Methods for transforming yeast cells with heterologous DNA to produce heterologous polypeptides are described, for example, in U.S. Pat. Nos. 4,599,311; 4,931,373; 4,870,008; 5,037,743 and 4,845,075. Further examples of suitable yeast cells are strains of *Kluyveromyces* (such as *K. lactis*), *Hansenula* (such as *H. polymorpha*) or *Pichia* (such as *P. pastoris*) (see Gleeson et al., 1986, *J. Gen. Microbiol.*, 132:3459-3465, and U.S. Pat. No. 4,882,279).

Examples of filamentous fungi host cells include *Aspergillus* spp., *Neurospora* spp., *Fusarium* spp. or *Trichoderma* spp., in particular strains of *A. oryzae*, *A. nidulans* and *A. niger*. The use of *Aspergillus* spp. for the expression of proteins is described in, for example, European Patent Application Nos. EP 272 277, EP 238 023 and EP 184 438. Transformation of *F. oxysporum* may, for instance, be carried out as described by Malardier et al., 1989, *Gene*, 78:147-156, and transformation of *Trichoderma* spp. may be performed for instance as described in European Patent Application No. EP 244 234.

Examples of suitable insect host cell lines include Lepidoptera cell lines, such as *Spodoptera frugiperda* cells or *Trichoplusia ni* cells (see U.S. Pat. No. 5,077,214). Transformation of insect cells to produce heterologous polypeptides may be performed, for example, as described in U.S. Pat. Nos. 4,745,051; 4,879,236; 5,155,037, and 5,162,222, and European Patent Application No. EP 397 485.

Once a transformed or transfected host cell that expresses the VAR2CSA polypeptide has been identified, it may be cultured in a suitable nutrient medium under conditions permitting expression of the VAR2CSA polypeptide. The medium used to culture the cells may be any conventional medium suitable for growing the host cells, such as minimal or complex media containing appropriate supplements. Suitable media are available from commercial suppliers or may be prepared according to published recipes (for example, in catalogues of the ATCC). The VAR2CSA polypeptide produced by the cells may then be recovered from the culture medium by conventional procedures such as centrifugation or filtration, and/or precipitation of the proteinaceous components of the supernatant or filtrate (for example by means of a salt, such as ammonium sulfate).

The VAR2CSA polypeptide isolated from the culture medium may be purified by a variety of procedures known in the art including, but not limited to, chromatography (for example, one or more of ion exchange, affinity, hydrophobic, chromatofocusing, or size exclusion), electrophoretic procedures (for example, preparative isoelectric focusing (IEF)), differential solubility (such as ammonium sulfate precipitation), or extraction (see, for example, *Protein Purification*, J.-C. Janson and Lars Ryden, editors, VCH Publishers, New York, 1989). In certain embodiments, the VAR2CSA polypeptides may be purified by affinity chromatography on an anti-VAR2CSA antibody column. Additional purification may be achieved by conventional chemical purification means, such as high-performance liquid chromatography. The skilled person will appreciate that other methods of purification known in the art may be applied to the purification of the VAR2CSA polypeptides in certain embodiments (see, for example, Scopes, R., *Protein Purification*, Springer-Verlag, N.Y., 1982).

Methods suitable for preparing VAR2CSA polypeptides have also been described in International Patent Application Nos. WO 2013/117705 and WO 2015/095952.

For therapeutic purposes, the VAR2CSA polypeptide is typically substantially pure. In some embodiments, the VAR2CSA polypeptides are purified to about 90 to 95% homogeneity. In some embodiments, the VAR2CSA polypeptides are purified to about 98% homogeneity. Purity may be assessed by, for example, gel electrophoresis and/or amino-terminal amino acid sequencing.

Toxins

The VDCs described herein comprise one or more toxins having anti-cancer activity conjugated to the VAR2CSA polypeptide. In certain embodiments, the toxin is a microtubule polymerization inhibitor. In some embodiments, the toxin is a depsipeptide microtubule polymerization inhibitor.

Examples of toxins capable of inhibiting microtubule polymerization include, but are not limited to, hemiasterlins, auristatins, tubulysins, dolastatins, maytansines, and analogues and derivatives thereof.

In certain embodiments, the toxin comprised by the VDCs is a hemiasterlin, auristatin, tubulysin, or an analogue or derivative thereof. In certain embodiments, the toxin comprised by the VDCs is a hemiasterlin or an auristatin, or an analogue or derivative thereof. In certain embodiments, the toxin comprised by the VDCs is a hemiasterlin, or a analogue or derivative thereof.

Hemiasterlins

Various analogues and derivatives of hemiasterlin having anti-cancer activity that may be included in the VDCs in some embodiments have been described (see, for example, International Patent Publication Nos. WO 1996/33211, WO 2004/026293 and WO 2014/144871).

U.S. Pat. No. 7,579,323 describes an analogue of hemiasterlin, referred to as HTI-286, that possesses potent antimitotic activity and which has been assessed in clinical trials for the treatment of cancer.

HTI-286

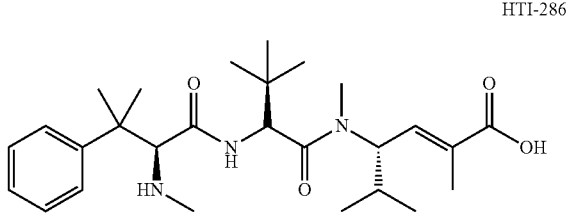

In certain embodiments, the toxin comprised by the VDCs is HTI-286 or an analogue or derivative thereof.

In certain embodiments, the toxin comprised by the VDCs is a hemiasterlin analogue selected from those described in International Patent Publication No. WO 2014/144871.

In certain embodiments, the toxin comprised by the VDCs is a compound having general formula (IV):

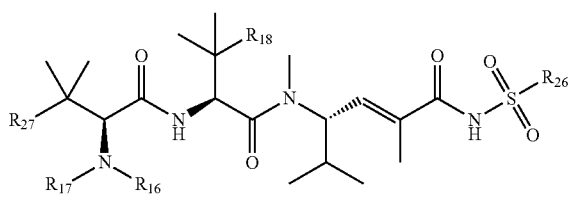

(IV)

wherein:

$R_{26}$ is selected from optionally substituted alkyl, optionally substituted alkylamino, optionally substituted cycloalkyl, optionally substituted aryl, optionally substituted heterocyclyl and optionally substituted heteroaryl;

$R_{27}$ is selected from optionally substituted alkyl, optionally substituted alkylamino, optionally substituted cycloalkyl, optionally substituted aryl, optionally substituted heterocyclyl and optionally substituted heteroaryl;

$R_{16}$ and $R_{17}$ are each independently H or $C_{1-6}$ alkyl, and $R_{18}$ is $C_{1-6}$ alkyl or —SH.

In the context of general formula (IV), the term "alkyl" refers to a straight or branched chain substituent consisting solely of carbon and hydrogen atoms, which is saturated or unsaturated and has from one to 12 carbon atoms; the term "alkylamino" refers to a substituent of the formula —$NHR_a$ or —$NR_aR_a$, where each $R_a$ is independently an alkyl substituent containing one to 12 carbon atoms; the term "cycloalkyl" refers to a stable non-aromatic monocyclic or polycyclic hydrocarbon substituent consisting solely of carbon and hydrogen atoms, which may include fused or bridged ring systems, having from 3 to 10 carbon atoms; the term "aryl" refers to a hydrocarbon ring substituent comprising hydrogen, 6 to 18 carbon atoms and at least one aromatic ring; the term "heterocyclyl" refers to a stable 3- to 18-membered non-aromatic ring substituent which comprises 2 to 12 carbon atoms and from one to 6 heteroatoms selected from N, O and S; the term "heteroaryl" refers to a 5- to 14-membered ring system substituent comprising hydrogen atoms, one to 13 carbon atoms, one to 6 heteroatoms selected from N, O and S, and at least one aromatic ring, and the term "aralkyl" refers to a group having the formula —$R_b$—$R_c$, where $R_b$ is an alkylene chain and $R_c$ is one or more aryl substituents.

In the context of general formula (IV), the term "optionally substituted" used with reference to a defined group means that the group is optionally substituted with one or more substituents selected from: $R_{14}$, =O, =S, —OH, —$OR_{15}$, —$O_2CR_{15}$, —SH, —$SR_{15}$, —$SOCR_{15}$, —$NH_2$, —$N_3$, —$NHR_{15}$, —$N(R_{15})_2$, —$NHCOR_{15}$, —$NR_{15}COR_{15}$, —I, —Br, —Cl, —F, —CN, —$CO_2H$, —$CO_2R_{15}$, —CHO, —$COR_{15}$, —$CONH_2$, —$CONHR_{15}$, —$CON(R_{15})_2$, —COSH, —$COSR_{15}$, —$NO_2$, —$SO_3H$, —$SOR_{15}$ or —$SO_2R_{15}$, wherein $R_{14}$ is optionally substituted $C_1$-$C_6$ alkyl or optionally substituted aryl, and each $R_{15}$ is independently alkyl optionally substituted with halogen, —OH or —SH.

In certain embodiments in compounds of general formula (IV):

$R_{26}$ is optionally substituted alkyl or optionally substituted aryl.

In certain embodiments in compounds of general formula (IV):

$R_{26}$ is optionally substituted phenyl or optionally substituted aralkyl.

In certain embodiments in compounds of general formula (IV):

$R_{27}$ is optionally substituted aryl.

In certain embodiments in compounds of general formula (IV):

$R_{26}$ is optionally substituted alkyl or optionally substituted aryl, and $R_{27}$ is optionally substituted aryl.

In certain embodiments in compounds of general formula (IV):

$R_{16}$ and $R_{17}$ are each independently H or methyl.

In certain embodiments in compounds of general formula (IV):

$R_{18}$ is $C_1$-$C_6$ alkyl.

In certain embodiments in compounds of general formula (IV):

$R_{16}$ is H, and $R_{17}$ and $R_{18}$ are each methyl.

Combinations of any of the foregoing embodiments for compounds of general formula (IV) are also contemplated and each combination forms a separate embodiment for the purposes of the present disclosure.

In certain embodiments, the toxin comprised by the VDCs is a compound of general formula (IV) and is conjugated to the VAR2CSA polypeptide, directly or through a linker, via the $R_{26}$ substituent. In some embodiments, the toxin comprised by the VDCs is a compound of general formula (IV) and is conjugated to the VAR2CSA polypeptide, directly or through a linker, via the $R_{27}$ substituent. In certain embodiments, the toxin comprised by the VDCs is a compound of general formula (IV) that has been modified by standard protocols to allow for conjugation to the VAR2CSA polypeptide, directly or through a linker.

In certain embodiments, the compound of general formula (IV) is selected from the following compounds:

Compound 1
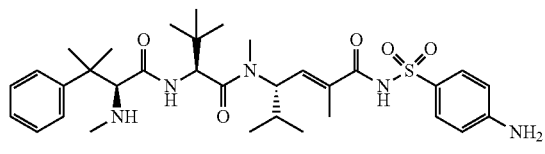
Compound 2
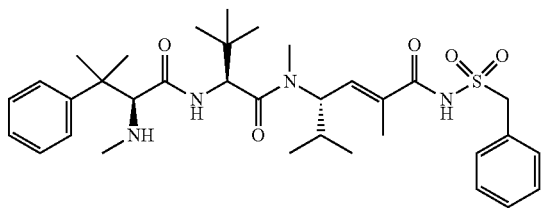
Compound 3
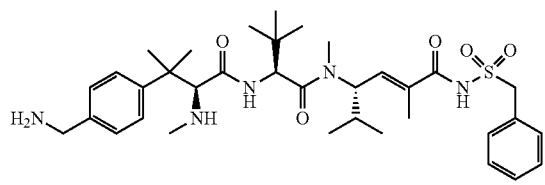
Compound 4
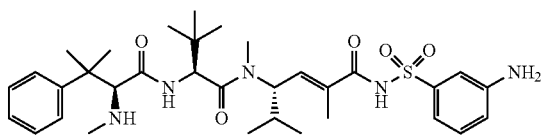
Compound 5
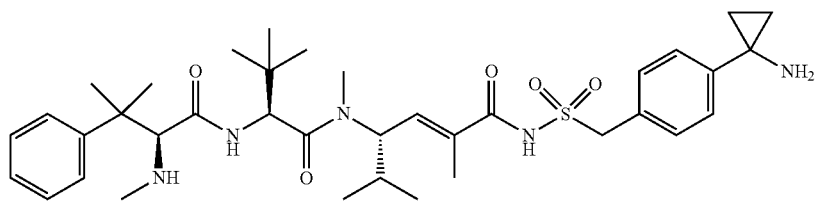
Compound 6
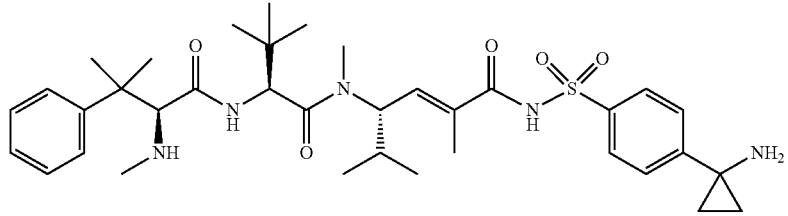
Compound 7
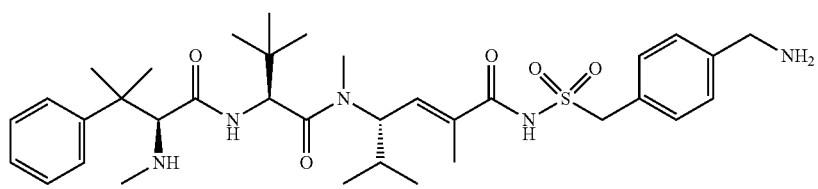
Compound 8
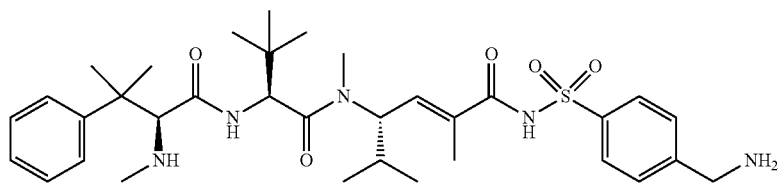
Compound 9
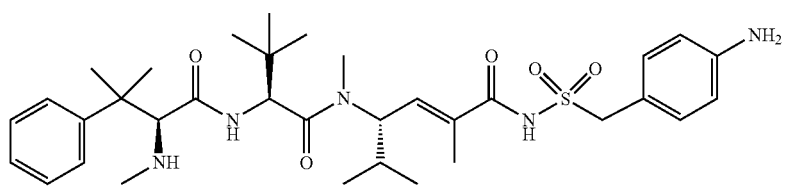

Compound 10

[Chemical structure of Compound 10]

Auristatins

Various auristatin analogues and derivatives having anti-cancer activity are known in the art and are suitable for inclusion in the VDCs in certain embodiments. Examples include, but are not limited to, auristatin E, auristatin F, auristatin EB (AEB), auristatin EVB (AEVB), auristatin F phenylenediamine (AFP), monomethylauristatin F (MMAF), and monomethylauristatin E (MMAE). The synthesis and structure of exemplary auristatins are described in U.S. Pat. Nos. 6,884,869; 7,098,308; 7,256,257; 7,423,116; 7,498,298 and 7,745,394.

The auristatin or auristatin analogue or derivative may be conjugated to the VAR2CSA polypeptide in the VDCs via the amino (N)-terminus or the carboxy (C)-terminus of the auristatin molecule.

Examples of auristatin analogues suitable for conjugation via the N-terminus of the toxin molecule include those described in U.S. Pat. Nos. 7,498,298 and 7,659,241. For example, MMAE or MMAF may be conjugated to the VAR2CSA polypeptide via the N-terminus of the toxin molecule as shown below, where the wavy line indicates the point of conjugation to the VAR2CSA polypeptide, which may be direct conjugation or via a linker:

[Chemical structure of MMAE]

MMAE

[Chemical structure of MMAF]

MMAF

Examples of auristatin analogues suitable for conjugation via the C-terminus of the toxin molecule include those described in International Patent Publication Nos. WO 2002/088172 and WO 2016/041082.

In certain embodiments, the toxin comprised by the VDCs is an auristatin analogue selected from those described in International Patent Publication No. WO 2016/041082.

In some embodiments, the toxin comprised by the VDCs is a compound of general formula (III):

[Chemical structure of formula (III)]

(III)

wherein:

$R^6$ is selected from $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl and heterocyclyl, each optionally substituted with one or more substituents selected from $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloalkyl, $C_1$-$C_6$ haloalkoxy, halo, hydroxyl, nitro, thio and thio-$C_1$-$C_6$ alkyl;

X is —C(O)NHCH(CH$_2$R$^7$)—, or X is absent;

$R^7$ is selected from aryl, heteroaryl and $C_3$-$C_7$ cycloalkyl, each optionally substituted with one substituent selected from amino and hydroxyl, and $R^4$ and $R^5$ are each independently H or $C_1$-$C_6$ alkyl.

In the context of general formula (III), the term "aryl" refers to a radical derived from a 6- to 12-membered mono- or bicyclic hydrocarbon ring system in which at least one ring is aromatic; the term "aryl-alkyl" refers to an alkyl group substituted with one aryl substituent; the term "cycloalkyl-alkyl" refers to an alkyl group substituted with one cycloalkyl substituent; the term "heteroaryl" refers to a radical derived from a 6- to 12-membered mono- or bicyclic ring system wherein at least one ring atom is a heteroatom, such as O, N or S, and at least one ring is aromatic; the term "heteroaryl-alkyl" refers to an alkyl group substituted with one heteroaryl substituent; the term "heterocyclyl" refers to a radical derived from a 3- to 12-membered mono- or bicyclic non-aromatic ring system wherein at least one ring atom is a heteroatom such as O, N or S; the term "alkoxy-carbonyl" refers to —C(O)O-alkyl; the term "alkylamino" refers to —NH-alkyl; the term "amino-alkyl" refers to an alkyl group substituted with one amino substituent; the term "amino-aryl" refers to an aryl group substituted with one amino substituent; the term "amino-cycloalkyl" refers to a cycloalkyl group substituted with one amino substituent; the term "carboxamide" refers to —C(O)NH$_2$; the term "haloalkyl" refers to an alkyl group substituted with one or more halo substituents; the term "haloalkoxy" refers to —O— haloalkyl, and the term "thio-alkyl" refers to —S-alkyl.

In certain embodiments, in compounds of general formula (III):
$R^6$ is aryl or aryl-$C_1$-$C_6$ alkyl, each optionally substituted with one or more substituents as defined above for general formula (III).

In certain embodiments, in compounds of general formula (III):
X is absent.

In certain embodiments, in compounds of general formula (III):
X is —C(O)NHCH(CH$_2$R$^7$)—, wherein R$^7$ is aryl optionally substituted with one substituent selected from amino and hydroxyl.

In certain embodiments, in compounds of general formula (III):
$R^4$ and $R^5$ are each $C_1$-$C_6$ alkyl.

In certain embodiments, in compounds of general formula (III):
$R^4$ and $R^5$ are each methyl.

In certain embodiments, in compounds of general formula (III):
$R^6$ is aryl or aryl-$C_1$-$C_6$ alkyl, each optionally substituted with one or more substituents as defined above for general formula (III);
X is absent, and
$R^4$ and $R^5$ are each $C_1$-$C_6$ alkyl.

In certain embodiments, in compounds of general formula (III):
$R^6$ is aryl or aryl-$C_1$-$C_6$ alkyl, each optionally substituted with one or more substituents selected from $C_1$-$C_6$ alkylamino, amino, amino-$C_1$-$C_6$ alkyl, amino-aryl and amino-$C_3$-$C_7$ cycloalkyl;
X is absent, and
$R^4$ and $R^5$ are each methyl.

Combinations of any of the foregoing embodiments for compounds of general formula (III) are also contemplated and each combination forms a separate embodiment for the purposes of the present disclosure.

In certain embodiments, the toxin comprised by the VDCs is a compound of general formula (III) and is conjugated to the VAR2CSA polypeptide via the $R^6$ group.

Tubulysins

In certain embodiments, the toxin comprised by the VDC is a tubulysin or analogue or derivative thereof. Naturally occurring tubulysins include, for example, tubulysins A, B, C, D, E, F, G, H, I, U, V, W and Z:

Tubulysin A: $R^1$=Ac; $R^2$=CH$_2$C(O)CH$_2$CH(CH$_3$)$_2$; $R^3$=OH
Tubulysin B: $R^1$=Ac; $R^2$=CH$_2$OC(O)CH$_2$CH$_2$CH$_2$; $R^3$=OH
Tubulysin C: $R^1$=Ac; $R^2$=CH$_2$OC(O)CH$_2$CH$_3$; $R^3$=OH
Tubulysin D: $R^1$=Ac; $R^2$=CH$_2$OC(O)CH$_2$CH(CH$_3$)$_2$; $R^3$=H
Tubulysin E: $R^1$=Ac; $R^2$=CH$_2$OC(O)CH$_2$CH$_2$CH$_2$; $R^3$=H
Tubulysin F: $R^1$=Ac; $R^2$=CH$_2$OC(O)CH$_2$CH$_3$; $R^3$=H
Tubulysin G: $R^1$=Ac; $R^2$=CH$_2$OC(O)CH=C(CH$_3$)$_2$; $R^3$=OH
Tubulysin H: $R^1$=Ac; $R^2$=CH$_2$OC(O)CH$_3$; $R^3$=H
Tubulysin I: $R^1$=Ac; $R^2$=CH$_2$OC(O) CH$_3$; $R^3$=OH
Tubulysin U: $R^1$=Ac; $R^2$=$R^3$=H
Tubulysin V: $R^1$=$R^2$=$R^3$=H
Tubulysin W: $R^1$=H; $R^2$=CH$_2$OC(O)CH$_2$CH$_2$CH$_2$; $R^3$=OH
Tubulysin X: $R^1$=Ac; $R^2$=H; $R^3$=OH
Tubulysin Z: $R^1$=$R^2$=H; $R^3$=OH Therapeutically useful analogues and derivatives of tubulysins have also been described (see, for example, International Patent Publication No. WO 2014/126836 and U.S. Patent Publication No. US 2016/0130299).

The tubulysin or tubulysin analogue or derivative may be conjugated to the antigen binding construct through a free hydroxyl group, or it may be modified to include an amine group that can be used for conjugation as described in U.S. Patent Publication No. US 2016/0130299.

In certain embodiments, the toxin comprised by the VDCs is a tubulysin analogue selected from those described in International Patent Application No. PCT/CA2016/051135, filed Sep. 29, 2016, and published as WO 2017/054080.

One skilled in the art will appreciate that certain compounds of general formula (III) or (IV) may exhibit tautomerism. It is to be understood that the structural formulae herein are intended to represent any tautomeric form of the depicted compound that has the requisite anti-cancer activity and are thus not limited to the specific compound form depicted by the structural formulae except in certain specific embodiments.

In addition, the skilled person will appreciate that certain compounds of general formula (III) or (IV) have one or more asymmetric (chiral) centres and/or one or more unsaturated bonds. As a consequence, these compounds can be present as racemates, individual enantiomers, mixtures of enantiomers, individual diastereomers, mixtures of diastereomers, individual isomers (for example, E and Z isomers) and mixtures of isomers. Certain embodiments of the invention thus relate to compounds of general formula (III) or (IV) in a substantially pure enantiomeric, diastereomeric or isomeric form. By "substantially pure" it is meant that the compound is in a form that is at least 80% optically pure, that is, a form that comprises at least 80% of a single isomer. In certain embodiments, chiral compounds may be in a form that is at least 85% optically pure, for example, at least 90%, at least 95%, at least 96%, at least 97%, at least 98%, or at least 99% optically pure. In some embodiments, however, it is contemplated that compounds of general formula (III) and (IV) may be provided as a mixture, including as a racemic mixture, of enantiomers, diastereomers or isomers.

In certain embodiments, the toxins described herein may possess a sufficiently acidic group, a sufficiently basic group, or both functional groups, and accordingly react with a number of organic and inorganic bases, or organic and inorganic acids, to form pharmaceutically acceptable salts. The term "pharmaceutically acceptable salt" as used herein, refers to a salt of a toxin compound described herein, which is substantially non-toxic to living organisms. Typical pharmaceutically acceptable salts include those salts prepared by reaction of a toxin with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulphuric acid, phosphoric acid, and the like, and organic acids such as p-toluenesulphonic acid, methanesulphonic acid, oxalic acid, p-bromophenylsulphonic acid, carbonic acid, succinic acid, citric acid, benzoic acid, acetic acid, and the like. Examples of such pharmaceutically acceptable salts are the sulphate, pyrosulphate, bisulphate, sulphite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulphonate, phenylacetate, phenylpropionate, phenylbutyrate, citrate, lactate, gamma-hydroxybutyrate, glycolate, tartrate, methanesulphonate, propanesulphonate, naphthalene-1-sulfonate, napththalene-2-sulfonate, mandelate and the like. Pharmaceutically acceptable acid addition salts of particular interest are those formed with mineral acids such as hydrochloric acid and hydrobromic acid, and those formed with organic acids such as maleic acid and methanesulphonic acid.

Salts of amine groups may also comprise quarternary ammonium salts in which the amino nitrogen carries a suitable organic group such as an alkyl, lower alkenyl, substituted lower alkenyl, lower alkynyl, substituted lower alkynyl, or aralkyl moiety.

Base addition salts include those derived from inorganic bases, such as ammonium or alkali or alkaline earth metal hydroxides, carbonates, bicarbonates, and the like. Bases useful in preparing pharmaceutically acceptable salts thus include sodium hydroxide, potassium hydroxide, ammonium hydroxide, potassium carbonate, sodium carbonate, sodium bicarbonate, potassium bicarbonate, calcium hydroxide, calcium carbonate, and the like.

One skilled in the art will understand that the particular counterion forming a part of a pharmaceutically acceptable salt is usually not of a critical nature, so long as the salt as a whole is pharmacologically acceptable and as long as the counterion does not contribute undesired qualities to the salt as a whole.

Certain embodiments relate to pharmaceutically acceptable solvates of a toxin described above. One skilled in the art will appreciate that certain toxins may combine with solvents such as water, methanol, ethanol and acetonitrile to form pharmaceutically acceptable solvates such as the corresponding hydrate, methanolate, ethanolate and acetonitrilate. Other examples of solvents that may be used to prepare solvates include isopropanol, dimethyl sulfoxide, ethyl acetate, acetic acid, ethanolamine, or acetone, as well as miscible formulations of solvate mixtures as would be known by the skilled artisan.

Linkers

In certain embodiments, the toxin is conjugated to the VAR2CSA polypeptide in the VDC via a linker. Linkers are bifunctional or multifunctional moieties capable of linking one or more toxins to a targeting moiety, such as a VAR2CSA polypeptide. In some embodiments, the linker may be bifunctional (or monovalent) such that it links a single toxin molecule to a single site on the VAR2CSA polypeptide. In some embodiments, the linker may be multifunctional (or polyvalent) such that it links more than one toxin molecule to a single site on the VAR2CSA polypeptide.

Attachment of a linker to the VAR2CSA polypeptide can be accomplished for example through conjugation to a surface lysine or cysteine residue. Alternatively, attachment of a linker to the VAR2CSA polypeptide may be achieved by modification of the VAR2CSA polypeptide to include additional cysteine residues or non-natural amino acids that provide reactive handles, such as selenomethionine, p-acetylphenylalanine, formylglycine or p-azidomethyl-L-phenylalanine, as has been described for antibodies (see, for example, Hofer et al., 2009, *Biochemistry* 48:12047-12057; Axup et al., 2012, *PNAS* 109:16101-16106; Wu et al., 2009, *PNAS* 106:3000-3005; Zimmerman et al., 2014, *Bioconj. Chem.* 25:351-361).

In certain embodiments, the VDC comprises a linker that conjugates the toxin to a cysteine residue on the VAR2CSA polypeptide.

Linkers include a functional group capable of reacting with the target group or groups on the VAR2CSA polypeptide and one or more functional groups capable of reacting with a target group on the toxin. Suitable functional groups are known in the art and include those described, for example, in *Bioconjugate Techniques* (G. T. Hermanson, 2013, Academic Press). Non-limiting examples of functional groups for reacting with free cysteines or thiols include maleimide, haloacetamide, haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. Also useful in this context are "self-stabilizing" maleimides as described in Lyon et al., (2014) *Nat. Biotechnol.* 32:1059-1062. Non-limiting examples of functional groups for reacting with surface lysines and amines include activated esters such as N-hydroxysuccinamide (NHS) esters or sulfo-NHS esters, imido esters such as Traut's reagent, isothiocyanates, aldehydes and acid anhydrides such as diethylenetriaminepentaacetic anhydride (DTPA). Other examples include succinimido-1,1,3,3-tetra-methyluronium tetrafluoroborate (TSTU) and benzotriazol-1-yloxytripyrrolidinophosphonium hexafluorophosphate (PyBOP). Non-limiting examples of functional groups capable of reacting with an electrophilic group on the VAR2CSA polypeptide or toxin (such as an aldehyde or ketone carbonyl group) include hydrazide, oxime, amino, hydrazine, thiosemicarbazone, hydrazine carboxylate and arylhydrazide.

A variety of linkers for linking drugs or toxins to targeting moieties such as peptides, polypeptides, antibodies and other antigen binding constructs are known in the art, including hydrazone-, disulfide- and peptide-based linkers.

Suitable linkers typically are more chemically stable to conditions outside the cell than to conditions inside the cell, although less stable linkers may be contemplated in certain situations, such as when the toxin is selective or targeted and has a low toxicity to normal cells. Suitable linkers include, for example, cleavable and non-cleavable linkers. A cleavable linker is typically susceptible to cleavage under intracellular conditions, for example, through lysosomal processes. Examples include linkers that are protease-sensitive, acid-sensitive or reduction-sensitive. Non-cleavable linkers by contrast, rely on the degradation of the targeting moiety in the cell, which typically results in the release of an amino acid-linker-toxin moiety.

In certain embodiments, the VDCs comprise a cleavable linker. Suitable cleavable linkers include, for example, peptide-containing linkers cleavable by an intracellular protease, such as lysosomal protease or an endosomal protease. In exemplary embodiments, the linker may be a dipeptide-containing linker, such as a valine-citrulline (Val-Cit) or a phenylalanine-lysine (Phe-Lys) linker. Other examples of suitable dipeptides for inclusion in linkers include Val-Lys, Ala-Lys, Phe-Lys, Val-Cit, Phe-Cit, Leu-Cit, Ile-Cit, Trp-Cit, Phe-Arg, Ala-Phe, Val-Ala, Met-Lys, Asn-Lys, Ile-Pro, Ile-Val, Asp-Val, His-Val, Met-(D)Lys, Asn-(D)Lys, Val-(D)Asp, NorVal-(D)Asp, Ala-(D)Asp, Me$_3$Lys-Pro, PhenylGly-(D)Lys, Met-(D)Lys, Asn-(D)Lys, Pro-(D)Lys and Met-(D)Lys. Linkers may also include longer peptide sequences in some embodiments, such as the tripeptides Met-Cit-Val, Gly-Cit-Val, (D)Phe-Phe-Lys or (D)Ala-Phe-Lys, or the tetrapeptides Gly-Phe-Leu-Gly or Ala-Leu-Ala-Leu.

Additional suitable cleavable linkers include disulfide-containing linkers. Examples of disulfide-containing linkers include, but are not limited to, N-succinimydyl-4-(2-pyridyldithio) butanoate (SPDB) and N-succinimydyl-4-(2-pyridyldithio)-2-sulfo butanoate (sulfo-SPDB). Disulfide-containing linkers may optionally include additional groups to provide steric hindrance adjacent to the disulfide bond in order to improve the extracellular stability of the linker, for example, inclusion of a geminal dimethyl group. Other suitable linkers include linkers hydrolyzable at a specific pH or within a pH range, such as hydrazone linkers. Linkers comprising combinations of these functionalities may also be useful, for example, linkers comprising both a hydrazone and a disulfide are known in the art.

A further example of a cleavable linker is a linker comprising a β-glucuronide, which is cleavable by β-glucuronidase, an enzyme present in lysosomes and the tumor interstitium (see, for example, De Graaf et al., 2002, *Curr. Pharm. Des.* 8:1391-1403).

Cleavable linkers may optionally further comprise one or more additional functionalities such as self-immolative groups, self-elimination groups, stretchers or hydrophilic moieties.

Self-immolative and/or self-elimination groups that find use in linkers include, for example, p-aminobenzyloxycarbonyl (PABC) and p-aminobenzyl ether (PABE) groups, and methylated ethylene diamine (MED). Other examples of self-immolative groups include, but are not limited to, aromatic compounds that are electronically similar to the PABC or PABE group such as heterocyclic derivatives, for example 2-aminoimidazol-5-methanol derivatives as described in U.S. Pat. No. 7,375,078. Other examples include groups that undergo cyclization upon amide bond hydrolysis, such as substituted and unsubstituted 4-aminobutyric acid amides (Rodrigues et al. (1995) *Chemistry Biology* 2:223-227) and 2-aminophenylpropionic acid amides (Amsberry, et al. (1990) *J. Org. Chem.* 55:5867-5877). Self-immolative/self-elimination groups, alone or in combination are often included in peptide-based linkers, but may also be included in other types of linkers.

In some embodiments, the linker may include one or more self-immolative and self-elimination groups, for example, a PABC group, a PABE group, or a combination of a PABC group and an MED group, or PABE group and an MED group. In some embodiments, the linker may not include any self-immolative or self-elimination groups.

Stretchers that find use in linkers include, for example, alkylene groups and stretchers based on aliphatic acids, diacids, amines or diamines, such as diglycolate, malonate, caproate and caproamide. Other stretchers include, for example, glycine based stretchers and polyethylene glycol (PEG) or monomethoxy polyethylene glycol (mPEG) stretchers. PEG and mPEG stretchers also function as hydrophilic moieties and may be particularly useful with hydrophobic drugs, although their use in linkers with other drugs is also contemplated in some embodiments.

In some embodiments, the linker included in the VDCs is a cleavable linker. Examples of commonly used cleavable linkers that may find use in the VDCs of the present disclosure in some embodiments include, for example, linkers comprising SPDB, sulfo-SPDB, hydrazone, Val-Cit, maleidocaproyl (MC or mc), mc-Val-Cit, mc-Val-Cit-PABC, Phe-Lys, mc-Phe-Lys or mc-Phe-Lys-PABC.

In some embodiments, the linker comprised by the VDCs may be a peptide-containing cleavable linker. In some embodiments, the linker may be a peptide-containing cleavable linker that further comprises a stretcher. In some embodiments, the linker may be a peptide-containing cleavable linker that further comprises one or more self-immolative and self-elimination groups. In some embodiments, the linker may be a peptide-containing cleavable linker that does not include any self-immolative or self-elimination groups.

In certain embodiments, the linker-toxin included in the VDCs comprises a peptide-based linker and has general formula (VI):

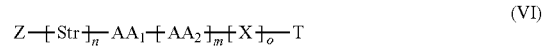

(VI)

wherein:
Z is a functional group capable of reacting with the target group on the VAR2CSA polypeptide;
Str is a stretcher;
AA$_1$ and AA$_2$ are each independently an amino acid, wherein AA$_1$-[AA$_2$]$_m$ forms a protease cleavage site;
X is a self-immolative group;
T is a toxin;
n is 0 or 1;
m is 1, 2 or 3, and
o is 0, 1 or 2.
In some embodiments, in general formula (VI):
Z is

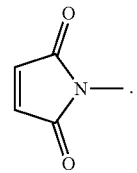

In some embodiments, in general formula (VI):
Str is

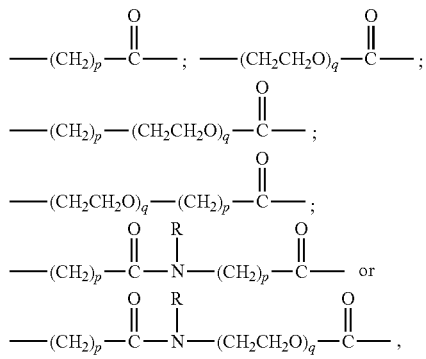

wherein
R is H or $C_1$-$C_6$ alkyl;
p is an integer from 2 to 10, and
q is an integer from 1 to 10.

In some embodiments, in general formula (VI):
Str is

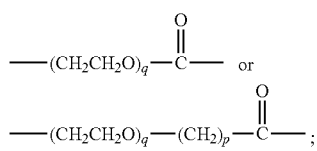

wherein:
p is an integer from 2 to 10, and
q is an integer from 1 to 10.

In some embodiments, in general formula (VI):
Str is

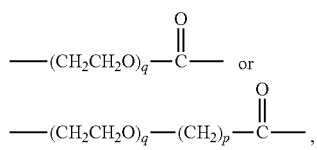

wherein p and q are each independently an integer from 2 to 4.

In some embodiments, in general formula (VI):
$AA_1$-$[AA_2]_m$ is selected from Val-Lys, Ala-Lys, Phe-Lys, Val-Cit, Phe-Cit, Leu-Cit, Ile-Cit, Trp-Cit, Phe-Arg, Ala-Phe, Val-Ala, Met-Lys, Asn-Lys, Ile-Pro, Ile-Val, Asp-Val, His-Val, Met-(D)Lys, Asn-(D)Lys, Val-(D)Asp, NorVal-(D)Asp, Ala-(D)Asp, $Me_3$Lys-Pro, PhenylGly-(D)Lys, Met-(D)Lys, Asn-(D)Lys, Pro-(D)Lys, Met-(D)Lys, Met-Cit-Val, Gly-Cit-Val, (D)Phe-Phe-Lys, (D)Ala-Phe-Lys, Gly-Phe-Leu-Gly and Ala-Leu-Ala-Leu.

In some embodiments, in general formula (VI):
m is 1 (i.e. $AA_1$-$[AA_2]_m$ is a dipeptide).

In some embodiments, in general formula (VI):
$AA_1$-$[AA_2]_m$ is a dipeptide selected from Val-Lys, Ala-Lys, Phe-Lys, Val-Cit, Phe-Cit, Leu-Cit, Ile-Cit and Trp-Cit.

In some embodiments, in general formula (VI):
each X is independently selected from p-aminobenzyloxycarbonyl (PABC), p-aminobenzyl ether (PABE) and methylated ethylene diamine (MED).

In some embodiments, in general formula (VI):
n is 1.

In some embodiments, in general formula (VI):
o is 1 or 2.

In some embodiments, in general formula (VI):
o is 0 (i.e. X is absent).

In some embodiments, in general formula (VI):
Z is

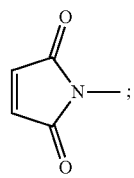

Str is

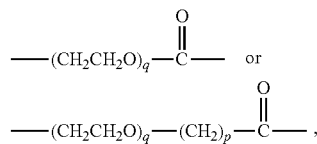

wherein p and q are each independently an integer from 2 to 4;
m is 1 and $AA_1$-$[AA_2]_m$ is a dipeptide selected from Val-Lys, Ala-Lys, Phe-Lys, Val-Cit, Phe-Cit, Leu-Cit, Ile-Cit and Trp-Cit;
each X is independently selected from p-aminobenzyloxycarbonyl (PABC), p-aminobenzyl ether (PABE) and methylated ethylene diamine (MED);
n is 1, and
o is 1 or 2.

In some embodiments, in general formula (VI):
Z is

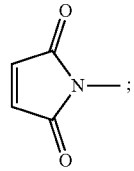

Str is

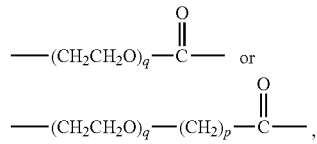

wherein p and q are each independently an integer from 2 to 4;
m is 1 and $AA_1$-$[AA_2]_m$ is a dipeptide selected from Val-Lys, Ala-Lys, Phe-Lys, Val-Cit, Phe-Cit, Leu-Cit, Ile-Cit and Trp-Cit;

n is 1, and o is 0.

Combinations of any of the foregoing embodiments for compounds of general formula (VI) are also contemplated and each combination forms a separate embodiment for the purposes of the present disclosure.

Various non-cleavable linkers are known in the art for linking drugs to targeting moieties and may be useful in the VDCs of the present disclosure in certain embodiments. Examples of non-cleavable linkers include linkers having an N-succinimidyl ester or N-sulfosuccinimidyl ester moiety for reaction with the VAR2CSA polypeptide, as well as a maleimido- or haloacetyl-based moiety for reaction with the toxin, or vice versa. An example of such a non-cleavable linker is based on sulfosuccinimidyl-4-[N-maleimidomethyl]cyclohexane-1-carboxylate (sulfo-SMCC). Sulfo-SMCC conjugation typically occurs via a maleimide group which reacts with sulfhydryls (thiols, —SH) on the toxin moiety, while the sulfo-NHS ester is reactive toward primary amines (as found in lysine and the polypeptide N-terminus). Other non-limiting examples of such linkers include those based on N-succinimidyl 4-(maleimidomethyl)cyclohexanecarboxylate (SMCC), N-succinimidyl-4-(N-maleimidomethyl)-cyclohexane-1-carboxy-(6-amidocaproate) ("long chain" SMCC or LC-SMCC), 11-maleimidoundecanoic acid N-succinimidyl ester (KMUA), 4-maleimidobutyric acid N-succinimidyl ester (GMBS), 6-maleimidocaproic acid N-hydroxysuccinimide ester (EMCS), m-maleimidobenzoyl-N-hydroxysuccinimide ester (MB S), N-(maleimidoacetoxy)-succinimide ester (AMAS), succinimidyl-6-(maleimidopropionamido)hexanoate (SMPH), N-succinimidyl 4-(p-maleimidophenyl)-butyrate (SMPB), and N-(p-maleimidophenyl)isocyanate (PMPI). Other examples include linkers comprising a haloacetyl-based functional group such as N-succinimidyl-4-(iodoacetyl)-aminobenzoate (SIAB), N-succinimidyl iodoacetate (SIA), N-succinimidyl bromoacetate (SBA) and N-succinimidyl 3-(bromoacetamido)propionate (SBAP).

Other examples of non-cleavable linkers include maleimidocarboxylic acids, such as maleimidocaproyl (MC).

In certain embodiments, the VDCs comprise a VAR2CSA polypeptide conjugated to the toxin via a sulphonamide-containing linker as described in International Patent Publication No. WO 2015/095953.

In some embodiments, the VDCs comprise a VAR2CSA polypeptide conjugated to the toxin via a linker and have general formula (VIII):

$$\text{(VIII)}$$

wherein:

$R^{10}$ is selected from optionally substituted alkyl, optionally substituted alkylamino, optionally substituted cycloalkyl, optionally substituted aryl, optionally substituted heterocyclyl, optionally substituted heteroaryl, —COR$^{11}$—, —CSR$^{11}$—, —OR$^{11}$— and —NHRH$^{11}$—, wherein each R$^{11}$ is independently selected from optionally substituted alkyl, optionally substituted alkylamino, optionally substituted cycloalkyl, optionally substituted aryl, optionally substituted heterocyclyl and optionally substituted heteroaryl;

$P^3$ is the toxin or a portion of the toxin;

$L^3$ is the remaining portion of the linker, and

V is the VAR2CSA polypeptide.

In some embodiments, the VDCs comprise a VAR2CSA polypeptide conjugated to the toxin via a peptide-containing linker and have general formula (IX):

$$\text{(IX)}$$

wherein -$L^3$-V has the structure:

wherein:

$P^3$ is a the toxin or a portion of the toxin;

the —NH— group bonded to $R^{12}$ forms a peptide bond (the junction peptide bond or JPB) with (AA)$^1$;

$R^{12}$ is selected from optionally substituted alkyl, optionally substituted alkylamino, optionally substituted cycloalkyl, optionally substituted aryl, optionally substituted heterocyclyl, optionally substituted heteroaryl, —COR$^{11}$—, —CSR$^{11}$—, —OR$^{11}$— and —NHR$^{11}$—, wherein each R$^{11}$ is independently selected from optionally substituted alkyl, optionally substituted alkylamino, optionally substituted cycloalkyl, optionally substituted aryl, optionally substituted heterocyclyl and optionally substituted heteroaryl;

each AA is independently an amino acid, wherein (AA)$^1$-(AA)$_x$ taken together comprise an amino acid sequence capable of facilitating cleavage of the JPB;

x is an integer from 0 to 25;

L' is the remaining portion of the linker or is absent;

V is the VAR2CSA polypeptide.

Selection of an appropriate linker for the VDC may be readily made by the skilled person having knowledge of the art and taking into account relevant factors, such as the site of attachment to the VAR2CSA polypeptide, any structural constraints of the toxin and the hydrophobicity of the toxin (see, for example, review in Nolting, Chapter 5, *Antibody—Drug Conjugates: Methods in Molecular Biology*, 2013, Ducry (Ed.), Springer).

In certain embodiments, the toxin comprised by the VDC is a hemiasterlin or analogue or derivative thereof, and the linker is a peptide-containing cleavable linker.

In certain embodiments, the toxin comprised by the VDC is a hemiasterlin or analogue or derivative thereof, and the linker-toxin has general formula (VI), as described in any one of the embodiments above.

In certain embodiments, the toxin comprised by the VDC is a compound of general formula (IV), as described in any one of the embodiments above, and the linker-toxin has general formula (VI), as described in any one of the embodiments above.

In certain embodiments, the toxin comprised by the VDC is an auristatin or analogue or derivative thereof, and the linker is a peptide-containing cleavable linker.

In certain embodiments, the toxin comprised by the VDC is an auristatin or analogue or derivative thereof, and the linker-toxin has general formula (VI), as described in any one of the embodiments above.

In certain embodiments, the toxin comprised by the VDC is a compound of general formula (III), as described in any one of the embodiments above, and the linker-toxin has general formula (VI), as described in any one of the embodiments above.

Preparation of VDCs

The VDCs may be prepared by one of several routes known in the art, employing organic chemistry reactions, conditions, and reagents known to those skilled in the art (see, for example, *Bioconjugate Techniques* (G. T. Hermanson, 2013, Academic Press)). For example, conjugation may be achieved by reaction of the VAR2CSA polypeptide (V) with a bivalent linker reagent (L) to form polypeptide-linker intermediate V-L via a covalent bond, followed by reaction with an activated toxin moiety (T); or reaction of the toxin moiety (T) with a linker reagent (L) to form toxin-linker intermediate T-L via a covalent bond, followed by reaction with the VAR2CSA polypeptide (V). Such conjugation methods may be employed with a variety of toxins and linkers to prepare the VDCs described herein. Various linkers, linker components and toxins are commercially available or may be prepared using standard synthetic organic chemistry techniques (see, for example, *March's Advanced Organic Chemistry* (Smith & March, 2006, Sixth Ed., Wiley); Toki et al., (2002) *J. Org. Chem.* 67:1866-1872; Frisch et al., (1997) *Bioconj. Chem.* 7:180-186; *Bioconjugate Techniques* (G. T. Hermanson, 2013, Academic Press)). In addition, a number of pre-formed drug-linkers suitable for reaction with a selected targeting moiety are also available commercially, for example, linker-toxins comprising MMAE or MMAF SA are available from Creative BioLabs (Shirley, N.Y.).

Methods of preparing certain hemiasterlin and auristatin analogues described herein, as well as linker-toxins comprising these analogues, may be found in International Patent Publication Nos. WO 2014/144871, WO 2015/095953 and WO 2016/041082.

The average number of toxins conjugated to the VAR2CSA polypeptide may be determined by standard techniques such as UV/VIS spectroscopic analysis, ELISA-based techniques, chromatography techniques such as hydrophobic interaction chromatography (HIC), UV-MALDI mass spectrometry (MS) and MALDI-TOF MS. In addition, distribution of toxin-linked forms (for example, the fraction of VAR2CSA polypeptides containing zero, one, two, three, etc. toxins) may also optionally be analyzed. Various techniques are known in the art to measure such distribution, including MS (with or without an accompanying chromatographic separation step), hydrophobic interaction chromatography, reverse-phase HPLC or iso-electric focusing gel electrophoresis (IEF) (see, for example, Wakankar et al., 2011, *mAbs* 3:161-172). Purity of the VDC may also be assessed by a variety of methods known in the art.

Testing

The VDCs may be tested for their ability to bind to oncofetal chondroitin sulfate (ofCS) by techniques known in the art. For example, placental tissue and most cancer cells are known to express ofCS (see Salanti et al., 2015, Cancer Cell, 28:500-514). The ability of the VDCs to bind ofCS may therefore be indirectly assessed by determining the ability of the VDC to bind to placental tissue but not to control tissue using standard immunohistochemistry techniques (see Salanti et al., 2015, ibid.). Inhibition of this binding by addition of chondroitin sulfate A (CSA) or removal of CS chains may also be tested.

Alternatively, the ability of the VDCs to bind ofCS may be indirectly assessed by determining the ability of the VDC to bind to cancer cells but not to normal cells using standard techniques, such as ELISA or flow cytometry (see Salanti et al., 2015, ibid.). The ability of CSA to inhibit this binding may also be tested. Representative cancer cell lines suitable for testing the VDCs include, but are not limited to, C32 melanoma cells, H1792 lung adenocarcinoma cells, PC-3 prostate cancer cells and UM-UC-6 bladder transitional cell carcinoma cells.

Kinetics of binding and calculation of $K_D$ for the VDCs for binding to ofCS on placental or cancer cells may also be assessed by standard techniques (see, for example, *Current Protocols in Protein Science*, ed. Coligan, J. E., et al., 1995 & updates, Wiley & Sons, New York, N.Y.). For example, such parameters may be assessed through the use of surface plasmon resonance (SPR) or quartz crystal microbalance (QCM) based techniques cytometry (see Salanti et al., 2015, ibid.).

Additionally, the VDCs may be tested to determine their effect on cancer cells. Initial determinations of the efficacy of the VDCs may made using one or more standard in vitro assays. For example, standard assays may be conducted to assess one or more of cytotoxicity, anti-proliferative activity or anchorage-independent growth inhibition. Such assays are well-known in the art (see, for example, *Current Protocols in Pharmacology*, ed. Enna, S. J., et al., 2005 & updates, John Wiley & Sons, New York, N.Y.) and include those described in the Examples herein.

The ability of the VDCs to inhibit tumor growth and/or proliferation in vivo may also be assessed in an appropriate animal model using standard techniques known in the art (see, for example, *Current Protocols in Pharmacology*, ibid.). In general, current animal models for screening anti-tumor compounds are xenograft models, in which a human tumor has been implanted into an animal. Examples of xenograft models of human cancer include, but are not limited to, human solid tumor xenografts, implanted by sub-cutaneous injection or implantation and used in tumor growth assays; human solid tumor isografts. implanted by fat pad injection and used in tumor growth assays; human solid tumor orthotopic xenografts, implanted directly into the relevant tissue and used in tumor growth assays; experimental models of lymphoma and leukaemia in mice, used in survival assays, and experimental models of lung metastasis in mice.

Pharmaceutical Compositions

The VDCs described herein are typically formulated for administration. Accordingly, certain embodiments relate to pharmaceutical compositions comprising a VDC and a pharmaceutically acceptable carrier, diluent, or excipient. The pharmaceutical compositions may be prepared by known procedures using well-known and readily available ingredients.

Pharmaceutical compositions comprising VDCs may be formulated for administration to a subject by one of a variety of standard routes, for example, orally, topically, parenterally, by inhalation or spray, rectally or vaginally, in dosage unit formulations containing conventional non-toxic pharmaceutically acceptable carriers, adjuvants and/or vehicles. The term parenteral as used herein includes in various embodiments subcutaneous injections, intradermal, intraarticular, intravenous, intramuscular, intravascular, intrasternal, intrathecal injection and infusion techniques. The pharmaceutical composition will typically be formulated in a format suitable for administration to the subject by the selected route, for example, as a syrup, elixir, tablet, troche, lozenge, hard or soft capsule, pill, suppository, oily or aqueous suspension, dispersible powder or granule, emulsion, injectable or solution.

In certain embodiments, the VDCs are formulated for administration via a systemic route, for example, intravenously, intramuscularly, intradermally, intraperitoneally, subcutaneously, or orally.

Compositions intended for oral use may be prepared in either solid or fluid unit dosage forms. Fluid unit dosage form can be prepared according to procedures known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations. An elixir is prepared by using a hydroalcoholic (for example, ethanol) vehicle with suitable sweeteners such as sugar or saccharin, together with an aromatic flavoring agent. Suspensions can be prepared with an aqueous vehicle with the aid of a suspending agent such as acacia, tragacanth, methylcellulose and the like.

Solid formulations such as tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate: granulating and disintegrating agents for example, corn starch, or alginic acid: binding agents, for example starch, gelatin or acacia, and lubricating agents, for example magnesium stearate, stearic acid or talc and other conventional ingredients such as dicalcium phosphate, magnesium aluminum silicate, calcium sulfate, starch, lactose, methylcellulose, and functionally similar materials. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Soft gelatin capsules are prepared by machine encapsulation of a slurry of the compound with an acceptable vegetable oil, light liquid petrolatum or other inert oil.

Aqueous suspensions contain the active ingredient in admixture with one or more excipients suitable for the manufacture of aqueous suspensions. Such excipients include suspending agents, for example sodium carboxylmethylcellulose, methyl cellulose, hydropropylmethylcellulose, sodium alginate, polyvinylpyrrolidone, gum tragacanth and gum acacia; and dispersing or wetting agents such as naturally-occurring phosphatides (for example, lecithin), condensation products of an alkylene oxide with fatty acids (for example polyoxyethylene stearate), condensation products of ethylene oxide with long chain aliphatic alcohols (for example hepta-decaethyleneoxycetanol), condensation products of ethylene oxide with partial esters derived from fatty acids and a hexitol (for example, polyoxyethylene sorbitol monooleate), or condensation products of ethylene oxide with partial esters derived from fatty acids and hexitol anhydrides (for example polyethylene sorbitan monooleate). The aqueous suspensions may also contain one or more preservatives, for example ethyl, or n-propyl-p-hydroxy benzoate, one or more colouring agents, one or more flavouring agents or one or more sweetening agents, such as sucrose or saccharin.

Oily suspensions may be formulated by suspending the active ingredient in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

Pharmaceutical compositions may also be in the form of oil-in-water emulsions. The oil phase may be a vegetable oil, for example olive oil or peanut oil, or a mineral oil, for example liquid paraffin, or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of such partial esters with ethylene oxide, for example polyoxyethylene sorbitan monooleate. The emulsions may also optionally contain sweetening and flavoring agents.

The pharmaceutical compositions may be in the form of a sterile injectable aqueous or oleaginous suspension. Such suspensions may be formulated as known in the art using suitable dispersing or wetting agents and suspending agents such as those mentioned above. The sterile injectable preparation may also be a sterile injectable solution or a suspension in a non-toxic parentally acceptable diluent or solvent, for example as a solution in 1,3-butanediol. Other acceptable vehicles and solvents that may be employed include, for example, water, Ringer's solution and isotonic sodium chloride solution. In addition, sterile, fixed oils may be employed as a solvent or suspending medium. Various bland fixed oils known to be suitable for this purpose may be employed including synthetic mono- or diglycerides. In addition, fatty acids such as oleic acid find use in the preparation of injectables. Adjuvants such as local anaesthetics, preservatives and buffering agents may also optionally be included in the injectable solution or suspension.

Other pharmaceutical compositions and methods of preparing pharmaceutical compositions are known in the art and are described, for example, in "*Remington: The Science and Practice of Pharmacy*" (formerly "*Remingtons Pharmaceutical Sciences*"); Gennaro, A., Lippincott, Williams & Wilkins, Philadelphia, Pa. (2000).

Methods of Use

Certain embodiments relate to the use of the VDCs to inhibit the growth and/or proliferation of platinum-drug resistant cancer cells. In certain embodiments, the platinum drug-resistant cancer shows elevated ofCS expression compared to a corresponding cancer which is not platinum drug resistant. In some embodiments, the platinum-drug resistant cancer cells have increased expression of CD44 compared to corresponding cancer cells that are not resistant to the platinum drug.

Certain embodiments relate to the use of the VDCs in the treatment of a platinum drug-resistant cancer. In this context, the VDCs may exert either a cytotoxic or cytostatic effect and such treatment may result in one or more of a reduction in the size of a tumor, the slowing or prevention of an increase in the size of a tumor, an increase in the disease-free survival time between the disappearance or removal of a tumor and its reappearance, prevention of an initial or subsequent occurrence of a tumor (e.g. metastasis), an increase in the time to progression, reduction of one or more adverse symptom associated with a tumor, or an increase in the overall survival time of the subject having the platinum drug-resistant cancer.

Platinum drugs ("platins") used in the treatment of cancer include, for example, cisplatin, carboplatin, oxaliplatin and nedaplatin. Other platins currently in clinical trials include, for example, satraplatin and picoplatin.

Certain embodiments relate to the use of the VDCs in the treatment of a cancer resistant to cisplatin, carboplatin, oxaliplatin or nedaplatin. Some embodiments relate to the use of the VDCs in the treatment of a cancer resistant to picoplatin or satraplatin. Some embodiments relate to the use of the VDCs in the treatment of a cancer resistant to cisplatin, carboplatin or oxaliplatin. Certain embodiments relate to the use of the VDCs in the treatment of a cancer resistant to cisplatin or carboplatin.

Cancers commonly treated with platins that are prone to developing resistance to these drugs include, but are not limited to, bladder cancer, colon cancer, small cell lung cancer (SCLC), non-small cell lung cancer (NSCLC), breast cancer, testicular cancer, melanoma, head and neck cancer, anal cancer, endometrial cancer, ovarian cancer, adrenocortical cancer and non-Hodgkin lymphoma.

Certain embodiments relate to the use of the VDCs in the treatment of a platinum drug-resistant bladder cancer, colon cancer, small cell lung cancer, NSCLC, breast cancer, testicular cancer, melanoma, head and neck cancer, anal cancer, endometrial cancer, ovarian cancer, adrenocortical cancer and non-Hodgkin lymphoma. Some embodiments relate to the use of the VDCs in the treatment of a platinum drug-resistant bladder cancer, SCLC, NSCLC, testicular cancer, melanoma, head and neck cancer or ovarian cancer.

In some embodiments, the cancer may be an advanced and/or metastatic cancer.

In some embodiments, the cancer may be a platinum drug-resistant cancer that shows an increased expression of CD44 as compared to a corresponding cancer that is not resistant to the platinum drug.

In some embodiments, the VDCs may be used as a second line therapy after a subject has received a prior treatment regimen comprising a platinum drug. In some embodiments, the prior treatment regimen comprising a platinum drug may have been a combination therapy that comprised the platinum drug in combination with one or more other therapeutics.

Examples of combination therapies currently in use that comprise platins include, but are not limited to, cisplatin and fluorouracil, cisplatin and etoposide, cisplatin and topotecan, cisplatin and docetaxel, cisplatin and gemcitabine, cisplatin and pemetrexed, cisplatin and vinorelbine, carboplatin and etoposide, carboplatin and paclitaxel, carboplatin and docetaxel, carboplatin and pemetrexed, carboplatin with vinorelbine, oxaliplatin and capecitabine, oxaliplatin with leucovorin and fluorouracil, cisplatin with dexamethasone and cytarabine ("DHAP"), cisplatin with etoposide, methylprednisolone and cytarabine ("ESHAP"), carboplatin with ifosfamide and etoposide ("ICE"), cisplatin with bleomycin and etoposide ("BEP"), cisplatin with methotrexate, vinblastine and doxorubicin ("MVAC") and cisplatin with methotrexate and vinblastine ("CMV").

In some embodiments, the subject has received a prior treatment regimen comprising a platinum drug and has progressed or relapsed after the prior treatment. In some embodiments, the subject received a prior treatment regimen comprising a platinum drug as a first line therapy.

Certain embodiments relate to the use of the VDCs in the treatment of platinum drug-resistant bladder cancer. In some embodiments, the platinum drug-resistant bladder cancer is advanced and/or invasive bladder cancer. In some embodiments, the platinum drug-resistant cancer is muscle-invasive bladder cancer (MIBC). In some embodiments, the platinum drug-resistant cancer is cisplatin- or carboplatin-resistant bladder cancer.

Certain embodiments relate to the use of the VDCs to treat a subject with platinum drug-resistant bladder cancer. In some embodiments, the VDCs are administered to the subject as a second-line therapy. In some embodiments, the subject has received a prior treatment regimen comprising cisplatin or carboplatin. In some embodiments, the prior treatment regimen was a combination therapy including cisplatin or carboplatin. In some embodiments, the prior treatment regimen was a first-line therapy. In some embodiments, the subject has platinum drug-resistant MIBC.

Pharmaceutical Kits

In certain embodiments, the VDCs may be provided as part of a pharmaceutical kit or pack. Individual components of the kit would typically be packaged in separate containers. Suitable containers include, for example, bottles, blister packs and the like. In certain embodiments, the container may be in a form allowing for administration to a subject, for example, an inhaler, syringe, pipette, eye dropper, pre-soaked gauze or pad, or other such like apparatus, from which the contents may be administered to the subject.

The kit may further comprise a label or package insert on or associated with the container(s). The term "package insert" is used to refer to instructions customarily included in commercial packages of therapeutic products, that contain information about the indications, usage, dosage, administration, contraindications and/or warnings concerning the use of such therapeutic products. The label or package insert may further include a notice in the form prescribed by a governmental agency regulating the manufacture, use or sale of pharmaceuticals or biological products, which notice reflects approval by the agency of manufacture, for use or sale for human or animal administration. The label or package insert indicates that the VDC is for use to treat the condition of choice, such as platinum drug resistant cancer.

If appropriate, one or more components of the kit may be lyophilized or provided in a dry form, such as a powder or granules, and the kit can additionally contain a suitable solvent for reconstitution of the lyophilized or dried component(s).

In some embodiments, a kit may provide a number of unit dosages. Such kits may include a card having the dosages oriented in the order of their intended use. An example of such a kit is a "blister pack." Blister packs are well known in the packaging industry and are widely used for packaging pharmaceutical unit dosage forms. When the VDC is intended for administration by infusion or injection, such multi-unit kits may comprise a plurality of vials, each containing one unit dosage. If desired, a memory aid can be provided, for example in the form of numbers, letters, or other markings, or as a calendar insert, designating the days in the treatment schedule in which the dosages can be administered.

To gain a better understanding of the invention described herein, the following examples are set forth. It will be understood that these examples are intended to describe illustrative embodiments of the invention and are not intended to limit the scope of the invention in any way.

EXAMPLES

General Procedures for Example 1

General Procedure 1: Trifluoroacetamide Installation

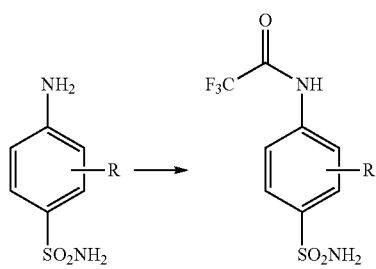

To a stirred suspension of the amine in 1,4-dioxane was added trifluoroacetic anhydride (1.1 equivalents). The reaction mixture transitioned from a suspension to a solution and back to a suspension again. The progress of the reaction was monitored by TLC and/or HPLC-MS for completion. Once the starting material was fully consumed, the reaction was diluted with hexanes or diethyl ether, filtered on a Buchner funnel and the resulting solids were dried under reduced pressure to give the pure trifluoroacetamide.

General Procedure 2: Trifluoroacetamide Saponification

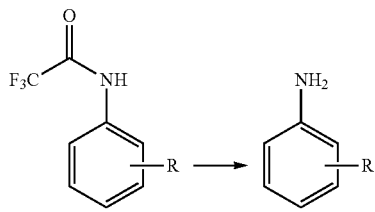

To a solution of the trifluoroacetamide-containing construct in 1,4-dioxane or methanol was added lithium hydroxide (10 equivalents) and water (10% v/v). The reaction was allowed to stir at room temperature or optionally heated to 50° C. Reaction course was monitored by HPLC-MS. Upon completion, volatiles were removed under reduced pressure and the aqueous layer was quenched with an aqueous solution of 5% w/v citric acid or 1 M hydrochloric acid. The resulting aqueous solution was washed successively with dichloromethane or ethyl acetate and the organic phases were pooled, dried over $MgSO_4$, filtered and concentrated. The reaction product was either used "as is" or purified by silica gel chromatography as necessary.

General Procedure 3: HATU Mediated Peptide Bond Formation

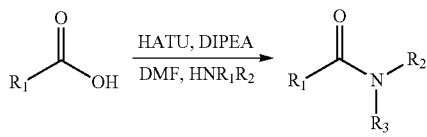

To a stirred solution of the carboxylic acid in a minimal amount of dichloromethane or N,N-dimethylformamide or mixture thereof, at 0° C. was added HATU (1.05-1.2 equivalents) and either N,N-diisopropylamine (2-4 equivalents) or 2,4,6-collidine (2-4 equivalents). Stirring was continued for a brief induction period (5-20 minutes) at which time the reaction was charged with a solution of the amine in dichloromethane. The reaction was allowed to warm to room temperature and monitored for progress by HPLC-MS. Upon completion, volatiles were removed under reduced pressure and the residual material was purified by silica gel chromatography or reverse phase HPLC to furnish amide in adequate purity.

General Procedure 4: Fmoc Group Removal

The Fmoc-protected compound was dissolved in 20% piperidine in N,N-dimethylformamide. The reaction course was monitored by HPLC-MS. When complete, all volatiles were removed under reduced pressure to yield a residue that was either purified by silica gel chromatography or used directly in the next step.

General Procedure 5: N-acylation of Amines Using NHS-Activated Esters

To a solution of the amine in a minimal amount of N,N-dimethylformamide was added the corresponding N-hydroxy succinimide containing ester (1.5 equivalents). The progress of the reaction was monitored by HPLC-MS (typically ~16 h) at which point all volatiles were removed under reduced pressure. The residue was then purified by either silica gel chromatography or reverse phase HPLC to give the desired amide product.

General Procedure 6: Boc Group Removal

To a solution of the Boc-protected compound in dichloromethane was added 10% v/v trifluoroacetic acid. Reaction course was monitored by HPLC-MS. Upon reaction completion, all volatiles were removed under reduced pressure. The residual material was purified either by reverse phase HPLC, silica gel chromatography or precipitation from a mixture of cold methanol/dichloromethane/diethyl ether.

Example 1: Preparation of MTvc886

Figure 8:
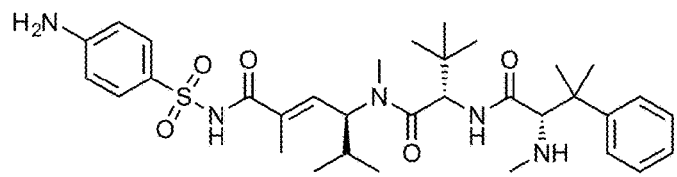
FIG. 8 shows (A) the structure of an exemplary hemiasterlin analogue (Compound 1); (B) the structure of linker-toxin MTvc886 comprising Compound 1 with a maleimido triethylene glycolate valine-citrulline linker, and (C) a schematic representation of the VAR2CSA drug conjugate VDC886.
Figure 8:
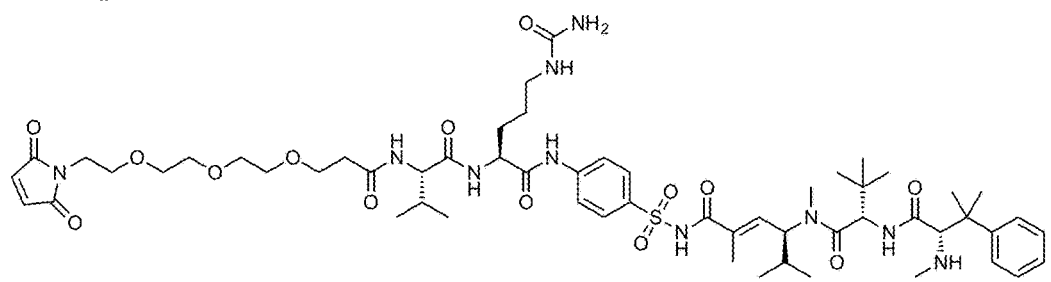
Figure 8:
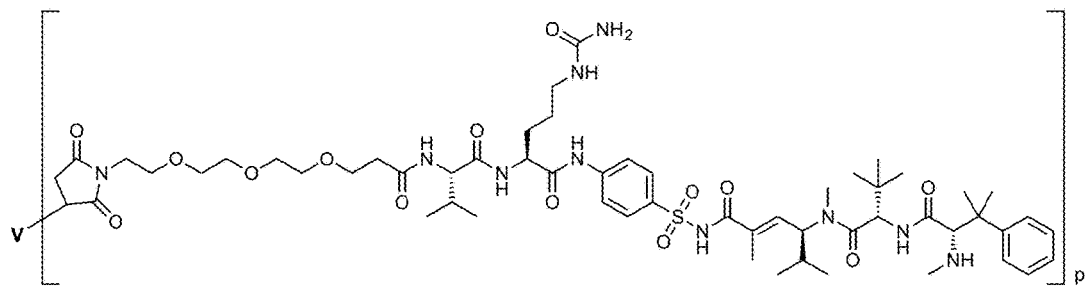

MTvc886 ((S,E)-N-((4-((14S,17S)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido) phenyl)sulfonyl)-2,5-dimethyl-4-((S)—N,3,3-trimethyl-2-((S)-3-methyl-2-(methyl amino)-3-phenylbutanamido) butanamido)hex-2-enamide; see FIG. 8B) can be prepared according to the protocol described in International Patent Publication No. WO 2015/095953. The general procedure is provided below.

Boc-HTI-286-OH: (6S,9S,12S,E)-9-tert-butyl-12-isopropyl-2,2,5,11,14-pentamethyl-4,7,10-trioxo-6-(2-phenylpropan-2-yl)-3-oxa-5,8,11-triazapentadec-13-en-15-oic acid

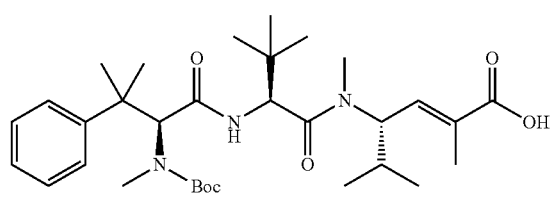 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)O]

The title compound was prepared according to Nieman et al., 2003, *J. Nat. Prod.*, 66:183-199.

Compound A:
2,2,2-trifluoro-N-(4-sulfamoylphenyl)acetamide

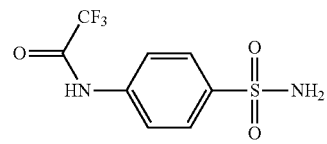 [SMILES: NS(=O)(=O)c1ccc(NC(=O)C(F)(F)F)cc1]

The title compound was synthesized from commercially available sulfanilamide and TFAA using General Procedure 1 in near quantitative yield.

Compound B: Tert-butyl (S)-1-((S)-1-(((S,E)-2,5-dimethyl-6-oxo-6-(4-(2,2,2-trifluoroacetamido)phenylsulfonamido)hex-4-en-3-yl)(methyl)amino)-3,3-dimethyl-1-oxobutan-2-ylamino)-3-methyl-1-oxo-3-phenylbutan-2-yl(methyl)carbamate

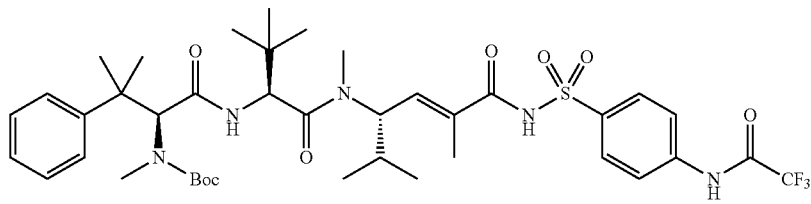 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)c1ccc(NC(=O)C(F)(F)F)cc1]

To a stirred solution of Boc-HTI-286-OH (0.400 g, 0.7 mmol) and Compound A (0.244, 1.3 equiv) in ethyl acetate (10 mL) was added N,N'-dicyclohexylcarbodiimide (0.202 g, 1.4 equiv) and N,N-dimethyl-4-aminopyridine (0.119 g, 1.4 equiv). Stirring was continued overnight at which point the reaction was diluted with diethyl ether (60 mL), the solids were filtered off, washed with diethyl ether (30 mL) and the filtrate concentrated to give a colourless oil. The oil was purified by silica gel chromatography using 5-50% EtOAc (containing 5% AcOH) in hexanes on a 25 g Isolera™ column over 25 column volumes. Fractions containing the desired material were pooled and concentrated to give the title compound (0.504 g, 86%) as a colourless foam.

Compound C: Tert-butyl (S)-1-((S)-1-(((S,E)-6-(4-aminophenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl (methyl)carbamate

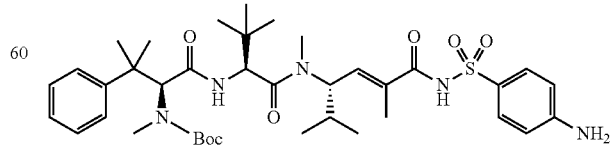

The title compound was prepared from Compound B according to General Procedure 2.

Compound D

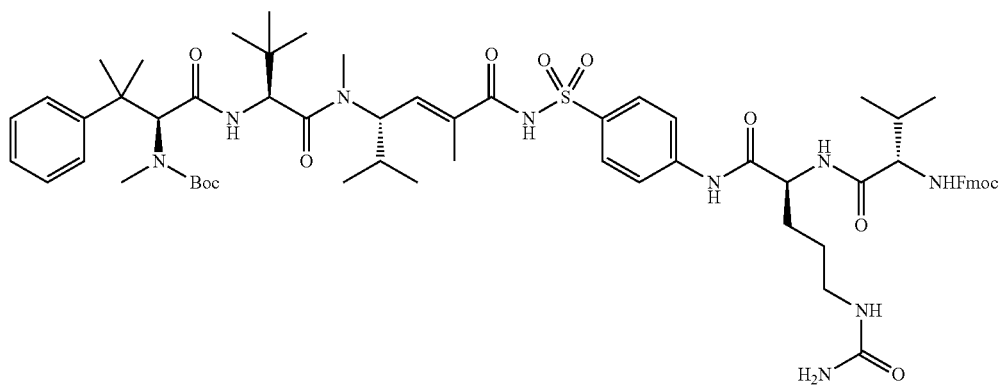

Compound D was synthesized from Compound C and Fmoc-Val-Cit-OH according to General Procedure 3.

Compound E: Tert-butyl (S)-1-((S)-1-(((S,E)-6-(4-((S)-2-(S)-2-amino-3-methylbutanamido)-5-ureidopentanamide)phenylsulfonamido)-2,5-dimethyl-6-oxohex-4-en-3-yl)(methyl)amino)-3,3-dimethyl-1-oxobutan-2 ylamino)-3-methyl-1-oxo-3-phenylbutan-2-yl(methyl)carbonate

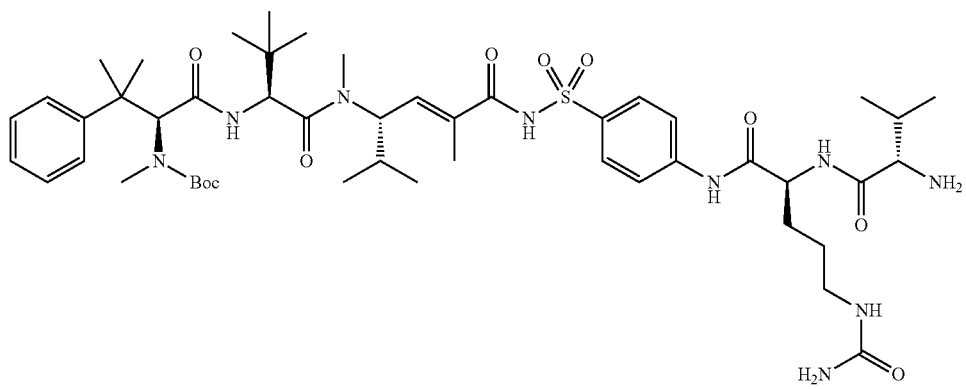 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)c1ccc(NC(=O)[C@H](CCCNC(N)=O)NC(=O)[C@@H](N)C(C)C)cc1]

The title compound was prepared from Compound D according to General Procedure 4.

Compound F. Tert-butyl (S)-1-(((S)-1-(((S,E)-6-(4-((14S,17S)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido) phenylsulfonamido)-2,5-dimethyl-6-oxohex-4-en-3-yl)(methyl)amino)-3,3-dimethyl-1-oxobutan-2-yl) amino)-3-methyl-1-oxo-3 phenylbutan-2-yl)(methyl) carbonate

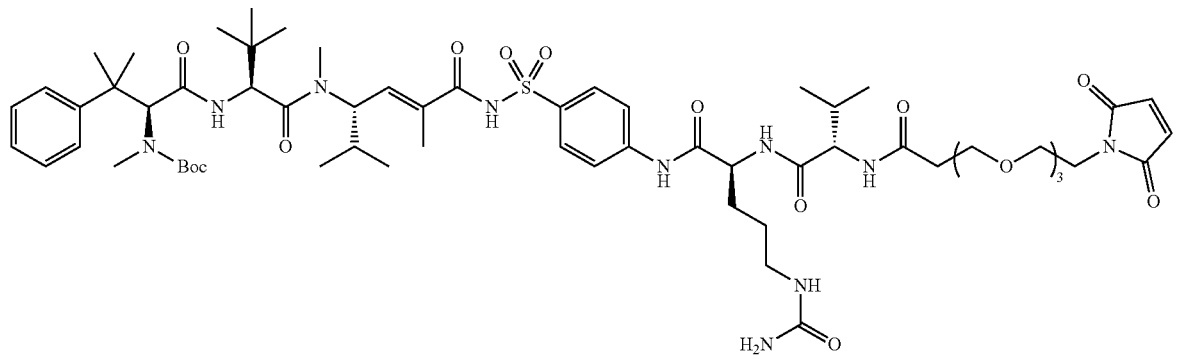

The title compound was prepared from Compound E and MT-NHS (2,5-dioxopyrrolidin-1-yl 3-(2-(2-(2-(2,5-dioxo-2,5-dihydro-1H-pyrrol-1-yl)ethoxy) ethoxy)ethoxy)propanoate) according to General Procedure 5.

MTvc886:

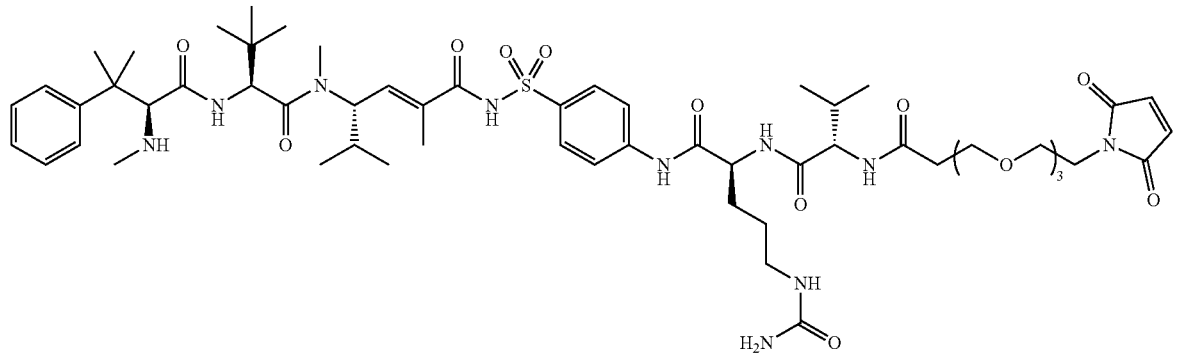

The title compound was prepared from Compound F according to General Procedure 6.

Material and Methods for Examples 2-5

Bladder Cancer Cohorts

Two independent cohorts in the same clinical setting were used (Table 1): A consecutive series of bladder cancer patients, diagnosed with muscle invasive bladder cancer (MIBC), received platin-based neoadjuvant chemotherapy (NAC) (at least 3 cycles) after transurethral resection of the primary tumor (TURBT) and underwent cystectomy with pelvic lymph node dissection at the Department of Urology, University of Bern, Switzerland; at the Vancouver General Hospital, Vancouver, BC, Canada, and the Department of Urology, University Hospital of Southampton, UK, respectively.

TABLE 1

Clinicopathological data of the three NAC cohorts used for tissue microarray (TMA) construction and gene expression analysis.

| | Bern (n = 65) | Vancouver (n = 58) | Southampton (n = 24) | p-value |
|---|---|---|---|---|
| Age (median, range) at surgery (years) | 64 (35-78) | 62 (39-78) | 69 (35-81) | 0.13 |
| Gender (female/male) | 20/45 | 16/42 | 7/17 | 0.9 |
| Median overall survival (years) | 4.5 | 3.0 | 4.1 | 0.8 |
| Cystectomy and lymphadenectomy data | | | | |
| Tumor stage (n) | | | | |
| ypT0/1 (%) | 14 (37) | 24 (38) | 9 (41) | 0.2 |
| ypT2 (%) | 12 (18) | 13 (25) | 6 (22) | |
| ypT3/4 (%) | 29 (45) | 21 (37) | 9 (37) | |

TABLE 1-continued

Clinicopathological data of the three NAC cohorts used for tissue microarray (TMA) construction and gene expression analysis.

| | Bern (n = 65) | Vancouver (n = 58) | Southampton (n = 24) | p-value |
|---|---|---|---|---|
| Lymph node stage (n) | | | | |
| ypN0 (%) | 37 (57) | 51 (88) | 19 (79) | <0.001 |
| ypN+ (%) | 28 (43) | 7 (12) | 5 (21) | |
| Response to NAC | | | | |
| Major response (<ypT2, ypNneg) (%) | 21 (32) | 24 (41) | 9 (38) | 0.6 |
| No response (≥ypT2, any ypNpos) (%) | 44 (68) | 34 (59) | 15 (62) | |

Figure 2:
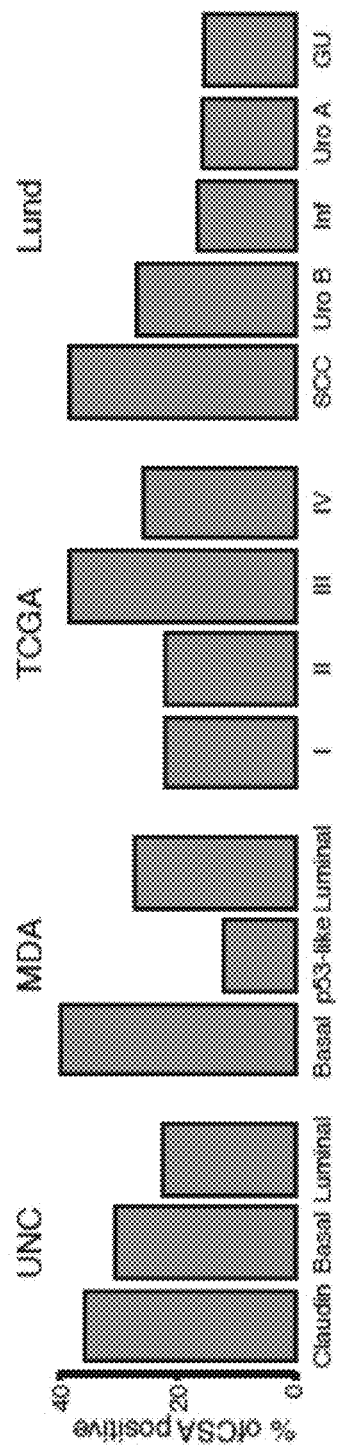
FIG. 2 shows an analysis of oncofetal chondroitin sulfate (ofCS) expression in chemotherapy-resistant bladder cancer (ypT). ofCS expression was present at all stages of chemoresistant-bladder cancer (ypT1-4, but elevated in later stage disease (ypT3-4). Moreover, high expression of ofCS correlated with poor outcome of patients in two independent cohorts.
Figure 3:
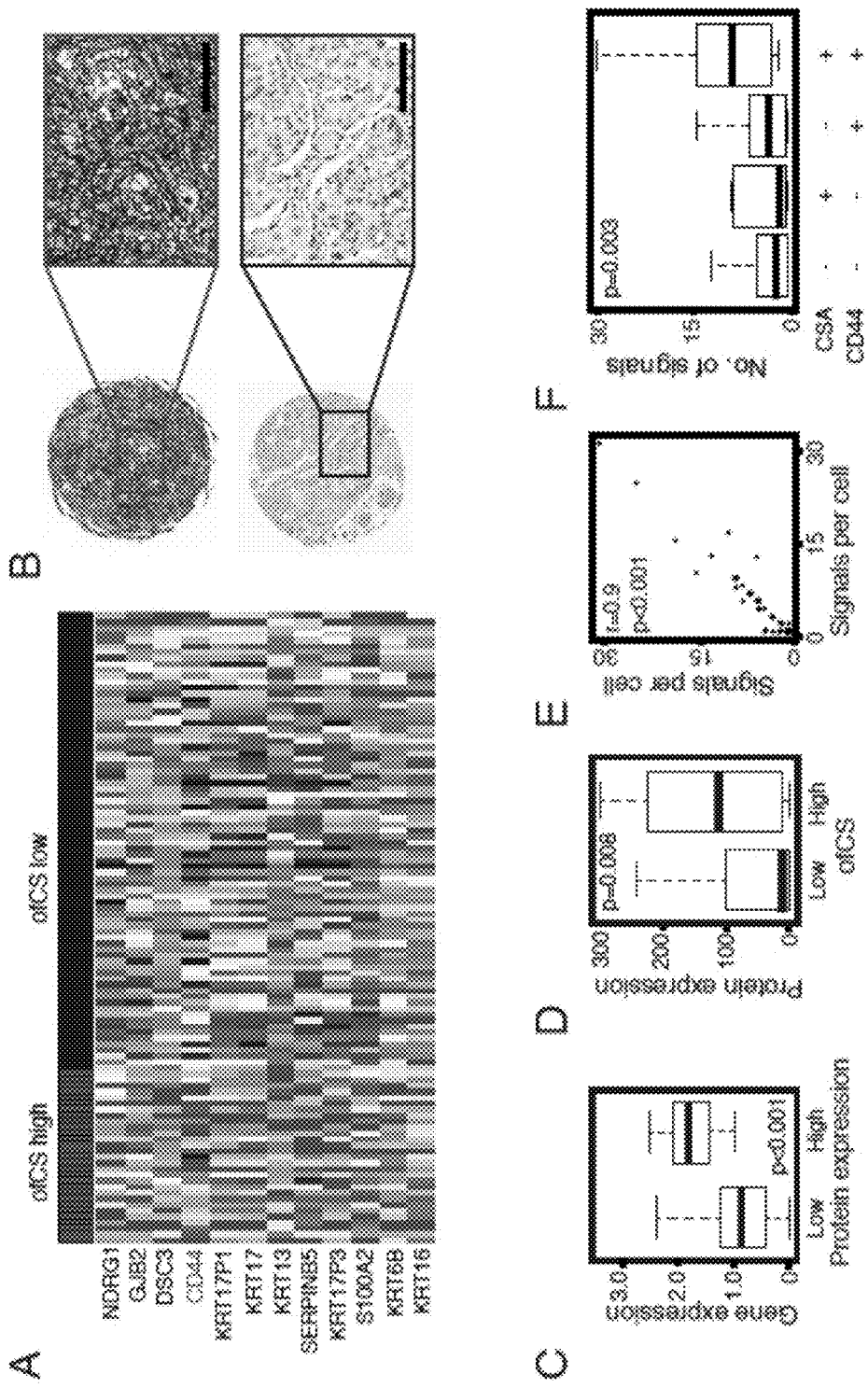
FIG. 3 shows oncofetal chondroitin sulfate (ofCS) carrying proteoglycans in bladder cancer: (A) Proteoglycan gene expression in ofCS$^{High}$ and ofCS$^{Low}$ chemotherapy naïve bladder cancer. Data are arranged so that each column represents an individual patient and each row represents a gene. The uppermost panel is divided into high (red) and low (blue) cellular ofCS expression (n=120 patients). In the heat map, difference in gene expression was calculated as fold change (log 2) and significantly overexpressed genes for each patient are highlighted in red. (B) Representative immunohistochemical (IHC) images showing high and low CD44 protein expression of bladder cancer. For statistical analysis, low expressing tumors ($1^{st}$-$3^{rd}$ quartile) were compared to high expression tumors ($4^{th}$ quartile), respectively. Scale bar represents 100 μm. (C) Box plot indicating gene expression (y-axes) in samples with low ($1^{st}$-$3^{rd}$ quartile) and high ($4^{th}$ quartile) CD44 protein expression, respectively. (D) Bar plot indicating the relation of CD44 protein expression with ofCS in ofCS$^{High}$ and ofCS$^{Low}$ groups. (E & F) Statistical evaluation of in situ tissue proximity ligation assay (PLA) between ofCS and CD44. The number of PLA signals between duplicate cores from a single patient (x axis; one tissue core and y axis; the other) and the average number of PLA signals per cell was compared to the status of IHC of individual biomarker (ofCS and CD44).

Table 1 shows that all parameters were virtually the same between cohorts. Bern had a significantly higher rate of lymph node involvement, however, the rate of response to NAC was not significantly different between cohorts. Due to this slightly lower risk in Vancouver and Southampton, these two cohorts were used for validation of ofCSA expression (Example 1; FIGS. 1 & 2). Analyses of gene and protein expression of CD44 (Example 2; FIG. 3) were performed in the entire dataset.

Tissue Microarrays (TMA)

The TMA were constructed as follows: Per patient, two samples were taken from the TURBT specimen (n=56 (Bern); n=82 (Vancouver/Southampton)) and, if still present, two from the cisplatin-resistant bladder cancer after NAC (ypT+, n=38 (Bern); n=40 (Vancouver/Southampton)).

Microarrays

With RNeasy kit (Qiagen, Valencia, Calif.), total RNA was extracted from FFPE TURBT tissue, amplified and labeled using the Ovation WTA FFPE system (NuGen, San Carlos, Calif.). Samples were profiled using GeneChip Human Exon 1.0 ST oligonucleotide microarrays (Affymetrix, Santa Clara, Calif.) according to the manufacturer's recommendations. The microarray data quality control was assessed by Affymetrix Power Tools packages. Array files for these cases are available from the National Center for Biotechnology Information's Gene Expression Omnibus (NCBI-GEO) database (www.ncbi.nlm.nih.gov/geo/).

Cell Lines

A panel of human bladder cancer cell lines was provided by the Pathology Core of the Bladder Cancer Specialized Program of Research Excellence (SPORE) at MD Anderson Cancer Center (RT112, UM-UC1, UM-UC5, UM-UC6, UM-UC14, UM-UC3 and UM-UC13). The cell lines were cultured as instructed by the supplier.

Immunohistochemistry

Freshly cut tissue microarray (TMA) sections were analyzed for ofCS and CD44 expression and all immunohistochemistry was performed using the Ventana Discovery platform. For ofCS staining, sections were incubated in citrate buffer (cell conditioning 2; CC2) at 95° C. for 32 minutes to retrieve antigenicity and stained with 500 picomolar V5-tagged rVAR2 (FIG. 7) at room temperature for 12 minutes, followed by 1:700 mouse monoclonal anti-V5 step, and Ventana UltraMap anti-mouse HRP, then visualization with Ventana Ultra ChromoMAP DAB kit.

CD44 immunohistochemistry was optimized and performed with a monoclonal mouse antibody against CD44 (R&D systems, BBA10, 1:500 dilution). In brief, tissue sections were incubated in CC2 for CD44 at 95° C. for 32 minutes to retrieve antigenicity, followed by incubation with a respective primary antibody at 37° C. for 1 hour. Bound primary antibodies were incubated with Ventana universal secondary antibody at 37° C. for 32 min and visualized using Ventana DAB Map detection kit.

Interpretation of all immunostainings was blinded for clinicopathological parameters and outcome data. ofCS expression was homogeneous and intensity was scored from 0 to 3. A score 2/3 was considered as ofCS high. An overall score, including tumor environment and cancer cells, as well as cellular score was determined for each spot (FIG. 1A-1C). CD44 expression was determined as the product of staining intensity and % of stained cancer cells. The tumors were grouped into quartiles of expression of the entire cohort and for statistical analysis, the $4^{th}$ quartile was compared with $1^{st}$-$3^{rd}$ quartile.

Western Blotting

Bladder cancer cell line lysates were separated electrophoretically on SDS polyacrylamide or Tris-Acetate Protein (NuPAGE® Novex®) gels and then transferred to Nitrocellulose membranes at 75 mA overnight at 4° C. on ice. Blots were blocked for 1 hour at room temperature and then incubated with the CD44 primary antibody (1:1000 dilution). After washing in TBS with 0.1% Tween 20, membranes were incubated with horseradish peroxidase (HRP)-conjugated secondary antibody (Santa Cruz Biotechnologies) at 1:5000 dilution for 1 hour at room temperature. Blots were developed using an enhanced chemiluminescence (ECL) substrate system for detection of HRP, SuperSignal West Femto Maximum Sensitivity Substrate (Thermo Scientific).

Flow Cytometry

Cells were grown to 70-80% confluency in appropriate growth media and harvested in an EDTA detachment solution (Cellstripper®). Cells were incubated with rVAR2 (200 nM-25 nM) in PBS containing 2% FBS for 30 min at 4° C. and binding was analyzed in a FACSCalibur (BD Biosciences) after a secondary incubation with anti-V5-FITC antibody. For inhibition studies, protein was co-incubated with the indicated concentration of chondroitin sulfate A (CSA).

Proximity Ligation Assay (PLA)

PLA uses a pair of primary target-specific antibodies, selected from two different host species to fixed cells or tissue sections. With Duolink technology (Olink Bioscience, Sweden), these antibodies can be conjugated with Duolink species-specific probes which contain unique DNA strands that template the hybridization of added oligonucleotides. When these two antibody-bound oligonucleotides are in close proximity (<40 nm), the oligonucleotides are ligated by a ligase to form a circular template. This template is subsequently amplified and detected using fluorescent or chromogenic-labeled complementary oligonucleotide probes (Soderberg, et al., 2006, *Nat. Methods*, 3:995-1000). The signal detection was performed either with a fluorescent label, for inverted confocal LSM-780 microscope (Zeiss), or horseradish peroxidase (HRP), for fixed-stage upright BX51W1 microscope (Olympus), for bright-field detection. The PLA signals were determined by Duolink Image Tool (Olink Bioscience, Sweden). For quantification, the median number of signals per cell was used for both tissue and cell lines.

rVAR2 Polypeptides

Two truncated versions of the VAR2CSA protein were prepared (FIG. 7). rVAR2 comprises the ID1, DBL2X and ID2a domains of the full-length malarial VAR2CSA protein linked to a C-terminal V5 tag. rVAR2' comprises the DBL1X, ID1, DBL2X and ID2a domains.

Briefly, rVAR2 protein was expressed in *E. coli* Shuffle cells harboring an IPTG inducible plasmid that expresses DBL1-ID2a with C terminal V5 and His tags. The cells were grown in rich media at 37° C. until mid-exponential growth phase where the temperature was decreased to 20° C. and 0.1 mM IPTG was added to the media, initiating overnight expression of the protein. The following morning the cells were harvested by centrifugation and stored at −20° C.

Protein purification was performed by dissolving the cells in Buffer A (10 mM NaP, 500 mM NaCl and 60 mM Imidazole pH7.2) supplemented with cOMPLETE™ protease inhibitor. The cells were lysed by sonication and insoluble material was removed by centrifugation and filtration. The cleared cell lysate was loaded onto a HIS-Trap column equilibrated with Buffer A and step eluted with Buffer B (10 mM NaP, 500 mM NaCl and 500 mM Imidazole pH7.2). The eluted protein was pooled and separated on size exclusion chromatography (Superdex S200 pg) equilibrated with the running buffer, PBS pH6.0. The monomeric peak was pooled and flash frozen in liquid nitrogen. The pooled protein was stored at −80° C. until further use.

All protein batches were analyzed by SDS-PAGE under reducing and non-reducing conditions. The binding affinity towards the proteoglycans decorin and heparin sulfate proteoglycan (HSPG) were determined using ELISA in which the plate was coated with the respective proteoglycan and a two-fold dilution series from 100 nM down to 1.5 nM of rVAR2 was analyzed. All proteins used showed specific binding towards decorin and only low binding towards HSPG. Binding of MyLa cancer cells by the proteins was determined by flow cytometry, with rVAR2 binding being detected using an anti-V5-FITC antibody. All proteins used showed saturated binding in the two-fold dilution series from 6.25 nM to 400 nM.

rVAR2-Hemiasterlin Drug Conjugate (VDC886)

The rVAR2' polypeptide was chemically conjugated with a hemiasterlin analogue (KT886; Compound 1 in FIG. 8A) as previously described (Salanti et al., 2015, ibid.). Briefly, to a solution of DBL1-1D2a in ice-cold PBS, pH7.4, was added MTvc886 (12 molar equivalents from a 10 mM stock solution in DMSO). The protein solution was mixed gently and allowed to stand on ice for a period of 90 min prior to concentration using a Pall Macrosep Advance Centrifugal Filter (30 KDa MWCO). The concentrated protein solution was purified over a Zeba Spin Desalting Column (40 kDa MWCO) preconditioned with sterile PBS, pH 6.0. Conjugates were sterile-filtered using a 0.22 um filter membrane. Composition and purity of the VDC were assessed by SDS-PAGE and SEC-UPLC-Esi-MS.

By capping of free cysteine residues on rVAR2' with a toxin-linker, an average of 4 KT886 toxins per rVAR2' molecule were conjugated to the recombinant protein. The protease-sensitive dipeptide linker (see FIG. 8B) used for conjugation is stable in circulation but cleaved upon internalization and trafficking to the lysosome.

In Vitro Cytotoxicity Assay of VDC886 in Human Bladder Cancer Cell Lines

Cells were removed from their culture vessel using Gibco® Trypsin-EDTA (Invitrogen #25300-054). Detached cells were diluted in respective growth medium (Invitrogen #: 11095-080)+10% Fetal bovine serum (Corning #: 35-015-CV) to 25000 cells/mL such that 100 uL/well dispensed 2500 cells/well. Cells were seeded into black walled, clear, flat bottomed 96-well plates (Costar #3595). Cells were incubated for one night at 37° C. in a 5% $CO_2$ atmosphere to allow the cells to attach to the microtitre plate surface. VDC886 was diluted directly in the appropriate cell growth medium and then titrated 1:3 over nine steps. A control with no VDC886 present (growth medium alone) was included in each microtiter plate in triplicates. 400 ug/ml CSA was used as a specificity control as well as a toxicity rescue assay. 25 ul/well of the prepared titrations was added in triplicate to each cell line assayed. The cells and titrations were incubated at 37° C. with 5% $CO_2$ for 48 hours. After the incubation, cell viability was measured using by a crystal violet proliferation assay. The collected relative light absorbance [LA] were converted to % cytotoxicity using the absorbance values measured from the growth medium alone control as follows: % Cytotoxicity=1−[Well LA/average medium alone control LA]. Data (% Cytotoxicity vs. Concentration of VDC (log 10 [nM])) were plotted and were analyzed by non-linear regression methods using GraphPad Prism software v. 5.02 to obtain $IC_{50}$ estimates.

Internalization Assay

UM-UC13 parental and ex vivo cells were seeded to cover slips and grown to 80% confluency. 100 nM rVAR2-V5 was incubated with the cells for 1 hour at 37° C. and 5% $CO_2$. Cells were subsequently washed with PBS prior to fixation with 4% paraformaldehyde for 15 min at room temperature followed by permeabilization with 0.5% trition for 3 mins and blocked with 3% BSA for 30 mins. Cells were then incubated with primary Anti-V5 antibody from ThermoFischer (R960-25) according to manufacturer's instructions followed by 1 hour incubation with anti-mouse AlexaFluor488 secondary antibody from Invitrogen (A-21202). Cover slips were washed with PBS and mounted in mounting media containing DAPI and analyzed by laser-scanning confocal microscopy.

Orthotopic Cisplatin-Resistant Bladder Cancer Xenografts

All animal work was approved by the Institutional Review Board of the University of British Columbia. Initially, 8-week-old nude mice (Harlan Laboratories, Indianapolis, Ind.) were anesthetized with 3% isoflurane. 30 μL of a cell suspension in Matrigel™ (BD Biosciences) containing $3.0 \times 10^4$ cells of UM-UC13 were inoculated into each of 12 mice using a 30 G needle by percutaneous injection with ultrasound guidance as previously described (Jager et al., 2013, *PlosOne*, 8(3):e59536). For in vivo imaging, cells previously underwent transduction with a lentiviral construct containing a firefly luciferase gene under blasticidin selection (Life Technologies). Bioluminescence was used to quantify tumor burden and was measured after intraperitoneal injection of 150 ug/kg luciferin (Caliper Lifesciences, Hopkinton, Mass.) starting on day 5 after tumor inoculation and then twice a week. Images were taken at 10 and 15 min after luciferin injection and the average counts were used for statistical analysis. In addition, starting on day 10, tumor volume was measured by transabdominal ultrasound. Once weekly, mice were treated with cisplatin 3 mg/kg by intraperitoneal injection. Before reaching the humane endpoint, the mouse with the fastest growing tumor was sacrificed, the tumor was minced in PBS, mixed with Matrigel™ (BD Biosciences) and reinjected in 4-6 nude mice (Harlan Laboratories, Indianapolis, Ind.). This passaging was performed for 6 successive cycles to generate cisplatin-resistant tumors. From each generation of tumor, an ex vivo cell line was created to use for in vitro experiments (binding-, toxicity- and internalisation assays). From the 6th in vivo cycle, the tumors of two mice were passed into 40, eight-week-old nude mice (Harlan Laboratories, Indianapolis, Ind.). Five mice did not develop cancers, the tumors of 2 mice did not show an increase in bioluminescence, 3 mice developed early peritoneal carcinomatosis and one mouse developed cancer of the urethra. At day 17, mice with growing tumors under cisplatin treatment were used for the subsequent experiment and assigned to the following treatment groups: Vehicle (n=7), rVar2' alone (n=7), KT886 (n=7) and VDC886 (n=8). The given treatment was administered twice per week by intravenous injection in the tail vein. Imaging by bioluminescence and ultrasound was continued twice and once per week, respectively. Fifty-two days after tumor injection, the time to reach the humane endpoint for the mice (hematuria, weight loss>15%, tumor burden greater than $10^\circ$ photons/sec, tumor seen as a visible bulge in the lower abdomen, irregular/labored respirations, severe diarrhea, ulcerated skin>1 cm patch, no response when stimulated, immobile, constantly shaking, vocalizations, severe self-mutilation/trauma) was noted for each of the VDC886 and Vehicle treated groups and used to generate a Kaplan Meier plot.

Statistical Analyses

Statistical analyses were conducted using R software package, version 3.1.0. All tests were two-sided with type I error probability of 5%. To compare continuous data, the non-parametric Wilcoxon rank-sum test and Kruskal-Wallis test were used to compare between two or more groups, respectively. Fisher's exact test was used for the analysis of contingency tables. Kaplan-Meier plots and log-rank tests were used to estimate overall survival (OS). For the patient cohort, OS was calculated from surgery to the date of death. Patients still alive were censored at the date of last follow-up. For the animal experiment, OS was calculated from tumor cell injection to time of reaching of the humane endpoint.

Example 2: Expression of Oncofetal Chondroitin Sulphate in Cisplatin-Resistant Bladder Cancer To analyze the oncofetal chondroitin sulphate (ofCS) expression landscape in bladder cancer pre- and post-treatment with cisplatin, immunohistochemical (IHC) analysis was performed on two independent cohorts of primary chemotherapy naïve transurethral resected bladder tumors (TURBT) and patient-matched cisplatin-resistant bladder cancer (ypT) samples using rVAR2 as the ofCS detection reagent (FIG. 1A). The discovery cohort was comprised of more advanced tumors as compared to the validation cohort (see Table 1).

In chemotherapy naïve TURBT bladder tumors, 25% (n=31/120) of the cancer cells showed high membranous expression of ofCS (ofCS$^{High}$) while 75% (n=89/120) showed low (ofCS$^{Low}$) positivity (FIG. 1B). When progressing into cisplatin-resistant disease (ypT), 40% (n=11/28; p=0.001) of those tumors became ofCS$^{High}$ in the discovery cohort (FIG. 1C, left) and 45% (n=15/33; p=0.01) in the validation cohort (FIG. 1C, right). Thus, the shift from ofCS$^{Low}$ to ofCS$^{High}$ in cisplatin-resistant disease was independent of tumor stage. In cisplatin-resistant bladder cancer, ofCS$^{High}$ was associated with extravesical extension of primary tumors in the discovery cohort (p=0.005) (FIG. 1D, left) and the similar trend was seen in the validation cohort (p=0.08) (FIG. 1D right and FIG. 1E). This shift in ofCS expression was associated with poor overall survival in the discovery cohort (p=0.04) (FIG. 1F, upper) but not in the validation cohort (p=0.5), which only had 6 years clinical follow-up (FIG. 1F, lower). Accordingly, these data indicate that ofCS is upregulated in cisplatin-resistant bladder cancer and this event is associated with poor outcome particularly in more advanced disease.

Example 3: Analysis of Proteoglycans Presenting Oncofetal Chondroitin Sulfate

At least 18 proteoglycans have the ability to carry ofCS GAG modifications (Salanti, et al., 2015, *Cancer Cell*, 28:500-14). To search for ofCS-modified proteoglycans in bladder cancer, gene expression data from ofCS$^{High}$ and ofCS$^{Low}$ expressing chemotherapy naïve bladder cancer was compared. CD44, previously reported to be ofCS modified (Salanti, et al., 2015, ibid.), was amongst the highest overexpressed genes in ofCS$^{High}$ tumors (FIG. 3A). CD44 protein expression (FIG. 3B) showed a strong correlation with gene expression (FIG. 3C) and was strongly correlated with ofCS$^{High}$ cases (FIG. 3D; p=0.008). Indeed, in situ proximity ligation assay (PLA) using anti-CD44 antibodies (probe 1) with ofCS-binding rVAR2 (probe 2) confirmed contiguity of CD44 and ofCS chains in primary bladder tumors, and duplicate cores from a single patient showed similar PLA signal count (FIG. 3E). Moreover, the PLA signal was highest in tumors with dual positivity for ofCS and CD44 (FIG. 3F). Together, these data suggest that CD44 is a major ofCS-presenting proteoglycan in human bladder cancer.

Importantly, however, CD44 protein was expressed in MIBC independent of cisplatin-sensitivity. In UM-UC3 cells, PLA positivity was low compared to ofCS positivity, relative to the UM-UC1 and UM-UC13 cells. This suggests that other proteoglycans in addition to CD44 likely contribute to ofCS presentation in MIBC.

Figure 4:
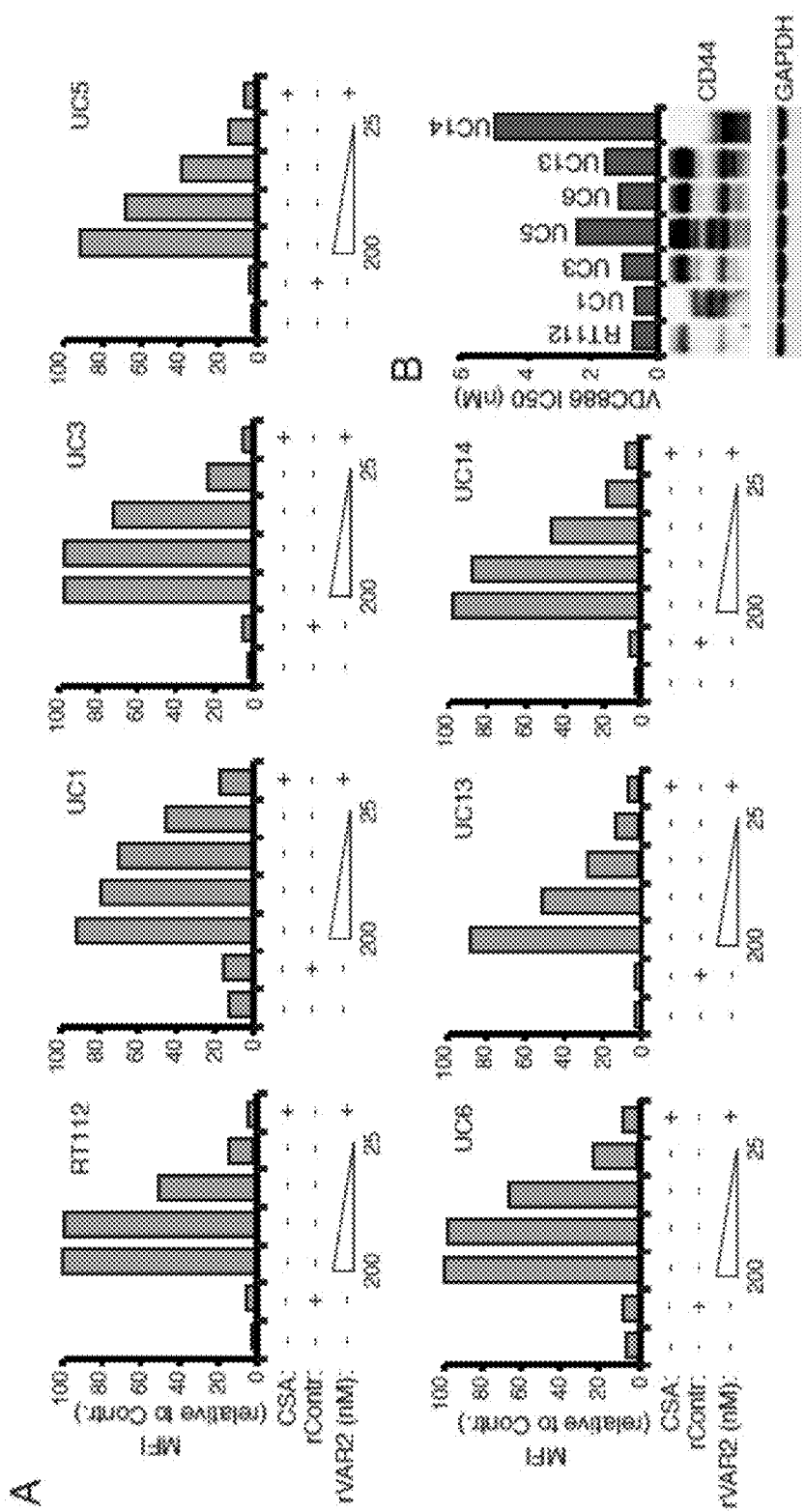
FIG. 4 shows rVar2 binding to human bladder cancer cells: (A) Relative mean fluorescence intensity (MFI) of a panel of bladder cancer cell lines incubated with recombinant control protein (rContr) or a VAR2CSA polypeptide (rVAR2) as indicated and detected by flow cytometry using anti-V5-FITC. (B) $IC_{50}$ kill-values for the VAR2CSA drug conjugate, VDC886, in various cancer cell lines (upper panel). CD44 protein expression in the same bladder cancer cell line panel; GAPDH as a loading control (lower panel). (C) Proximity ligation assay (PLA) analysis of CD44 and ofCS in UM-UC1, UM-UC3 and UM-IC13 parental bladder cancer cell lines. rVAR2 alone is used as a negative control and soluble CSA for competitive inhibition of the interaction. Scale bar represents 10 μm.
Figure 4:
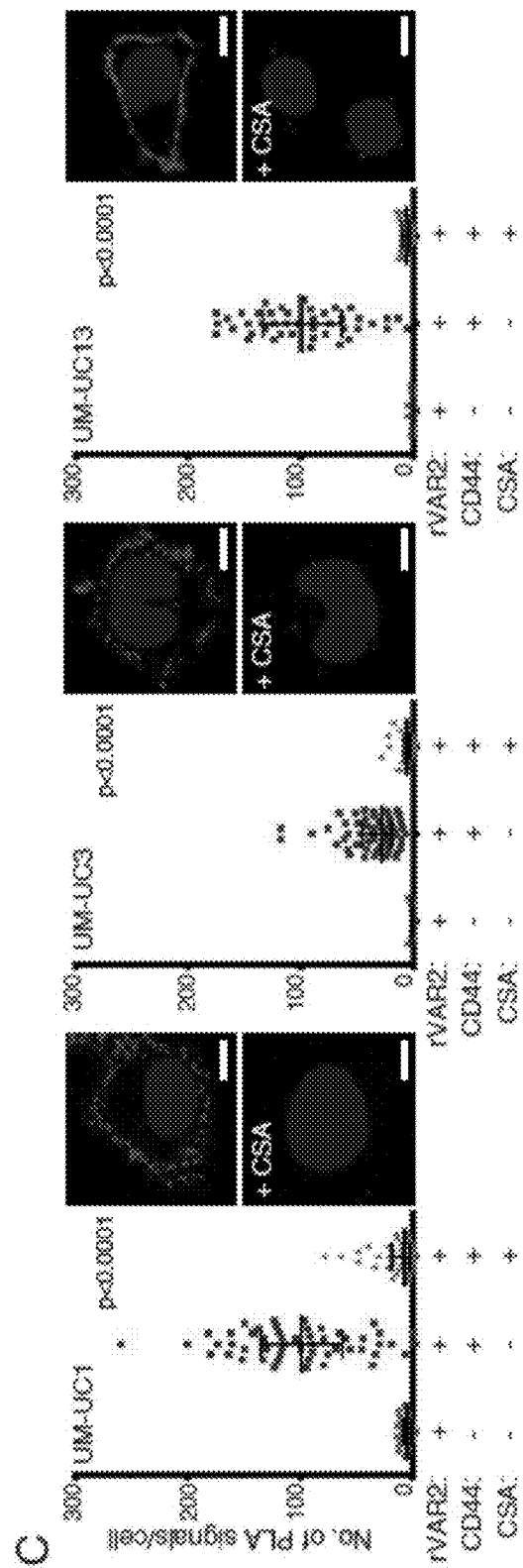

Example 4: Oncofetal Chondroitin Sulfate Expression in Bladder Cancer Cell Lines A panel of 7 bladder cancer cell lines derived from MIBC patients was analyzed for ofCS expression by flow cytometry using rVAR2 as ofCS detection reagent. Remarkably, all bladder cancer cell lines analyzed expressed ofCS, although to various degrees (FIG. 4A). This expression was associated with sensitivity to the ofCS targeting rVAR2 drug conjugate (VDC) VDC886 in the low-nanomolar IC$_{50}$ concentration range and with expression of CD44 (FIG. 4B). VDC886 comprises the DBL1X-ID2a domains of the full-length malarial VAR2CSA protein loaded with an average of 3 KT886 hemiasterlin toxin analogs (see Materials and Methods above, and Salanti, et al., 2015, ibid.).

As in primary human MIBC specimens (FIGS. 3E and 3F), CD44 produced a robust PLA signal with ofCS in bladder cancer cells, which could be efficiently blocked by soluble CSA competition (FIG. 4C). Thus, human bladder cancer cells present ofCS modifications on membrane-associated proteoglycans, including CD44, which can be targeted by VDCs.

Example 5: Efficacy of rVar2 Drug Conjugate Against Cisplatin-Resistant Muscle Invasive Bladder Cancer In Vivo In view of the results described in Examples 2 and 4 indicating that human cisplatin-resistant MIBC upregulates presentation of ofCS and that MIBC cells are sensitive to VDCs in vitro, VDC886 efficacy against cisplatin-resistant MIBC was tested in vivo.

Figure 5:
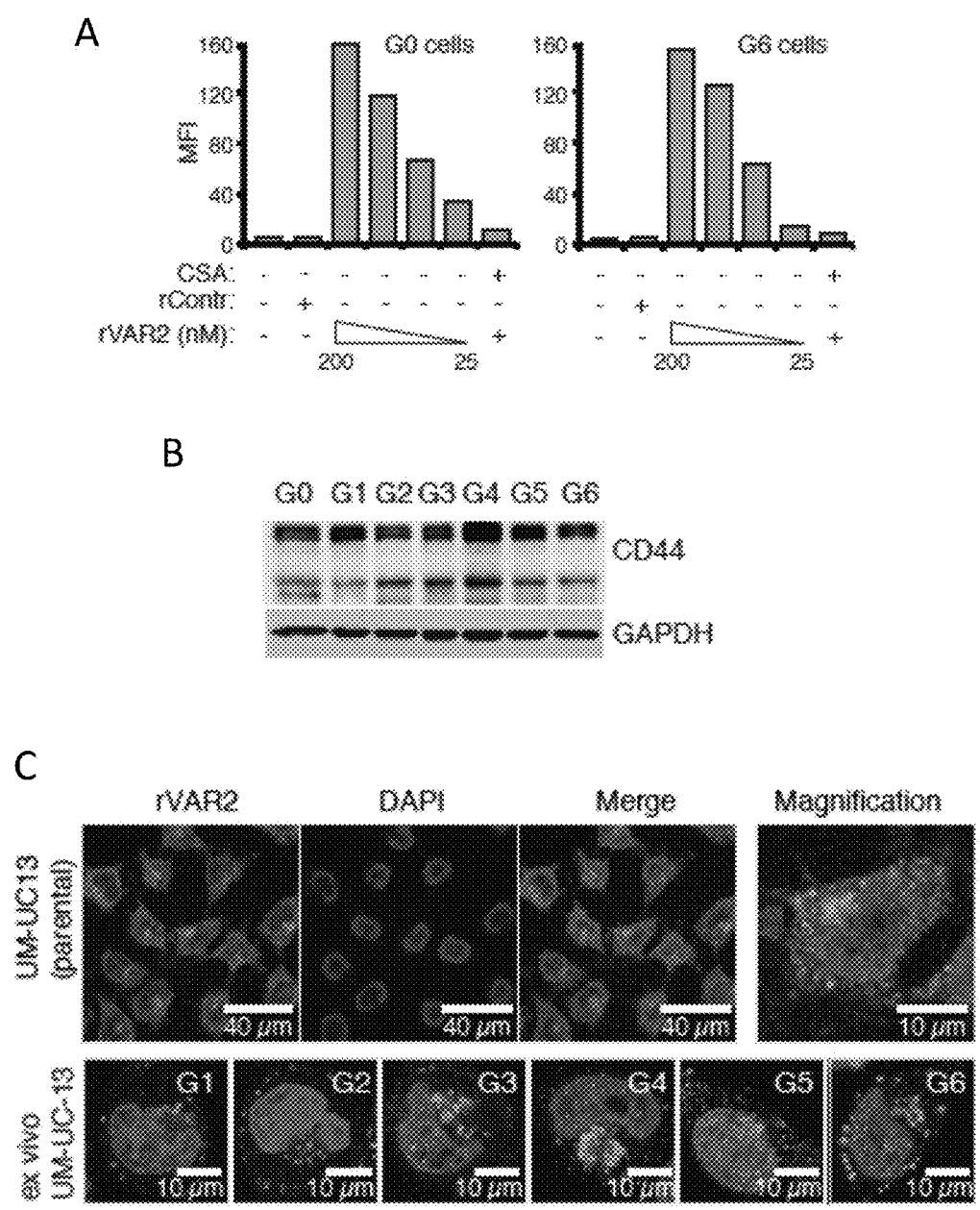
FIG. 5 demonstrates the potential of the VAR2CSA drug conjugate, VDC886, for targeted therapy of cisplatin-resistant bladder cancer: (A) Binding of rVAR2 to UM-UC13 parental and ex vivo cells (generation 6). Relative mean fluorescence intensity (MFI) after incubation with recombinant control protein (rContr) or rVAR2 as indicated and detection by flow cytometry using anti-V5-FITC. (B) CD44 protein expression in UM-UC-13 parental (G0) and the ex vivo cell lines (G1 to G6); GAPDH as a loading control. (C) Internalization of Alexa488-labelled rVAR2 in parental (upper panel) and ex vivo (lower panel) UM-UC13 bladder cancer cells detected by confocal microscopy 30 minutes after addition of rVAR2-FITC (green) and DAPI (blue). (D) Indicated human bladder cancer cell lines were seeded in 96-well plates and treated with VDC886 in concentrations ranging from 0.01 pM to 200 nM. The column graph displays $IC_{50}$ kill-values of VDC886 performance. (E) Comparing tumor growth between VDC886-treated and control groups. The noted treatment was administered intravenously twice per week (red arrow heads) as indicated. (F) Representative ultrasound images of each group at day 17, 31 and 45. (G) Kaplan-Meier curve of VDC886 and Vehicle treated mice from (E).
Figure 5:
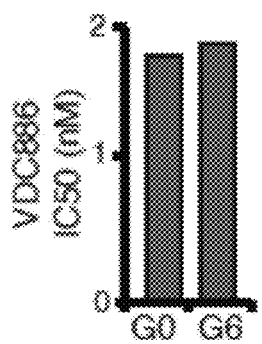
Figure 5:
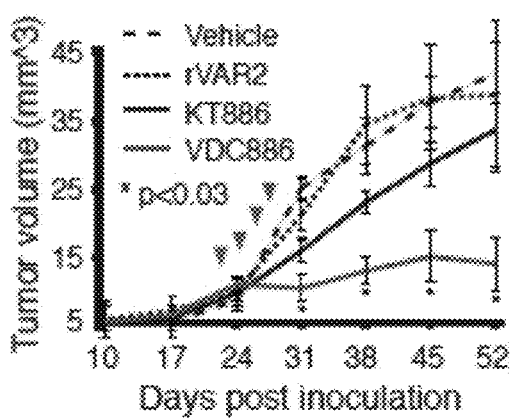
Figure 5:
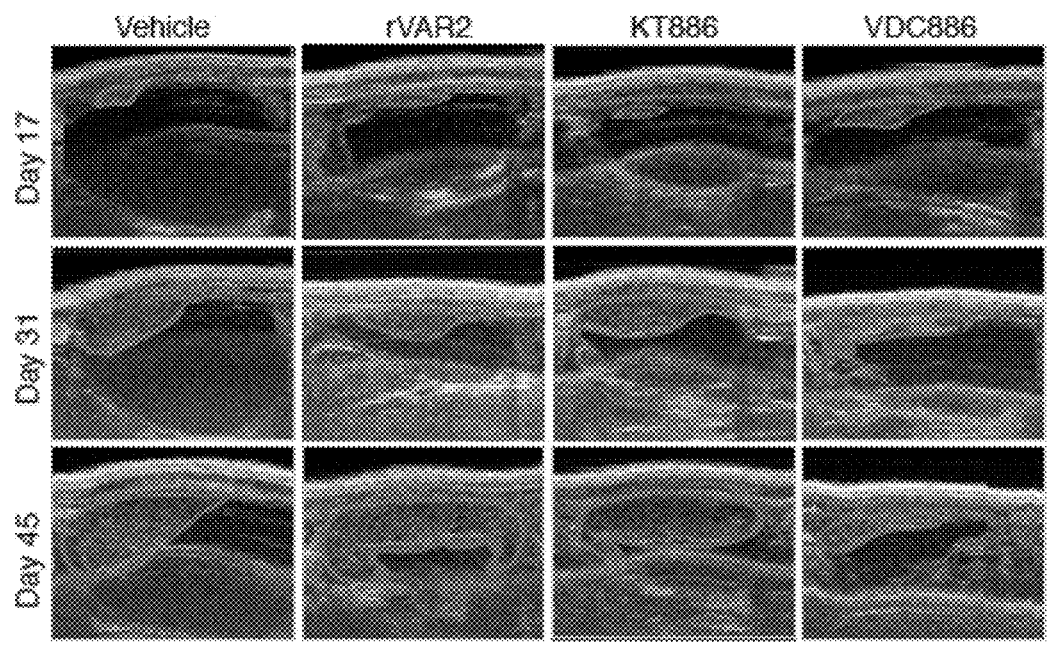
Figure 5:
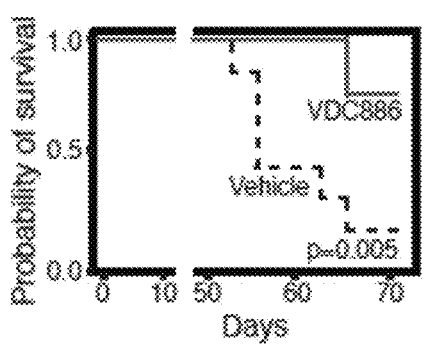

UM-UC13 cells were inoculated directly into the bladder wall of Nude mice guided by ultrasound and tumor sizes were subsequently monitored using ultrasound. As the UM-UC13 tumors developed, the mice were subjected repeating cycles of cisplatin treatment while passaged directly from one mouse to the next over 6 tumor generations (G0-G6). Ex vivo and in situ G0-G6 tumor cells expressed similar levels of ofCS and CD44 (FIGS. 5A and 5B) and retained internalization capacity of the rVAR2 protein (FIG. 5C). Importantly, the completely cisplatin-resistant G6 and cisplatin-sensitive G0 cells showed equal sensitivity to VDC886 ex vivo (FIG. 5D).

Figure 6:
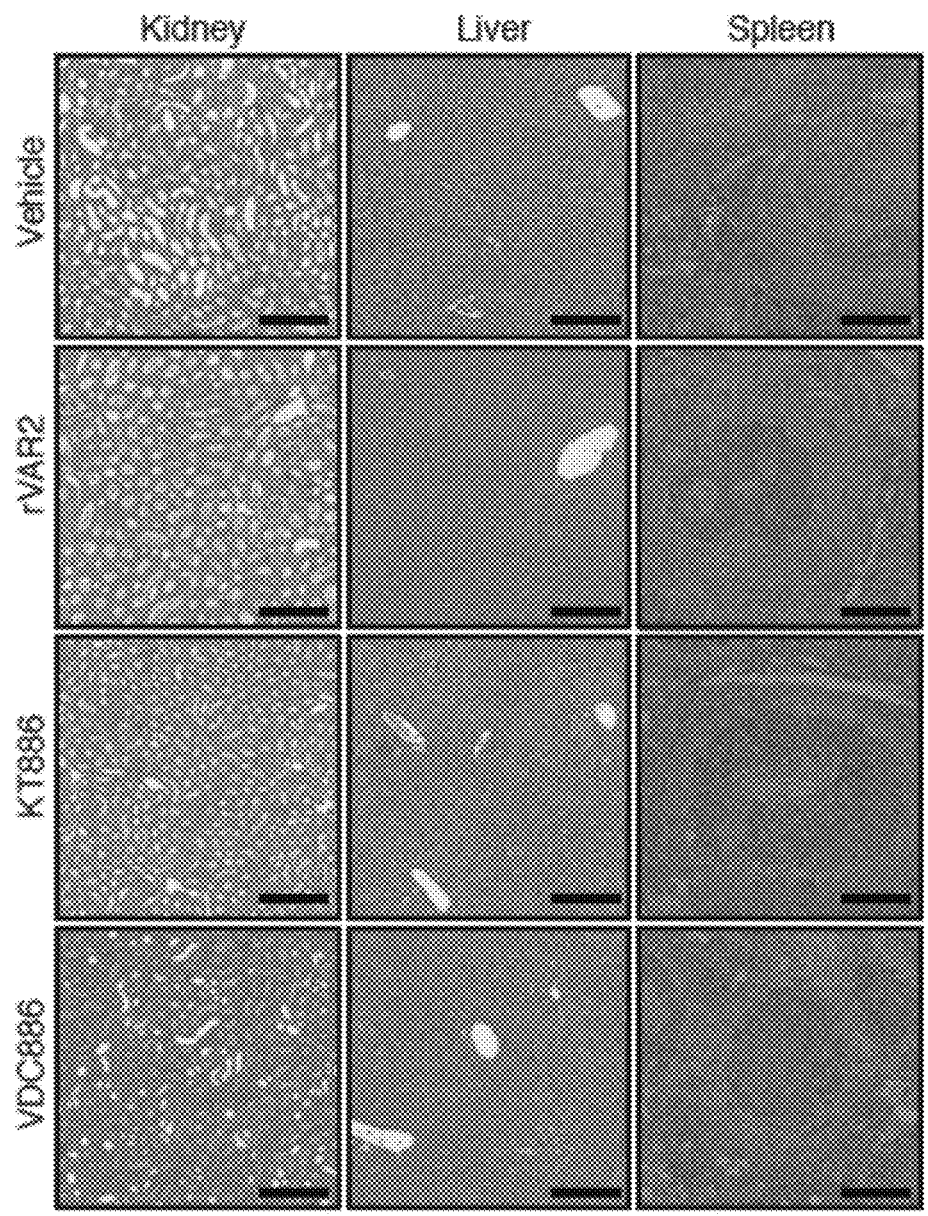
FIG. 6 shows representative hematoxylin and eosin stained (H&E) images of kidney, liver and spleen extracted from VDC886-treated and control mice from FIG. 5F. Histological examination of kidney, liver and spleen was performed on 3 mice per group to assess toxicity to treatment. During the experiment, no side effects were observed to any of the treatments. Except locally in the pelvis, no pathologically suspicious lesions were observed by macroscopic examination of organs from all mice at harvesting. Scale bar represents 200 um.

Next, mice with established G6-initiated cisplatin-resistant tumors were randomized into 4 groups and treated bi-daily (4 treatments in total) with vehicle, rVAR2, KT886, or VDC886. Remarkably, VDC886 treatment strongly retarded tumor growth (FIGS. 5E & F) and significantly prolonged survival of the mice (FIG. 5G). Importantly, clinic-pathological examination of VDC886-treated mice demonstrated no organ toxicity in the mice (FIG. 6). In the VDC886 treated group, one mouse had complete response, one mouse presented with significant tumor regression and 4 mice had cytostatic tumors during the experiment, but viable tumor cells in histology.

In summary, Examples 2-5 demonstrate a new approach for treating cisplatin-resistant MIBC using the protein, VAR2CSA, which specifically binds a secondary ofCS modification on a subset of cancer-associated proteoglycans. The results show that presentation of ofCS is related to cisplatin-resistance and poor survival of human MIBC patients. Two different cohorts of patients with slightly different clinical compositions were analyzed—the discovery cohort comprised more advanced disease with >10 years of clinical follow-up, while the validation cohort had less advanced disease and only 6 years of follow-up. In both cohorts, ofCS was significantly correlated with cisplatin-resistance. The advanced disease discovery cohort produced a robust and significant relationship between high ofCS levels, tumor stage and survival. This relationship did not reach statistical significance in the validation cohort, which exhibited less advanced disease cases and shorter follow-up. This indicates that high ofCS is broadly associated with cisplatin-resistance independent of disease progression, and also that high ofCS expression is related to survival in more advanced MIBC.

Overall, 90% of all MIBC showed high ofCS expression. Interestingly, the cellular ofCS expression significantly increased in cisplatin-resistant MIBC when compared to paired chemotherapy naïve MIBC. Therapeutic approaches that target ofCS with Var2CSA drug conjugates, therefore, could be particularly useful in cisplatin-resistant MIBC. VDC886 eliminated all bladder cancer cell lines in the picoM to low nM $IC_{50}$ concentration range. In an animal model of cisplatin-resistant MIBC, VDC886 was able to efficiently target established cisplatin-resistant tumors and rescue the mice from tumor-associated morbidity and death.

Example 6: Other Platinum Drug-Resistant Cancers

Platinum is front line treatment in several malignancies other than bladder cancer, including non-small cell lung cancer (NSCLC). Cisplatin-resistant NSCLC that over-expresses ofCS is expected to be susceptible to treatment with VDCs as described herein. To test the efficacy of VDCs in cisplatin-resistant NSCLC, cisplatin-resistant human A549 NSCLC cells are inoculated subcutaneously on the back of immune compromised Foxn1nu mice and allowed to establish tumors of ~100 $mm^3$. Tumor-bearing mice are segregated into 4 groups and subjected 3 treatments of vehicle (group 1), un-modified rVAR2 (group 2), KT886 alone (group 3), and VDC886 (group 4). Tumor sizes are monitored with a caliper for 50 days or until reaching a humane endpoint.

The disclosures of all patents, patent applications, publications and database entries referenced in this specification are hereby specifically incorporated by reference in their entirety to the same extent as if each such individual patent, patent application, publication and database entry were specifically and individually indicated to be incorporated by reference.

Modifications of the specific embodiments described herein that would be apparent to those skilled in the art are intended to be included within the scope of the following claims.

SEQUENCES

```
>fcr3 745 amino acids|640 aa; underlined sequence corresponds to the ID1 domain of
FCR3. Sequence in bold corresponds to DBL2Xb domain of FCR3. Remaining sequence is
ID2a (SEQ ID NO: 1)
NYIKGDPYFAEYATKLSFILNPSDANNPSGETANHNDEACNCNESGISSVGQAQTSGPSSNKTCIT
HSSIKTNKKKECKDVKLGVRENDKDLKICVIEDTSLSGVDNCCCQDLLGILQENCSDNKRGSSSN
DSCDNKNQDECQKKLEKVFASLTNGYKCDKCKSGTSRSKKKWIWKKSSGNEEGLQEEYAN
TIGLPPRTQSLYLGNLPKLENVCEDVKDINFDTKEKFLAGCLIVSFHEGKNLKKRYPQNKNS
GNKENLCKALEYSFADYGDLIKGTSIWDNEYTKDLELNLQNNFGKLFGKYIKKNNTAEQD
TSYSSLDELRESWWNTNKKYIWTAMKHGAEMNITTCNADGSVTGSGSSCDDIPTIDLIPQY
LRFLQEWVENFCEQRQAKVKDVITNCKSCKESGNKCKTECKTKCKDECEKYKKFIEACGT
AGGGIGTAGSPWSKRWDQIYKRYSKHIEDAKRNRKAGTKNCGTSSTTNAAASTDENKCVQ
SDIDSFFKHLIDIGLTTPSSYLSNVLDDNICGADKAPWTTYTTYTTTEKCNKERDKSKSQSSD
TLVVVNVPSPLGNTPYRYKYACQCKIPTNEETCDDRKEYMNQWSCGSARTMKRGYKNDNYE
LCKYNGVDVKPTTVRSNSSKLD >gi|254952610|gb|ACT97135.1|VAR2CSA [Plasmodium falciparum] |341 aa (SEQ ID NO: 2)
KCDKCKSGTSRSRKIWTWRKSSGNKEGLQEEYANTIGLSPRTQLLYLGNLRKLENVCEDVTDIN
FDTKEKFLAGCLIAAFHEGKNLKKRYLEKKKGDNNSKLCKDLKYSFADYGDLIKGTSIWDNDFT
KDLELNLQQIFGKLFRKYIKKKNISTEQDTSYSSLDELRESWWNTNKKYIWLAMKHGAGMNSTT
CSCSGDSSSGENQTNSCDDIPTIDLIPQYLRFLQEWVEHFCEQRQAKVKDVITNCNSCKESGGTCN
SDCEKKCKNKCDAYKTFIEDCKGVGGTGTAGSSWVKRWYQIYMRYSKYIEDAKRNRKAGTKS
CGTSSTTNVSVSTDENKCVQS- >M24 745 amino acids |656 aa (SEQ ID NO: 3)
DYIKGDPYFAEYATKLSFILNSSDANNPSGETANHNDEVCNPNESEISSVGQAQTSDPSSNKT
CNTHSSIKANKKKVCKHVKLGINNNDKVLRVCVIEDTSLSGVENCCFKDLLGILQENCSDN
KSGSSSNGSCNNKNQEACEKNLEKVLASLTNCYKCDKCKSGTSTVNKNWIWKKSSGNKEG
LQKEYANTIGLPPRTHSLYLGNLPKLENVCEDVKDINFDTKEKFLAGCLIAAFHEGKNLKK
RYPQNKNDDNNSKLCKALEYSFADYGDLIKGTSIWDNEYTKDLELNLQQIFGKLFRKYIKK
```

| SEQUENCES |
|---|
| NISTEQDTLYSSLDELRESWWNTNKKYIWLAMKHGAGMNITTCCGDGSVTGSGSSCDDIPT
IDLIPQYLRFLQEWVEHFCKQRQEKVKDVINSCNSCKNTSSKTKLGDTCNSDCEKKCKIEC
EKYKKFIEECRTAVGGTAGSSWSKRWDQIYKMYSKHIEDAKRNRKAGTKNCGITTGTISG
ESSGANSGVTTTENKCVQSDIDSFFKHLIDIGLTTPSSYLSIVLDDNICGDDKAPWTTYTTYT
TYTTTEKCNKERDKSKSQQSNTSVVVNVPSPLGNTPHGYKYACQCKIPTNEETCDDRKEYMN
QWISDTSKNPKGSGSTNNDYELYTYNGVKETKLPKKLNSPKLD

>KMWII 745 amino acids|643 aa (SEQ ID NO: 4)
DYIKDDPYSKEYTTKLSFILNSSDANTSSGETANHNDEACNCNESEISSVGQAQTSGPSSNKT
CITHSFIKANKKKVCKDVKLGVRENDKVLRVCVIEDTSLSGVDNCCCQDLLGILQENCSDN
KRGSSSNGSCNNKNQDECQKKLEKVFVSLTNGYKCDKCKSGTSTVNKKWIWKKSSGNEK
GLQKEYANTIGLPPRTQSLYLGNLPKLGNVCEDVTDINFDTKEKFLAGCLIAAFHEGKNLKI
SHEKKKGDNGKKLCKALEYSFADYGDLIKGTSIWDNEYTKDLELNLQKAFGKLFGKYIKK
NIASDENTSYSSLDELRESWWNTNKKYIWTAMKHGAEMNSTMCNADGSVTGSGSSCDDIP
TTDFIPQYLRFLQEWVEHFCKQRQEKVNAVIENCNSCKNTSGERKIGGTCNGDCKTECKN
KCEAYKNFIEDCKGGDGTAGSSWVKRWDQIYKRYSKHIEDAKRNRKAGTKSCGPSSITNAS
VSTDENKCVQSDIDSFFKHLIDIGLTTPSSYLSIVLDENNCGEDNAPWTTYTTYTTTEKCNKD
KKKSKSQSCNTAVVVNVPSPLGNTPHEYKYACQCKIPTTEETCDDRKEYMNQWISDTSKKQK
GSGSTNNDYELYTYTGVKETKLPKKLNSPKLD 1248 745 amino acids|640 aa (SEQ ID NO: 5)
SYVKNDPYSKEYVTKLSFILNPSDANNPSGETANHNDEACNPNESEIASVGQAQTSDRLSQK
ACITHSFIGANKKIVCKDVKLGVREKDKDLKICVIEDDSLRGVENCCFKDLLGILQENCSDN
KSGSSSNGSCNNKNQDECQKKLDEALASLHNGYKCDKCKSGTSRSKKIWTWRKFPGNGEG
LQKEYANTIGLPPRTQSLYLGNLRKLENVCKGVTDINFDTKEKFLAGCLIAAFHEGKNLKIS
NKKKNDDNGKKLCKDLKYSFADYGDLIKGTSIWDNEYTKDLELNLQKIFGKLFRKYIKKNI
ASDENTLYSSLDELRESWWNTNKKYIWLAMKHGTTCSSGSGDNGDGSVTGSGSSCDDMST
IDLIPQYLRFLQEWVEHFCKQRQEKVKDVIENCKSCKNTSGERIIGGTCGSDCKTKCKGEC
DAYKNFIEECKRGDGTAGSPWSKRWDQIYMRYSKYIEDAKRNRKAGTKNCGTSSTTNAAE
NKCVQSDIDSFFKHLIDIGLTTPSSYLSIVLDENICGDDKAPWTTYTTYTTTEKCNKETDKSK
SQSCNTAVVVNVPSPLGNTPHGYKYACECKIPTTEETCDDRKEYMNQWISDTSKKPKGGRSTN
NDYELYTYNGVKETKLPKKSSSSKLD >gi|254952618|gb|ACT97139.1|VAR2CSA [Plasmodium falciparum] |358 aa (SEQ ID NO: 6)
KCEKCKSEQSKKNNNIWIWRKFPGNGEGLQKEYANTIGLPPRTHSLYLGNLPKLENVCKDVKDI
NFDTKEKFLAGCLIAAFHEGKNLKTTYPQNKNADNNSKLCKDLKYSFADYGDLIKGTSIWDNDF
TKDLELNLQKIFGKLFRKYIKKNIASDENTLYSSLDELRESWWNTNKKYIWLAMKHGAEMNST
MCNGDGSVTGSSDSGSTTCSGDNGSISCDDIPTIDLIPQYLRFLQEWVEHFCKQRQEKVKPVIENC
KSCKNTSGERIIGGTCGSDCEKKCKGECDAYKKFIEECKGGGGGTGTAGSPWSKRWDQIYKRYS
KYIEDAKRNRKAGTKSCGPSSTTNAAASTTESKCVQS >gi|254952592|gb|ACT97126.1|VAR2CSA [Plasmodium falciparum] |333 aa (SEQ ID NO: 7)
KCDKCKSEQSKKNNKNWIWKQFPGNGEGLQKEYANTIGLPPRTHSLYLGNLPKLENVCKGVTDI
NFDTKEKFLAGCLIAAFHEGKNLKTSHEKKKGDNGKKLCKDLKYSFADYGDLIKGTSIWDNDFT
KDLELNLQQIFGKLFRKYIKKNISAEQDTSYSSLDELRESWWNTNKKYIWLAMKHGTTCSSGSG
DNGDGSVTGSGSSCDDMPTTDFIPQYLRFLQEWVEHFCKQRQEKVNAVITNCKSCKESGGTCNS
DCEKKCKDECEKYKKFIEECRTAADGTAGSSWSKRWDQIYKMYSKHIEDAKRNRKAGTKNCGT
SSTTNAAENKCVQS >gi|90193467|gb|ABD92329.1|erythrocyte membrane protein| [Plasmodium falciparum] |
269 aa (SEQ ID NO: 8)
DYIKDDPYSKEYTTKLSFILNSSDANTSSGETANHNDEACNCNESEIASVEQASISDRSSQKAYITH
SSIKTNKKKVCKYVKLGINNNDKVLRVCVIEDTSLSGVENCCFKDLLGILQENCSDNKRGSSFND
SCNNNNEEACQKKLEKVLASLTNGYKCEKCKSGTSRSKKKWIWKKSSGKEGGLQKEYANTIGL
PPRTQSLYLGNLPKLENVCKGVTDINFDTKEKFLAGCLIAAFHEGKNLKPSHQNKNDDNNSKLC
KDLKYSFADY >gi|254952616|gb|ACT97138.1|VAR2CSA [Plasmodium falciparum] |333 aa (SEQ ID NO: 9)
KCDKCKSGTSRSKKKWTWRKSSGNKEGLQKEYANTIGLPPRTHSLYLGNLRKLENVCEDVTDIN
FDTKEKFLAGCLIAAFHEGKNLKTTYPQNKNDDNNSKLCKALKYSFADYGDLIKGTSIWDNDFT
KDLELNLQKIFGKLFRKYIKKNISTEQHTSYSSLDELRESWWNTNKKYIWLAMKHGAEMNGTTC
SCSGDSSDDIPTIDLIPQYLRFLQEWVEHFCKQRQAKVNAVINSCNSCKNTSGERKLGGTCGSEC
KTECKNKCDAYKEFIDGTGSGGGTGTAGSSWVKRWDQIYKRYSKYIEDAKRNRKAGSKNCGTS
STTNAAESKCVQS >hb31 745 amino acids |650 aa (SEQ ID NO: 10)
SYVKNNPYSAEYVTKLSFILNSSDANTSSETPSKYYDEVCNCNESEISSVGQAQTSGPSSNKT
CITHSSIKTNKKKVCKDVKLGINNNDKVLRVCVIEDTSLSGVDNCCCQDLLGILQENCSDKN
QSGSSSNGSCNNKNQDECQKKLEKVFASLTNGYKCDKCKSGTSRSKKKWIWRKSSGNEEG
LQKEYANTIGLPPRTQSLYLGNLRKLENVCKGVTDINFDTKEKFLAGCLIAAFHEGKNLKT
TYPQNKKKLCKDLKYSFADYGDLIKGTSIWDNEYTKDLELNLQKAFGKLFRKYIKKNISTE
QHTLYSSLDELRESWWNTNKKYIWLAMKHGAGMNSTTCCGDGSVTGSGSSCDDIPTIDLIP
QYLRFLQEWVEHFCKQRQEKVNAVIENCNSCKECGDTCNGECKTECEKKCKIECEKYKTF
IEECVTAVGGTSGSPWSKRWDQIYKRYSKYIEDAKRNRKAGTKNCGITTGTISGESSGANS
GVTTTENKCVQSDIDSFFKHLIDIGLTTPSSYLSIVLDDNICGADNAPWTTYTTYTTTYTTTKN
CDIKKKTPKSQPINTSVVVNVPSPLGNTPHGYKYACQCKIPTTEESCDDRKEYMNQWIIDTSK
KQKGSGSTNNDYELYTYNGVKETKLPKKSSSSKLD |

| SEQUENCES |
|---|

>hb32 745 amino acids |643 aa (SEQ ID NO: 11)
SYVKDDPYSAEYVTKLSFILNSSDANTSSETPSKYYDEVCNCNESEISSVGQAQTSGPSSNKT
CITHSSIKTNKKKVCKDVKLGINNNDKVLRVCVIEDTSLSGVDNCCCQDLLGILQENCSDKN
QSGSSSNGSCNNKNQDECQKKLEKVFASLTNGYKCDKCKSGTSRSKKKWIWRKSSGNEEG
LQKEYANTIGLPPRTQSLYLGNLPKLENVCKGVTDIIYDTKEKFLSGCLIAAFHEGKNLKTS
HEKKNDDNGKKLCKALEYSFADYGDLIKGTSIWDNDFTKDLELNLQKIFGKLFRKYIKKN
NTAEQDTSYSSLDELRESWWNTNKKYIWTAMKHGAGMNSTTCSGDGSVTGSGSSCDDMP
TIDLIPQYLRFLQEWVEHFCKQRQEKVKDVITNCNSCKECGDTCNGECKTECKTKCKGEC
EKYKNFIEECNGTADGGTSGSSWSKRWDQIYKRYSKYIEDAKRNRKAGTKNCGTSSTTNA
AASTTENKCVQSDIDSFFKHLIDIGLTTPSSYLSNVLDDNICGEDKAPWTTYTTYTTKNCDIQ
KKTPKPQSCDTLVVVNVPSPLGNTPHGYKYVCECKIPTTEETCDDRKEYMNQWIIDTSKKQK
GSGSTNNDYELYTYNGVQIKQAAGTLKNSKLD >gi|90193475|gb|ABD92333.1|erythrocyte membrane protein 1 [Plasmodium falciparum] |
269 aa (SEQ ID NO: 12)
NYIKGDPYSAEYATKLSFILNSSDTENASEKIQKNNDEVCNCNESEIASVEQAPISDRSSQKACITH
SSIKANKKKVCKHVKLGVRENDKDLKICVIEDTSLSGVDNCCCQDLLGILQENCSDNKSGSSSNG
SCNNNNEEICQKKLEKVLASLTNGYKCDKCKSGTSTVNKNWIWKKYSGKEGGLQEEYANTIGL
PPRTQSLYLGNLPKLENVCEDVKDINFDTKEKFLAGCLIAAFHEGKNLKTSNKKKNDDNNSKLC
KALKYSFADY >gi|254952600|gb|ACT97130.1|VAR2CSA [Plasmodium falciparum+] |344 aa (SEQ ID NO: 13)
KCDKCKSGTSTVNKKWIWKKYSGTEGGLQEEYANTIALPPRTQSLYLGNLPKLENVCKDVTDIN
FDTKEKFLAGCLIAAFHEGKNLKTTYLEKKKGDNGKKNDDNNSKLCKALKYSFADYGDLIKGT
SIWDNDFTKDLELNLQQIFGKLFRKYIKKNIASDENTLYSSLDELRESWWNTNKKYIWLAMKHG
AGMNSTMCNADGSVTGSGSSCDDIPTIDLIPQYLRFLQEWVEHFCKQRQAKVKDVITNCNSCKE
CGGTCNGECKTECEKKCKGECDAYKKFIEECKGKADEGTSGSSWSKRWDQIYKRYSKYIEDAK
RNRKAGTKNCGPSSTTSTAESKCVQS >gi|254952598|gb|ACT97129.1|VAR2CSA [Plasmodium falciparum] |334 aa (SEQ ID NO: 14)
KCDKCKSEQSKKNNNIWIWKKSSSGTEGGLQKEYANTIALPPRTQSLYLGNLRKLENVCEDVKDI
NFDTKEKFLAGCLIAAFHEGKNLKKRYLEKKNGDNNSKLCKALKYSFADYGDLIKGTSIWDNEY
TKDLELNLQKIFGKLFRKYIKKNNTAEQHTSYSSLDELRESWWNTNKKYIWLAMKHGTTCSSGS
GDNGSISCDDIPTIDLIPQYLRFLQEWVEHFCEQRQGKVNAVIENCNSCKNTSSKTLGGTCNGE
CKTECKGECDAYKEFIEKCKGTAAEGTSGSSWVKRWYQIYMRYSKYIEDAKRNRKAGTKNCGT
SSTTSTAESKCVQS >gi|254952596|gb|ACT97128.1|VAR2CSA [Plasmodium falciparum+] |332 aa (SEQ ID NO: 15)
KCDKCKSEQSKKNNNIWIWKKSSGTEGGLQKEYANTIALPPRTQSLYLGNLRKLENVCEDVKDI
NFDTKEKFLAGCLIAAFHEGKNLKKRYLEKKNGDNNSKLCKALKYSFADYGDLIKGTSIWDNEY
TKDLELNLQKIFGKLFRKYIKKNNTAEQDTSYSSLDELRESWWNTNKKYIWTAMKHGTTCSSGS
GDNGSISCDDIPTIDLIPQYLRFLQEWVEHFCEQRQEKVKDVIKNCNSCKECGGTCNGECKTECK
NKCKDECDAYKKFIEECEGKAAEGTSGSSWSKRWDQIYKRYSKYIEDAKRNRKAGTKNCGTSS
TTSTAENKCVQS >gi|90193465|gb|ABD92328.1|erythrocyte membrane protein 1 [Plasmodium falciparum]
| 267 aa (SEQ ID NO: 16)
NYIKDDPYSAEYTTKLSFILNSSDTENASEKIQKNNDEVCNPNESGIACVELAQTSGSSSNKTCNT
HSFIKANKKKVCKDVKLGINKKDKDLKICVIEDDSLRGVDNCCCQDLLGILQENCSDKNQSGSSS
NGSCNNKNQEACQKKLENVFASLTNGYKCEKCKSEQSKKNNKNWIWKKYSVKEEGLQKEYAN
TIALPPRTQSLYLGNLPKLGNVCKGVTDINFDTKEKFLAGCLIAAFHEGKNLKTTYLQNKKKLCK
ALKYSFADY >gi|90193477|gb|ABD92334.1|erythrocyte membrane protein 1 [Plasmodium falciparum]
| 263 aa (SEQ ID NO: 17)
DYIKGDPYFAEYATKLSFILNSSDANTSSGETANHNDEACNPNESEIASVEQASISDRSSQKACNT
HSSIKANKKKECKHVKLGVRENDKDLKICVIEDTSLSGVDNCCCQDLLGILQENCSDNKRGSSSN
GSCDKNSEEICQKKLDEALASLHNGYKNQKCKSEQSKKNKNKWIWKKSSGNEKGLQKEYANTI
GLPPRTQSLYLGNLPKLENVCEDVTDINFDTKEKFLAGCLIAAFHEGKNLKTTYPQNKNDDNGK
KLCKD >gi|254952594|gb|ACT97127.1|VAR2CSA [Plasmodium falciparum] |338 aa (SEQ ID NO: 18)
KCDKCKSEQSKKNNNIWIWKKSSGNKKGLQKEYANTIGLPPRTQSLYLGNLPKLENVCKDVTDI
NFDTKEKFLAGCLIAAFHEGKNLKISNEKKNDDNGKKLCKDLKYSFADYGDLIKGTSIWDNEYT
KDLELNLQNNFGKLFRKYIKKNNTAEQHTLYSSLDELRESWWNTNKKYIWLAMKHGTTCSSGS
GDNGDGSVTGSGSSCDDMSTIDLIPQYLRFLQEWVEHFCKQRQEKVNAVIENCNSCKNTSSKTK
LGGTCNGECKTECEKKCKDECEKYKEFIEECKRGDGTAGSPWVKRWDQIYMRYSKYIEDAKRN
RKAGTKSCGTSAAENKCVQS >gi|254952602|gb|ACT97131.1|VAR2CSA [Plasmodium falciparum] |341 aa (SEQ ID NO: 19)
KCDKCKSEQSKKNNNIWIWKKSSGDEKGLQKEYANTIALPPRTQSLYLGNLPKLENVCKDVTDI
NFDTKEKFLAGCLIAAFHEGKNLKTSHQNKNADNGKKNDDNGKKLCKALKYSFADYGDLIKGT
SIWDNEYTKDLELNLQQIFGKLFRKYIKRNNTAEQHTLYSSLDELRESWWNTNKKYIWLAMKH
GTTCSSGSGDNGDGSVTGSGSSCDDMSTIDLIPQYLRFLQEWVEHFCKQRQEKVKDVITNCNSC
KECGGTCGSDCKTKCEAYKKFIEECNGTADGGTSGSSWSKRWDQIYKRYSKYIEDAKRNRKAG
TKNCGPSSGANSGVTTTENKCVQS

| SEQUENCES |
|---|

>gi|254952660|gb|ACT97160.1|VAR2CSA [*Plasmodium falciparum*] |352 aa (SEQ ID NO: 20)
KCEKCESEQSKNNKYWIWKKSSGNGEGLQEEYANTIALPPRTHSLCLVCLHEKEGKKTQELKN
IRTNSELLKERIIAAFHEGKNLKTSPQNKNDNGKKLCKDLKYSFADYGDLIKGTSIWDNEYTKDL
ELNLQKIFGKLFRKYIKKNNTAEQHTLYSSLDELRESWWNTNKKYIWLAMKHGAGMNSTMCN
ADGSVTGSSDSGSTTCCGDNGSISCDDMPTIDLIPQYLRFLQEWVEHFCEQRQEKVNAVITNCKS
CKEKCGGTCNSDCEKKCKAYKEFIEKCKGGGTEGTSGSSWSKRWDQIYKRHSKHIEDAKRNRKA
GTKNCGITTGTISGESSGANSGVTTTENKCVQS >gi|254952652|gb|ACT97156.1|VAR2CSA [*Plasmodium falciparum*] |344 aa (SEQ ID NO: 21)
KCDKCKSGTSRSRKIWTWRKFRGNGEGLQKEYANTIGLSPRTQLLYLVCLHEKGKKTQELKNIS
TNSELLKEWIIAAFHEGKNLKTTYPQKKNDDNGKKLCKALKYSFADYGDLIKGTSIWDNDFTKD
LELNLQKIFGKLFRKYIKKNIASDENTSYSSLDELRESWWNTNKKYIWTAMKHGAGMNGTTCC
GDGSVTGSSDSGSTTCCGDGSVTGSGSSCDDIPTIDLIPQYLRFLQEWVEHFCEQRQEKVKDVITN
CKSCKESEKKCKNKCDAYKEFIDGTGSGGGTGTAGSSWSKRWDQIYMRYSKYIEDAKRNRKAG
TKNCGTSSGANSGVTTTENKCVQS >gi|254952622|gb|ACT97141.1|VAR2CSA [*Plasmodium falciparum*] |350 aa (SEQ ID NO: 22)
KCEKCKSEQSKKNNKIWTWRKFPGNGEGLQKEYANTIGLSPRTQLLYLVCLHEKGKKTQHKTIS
TNSELLKEWIIAAFHEGKNLKKRYLEKKKGDNNSKLCKDLKYSFADYGDLIKGTSIWDNDFTKD
LELNLQQIFGKLFRKYIKKNIASDENTSYSSLDELRESWWNTNKKYIWTAMKHGAGMNSTMCN
GDGSVTGSSDSGSTTCSGDNGSISCDDIPTIDLIPQYLRFLQEWVEHFCEQRQEKVKDVIKNCNSC
KECGGTCNGECKTECKNKCKDECEKYKNFIEVCTGGDGTAGSPWSKRWYQIYMRYSKYIEDAK
RNRKAGTKSCGTSSGANSGVTTTESKCVQS >gi|254952626|gb|ACT97143.1|VAR2CSA [*Plasmodium falciparum*] |359 aa (SEQ ID NO: 23)
KCEKCKSEQSKKNNKNWIWRKFPGNGEGLQKEYANTIGLPPRTHSLYLVCLHEKGKKTQELKNI
RTNSELLKEWIIAAFHEGKNLKKRYHQNNNSGNKKKLCKALEYSFADYGDLIKGTSIWDNEYTK
DLELNLQQIFGKLFRKYIKKNISTEQDTLYSSLDELRESWWNTNKKYIWLAMKHGAGMNSTTCC
GDGSVTGSSDSGSTTCSGDNGSISCDDMPTIDLIPQYLRFLQEWVEHFCEQRQEKVKDVIENCKS
CKNTSGERIIGGTCNGECKTECEKKCKAACEAYKTFIEECEGKAAEGTSGSSWSKRWYQIYMRY
SKYIEDAKRNRKAGTKNCGKSSGANSGVTTTENKCVQS >gi|90193469|gb|ABD92330.1|erythrocyte membrane protein 1 [*Plasmodium falciparum*]
1 270 aa (SEQ ID NO: 24)
NYIKDDPYSKEYVTKLSFIPNSSDANNPSGETANHNDEVCNPNESEISSVEHAQTSVLLSQKAYIT
HSSIKANKKKVCKYVKLGVRENDKDLKICVIEDDSLRGVENCCFKDFLRILQENCSDNKRESSSN
GSCNNNNEEACEKNLDEALASLTNCYKNQKCKSGTSTVNNNKWIWKKSSGKEGGLQKEYANTI
GLPPRTQSLCLVVCLDEKEGKTQELKNIRTNSELLKEWIIAAFHEGKNLKKRYHQNKDDNNSK
LCKALKYSFADY >gi|254952644|gb|ACT97152.1|VAR2CSA [*Plasmodium falciparum*] |334 aa (SEQ ID NO: 25)
KCDKCKSEQSKKNNKYWIWKKYSVKEGGLQKEYANTIALPPRTQSLCLVVCLDEKEGKTQELK
NIRTNSELLKERIIAAFHEGKNLKTYHEKKKGDDGKKLCKDLKYSFADYGDLIKGTSIWDNDFTK
DLELNLQKIFGKLFRKYIKKNNTAEQHTSYSSLDELRESWWNTNKKYIWTAMKHGAEMNGTTC
SCSGDSSNDIPTIDLIPQYLRFLQEWVEHFCEQRQAKVNAVIKNCKSCKECGGTCNGECKTECKT
KCKGECEKYKEFIEKCEGQAAEGTSGSSWSKRWYQIYMRYSKYIEDAKRNRKAGTKNCGTSSG
ANSGVTTTENKCVQS >gi|254952642|gb|ACT97151.1|VAR2CSA [*Plasmodium falciparum*] |351 aa (SEQ ID NO: 26)
KCDKCKSEQSKKNNKNWIWKKYSGTEGGLQKEYANTIALPPRTQSLYLVCLHEKEEKTQELKNI
STNSELLKEWIIAAFHEGKNLKISPQNKNDNGKNLCKDLKYSFADYGDLIKGTSIWDNDFTKDLE
LNLQQIFGKLFRKYIKKNNTAEQDTLYSSLDELRESWWNTNKKYIWTAMKHGAGMNGTTCCG
DGSVTGSSDSGSTTCCGDGSVTGSGSSCDDIPTIDLIPQYLRFLQEWVEHFCEQRQAKVKDVIKN
CNSCKECGGTCNGECKTECEKKCKGECEAYKKFIEKCNGGGGEGTSGSSWSKRWDQIYMRYSK
YIEDAKRNRKAGTKNCGTSSTTNAAENKCVQS >giV254952658|gb|ACT97159.1|VAR2CSA [*Plasmodium falciparum*] |353 aa (SEQ ID NO: 27)
KCDKCKSGTSTVNKKWIWKKFPGKEGGLQEEYANTIALPPRTQSLCLVVCLDEKEGKTQHKTIS
TNSELLKEWIIAAFHEGKNLKISNKKKNDENNSKLCKDLKYSFADYGDLIKGTSIWDNDFTKDLE
LNLQKIFGKLFRKYIKKNNTAEQDTSYSSLDELRESWWNTNKKYIWLAMKHGYTTCSSGSGDNG
DGSVTGSSDSGSTTCCGDGSVTGSGSSCDDIPTIDLIPQYLRFLQEWVEHFCKQRQAKVKDVIEN
CKSCKNTSSKTKLGDTCNSDCKTKCKVACEKYKEFIEKCVSAAGGTSGSSWVKRWDQIYMRYS
KYIEDAKRNRKAGTKNCGPSSTTSTAESKCVQS >gi|254952640|gb|ACT97150.1|VAR2CSA [*Plasmodium falciparum*] |327 aa (SEQ ID NO: 28)
KCDKCKSGTSTVNKKWIWKKYSGKEGGLQKEYANTIGLPPRTQSLCLVCLHEKEGKTQELKNIS
TNSELLKEWIIAAFHEGKNLKISNKKKNDDNGKKLCKDLKYSFADYGDLIKGTSIWDNDFTKDL
ELNLQKIFGKLFRKYIKKNNTAEQDTLYSSLDELRESWWNTNKKYIWTAMKHGAGMNSTTCSC
SGDSSNDIPTIDLIPQYLRFLQEWVEHFCKQRQEKVNAVITNCKSCKESGGTCNSDCEKKCKIECE
KYKNFIEKCVTAAGGTSGSSWSKRWDQIYKMYSKYIEDAKRNRKAGTKNCGPSSTTNAAASTD
ENKCVQS >dd2full 745 amino acids |628 an (SEQ ID NO: 29)
NYIKGDPYFAEYATKLSFILNSSDTENASETPSKYYDEACNCNESEIASVGQAQTSGPSSNKT
CITHSSIKTNKKKECKDVKLGINNNDKVLRVCVIEDTSLSGVDNCCCQDLLGILQENCSDNK
RGSSSNGSCDKNSEEICQKKLEKVFASLTNGYKCDKCKSGTSRSKKKWIWKKSSGNEEGL

| SEQUENCES |
|---|
| QKEYANTIGLPPRTQSLCLVCLHEKEGKTQHKTISTNSELLKEWIIAAFHEGKNLKTSHEK<br>KNDDNGKKLCKALEYSFADYGDLIKGTSIWDNEYTKDLELNLQKIFGKLFRKYIKKNNTAE<br>QHTSYSSLDELRESWWNTNKKYIWTAMKHGAGMNGTTCSCSGDSSNDMPTIDLIPQYLRF<br>LQEWVEHFCKQRQEKVNAVIENCNSCKESGGTCNSDCKTECKNKCEAYKEFIEDCKGGGT<br>GTAGSPWSKRWDQIYKRYSKHIEDAKRNRKAGTKNCGTSSTTNAAASTDENKCVQSDVDS<br>FFKHLIDIGLTTPSSYLSNVLDDNICGADKAPWTTYTTYTTTKNCDIQKKTPKSQSCDTLVV<br>VNVPSPLGNTPHEYKYACECKIPTTEETCDDRKEYMNQWSCGSAQTVRGRSGKDDYELYTYN<br>GVKETKPLGTLKNSKLD<br><br>>gi\|254952636\|gb\|ACT97148.1\|VAR2CSA [*Plasmodium falciparum*] \|350 aa (SEQ ID NO: 30)<br>KCEKCKSEQSKKNNKNWIWRKFRGTEGGLQEEYANTIGLPPRTQSLVVCLDEKGKKTQELK<br>NIRTNSELLKEWIIAAFHEGKNLKPSHQNKNSGNKENLCKALKYSFADYGDLIKGTSIWDNDFTK<br>DLELNLQKIFGKLFRKYIKKNNTAEQHTSYSSLDELRESWWNTNKKYIWTAMKHGAEMNGTTC<br>NADGSVTGSSDSGSTTCSGDNGSISCDDIPTIDLIPQYLRFLQEWVEHFCKQRQEKVNAVINSCNS<br>CKNTSSKTKLGDTCNSDCKTKCKIECEKYKTFIEKCVTAAGGTSGSPWSKRWDQIYKRYSKYIE<br>DAKRNRKAGTKNCGPSSTTSTAESKCVQS<br><br>>gi\|254952638\|gb\|ACT97149.1\|VAR2CSA [*Plasmodium falciparum*] \|330 aa (SEQ ID NO: 31)<br>KCDKCKSEQSKKNNKNWIWRKYSGNGEGLQKEYANTIGLPPRTHSLYLVCLHEKEGKTQELKN<br>IRTNSELLKEWIIAAFHEGKNLKTTYLENKNDENKKKLCKALKYSFADYGDLIKGTSIWDNDFTK<br>DLELNLQKIFGKLFRKYIKKNIASDENTLYSSLDELRESWWNTNKKYIWTAMKHGAEMNGTTCS<br>SGSGDNGSISCDDIPTIDLIPQYLRFLQEWVGHFCKQRQEKVNAVITNCNSCKESGGTCNSDCEK<br>KCKIECEKYKKFIEECRTAAGGTSGSPWSKRWDQIYKMYSKYIEDAKRNRKAGTKNCGPSSTTS<br>TAESKCVQS<br><br>>gi\|254952628\|gb\|ACT97144.1\|VAR2CSA [*Plasmodium falciparum*] \|334 aa (SEQ ID NO: 32)<br>KCDKCKSEQSKKNNKNWIWRKYSGNGEGLQKEYANTIGLPPRTHSLYLVCLHEKEGKTQHKTIS<br>TNSELLKEWIIAAFHEGKNLKKRYPQNNNSGNKKKLCKDLKYSFADYGDLIKGTSIWDNEYTKD<br>LELNLQKAFGKLFRKYIKKNIASDENTLYSSLDELRESWWNTNKKYIWLAMKHGAEMNGTMC<br>NADGSVTGSGSSCDDMSTIDLIPQYLRFLQEWVEHFCEQRQAKVKDVINSCKSCKESGDTCNSD<br>CEKKCKNKCDAYKTFIEEFCTADGGTAGSPWSKRWDQIYKRYSKYIEDAKRNRKAGTKNCGTS<br>SGANSGVTTTENKCVQS<br><br>>gi\|254952630\|gb\|ACT97145.1\|VAR2CSA [*Plasmodium falciparum*] \|350 aa (SEQ ID NO: 33)<br>KCDKCKSGTSTVNKNWIWKKYSGKEEGLQKEYANTIALPPRTHSLYLVCLHEKGKKTQELKNIR<br>TNSELLKEWIIAAFHEGKNLKTSPQNNNSGNKKKLCKALKYSFADYGDLIKGTSIWDNDFTKDL<br>ELNLQKIFGKLFRKYIKKNNTAEQHTSYSSLDELRESWWNTNKKYIWLAMKHGAEMNGTTCCG<br>DGSVTGSSDSGSTTCSGDNGSISCDDMPTTDFIPQYLRFLQEWVEHFCKQRQEKVKHVMESCKS<br>CKECGDTCNGECKTECEKKCKNKCEAYKTFIEKCVSADGGTSGSSWSKRWDQIYMRYSKYIED<br>AKRNRKAGTKNCGTSSTTNAAASTAENKCVQS<br><br>>P13 745 amino acids \|647 an (SEQ ID NO: 34)<br>DYIKDDPYSAEYATKLSFILNPSDANTSSGETANHNDEVCNCNESEIASVELAPISDSSSNKTC<br>ITHSFIGANKKKECKDVKLGVREKDKDLKICVIEDDSLRGVENCCCQDLLGILQENCSDNK<br>SGSSSNGSCDKNSEDECQKKLENVFASLKNGYKCDKCKSGTSTVNKKWIWRKYSGNGEGL<br>QKEYANTIGLPPRTHSLYLVCLHEKEGKTQHKTISTNSELLKEWIIAAFHEGKNLKTSHQN<br>NNSGNKKKLCKALKYSFADYGDLIKGTSIWDNDFTKDLELNLQKIFGKLFRKYIKKNIASD<br>ENTSYSSLDELRESWWNTNKKYIWLAMKHGAEMNSTMCNGDGSVTGSSDSGSTTCSGDN<br>GSISCDDIPTIDLIPQYLRFLQEWVEHFCKQRQEKVKDVITNCKSCKESGDTCNSDCEKKCK<br>NKCEAYKKFIEERRTAAQGTAESSWVKRWDQIYMRYSKYIEDAKRNRKAGTKSCGPSSTT<br>NAAASTAENKCVQSDIDSFFKHLIDIGLTTPSSYLSIVLDDNICGADNAPWTTYTTYTTTKNC<br>DIKKKTPKPQSCDTLVVVNVPSPLGNTPHEYKYACQCRTPNKQESCDDRKEYMNQWSSGSA<br>QTVRGRSTNNDYELYTYNGVKETKPLGTLKNSKLD<br><br>>gi\|254952608\|gb\|ACT97134.1\|VAR2CSA [*Plasmodium falciparum*] \|341 aa (SEQ ID NO: 35)<br>KCDKCKSGTSTVNKKWIWRKSSGNKEGLQKEYANTIGLPPRTQSLYLGNLPKLENVCEDVKDIN<br>FDTKEKFLAGCLIVSFHEGKNLKTSHEKKNDDNGKKLCKALEYSFADYGDLIKGTSIWDNEYTK<br>DLELNLQKIFGKLFRKYIKKNNTAEQDTSYSSLDELRESWWNTNKKYIWTAMKHGAGMNITTC<br>CGDGSSGENQTNSCDDIPTIDLIPQYLRFLQEWVEHFCKQRQEKVNAVVTNCKSCKESGGTCNG<br>ECKTKCKNKCEVYKTFIDNVGDGTAGSPWVKRWDQIYKRYSKHIEDAKRNRKAGTKNCGITTG<br>TISGESSGATSGVTTTENKCVQS<br><br>>7g8 745 amino acids \|632 aa (SEQ ID NO: 36)<br>NYIKDDPYSKEYVTKLSFIPNSSDANTSSEKIQKNNDEVCNPNESGISSVEQAQTSGPSSNKTC<br>ITHSSIKANKKKECKDVKLGVRENDKDLKICVIEDTSLSGVDNCCCQDLLGILQENCSDNKR<br>GSSSNDSCDNKNQDECQKKLDEALESLHNGYKNQKCKSGTSTVNKKWIWKKSSGNKEGL<br>QKEYANTIGLPPRTQSLYLGNLPKLENVSKGVTDIIYDTKEKFLAGCLIVSFHEGKNLKTSH<br>EKKNDDNGKKLCKALEYSFADYGDLIKGTSIWDNEYTKDLELNLQKAFGKLFRKYIKKNIS<br>AEQDTSYSSLDELRESWWNTNKKYIWIAMKHGAGMNGTTCCGDGSSGENQTNSCDDIPTI<br>DLIPQYLRFLQEWVEHFCEQRQAKVKDVITNCKSCKNTSGERKIGGTCNGECKTKCKNKC<br>EAYKTFIEHCKGGDTAGSSWVKRWDQIYKRYSKHIEDAKRNRKAGTKSCGTSTAENKCV<br>QSDIDSFFKHLIDIGLTTPSSYLSIVLDENNCGEDKAPWTTYTTTKNCDIQKDKSKSQSSDTL<br>VVVNVPSPLGNTPHGYKYACQCKIPTTEETCDDRKEYMNQWSCGSARTMKRGYKNDYELC<br>KYNGVDVKPTTVRSSSTKLD

SEQUENCES

Ando 745 amino acids |639 aa (SEQ ID NO: 37)
DYIKGDPYSAEYVTKLSFIPNSSDANNPSEKIQKNNDEVCNCNESEISSVGQASISDPSSNKTC
NTHSSIKANKKKVCKDVKLGVRENDKVLKICVIEHTSLRGVDNCCFKDLLGILQEPRIDKN
QSGSSSNGSCDKNSEEACEKNLEKVLASLTNGYKCDKCKSGTSRSKKKWIWKKYSGKEGG
LQEEYANTIGLPPRTQSLCLVVCLDEKEGKTQELKNISTNSELLKEWIIAAFPEGKNLKPSP
EKKKGDNGKKLCKDLKYSFADYGDLIKGTSIWDNEYTKDLELNLQKIFGKLFRKYIKKNIA
SDENTLYSSLDELRESWWNTNKKYIWLAMKHGAGMNSTMCNADGSVTGSGSSCDDMPTI
DLIPQYLRFLQEWVEHFCKQRQEKVKPVIENCNSCKNTSSERKIGGTCNSDCKTECKNKCE
VYKKFIEDCKGGDGTAGSSWSKRWDQIYKRYSKYIEDAKRNRKAGTKNCGPSSTTNAAEN
KCVQSDIDSFFKHLIDIGLTTPSSYLSTVLDDNICGEDNAPWTTYTTYTTTKNCDKDKKKSK
SQSCDTLVVVNVPSPLGNTPHEYKYACECRTPNKQESCDDRKEYMNQWISDNTKNPKGSGSG
KDYYELYTYNGVDVKPTTVRSSSTKLD >MC 745 amino acids |655 aa (SEQ ID NO: 38)
DYIKGDPYFAEYATKLSFILNSSDANTSSGETANHHDEACNCNESEISSVEHASISDPSSNKTC
NTHSSIKANKKKVCKHVKLGVRENDKDLRVCVIEHTSLSGVENCCFKDFLRILQENCSDNK
SGSSSNGSCDKNNEEACEKNLEKVFASLTNCYKCEKCKSEQSKKNNKKWTWRKSSGNKG
GLQEEYANTIGLPPRTQSLCLVVCLDEKEGKKTQELKNIRTNSELLKEWIIAAFHEGKNLK
PSHEKKNDDNGKKNDDNNSKLCKDLKYSFADYGDLIKGTSIWDNEYTKDLELNLQKIFGK
LFRKYIKKNIASDENTLYSSLDELRESWWNTNKKYIWLAMKHGAEMNGTTCNADGSVTGS
GSSCDDIPTIDLIPQYLRFLQEWVEHFCKQRQAKVKDVIENCKSCKESGNKCKTECKNKCE
AYKKFIENCKGGDGTAGSSWVKRWDQIYMRYSKYIEDAKRNRKAGTKNCGPSSITNVSAS
TDENKCVQSDIDSFFKHLIDIGLTTPSSYLSIVLDDNICGDDKAPWTTYTTYTTYTTYTT
YTTYTTTKNCDKERDKSKSQSCNTAVVVNVPSPLGNTPHEYKYACECRTPSNKELCDDRKEY
MNQWSSGSAQTVRDRSGKDYYELYTYNGVKETKLPKKLNSSKLD >gi|254952650|gb|ACT97155.1|VAR2CSA [Plasmodium falciparum] |347 aa (SEQ ID NO: 39)
KCDKCKSEQSKKNNKYWIWKKSSVKEEGLQKEYANTIALPPRTHSLCLVVCLDEKGKKTQELK
NISTNSELLKERIIAAFHEGKNLKTTYLEKKNADNNSKLCKALKYSFADYGDLIKGTSIWDNEYT
KDLELNLQQIFGKLFRKYIKKNNTAEQHTLYSSLDELRESWWNTNKKYIWLAMKHGAGMNGTT
CCGDGSVTGSSDSGSTTCSGDNGSISCDDMPTTDFIPQYLRFLQEWVEHFCKQRQEKVKDVIENC
NSCKNNLGKTEINEKCKTECKNKCEAYKNFIEKFCTADGGTSGSPWSKRWDQIYKRYSKYIEDA
KRNRKAGTKNCGTSSTTSTAENKCVQS >gi|254952648|gb|ACT97154.1|VAR2CSA [Plasmodium falciparum] |335 aa (SEQ ID NO: 40)
KCEKCKSGTSTVNKYWIWRKSSGNKEGLQKEYANTIALPPRTHSLCLVVCLDEKEGKTQELKNI
STNSELLKERIIAAFHEGENLKTSHEKKKGDDGKKNADNNSKLCKALKYSFADYGDLIKGTSIW
DNEYTKDLELNLQKIFGKLFRKYIKKNIASDENTSYSSLDELRESWWNTNKKYIWLAMKHGAG
MNGTTCSCSGDSSDDMPTTDFIPQYLRFLQEWVEHFCKQRQENVNAVIENCNSCKECGGTCNSD
CEKKCKTECKNKCEAYKNFIEKFCTADGGTSGYSWSKRWDQIYKRYSKYIEDAKRNRKAGTKS
CGTSSTTSTAESKCVQS >ghana2 745 amino acids |667 aa (SEQ ID NO:41)
SYVKNNPYSKEYVTKLSFILNPSDANNPSETPSKYYDEVCNCNESGIACVGQAQTSGPSSNKT
CITHSFIGANKKKVCKDVKLGVREKDKDLKICVIEDTYLSGVDNCCFKDFLGMLQENCSDN
KSGSSSNGSCNNKNQDECEKNLDEALASLTNGYKCEKCKSGTSTVNKYWIWRKSSGNKEG
LQKEYANTIALPPRTHSLCLVVCLDEKEGKTQHKTISTNSELLKEWIIAAFHEGKNLKTSHE
KKKGDDGKKNADNNSKLCKALKYSFADYGDLIKGTSIWDNDFTKDLELNLQKIFGKLFRK
YIKKNIASDENTSYSSLDELRESWWNTNKKYIWLAMKHGAGMNSTTCCGDGSVTGSSDSG
STTCCGDGSVTGSGSSCDDMPTTDFIPQYLRFLQEWVEHFCKQRQENVNAVIENCNSCKEC
GGTCNSDCEKKCKTECKGECDAYKEFIEKCNGGAAEGTSGSSWSKRWDQIYKRYSKYIED
AKRNRKAGTKNCGTSSTTSTAESKCVQSDIDSFFKHLIDIGLTTPSSYLSIVLDENICGADNAP
WTTYTTYTTYTTTYTTTEKCNKETDKSKLQQCNTSVVVNVPSPLGNTPHGYKYVCECRTPNK
QETCDDRKEYMNQWISDNTKNPKGSRSTNNDYELYTYNGVQIKPTTVRSNSTKLD >gi|254952634|gb|ACT97147.1|VAR2CSA [Plasmodium falciparum] |348 aa (SEQ ID NO: 42)
KCDKCKSEQSKKNNKNWIWKKSSGNEKGLQKEYANTIGLPPRTQSLCLVVCLDEKEGKTQELK
NIRTNSELLKEWIIAAFHEGKNLKTSHEKKKGDNNSKLCKDLKYSFADYGDLIKGTSIWDNEYTK
DLELNLQNNFGKLFRKYIKKNIASDENTSYSSLDELRESWWNTNKKYIWLAMKHGAGMNSTTC
SSGSGSTTCSSGSGSTTCSSGSGSDSCDDMPTIDLIPQYLRFLQEWVEHFCKQRQEKVNAVIKNCNS
CKESGGTCNGECKTECKNKCEAYKTFIEEFCTADGGTSGSPWSKRWDQIYKMYSKHIEDAKRNR
KAGTKNCGPSSTTNVSVSTDENKCVQS >ghana1 745 amino acids |652 aa (SEQ ID NO:43)
DYIKDDPYFAEYVTKLSFILNSSDANNPSGETANHNDEVCNPNESGIASVEQAQTSDPSSNKT
CNTHSSIKANKKKVCKHVKLGVRENDKDLKICVIEHTSLSGVENCCCQDFLRILQENCSDN
KSGSSSNGSCNNKNQEACEKNLEKVLASLTNCYKCDKCKSEQSKKNNKNWIWKKSSGNEK
GLQKEYANTIGLPPRTQSLCLVVCLDEKEGKTQELKNIRTNSELLKEWIIAAFHEGKNLKK
RYPQNKNDDNNSKLCKDLKYSFADYGDLIKGTSIWDNEYTKDLELNLQNNFGKLFRKYIK
KNISTEQDTLYSSLDELRESWWNTNKKYIWLAMKHGAGMNSTTCSSGSGSTTCSSGSGSTT
CSSGSGDSCDDMPTTDFIPQYLRFLQEWVEHFCKQRQEKVNAVIKNCNSCKESGGTCNGE
CKTECKNKCEAYKTFIEEFCTADGGTSGSPWSKRWDQIYKMYSKHIEDAKRNRKAGTKNC
GPSSTTNVSVSTDENKCVQSDIDSFFKHLIDIGLTTPSSYLSIVLDDNICGEDKAPWTTYTTYT
TTKKCNKETDKSKSQSCNTAVVVNVPSPLGNTPHGYKYACECKIPTTEETCDDRKEYMNQWI
IDTSKKQKGSGSGKDDYELYTYNGVDVKPTTVRSNSTKLD

| SEQUENCES |
| --- |

>V1S1 745 amino acids |628 aa (SEQ ID NO: 44)
DYIKDDPYSAQYTTKLSFILNPSDANTSSEKIQKNNDEACNCNESGISSVGQAQTSGPSSNKT
CITHSSIKANKKKVCKDVKLGINNNDKVLRVCVIEDTSLSGVDNCCCQDLLGILQENCSDNK
RGSSSNGSCNNNNEEACEKNLDEAPASLHNGYKNQKCKSGTSRSKKKWIWKKSSGNEKGL
QEEYANTIGLPPRTQSLCLVCLHEKEGKTQHKTISTNSELLKEWIIAAFHEGKNLKTSHEK
KNDDNGKKLCKALEYSFADYGDLIKGTSIWDNEYTKDLELNLQKAFGKLFRKYIKKNNTA
EQDTSYSSLDELRESWWNTNKKYIWIAMKHGAGMNGTTCSCSGDSSNDMPTIDLIPQYLRF
LQEWVEHFCEQRQAKVKDVITNCKSCKESGNKCCKTECKTKCCKDECEKYKTFIEDCNGGG
TGTAGSSWVKRWDQIYKRYSKHIEDAKRNRKAGTKNCGPSSITNAAASTDENKCVQSDIDS
FFKHLIDIGLTTPSSYLSNVLDENSCGDDKAPWTTYTTYTTTKNCDIQKDKSKSQPINTSVVV
NVPSPLGNTPYRYKYACECKIPTTEESCDDRKEYMNQWSCGSARTMKRGYKNDNYELCKYNG
VDVKPTTVRSNSSKLD >raj116_var25 745 amino acids |653 aa (SEQ ID NO: 45)
DYIKGDPYFAEYATKLSFILNPSDTENASETPSKYYDEACNPNESEIASVEQAQTSGPSSNKT
CITHSSIKTNKKKECKDVKLGVRENDKDLKICVIEDTSLSGVDNCCFKDLLGILQENCSDNK
RGSSSNDSCNNNNEEACEKNLDEALASLTNGYKCDKCKSGTSTVNKKWTWRKSSGNEEGL
QKEYANTIGLPPRTQSLCLVCLHEKEGKTKHKTISTNSELLKEWIIAAFHEGKNLKTSHEK
KNDDNGKKLCKALEYSFADYGDLIKGTSIWDNEYTKDLELNLQKAFGKLFRKYIKKNNTA
EQDTSYSSLDELRESWWNTNKKYIWTAMKHGAEMNGTTCSSGSGDNGDSSITGSSDSGSTT
CSGDNGSISCDDIPTTDFIPQYLRFLQEWVEHFCEQRQAKVKDVINSCNSCNESGGTCNGEC
KTKCKDECEKYKKFIEDCNGGDGTAGSSWVKRWDQIYKRYSKHIEDAKRNRKAGTKNCG
PSSITNAAASTDENKCVQSDVDSFFKHLIDIGLTTPSSYLSIVLDENSCGDDKAPWTTYTTYT
TTEKCNKERDKSKSQSSDTLVVVNVPSPLGNTPHEYKYACECKIPTNEETCDDRKDYMNQWI
SDTSKKQKGSGSGKDYYELYTYNGVQIKQAAGRSSSTKLD >gi|31323048|gb|AAP37940.1|var2csa [Plasmodium falciparum] |490 aa (SEQ ID NO: 46)
KCDKCKSEQSKKNNNKWIWKKYSGNGEGLQKEYANTIGLPPRTQSLCLVCLHEKEGKTQHKTIS
TNSELLKEWIIAAFHEGKNLKRYPQNKNDDNNSKLCKALEYSFADYGDLIKGTSIWDNEYTKD
LELNLQKAFGKLFRKYIKKNNTAEQDTSYSSLDELRESWWNTNKKYIWTAMKHGAEMNGTTCS
SGSGDNGDSSCDDIPTIDLIPQYLRFLQEWVEHFCKQRQAKVKDVINSCNSCKNTSGERKIGGTC
NSDCEKKCKVACDAYKTFIEECRTAVGGTAGSSWVKRWDQIYKRYSKHIEDAKRNRKAGTKNC
GPSSTTNAAENKCVQSDIDSFFKHLIDIGLTTPSSYLSNVLDENSCGADKAPWTTYTTYTTYTTYT
TYTTTEKCNKERDKSKSQQSNTSVVVNVPSPLGNTPHEYKYACECKIPTTEETCDDRKEYMNQW
IIDNTKNPKGSGSTDNDYELYTYNGVQIKQAAGRSSSTKLD >gi|254952620|gb|ACT97140.1|VAR2CSA [Plasmodium falciparum] |335aa (SEQ ID NO: 47)
KCEKCKSGTSTVNNKWIWRKSSGKEGGLQKEYANTIGLPPRTQSLYLGNLPKLENVCKGVTDII
YDTKEKFLSGCLIAAFHEGKNLKTTYLEKKNDDNGKKLCKALEYSFADYGDLIKGTSIWDNEYT
KDLELNLQKIFGKLFRKYIKKNNTAEQDTSYSSLDELRESWWNTNKKYIWIAMKHGAGMNGTT
CSSGSGDSSNDIPTTDFIPQYLRFLQEWVENFCEQRQAKVKPVIENCNSCKESGGTCNGECKTKC
KVACDAYKKFIDGTGSGGGSRPTGIAGSSWSKRWDQIYKRYSKHIEDAKRNRKAGTKNCGPSSI
TNVSVSTDENKCVQS >T2C6 745 amino acids |637 an (SEQ ID NO: 48)
NYIKDDPYSKEYVTKLSFIPNSSDANTSSEKIQKNNDEVCNPNESGISSVEQAQTSDPSSNKTC
ITHSSIKANKKKECKDVKLGVRENDKDLKICVIEHTSLSGVDNCCFKDFLRMLQEPRIDKN
QRGSSSNGSCDKNSEEACEKNLDEALASLTNGYKCDKCKSEQSKKNNNKWIWKKFPGKEG
GLQEEYANTIGLPPRTQYLCLVVCLDEKEGKTQELKNIRTNSELLKEWIIAAFHEGKNLKT
TYPQKKNDDNGKKLCKDLKYSFADYGDLIKGTSIWDNEYTKNVELNLQNNFGKLFRKYIK
KNNTAEQDTSYSSLDELRESWWNTNKKYIWLAMKHGAEMNSTTCCGDGSVTGSGSSCDDI
PTIDLIPQYLRFLQEWVEHFCKQRQAKVKDVITNCNSCKESGNKCKTECKNKCKDECEKY
KKFIEACGTAVGGTGTAGSPWSKRWDQIYKRYSKHIEDAKRNRKAGTKNCGPSSTTNAAE
NKCVQSDIDSFFKHLIDIGLTTPSSYLSIVLDDNICGADKAPWTTYTTYTTENCDIQKKTPKS
QSCDTLVVVNVPSPLGNTPHGYKYACQCRTPNKQESCDDRKEYMNQWIIDNTKNPKGSGSGK
DYYELCKYNGVKETKPLGTLKNSKLD >gi|254952632|gb|ACT97146.1|VAR2CSA [Plasmodium falciparum] |330 aa (SEQ ID NO: 49)
KCDKCKSEQSKKNNNKWIWRKFPGKEGGLQKEYANTIGLPPRTQSLCLVCLHEKEGKTQHKTIS
TNSELLKEWIIAAFHEGKNLKTTYLEKKNAENKKKLCKALKYSFADYGDLIKGTSIWDNEYTKD
LELNLQKIFGKLFRKYIKKNNTAEQDTSYSSLDELRESWWNTNKKYIWTAMKHGAGMNGTMC
NADGSVTGSGSSCDDMPTTDFIPQYLRFLQEWVEHFCKQRQAKVKDVIENCKSCKESGNKCKTE
CKNKCDAYKTFIEECGTAVGGTAGSSWVKRWDQIYKRYSKHIEDAKRNRKAGTKNCGTSSTTN
AAASTAENKCVQS >gi|90193487|gb|ABD92339.1|erythrocyte membrane protein 1 [Plasmodium falciparum]
| 269 aa (SEQ ID NO: 50)
NYIKDDPYSKEYVTKLSFILNSSDAENASETPSKYYDEACNCNESGISSVEQASISDRSSQKACNT
HSFIGANKKKVCKHVKLGVRENDKDLKICVIEDDSLRGVENCCFKDFLRMLQEPRIDKNQRGSS
SNDSCNNNNEEACEKNLDEALASLHNGYKNQKCKSEQSKKNNNKWIWKKSSGKEGGLQKEYA
NTIGLPPRTQSLCLVCLHEKEGKTQHKTISTNSELLKEWIIDAFHEGKNLKTTYLEKKKGDNGKK
LCKALKYSFADY >gi|254952646|gb|ACT97153.1|VAR2CSA [Plasmodium falciparum] |347 aa (SEQ ID NO: 51)
KCDKCKSEQSKKNNKNWIWKKSSGKEGGLQKEYANTIALPPRTQSLCLVVCLHEKEGKTQHKTI
STNSELLKEWIIDAFHEGKNLKTTYLEKQNADNGKKNADNNSKLCKDLKYSFADYGDLIKGTSI
WDNEYTKDLELNLQQIFGKLFRKYIKKNIASDENTLYSSLDELRESWWNTNKKYIWTAMKHGA

| SEQUENCES |
|---|
| EMNGTTCSSGSGDSSSGENQTNSCDDIPTIDLIPQYLRFLQEWVEHFCEQRQAKVKDVITNCKSC<br>KESGGTCNSDCKTKCKGECEKYKKFIEKCKGGGTEGTSGSSWVKRWYQIYMRYSKYIEDAKRN<br>RKAGTKSCGTSSGANSGVTTTESKCVQS<br><br>>gi\|90193485\|gb\|ABD92338.1\|erythrocyte membrane protein 1 [*Plasmodium falciparum*]<br>\| 269 aa (SEQ ID NO: 52)<br>DYIKDDPYSKEYTTKLSFILNSSDANTSSEKIQKNNDEVCNPNESEISSVEQAQTSRPSSNKTCITH<br>SSIKANKKKVCKDVKLGVRENDKVLRVCVIEHTSLSGVENCCCQDLLGILQENCSDNKRGSSSN<br>GSCDKNSEEACEKNLDEALASLTNCYKNQKCKSEQSKKNNNKWIWKKSSGNEKGLQKEYANTI<br>GLPPRTQSLCLVCLHEKEGKTQELKNISTNSELLKEWIIAAFHEGKNLKTTYPQNKNDDNGKKLF<br>KDLKYSFADY<br><br>>MTS\| 745 amino acids 1646 aa (SEQ ID NO: 53)<br>DYIKDDPYSKEYTTKLSFILNSSDANTSSEKIQKNNDEVCNPNESEISSVEQAQTSRPSSNKTC<br>ITHSSIKANKKKVCKDVKLGVRENDKVLRVCVIEHTSLSGVENCCCQDLLGILQENCSDNK<br>RGSSSNGSCDKNSEEACEKNLDEALASLTNCYKNQKCKSEQSKKNNNKWIWKKSSGKEGG<br>LQKEYANTIGLPPRTQSLYLGNLPKLENVCKGVTDINFDTKEKFLAGCLIAAFHEGKNLKT<br>TYLEKKNDDNGKKLCKALEYSFADYGDLIKGTSIWDNEYTKDLELNLQKAFGKLFRKYIK<br>KNNTAEQDTSYSSLDELRESWWNTNKKYIWTAMKHGAGMNGTTCSSGSGDSSNDIPTTDFI<br>PQYLRFLQEWVENFCEQRQAKVKDVIENCNSCKNTSGERKIGDTCNSDCEKKCKDECEKY<br>KKFIEDCKGGDTAGSSWVKRWDQIYKRYSKHIEDAKRNRKAGTKNCGITTGTISGESSGA<br>TSGVTTTENKCVQSDIDSFFKHLIDIGLTTPSSYLSNVLDDNICGEDNAPWTTYTTYTTEKCN<br>KETDKSKSQQSNTAVVVNVPSPLGNTPHGYKYACECKIPTTEETCDDRKEYMNQWSCGSAQT<br>VRDRSGKDDYELCKYNGVQIKQAAGTLKNSKLD<br><br>>Q8I639 (Q8I639_PLAF7) *Plasmodium falciparum* (isolate 3D7), 632 aa extracellular part<br>(SEQ ID NO: 54)<br>NYIKGDPYFAEYATKLSFILNSSDANNPSEKIQKNNDEVCNCNESGIASVEQEQISDPSSNKTC<br>ITHSSIKANKKKVCKHVKLGVRENDKDLRVCVIEHTSLSGVENCCCQDFLRILQENCSDNK<br>SGSSSNGSCNNKNQEACEKNLEKVLASLTNCYKCDKCKSEQSKKNNKNWIWKKSSGKEGG<br>LQKEYANTIGLPPRTQSLCVVCLDEKGKKTQELKNIRTNSELLKEWIIAAFHEGKNLKPS<br>HEKKNDDNGKKLCKALEYSFADYGDLIKGTSIWDNEYTKDLELNLQKIFGKLFRKYIKKN<br>NTAEQDTSYSSLDELRESWWNTNKKYIWLAMKHGAGMNSTTCCGDGSVTGSGSSCDDIPT<br>IDLIPQYLRFLQEWVEHFCKQRQEKVKPVIENCKSCKESGGTCNGECKTECKNKCEVYKK<br>FIEDCKGGDTAGSSWVKRWDQIYKRYSKYIEDAKRNRKAGTKNCGPSSTTNAAENKCVQ<br>SDIDSFFKHLIDIGLTTPSSYLSIVLDDNICGADKAPWTTYTTYTTTEKCNKETDKSKLQQCN<br>TAVVVNVPSPLGNTPHGYKYACQCKIPTNEETCDDRKEYMNQWSCGSARTMKRGYKNDNYE<br>LCKYNGVDVKPTTVRSNSSKLD<br><br>>Q8I639 (Q8I639_PLAF7) *Plasmodium falciparum* (isolate 3D7), complete 2730 aa<br>extracellular part (SEQ ID NO: 55)<br>MDKSSIANKIEAYLGAKSDDSKIDQSLKADPSEVQYYGSGGDGYYLRKNICKITVNHSDSGTNDP<br>CDRIPPPYGDNDQWKCAIILSKVSEKPENVFVPPRRQRMCINNLEKLNVDKIRDKHAFLADVLLT<br>ARNEGERIVQNHPDTNSSNVCNALERSFADIADIIRGTDLWKGTSNSNLEQNLKQMFAKIRENDK<br>VLQDKYPKDQNYRKLREDWWNANRQKVWEVITCGARSNDLLIKRGWRTSGKSNGDNKLELCR<br>KCGHYEEKVPTKLDYVPQFLRWLTEWIEDFYREKQNLIDDMERHREECTSEDHKSKEGTSYCST<br>CKDKCKKYCECVKKWKSEWENQKNKYTELYQQNKNETSQKNTSRYDDYVKDFFKKLEANYS<br>SLENYIKGDPYFAEYATKLSFILNSSDANNPSEKIQKNNDEVCNCNESGIASVEQEQISDPSSNKTC<br>ITHSSIKANKKKVCKHVKLGVRENDKDLRVCVIEHTSLSGVENCCCQDFLRILQENCSDNKSGSS<br>SNGSCNNKNQEACEKNLEKVLASLTNCYKCDKCKSEQSKKNNKNWIWKKSSGKEGGLQKEYA<br>NTIGLPPRTQSLCVVCLDEKGKKTQELKNIRTNSELLKEWIIAAFHEGKNLKPSHEKKNDDNGK<br>KLCKALEYSFADYGDLIKGTSIWDNEYTKDLELNLQKIFGKLFRKYIKKNNTAEQDTSYSSLDEL<br>RESWWNTNKKYIWLAMKHGAGMNSTTCCGDGSVTGSGSSCDDIPTIDLIPQYLRFLQEWVEHF<br>CKQRQEKVKPVIENCKSCKESGGTCNGECKTECKNKCEVYKKFIEDCKGGDTAGSSWVKRWD<br>QIYKRYSKYIEDAKRNRKAGTKNCGPSSTTNAAENKCVQSDIDSFFKHLIDIGLTTPSSYLSIVLD<br>DNICGADKAPWTTYTTYTTTEKCNKETDKSKLQQCNTAVVVNVPSPLGNTPHGYKYACQCKIP<br>TNEETCDDRKEYMNQWSCGSARTMKRGYKNDNYELCKYNGVDVKPTTVRSNSSKLDDKDVTF<br>FNLFEQWNKEIQYQIEQYMTNTKISCNNEKNVLSRVSDEAAQPKFSDNERDRNSITHEDKNCKE<br>KCKCYSLWIEKINDQWDKQKDNYNKFQRKQIYDANKGSQNKKVVSLSNFLFFSCWEEYIQKYF<br>NGDWSKIKNIGSDTFEFLIKKCGNDSGDGETIFSEKLNNAEKKCKENESTNNKMKSSETSCDCSE<br>PIYIRGCQPKIYDGKIFPGKGGEKQWICKDTIIHGDTNGACIPPRTQNLCVGELWDKRYGGRSNIK<br>NDTKESLKQKIKNAIQKETELLYEYHDKGTAIISRNPMKGQKEKEEKNNDSNGLPKGFCHAVQR<br>SFIDYKNMILGTSVNIYEYIGKLQEDIKKIIEKGTTKQNGKTVGSGAENVNAWWKGIEGEMWDA<br>VRCAITKINKKQKKNGTFSIDECGIFPPTGNDEDQSVSWFKEWSEQFCIERLQYEKNIRDACTNNG<br>QGDKIQGDCRKCEEYKKYISEKKQEWDKQKTKYENKYVGKSASDLLKENYPECISANFDFIFN<br>DNIEYKTYYPYGDYSSICSCEQVKYYEYNNAEKKNNKSLCHEKGNDRTWSKKYIKKLENGRTL<br>EGVYVPPRRQQLCLYELFPIIIKNKNDITNAKKELLETLQIVAEREAYYLWKQYHAHNDTTYLAH<br>KKACCAIRGSFYDLEDIIKGNDLVHDEYTKYIDSKLNEIFDSSNKNDIETKRARTDWWENEAIAV<br>PNITGANKSDPKTIRQLVWDAMQSGVRKAIDEEKEKKKPNENFPPCMGVQHIGIAKPQFIRWLEE<br>WTNEFCEKYTKYFEDMKSNCNLRKGADDCDDNSNIECKKACANYTNWLNPKRIEWNGMSNYY<br>NKIYRKSNKESEDGKDYSMIMEPTVIDYLNKRCNGEINGNYICCSCKNIGENSTSGTVNKLQKK<br>ETQCEDNKGPLDLMNKVLNKMDPKYSEHKMKCTEVYLEHVEEQLKEIDNAIKDYKLYPLDRCF<br>DDKSKMKVCDLIGDAIGCKHKTKLDELDEWNDVDMRDPYNKYKGVLIPPRRRQLCFSRIVRGP<br>ANLRNLKEFKEEILKGAQSEGKFLGNYYNEDKDKEKALEAMKNSFYDYEYIIKGSDMLTNIQFK<br>DIKRKLDRLLEKETNNTEKVDDWWETNKKSIWNAMLCGYKKSGNKIIDPSWCTIPTTETPPQFL<br>RWIKEWGTNVCIQKEEHKEYVKSKCSNVTNLGAQESESKNCTSEIKKYQEWSRKRSIQWEAISE<br>GYKKYKGMDEFKNTFKNIKEPDANEPNANEYLKKHCSKCPCGFNDMQEITKYTNIGNEAFKQIK |

| SEQUENCES |
|---|
| EQVDIPAELEDVIYRLKHHEYDKGNDYICNKYKNINVNMKKNNDDTWTDLVKNSSDINKGVLL<br>PPRRKNLFLKIDESDICKYKRDPKLFKDFIYSSAISEVERLKKVYGEAKTKVVHAMKYSFADIGSII<br>KGDDMMENNSSDKIGKILGDGVGQNEKRKKWWDMNKYHIWESMLCGYKHAYGNISENDRKM<br>LDIPNNDDEHQFLRWFQEWTENFCTKRNELYENMVTACNSAKCNTSNGSVDKKECTEACKNYS<br>NFILIKKKEYQSLNSQYDMNYKETKAEKKESPEYFKDKCNGECSCLSEYFKDETRWKNPYETLD<br>DTEVKNNCMCKPPPPASNNTSDILQKTIPFGIALALGSIAFLFMKKKPKTPVDLLRVLDIPKGDYG<br>IPTPKSSNRYIPYASDRYKGKTYIYMEGDTSGDDDKYIWDL<br><br>>FCR3 (SEQ ID NO: 56) complete 2734 aa extracellular part (577 aa highlighted con.<br>ID1-DBL2b)<br>MDSTSTIANKIEEYLGAKSDDSKIDELLKADPSEVEYYRSGGDGDYLKNNICKITVNHSDSGKYD<br>PCEKKLPPYDDNDQWKCQQNSSDGSGKPENICVPPRRERLCTYNLENLKFDKIRDNNAFLADVL<br>LTARNEGEKIVQNHPDTNSSNVCNALERSFADLADIIRGTDQWKGTNSNLEKNLKQMFAKIREN<br>DKVLQDKYPKDQKYTKLREAWWNANRQKVWEVITCGARSNDLLIKRGWRTSGKSDRKKNFEL<br>CRKCGHYEKEVPTKLDYVPQFLRWLTEWIEDFYREKQNLIDDMERHREECTREDHKSKEGTSYC<br>STCKDKCKKYCECVKKWKTEWENQENKYKDLYEQNKNKTSQKNTSRYDDYVKDFFEKLEAN<br>YSSLENYIKGDPYFAEYATKLSFILNPSDANNPSGETANHNDEACNCNESGISSVGQAQTSGP<br>SSNKTCITHSSIKTNKKKECKDVKLGVRENDKDLKICVIEDTSLSGVDNCCCQDLLGILQEN<br>CSDNKRGSSSNDSCDNKNQDECQKKLEKVFASLTNGYKCDKCKSGTSRSKKKWIWKKSSG<br>NEEGLQEEYANTIGLPPRTQSLYLGNLPKLENVCEDVKDINFDTKEKFLAGCLIVSFHEGKN<br>LKKRYPQNKNSGNKENLCKALEYSFADYGDLIKGTSIWDNEYTKDLELNLQNNFGKLFGK<br>YIKKNNTAEQDTSYSSLDELRESWWNTNKKYIWTAMKHGAEMNITTCNADGSVTGSGSSC<br>DDIPTIDLIPQYLRFLQEWVENFCEQRQAKVKDVITNCKSCKESGNKCKTECKTKCKDECE<br>KYKKFIEACGTAGGGIGTAGSPWSKRWDQIYKRYSKHIEDAKRNRKAGTKNCGTSSTTNA<br>AASTDENKCVQSDIDSFFKHLIDIGLTTPSSYLSNVLDDNICGADKAPWTTYTTYTTTEKCN<br>KERDKSKSQSSDTLVVVNVPSPLGNTPYRYKYACQCKIPTNEETCDDRKEYMNQWSCGSART<br>MKRGYKNDNYELCKYNGVDVKPTTVRSNSSKLDGNDVTFFNLFEQWNKEIQYQIEQYMTNANI<br>SCIDEKEVLDSVSDEGTPKVRGGYEDGRNNNTDQGTNCKEKCKCYKLWIEKINDQWGKQKDN<br>YNKFRSKQIYDANKGSQNKKVVSLSNFLFFSCWEEYIQKYFNGDWSKIKNIGSDTFEFLIKKCGN<br>NSAHGEEIFNEKLKNAEKKCKENESTDTNINKSETSCDLNATNYIRGCQSKTYDGKIFPGKGGEK<br>QWICKDTIIHGDTNGACIPPRTQNLCVGELWDKSYGGRSNIKNDTKELLKEKIKNAIHKETELLY<br>EYHDTGTAIISKNDKKGQKGKNDPNGLPKGFCHAVQRSFIDYKNMILGTSVNIYEHIGKLQEDIK<br>KIIEKGTPQQKDKIGGVGSSTENVNAWWKGIEREMWDAVRCAITKINKKNNNSIFNGDECGVSP<br>PTGNDEDQSVSWFKEWGEQPCIERLRYEQNIREACTINGKNEKKCINSKSGQGDKIQGACKRKC<br>EKYKKYISEKKQEWDKQKTKYENKYVGKSASDLLKENYPECISANFDFIFNDNIEYKTYYPYGD<br>YSSICSCEQVKYYKYNNAEKKNNKSLCYEKDNDMTWSKKYIKKLENGRSLEGVYVPPRRQQLC<br>LYELFPIIIKNEEGMEKAKEELLETLQIVAEREAYYLWKQYNPTGKGIDDANKKACCAIRGSFYD<br>LEDIIKGNDLVHDEYTKYIDSKLNEIFGSSDTNDIDTKRARTDWWENETITNGTDRKTIRQLVWD<br>AMQSGVRYAVEEKNENFPPLCMGVEHIGIAKPQFIRWLEEWTNEFCEKYTKYFEDMKSKCDPPK<br>RADTCGDNSNIECKKACANYTNWLNPKRIEWNGMSNYYNKIYRKSNKESEGGKDYSMIMAPTV<br>IDYLNKRCHGEINGNYICCSCKNIGAYNTTSGTVNKKLQKKETECEEEKGPLDLMNEVLNKMDK<br>KYSAHKMKCTEVYLEHVEEQLNEIDNAIKDYKLYPLDRCFDDQTKMKVCDLIADAIGCKDKTK<br>LDELDEWNDMDLRGTYNKHKGVLIPPRRRQLCFSRIVRGPANLRSLNEFKEEILKGAQSEGKFLG<br>NYYKEHKDKEKALEAMKNSFYDYEDIIKGTDMLTNIEFKDIKIKLDRLLEKETNNTKKAEDWW<br>KTNKKSIWNAMLCGYKKSGNKIIDPSWCTIPTTETPPQFLRWIKEWGTNVCIQKQEHKEYVKSK<br>CSNVTNLGAQASESNNCTSEIKKYQEWSRKRSIRWETISKRYKKYKRMDILKDVKEPDANTYLR<br>EHCSKCPCGFNDMEEMNNNEDNEKEAFKQIKEQVKIPAELEDVIYRIKHHEYDKGNDYICNKYK<br>NIHDRMKKNNGNFVTDNFVKKSWEISNGVLIPPRRKNLFLYIDPSKICEYKKDPKLFKDFIYWSA<br>FTEVERLKKAYGGARAKVVHAMKYSFTDIGSIIKGDDMMEKNSSDKIGKILGDTDGQNEKRKK<br>WWDMNKYHIWESMLCGYREAEGDTETNENCRFPDIESVPQFLRWFQEWSENFCDRRQKLYDK<br>LNSECISAECTNGSVDNSKCTHACVNYKNYILTKKTEYEIQTNKYDNEFKNKNSNDKDAPDYLK<br>EKCNDNKCECLNKHIDDKNKTWKNPYETLEDTFKSKCDCPKPLPSPIKPDDLPPQADEPFDPTIL<br>QTTIPFGIALALGSIAFLFMKVIYIYIYVCCICMYVCMYVCMYVCMYVCMHVCMLCVYVI<br>YVFKICIYIEKEKRKK<br><br>>ID1 and DBL2Xb domains of FCR3 (SEQ ID NO: 57)<br>NYIKGDPYFAEYATKLSFILNPSDANNPSGETANHNDEACNCNESGISSVGQAQTSGPSSNKTCIT<br>HSSIKTNKKKECKDVKLGVRENDKDLKICVIEDTSLSGVDNCCCQDLLGILQENCSDNKRGSSSN<br>DSCDNKNQDECQKKLEKVFASLTNGYKCDKCKSGTSRSKKKWIWKKSSGNEEGLQEEYANTIG<br>LPPRTQSLYLGNLPKLENVCEDVKDINFDTKEKFLAGCLIVSFHEGKNLKKRYPQNKNSGNKENL<br>CKALEYSFADYGDLIKGTSIWDNEYTKDLELNLQNNFGKLFGKYIKKNNTAEQDTSYSSLDELR<br>ESWWNTNKKYIWTAMKHGAEMNITTCNADGSVTGSGSSCDDIPTIDLIPQYLRFLQEWVENFCE<br>QRQAKVKDVITNCKSCKESGNKCKTECKTKCKDECEKYKKFIEACGTAGGGIGTAGSPWSKRW<br>DQIYKRYSKHIEDAKRNRKAGTKNCGTSSTTNAAASTDENKCVQSDIDSFFKHLIDIGLTTPSSYL<br>SNVLDDNICGADKAPWTTYTTYTTTEKCNKERDKSKSQSSDTLVVVNVPSPLGNTPYRYKY<br><br>>DBL1X-ID2a region of VAR2CSA including V5 tag (bold) and histidine tag (underlined)<br>(SEQ ID NO: 58)<br>GHSDSGKYDPCEKKLPPYDDNDQWKCQQNSSDGSGKPENICVPPRRERLCTYNLENLKFDKIRD<br>NNAFLADVLLTARNEGEKIVQNHPDTNSSNVCNALERSFADLADIIRGTDQWKGTNSNLEKNLK<br>QMFAKIRENDKVLQDKYPKDQKYTKLREAWWNANRQKVWEVITCGARSNDLLIKRGWRTSGK<br>SDRKKNFELCRKCGHYEKEVPTKLDYVPQFLRWLTEWIEDFYREKQNLIDDMERHREECTREDH<br>KSKEGTSYCSTCKDKCKKYCECVKKWKTEWENQENKYKDLYEQNKNKTSQKNTSRYDDYVK<br>DPFEKLEANYSSLENYIKGDPYFAEYATKLSFILNPSDANNPSGETANHNDEACNCNESGISSVGQ<br>AQTSGPSSNKTCITHSSIKTNKKKECKDVKLGVRENDKDLKICVIEDTSLSGVDNCCCQDLLGILQ<br>ENCSDNKRGSSSNDSCDNKNQDECQKKLEKVFASLTNGYKCDKCKSGTSRSKKKWIWKKSSGN<br>EEGLQEEYANTIGLPPRTQSLYLGNLPKLENVCEDVKDINFDTKEKFLAGCLIVSFHEGKNLKKR |

SEQUENCES

```
YPQNKNSGNKENLCKALEYSFADYGDLIKGTSIWDNEYTKDLELNLQNNFGKLFGKYIKKNNTA
EQDTSYSSLDELRESWWNTNKKYIWTAMKHGAEMNITTCNADGSVTGSGSSCDDIPTIDLIPQYL
RFLQEWVENFCEQRQAKVKDVITNCKSCKESGNKCKTECKTKCKDECEKYKKFIEACGTAGGGI
GTAGSPWSKRWDQIYKRYSKHIEDAKRNRKAGTKNCGTSSTTNAAASTDENKCVQSDIDSFFKH
LIDIGLTTPSSYLSNVLDDNICGADKAPWTTYTTYTTTEKCNKERDKSKSQSSDTLVVVNVPSPL
GNTPYRYKYACQCKIPTNEETCDDRKEYMNQWSCGSARTMKRGYKNDNYELCKYNGVDVKPT
TVRSNSSKLDSGRGELEGKPIPNPLLGLDSTRTG<u>HHHHHH</u>
```

We claim:

1. A method of treating a platinum drug-resistant cancer in a subject comprising administering to the subject an effective amount of a VAR2CSA-drug conjugate (VDC), the VDC comprising:
   a) a VAR2CSA polypeptide that specifically binds to oncofetal chondroitin sulfate (ofCS), and
   b) one or more toxins having anti-cancer activity conjugated to the VAR2CSA polypeptide,
   wherein the VAR2CSA polypeptide is a functional fragment of an extracellular portion of a native VAR2CSA protein, and wherein the functional fragment is between about 550 amino acids and about 1100 amino acids in length and comprises a sequential amino acid sequence of ID1 and DBL2Xb domains of the native VAR2CSA protein.

2. The method according to claim 1, wherein the platinum drug is cisplatin, carboplatin or oxaliplatin.

3. The method according to claim 1, wherein the cancer is bladder cancer, colon cancer, small cell lung cancer (SCLC), non-small cell lung cancer (NSCLC), breast cancer, testicular cancer, melanoma, head and neck cancer, endometrial cancer, ovarian cancer, adrenocortical cancer or non-Hodgkin lymphoma.

4. The method according to claim 3, wherein the cancer is an advanced and/or metastatic cancer.

5. The method according to claim 1, wherein the platinum drug-resistant cancer has an increased expression of CD44 as compared to a corresponding cancer that is not resistant to platinum-drugs.

6. The method according to claim 1, wherein the platinum drug is cisplatin.

7. The method according to claim 1, wherein the cancer is bladder cancer.

8. The method according to claim 6, wherein the cancer is bladder cancer.

9. The method according to claim 7, wherein the cancer is muscle invasive bladder cancer.

10. The method according to claim 1, wherein the subject has undergone a prior treatment regimen comprising the platinum drug.

11. The method according to claim 10, wherein the subject relapsed or progressed following the prior treatment regimen.

12. The method according to claim 1, wherein the VDC is a compound of general formula (I):

$$V-[(L)_n-(T)_m]_p \quad (I)$$

wherein
V is the VAR2CSA polypeptide;
L is a linker;
T is the toxin;
n is 0 or 1;
m is an integer between 1 and 8, and
p is an integer between 1 and 12.

13. The method according to claim 12, wherein n is 1.

14. The method according to claim 13, wherein m is 1.

15. The method according to claim 12, wherein p is an integer from 1 to 10.

16. The method according to claim 14, wherein p is an integer from 1 to 4.

17. The method according to claim 1, wherein the extracellular portion of the native VAR2CSA protein has a sequence as set forth in SEQ ID NO:55 or 56.

18. The method according to claim 1, wherein the VAR2CSA polypeptide comprises a sequential amino acid sequence of the ID1 and DBL2Xb domains and all or a N-terminal portion of an ID2a domain.

19. The method according to claim 1, wherein the VAR2CSA polypeptide comprises an amino acid sequence having at least 90% sequence identity with the amino acid sequence as set forth in any one of SEQ ID NO:1, SEQ ID NO:3, SEQ ID NO:4, SEQ ID NO:5, SEQ ID NO:10, SEQ ID NO:11, SEQ ID NO:29, SEQ ID NO:34, SEQ ID NO:36, SEQ ID NO:37, SEQ ID NO:38, SEQ ID NO:41, SEQ ID NO:43, SEQ ID NO:44, SEQ ID NO:45, SEQ ID NO:48, SEQ ID NO:53, SEQ ID NO:54 or SEQ ID NO:57.

20. The method according to claim 1, wherein the VAR2CSA polypeptide comprises an amino acid sequence having at least 90% sequence identity with the amino acid sequence as set forth in SEQ ID NO:57.

21. The method according to claim 1, wherein the toxin is a microtubule polymerization inhibitor.

22. The method according to claim 1, wherein the toxin is a hemiasterlin, an auristatin, a tubulysin, or an analogue or derivative thereof.

23. The method according to claim 1, wherein the toxin is a compound of general formula (IV):

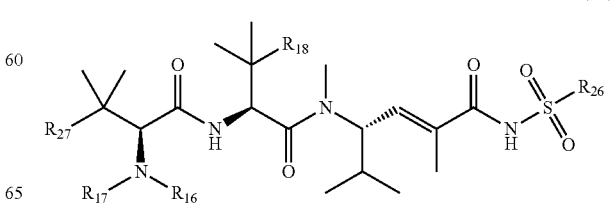

wherein:

R$_{26}$ is selected from optionally substituted alkyl, optionally substituted alkylamino, optionally substituted cycloalkyl, optionally substituted aryl, optionally substituted heterocyclyl and optionally substituted heteroaryl;

R$_{27}$ is selected from optionally substituted alkyl, optionally substituted alkylamino, optionally substituted cycloalkyl, optionally substituted aryl, optionally substituted heterocyclyl and optionally substituted heteroaryl;

R$_{16}$ and R$_{17}$ are each independently H or C$_{1-6}$ alkyl, and R$_{18}$ is C$_{1-6}$ alkyl or SH, and wherein the compound of general formula (IV) is conjugated to the VAR2CSA polypeptide via the R$_{26}$ substituent or the R$_{27}$ substituent.

24. The method according to claim 23, wherein R$_{26}$ is optionally substituted alkyl or optionally substituted aryl.

25. The method according to claim 23, wherein R$_{26}$ is optionally substituted phenyl or optionally substituted aralkyl.

26. The method according to claim 23, wherein R$_{27}$ is optionally substituted aryl.

27. The method according to claim 24, wherein R$_{27}$ is optionally substituted aryl.

28. The method according to claim 23, wherein R$_{16}$ and R$_{17}$ are each independently H or methyl.

29. The method according to claim 23, wherein R$_{18}$ is C$_1$-C$_6$ alkyl.

30. The method according to claim 23, wherein R$_{16}$ is H, and R$_{17}$ and R$_{18}$ are each methyl.

31. The method according to claim 24, wherein the compound of general formula (IV) is a compound selected from Compounds 1, 3, 4, 5, 6, 7, 8, 9 and 10:

Compound 1

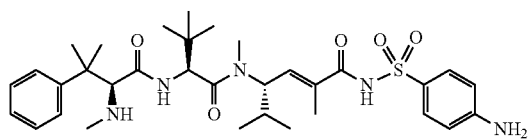

Compound 3

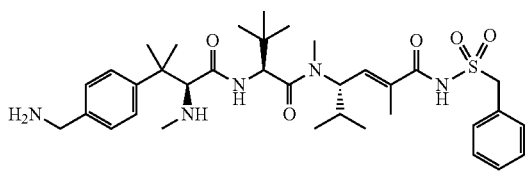

Compound 4

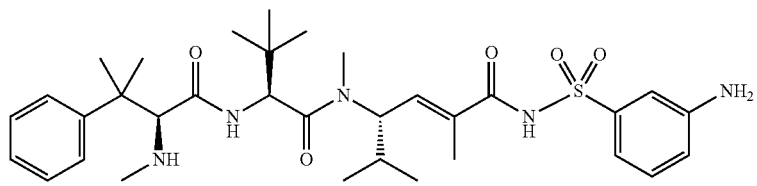

Compound 5

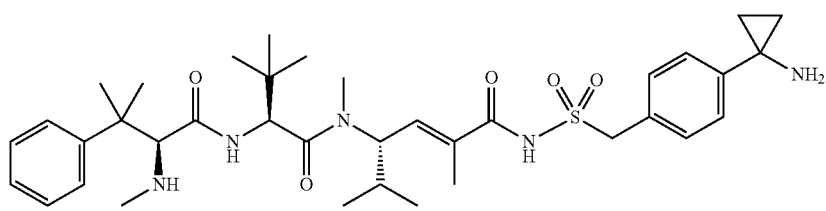

Compound 6

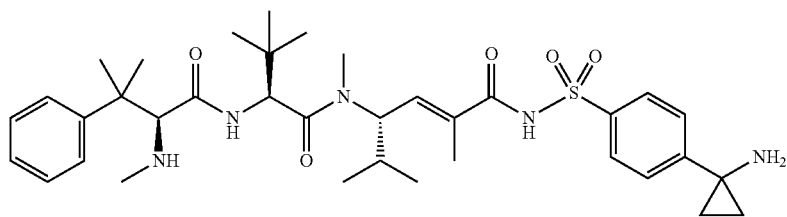

Compound 7

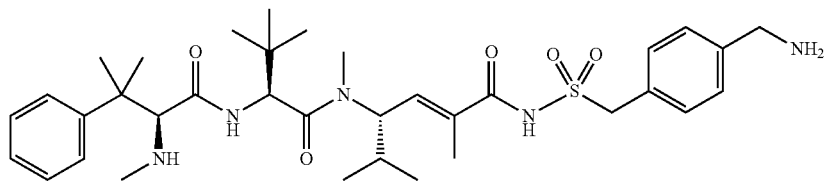

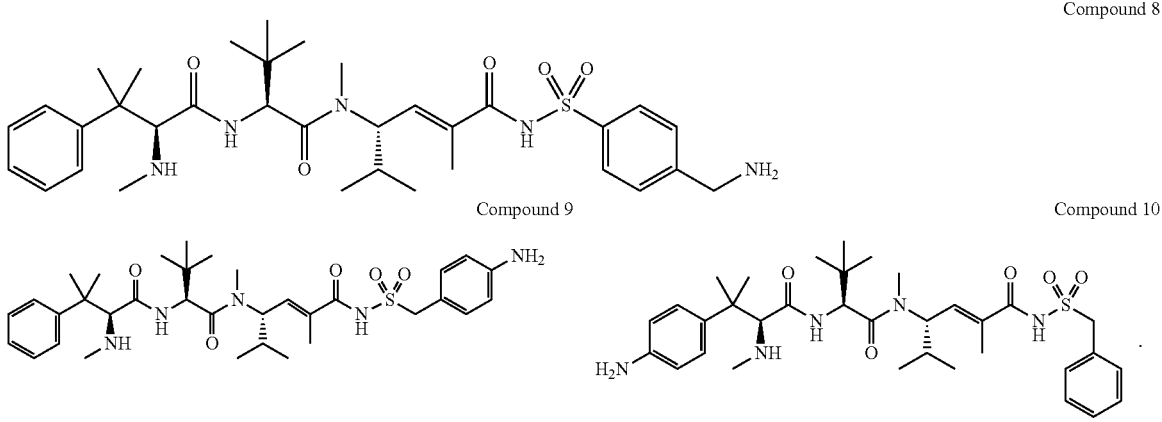

Compound 8

Compound 9

Compound 10

32. The method of claim 12, wherein the VDC has the structure:

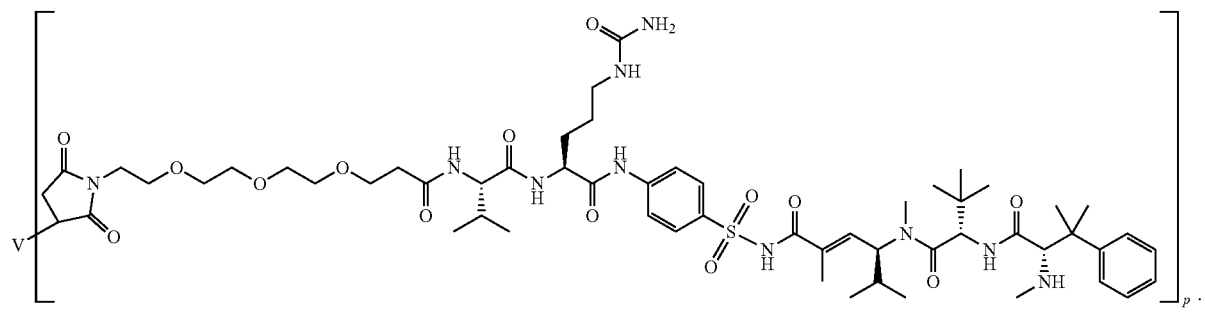

33. The method according to claim 12, wherein n is 1 and L is a cleavable linker.

34. The method according to claim 33, wherein L-T has the general formula (VI):

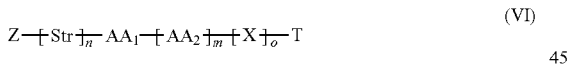

(VI)

wherein:
Z is a functional group capable of reacting with a target group on the VAR2CSA polypeptide;
Str is a stretcher;
$AA_1$ and $AA_2$ are each independently an amino acid, wherein $AA_1$-$[AA_2]_m$ forms a protease cleavage site;
X is a self-immolative group;
T is the toxin;
n is 0 or 1;
m is 1, 2 or 3, and
o is 0, 1 or 2.

35. The method according to claim 33, wherein the VDC has the general formula (VIII):

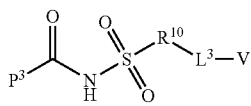

(VIII)

wherein:
$R^{10}$ is selected from optionally substituted alkyl, optionally substituted alkylamino, optionally substituted cycloalkyl, optionally substituted aryl, optionally substituted heterocyclyl, optionally substituted heteroaryl, —$COR^{11}$—, —$CSR^{11}$—, —$OR^{11}$— and —$NHR^{11}$—, wherein each $R^{11}$ is independently selected from optionally substituted alkyl, optionally substituted alkylamino, optionally substituted cycloalkyl, optionally substituted aryl, optionally substituted heterocyclyl and optionally substituted heteroaryl;
$P^3$ is the toxin or a portion of the toxin;
$L^3$ is the remaining portion of the linker, and
V is the VAR2CSA polypeptide.

36. A method of treating cancer in a subject who has received a prior treatment regimen comprising a platinum drug, the method comprising administering to the subject an effective amount of a VAR2CSA-drug conjugate (VDC), the VDC comprising:
a) a VAR2CSA polypeptide that specifically binds to oncofetal chondroitin sulfate (ofCS), and
b) one or more toxins having anti-cancer activity conjugated to the VAR2CSA polypeptide,
wherein the VAR2CSA polypeptide is a functional fragment of an extracellular portion of a native VAR2CSA protein, and wherein the functional fragment is between about 550 amino acids and about 1100 amino acids in length and comprises a sequential amino acid sequence of ID1 and DBL2Xb domains of the native VAR2CSA protein.

37. The method according to claim 36, wherein the subject relapsed or progressed following the prior treatment regimen.

38. A method of inhibiting growth of a platinum drug-resistant tumor in a subject comprising administering to the subject an effective amount of a VAR2CSA-drug conjugate (VDC), the VDC comprising:
   a) a VAR2CSA polypeptide that specifically binds to oncofetal chondroitin sulfate (ofCS), and
   b) one or more toxins having anti-cancer activity conjugated to the VAR2CSA polypeptide,
   wherein the VAR2CSA polypeptide is a functional fragment of an extracellular portion of a native VAR2CSA protein, and wherein the functional fragment is between about 550 amino acids and about 1100 amino acids in length and comprises a sequential amino acid sequence of ID1 and DBL2Xb domains of the native VAR2CSA protein.

39. A method of inhibiting the proliferation of platinum drug-resistant cancer cells comprising contacting the cells with an effective amount of a VAR2CSA-drug conjugate (VDC), the VDC comprising:
   a) a VAR2CSA polypeptide that specifically binds to oncofetal chondroitin sulfate (ofCS), and
   b) one or more toxins having anti-cancer activity conjugated to the VAR2CSA polypeptide,
   wherein the VAR2CSA polypeptide is a functional fragment of an extracellular portion of a native VAR2CSA protein, and wherein the functional fragment is between about 550 amino acids and about 1100 amino acids in length and comprises a sequential amino acid sequence of ID1 and DBL2Xb domains of the native VAR2CSA protein.

40. The method according to claim 1, wherein the functional fragment is between about 570 amino acids and about 1000 amino acids in length.

41. The method according to claim 1, wherein the VAR2CSA polypeptide comprises the amino acid sequence as set forth in amino acids 1-969 of SEQ ID NO:58.

42. The method according to claim 36, wherein the VAR2CSA polypeptide comprises an amino acid sequence having at least 90% sequence identity with the amino acid sequence as set forth in any one of SEQ ID NO:1, SEQ ID NO:3, SEQ ID NO:4, SEQ ID NO:5, SEQ ID NO:10, SEQ ID NO:11, SEQ ID NO:29, SEQ ID NO:34, SEQ ID NO:36, SEQ ID NO:37, SEQ ID NO:38, SEQ ID NO:41, SEQ ID NO:43, SEQ ID NO:44, SEQ ID NO:45, SEQ ID NO:48, SEQ ID NO:53, SEQ ID NO:54 or SEQ ID NO:57.

43. The method according to claim 36, wherein the VAR2CSA polypeptide comprises an amino acid sequence having at least 90% sequence identity with the amino acid sequence as set forth in SEQ ID NO:57.

44. The method according to claim 36, wherein the VAR2CSA polypeptide comprises the amino acid sequence as set forth in amino acids 1-969 of SEQ ID NO:58.

45. The method according to claim 38, wherein the VAR2CSA polypeptide comprises an amino acid sequence having at least 90% sequence identity with the amino acid sequence as set forth in any one of SEQ ID NO:1, SEQ ID NO:3, SEQ ID NO:4, SEQ ID NO:5, SEQ ID NO:10, SEQ ID NO:11, SEQ ID NO:29, SEQ ID NO:34, SEQ ID NO:36, SEQ ID NO:37, SEQ ID NO:38, SEQ ID NO:41, SEQ ID NO:43, SEQ ID NO:44, SEQ ID NO:45, SEQ ID NO:48, SEQ ID NO:53, SEQ ID NO:54 or SEQ ID NO:57.

46. The method according to claim 38, wherein the VAR2CSA polypeptide comprises an amino acid sequence having at least 90% sequence identity with the amino acid sequence as set forth in SEQ ID NO:57.

47. The method according to claim 38, wherein the VAR2CSA polypeptide comprises the amino acid sequence as set forth in amino acids 1-969 of SEQ ID NO:58.

48. The method according to claim 39, wherein the VAR2CSA polypeptide comprises an amino acid sequence having at least 90% sequence identity with the amino acid sequence as set forth in any one of SEQ ID NO:1, SEQ ID NO:3, SEQ ID NO:4, SEQ ID NO:5, SEQ ID NO:10, SEQ ID NO:11, SEQ ID NO:29, SEQ ID NO:34, SEQ ID NO:36, SEQ ID NO:37, SEQ ID NO:38, SEQ ID NO:41, SEQ ID NO:43, SEQ ID NO:44, SEQ ID NO:45, SEQ ID NO:48, SEQ ID NO:53, SEQ ID NO:54 or SEQ ID NO:57.

49. The method according to claim 39, wherein the VAR2CSA polypeptide comprises an amino acid sequence having at least 90% sequence identity with the amino acid sequence as set forth in SEQ ID NO:57.

50. The method according to claim 39, wherein the VAR2CSA polypeptide comprises the amino acid sequence as set forth in amino acids 1-969 of SEQ ID NO:58.

\* \* \* \* \*

SEQUENCE LISTING

<160> NUMBER OF SEQ ID NOS: 58

<210> SEQ ID NO 1
<211> LENGTH: 640
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: ID1 of FCR3, DBL2Xb of FCR3 and ID2a

<400> SEQUENCE: 1

```
Asn Tyr Ile Lys Gly Asp Pro Tyr Phe Ala Glu Tyr Ala Thr Lys Leu
1               5                   10                  15

Ser Phe Ile Leu Asn Pro Ser Asp Ala Asn Asn Pro Ser Gly Glu Thr
            20                  25                  30

Ala Asn His Asn Asp Glu Ala Cys Asn Cys Asn Glu Ser Gly Ile Ser
        35                  40                  45

Ser Val Gly Gln Ala Gln Thr Ser Gly Pro Ser Ser Asn Lys Thr Cys
    50                  55                  60

Ile Thr His Ser Ser Ile Lys Thr Asn Lys Lys Glu Cys Lys Asp
65                  70                  75                  80

Val Lys Leu Gly Val Arg Glu Asn Asp Lys Asp Leu Lys Ile Cys Val
                85                  90                  95

Ile Glu Asp Thr Ser Leu Ser Gly Val Asp Asn Cys Cys Cys Gln Asp
            100                 105                 110

Leu Leu Gly Ile Leu Gln Glu Asn Cys Ser Asp Asn Lys Arg Gly Ser
        115                 120                 125

Ser Ser Asn Asp Ser Cys Asp Asn Lys Asn Gln Asp Glu Cys Gln Lys
    130                 135                 140

Lys Leu Glu Lys Val Phe Ala Ser Leu Thr Asn Gly Tyr Lys Cys Asp
145                 150                 155                 160

Lys Cys Lys Ser Gly Thr Ser Arg Ser Lys Lys Trp Ile Trp Lys
                165                 170                 175

Lys Ser Ser Gly Asn Glu Glu Gly Leu Gln Glu Glu Tyr Ala Asn Thr
            180                 185                 190

Ile Gly Leu Pro Pro Arg Thr Gln Ser Leu Tyr Leu Gly Asn Leu Pro
        195                 200                 205

Lys Leu Glu Asn Val Cys Glu Asp Val Lys Asp Ile Asn Phe Asp Thr
    210                 215                 220

Lys Glu Lys Phe Leu Ala Gly Cys Leu Ile Val Ser Phe His Glu Gly
225                 230                 235                 240

Lys Asn Leu Lys Lys Arg Tyr Pro Gln Asn Leu Asn Ser Gly Asn Lys
                245                 250                 255

Glu Asn Leu Cys Lys Ala Leu Glu Tyr Ser Phe Ala Asp Tyr Gly Asp
```

```
                260                 265                 270
Leu Ile Lys Gly Thr Ser Ile Trp Asp Asn Glu Tyr Thr Lys Asp Leu
            275                 280                 285

Glu Leu Asn Leu Gln Asn Asn Phe Gly Lys Leu Phe Gly Lys Tyr Ile
290                 295                 300

Lys Lys Asn Asn Thr Ala Glu Gln Asp Thr Ser Tyr Ser Ser Leu Asp
305                 310                 315                 320

Glu Leu Arg Glu Ser Trp Trp Asn Thr Asn Lys Lys Tyr Ile Trp Thr
            325                 330                 335

Ala Met Lys His Gly Ala Glu Met Asn Ile Thr Thr Cys Asn Ala Asp
            340                 345                 350

Gly Ser Val Thr Gly Ser Gly Ser Ser Cys Asp Asp Ile Pro Thr Ile
            355                 360                 365

Asp Leu Ile Pro Gln Tyr Leu Arg Phe Leu Gln Glu Trp Val Glu Asn
            370                 375                 380

Phe Cys Glu Gln Arg Gln Ala Lys Val Lys Asp Val Ile Thr Asn Cys
385                 390                 395                 400

Lys Ser Cys Lys Glu Ser Gly Asn Lys Cys Lys Thr Glu Cys Lys Thr
                405                 410                 415

Lys Cys Lys Asp Glu Cys Glu Lys Tyr Lys Lys Phe Ile Glu Ala Cys
            420                 425                 430

Gly Thr Ala Gly Gly Ile Gly Thr Ala Gly Ser Pro Trp Ser Lys
            435                 440                 445

Arg Trp Asp Gln Ile Tyr Lys Arg Tyr Ser Lys His Ile Glu Asp Ala
            450                 455                 460

Lys Arg Asn Arg Lys Ala Gly Thr Lys Asn Cys Gly Thr Ser Ser Thr
465                 470                 475                 480

Thr Asn Ala Ala Ala Ser Thr Asp Glu Asn Lys Cys Val Gln Ser Asp
                485                 490                 495

Ile Asp Ser Phe Phe Lys His Leu Ile Asp Ile Gly Leu Thr Thr Pro
                500                 505                 510

Ser Ser Tyr Leu Ser Asn Val Leu Asp Asp Asn Ile Cys Gly Ala Asp
            515                 520                 525

Lys Ala Pro Trp Thr Thr Tyr Thr Thr Tyr Thr Thr Thr Glu Lys Cys
            530                 535                 540

Asn Lys Glu Arg Asp Lys Ser Lys Ser Gln Ser Ser Asp Thr Leu Val
545                 550                 555                 560

Val Val Asn Val Pro Ser Pro Leu Gly Asn Thr Pro Tyr Arg Tyr Lys
                565                 570                 575

Tyr Ala Cys Gln Cys Lys Ile Pro Thr Asn Glu Glu Thr Cys Asp Asp
                580                 585                 590

Arg Lys Glu Tyr Met Asn Gln Trp Ser Cys Gly Ser Ala Arg Thr Met
            595                 600                 605

Lys Arg Gly Tyr Lys Asn Asp Asn Tyr Glu Leu Cys Lys Tyr Asn Gly
            610                 615                 620

Val Asp Val Lys Pro Thr Thr Val Arg Ser Asn Ser Ser Lys Leu Asp
625                 630                 635                 640
```

<210> SEQ ID NO 2
<211> LENGTH: 341
<212> TYPE: PRT
<213> ORGANISM: Plasmodium falciparum

<400> SEQUENCE: 2

```
Lys Cys Asp Lys Cys Lys Ser Gly Thr Ser Arg Ser Arg Lys Ile Trp
1               5                   10                  15

Thr Trp Arg Lys Ser Ser Gly Asn Lys Glu Gly Leu Gln Glu Glu Tyr
            20                  25                  30

Ala Asn Thr Ile Gly Leu Ser Pro Arg Thr Gln Leu Leu Tyr Leu Gly
        35                  40                  45

Asn Leu Arg Lys Leu Glu Asn Val Cys Glu Asp Val Thr Asp Ile Asn
50                  55                  60

Phe Asp Thr Lys Glu Lys Phe Leu Ala Gly Cys Leu Ile Ala Ala Phe
65                  70                  75                  80

His Glu Gly Lys Asn Leu Lys Lys Arg Tyr Leu Glu Lys Lys Lys Gly
                85                  90                  95

Asp Asn Asn Ser Lys Leu Cys Lys Asp Leu Lys Tyr Ser Phe Ala Asp
                100                 105                 110

Tyr Gly Asp Leu Ile Lys Gly Thr Ser Ile Trp Asp Asn Asp Phe Thr
            115                 120                 125

Lys Asp Leu Glu Leu Asn Leu Gln Gln Ile Phe Gly Lys Leu Phe Arg
130                 135                 140

Lys Tyr Ile Lys Lys Lys Asn Ile Ser Thr Glu Gln Asp Thr Ser Tyr
145                 150                 155                 160

Ser Ser Leu Asp Glu Leu Arg Glu Ser Trp Trp Asn Thr Asn Lys Lys
                165                 170                 175

Tyr Ile Trp Leu Ala Met Lys His Gly Ala Gly Met Asn Ser Thr Thr
            180                 185                 190

Cys Ser Cys Ser Gly Asp Ser Ser Gly Glu Asn Gln Thr Asn Ser
            195                 200                 205

Cys Asp Asp Ile Pro Thr Ile Asp Leu Ile Pro Gln Tyr Leu Arg Phe
210                 215                 220

Leu Gln Glu Trp Val Glu His Phe Cys Glu Gln Arg Gln Ala Lys Val
225                 230                 235                 240

Lys Asp Val Ile Thr Asn Cys Asn Ser Cys Lys Glu Ser Gly Gly Thr
            245                 250                 255

Cys Asn Ser Asp Cys Glu Lys Cys Lys Asn Lys Cys Asp Ala Tyr
            260                 265                 270

Lys Thr Phe Ile Glu Asp Cys Lys Gly Val Gly Gly Thr Gly Thr Ala
            275                 280                 285

Gly Ser Ser Trp Val Lys Arg Trp Tyr Gln Ile Tyr Met Arg Tyr Ser
            290                 295                 300

Lys Tyr Ile Glu Asp Ala Lys Arg Asn Arg Lys Ala Gly Thr Lys Ser
305                 310                 315                 320

Cys Gly Thr Ser Ser Thr Thr Asn Val Ser Val Ser Thr Asp Glu Asn
                325                 330                 335

Lys Cys Val Gln Ser
            340

<210> SEQ ID NO 3
<211> LENGTH: 656
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: M24 745 amino acids

<400> SEQUENCE: 3
```

-continued

```
Asp Tyr Ile Lys Gly Asp Pro Tyr Phe Ala Glu Tyr Ala Thr Lys Leu
1               5                   10                  15
Ser Phe Ile Leu Asn Ser Ser Asp Ala Asn Asn Pro Ser Gly Glu Thr
            20                  25                  30
Ala Asn His Asn Asp Glu Val Cys Asn Pro Asn Glu Ser Glu Ile Ser
        35                  40                  45
Ser Val Gly Gln Ala Gln Thr Ser Asp Pro Ser Ser Asn Lys Thr Cys
    50                  55                  60
Asn Thr His Ser Ser Ile Lys Ala Asn Lys Lys Val Cys Lys His
65                  70                  75                  80
Val Lys Leu Gly Ile Asn Asn Asn Asp Lys Val Leu Arg Val Cys Val
                85                  90                  95
Ile Glu Asp Thr Ser Leu Ser Gly Val Glu Asn Cys Cys Phe Lys Asp
            100                 105                 110
Leu Leu Gly Ile Leu Gln Glu Asn Cys Ser Asp Asn Lys Ser Gly Ser
        115                 120                 125
Ser Ser Asn Gly Ser Cys Asn Asn Lys Asn Gln Glu Ala Cys Glu Lys
    130                 135                 140
Asn Leu Glu Lys Val Leu Ala Ser Leu Thr Asn Cys Tyr Lys Cys Asp
145                 150                 155                 160
Lys Cys Lys Ser Gly Thr Ser Thr Val Asn Lys Asn Trp Ile Trp Lys
                165                 170                 175
Lys Ser Ser Gly Asn Lys Glu Gly Leu Gln Lys Glu Tyr Ala Asn Thr
            180                 185                 190
Ile Gly Leu Pro Pro Arg Thr His Ser Leu Tyr Leu Gly Asn Leu Pro
        195                 200                 205
Lys Leu Glu Asn Val Cys Glu Asp Val Lys Asp Ile Asn Phe Asp Thr
    210                 215                 220
Lys Glu Lys Phe Leu Ala Gly Cys Leu Ile Ala Ala Phe His Glu Gly
225                 230                 235                 240
Lys Asn Leu Lys Lys Arg Tyr Pro Gln Asn Lys Asn Asp Asp Asn Asn
                245                 250                 255
Ser Lys Leu Cys Lys Ala Leu Glu Tyr Ser Phe Ala Asp Tyr Gly Asp
            260                 265                 270
Leu Ile Lys Gly Thr Ser Ile Trp Asp Asn Glu Tyr Thr Lys Asp Leu
        275                 280                 285
Glu Leu Asn Leu Gln Gln Ile Phe Gly Lys Leu Phe Arg Lys Tyr Ile
    290                 295                 300
Lys Lys Asn Ile Ser Thr Glu Gln Asp Thr Leu Tyr Ser Ser Leu Asp
305                 310                 315                 320
Glu Leu Arg Glu Ser Trp Trp Asn Thr Asn Lys Lys Tyr Ile Trp Leu
                325                 330                 335
Ala Met Lys His Gly Ala Gly Met Asn Ile Thr Thr Cys Cys Gly Asp
            340                 345                 350
Gly Ser Val Thr Gly Ser Gly Ser Ser Cys Asp Asp Ile Pro Thr Ile
        355                 360                 365
Asp Leu Ile Pro Gln Tyr Leu Arg Phe Leu Gln Glu Trp Val Glu His
    370                 375                 380
Phe Cys Lys Gln Arg Gln Glu Lys Val Lys Asp Val Ile Asn Ser Cys
385                 390                 395                 400
Asn Ser Cys Lys Asn Thr Ser Ser Lys Thr Lys Leu Gly Asp Thr Cys
                405                 410                 415
Asn Ser Asp Cys Glu Lys Lys Cys Lys Ile Glu Cys Glu Lys Tyr Lys
```

```
                420             425             430
Lys Phe Ile Glu Glu Cys Arg Thr Ala Val Gly Gly Thr Ala Gly Ser
            435                 440                 445

Ser Trp Ser Lys Arg Trp Asp Gln Ile Tyr Lys Met Tyr Ser Lys His
    450                 455                 460

Ile Glu Asp Ala Lys Arg Asn Arg Lys Ala Gly Thr Lys Asn Cys Gly
465                 470                 475                 480

Ile Thr Thr Gly Thr Ile Ser Gly Glu Ser Gly Ala Asn Ser Gly
                485                 490                 495

Val Thr Thr Thr Glu Asn Lys Cys Val Gln Ser Asp Ile Asp Ser Phe
            500                 505                 510

Phe Lys His Leu Ile Asp Ile Gly Leu Thr Thr Pro Ser Ser Tyr Leu
        515                 520                 525

Ser Ile Val Leu Asp Asp Asn Ile Cys Gly Asp Lys Ala Pro Trp
    530                 535                 540

Thr Thr Tyr Thr Thr Tyr Thr Thr Tyr Thr Thr Thr Glu Lys Cys Asn
545                 550                 555                 560

Lys Glu Arg Asp Lys Ser Lys Ser Gln Gln Ser Asn Thr Ser Val Val
                565                 570                 575

Val Asn Val Pro Ser Pro Leu Gly Asn Thr Pro His Gly Tyr Lys Tyr
            580                 585                 590

Ala Cys Gln Cys Lys Ile Pro Thr Asn Glu Glu Thr Cys Asp Asp Arg
        595                 600                 605

Lys Glu Tyr Met Asn Gln Trp Ile Ser Asp Thr Ser Lys Asn Pro Lys
            610                 615                 620

Gly Ser Gly Ser Thr Asn Asn Asp Tyr Glu Leu Tyr Thr Tyr Asn Gly
625                 630                 635                 640

Val Lys Glu Thr Lys Leu Pro Lys Lys Leu Asn Ser Pro Lys Leu Asp
                645                 650                 655

<210> SEQ ID NO 4
<211> LENGTH: 643
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: KMWII 745 amino acids

<400> SEQUENCE: 4

Asp Tyr Ile Lys Asp Asp Pro Tyr Ser Lys Glu Tyr Thr Thr Lys Leu
1               5                   10                  15

Ser Phe Ile Leu Asn Ser Ser Asp Ala Asn Thr Ser Ser Gly Glu Thr
            20                  25                  30

Ala Asn His Asn Asp Glu Ala Cys Asn Cys Asn Glu Ser Glu Ile Ser
        35                  40                  45

Ser Val Gly Gln Ala Gln Thr Ser Gly Pro Ser Ser Asn Lys Thr Cys
    50                  55                  60

Ile Thr His Ser Phe Ile Lys Ala Asn Lys Lys Val Cys Lys Asp
65                  70                  75                  80

Val Lys Leu Gly Val Arg Glu Asn Asp Lys Val Leu Arg Val Cys Val
                85                  90                  95

Ile Glu Asp Thr Ser Leu Ser Gly Val Asp Asn Cys Cys Gln Asp
            100                 105                 110

Leu Leu Gly Ile Leu Gln Glu Asn Cys Ser Asp Asn Lys Arg Gly Ser
```

```
                115                     120                     125
    Ser Ser Asn Gly Ser Cys Asn Asn Lys Asn Gln Asp Glu Cys Gln Lys
    130                     135                     140
    Lys Leu Glu Lys Val Phe Val Ser Leu Thr Asn Gly Tyr Lys Cys Asp
145                     150                     155                     160
    Lys Cys Lys Ser Gly Thr Ser Thr Val Asn Lys Lys Trp Ile Trp Lys
                165                     170                     175
    Lys Ser Ser Gly Asn Glu Lys Gly Leu Gln Lys Glu Tyr Ala Asn Thr
                180                     185                     190
    Ile Gly Leu Pro Pro Arg Thr Gln Ser Leu Tyr Leu Gly Asn Leu Pro
                195                     200                     205
    Lys Leu Gly Asn Val Cys Glu Asp Val Thr Asp Ile Asn Phe Asp Thr
    210                     215                     220
    Lys Glu Lys Phe Leu Ala Gly Cys Leu Ile Ala Ala Phe His Glu Gly
    225                     230                     235                     240
    Lys Asn Leu Lys Ile Ser His Glu Lys Lys Gly Asp Asn Gly Lys
                            245                     250                     255
    Lys Leu Cys Lys Ala Leu Glu Tyr Ser Phe Ala Asp Tyr Gly Asp Leu
                260                     265                     270
    Ile Lys Gly Thr Ser Ile Trp Asp Asn Glu Tyr Thr Lys Asp Leu Glu
                275                     280                     285
    Leu Asn Leu Gln Lys Ala Phe Gly Lys Leu Phe Gly Lys Tyr Ile Lys
                290                     295                     300
    Lys Asn Ile Ala Ser Asp Glu Asn Thr Ser Tyr Ser Ser Leu Asp Glu
    305                     310                     315                     320
    Leu Arg Glu Ser Trp Trp Asn Thr Asn Lys Lys Tyr Ile Trp Thr Ala
                            325                     330                     335
    Met Lys His Gly Ala Glu Met Asn Ser Thr Met Cys Asn Ala Asp Gly
                340                     345                     350
    Ser Val Thr Gly Ser Gly Ser Ser Cys Asp Asp Ile Pro Thr Thr Asp
                355                     360                     365
    Phe Ile Pro Gln Tyr Leu Arg Phe Leu Gln Glu Trp Val Glu His Phe
                370                     375                     380
    Cys Lys Gln Arg Gln Glu Lys Val Asn Ala Val Ile Glu Asn Cys Asn
    385                     390                     395                     400
    Ser Cys Lys Asn Thr Ser Gly Glu Arg Lys Ile Gly Gly Thr Cys Asn
                            405                     410                     415
    Gly Asp Cys Lys Thr Glu Cys Lys Asn Lys Cys Glu Ala Tyr Lys Asn
                420                     425                     430
    Phe Ile Glu Asp Cys Lys Gly Gly Asp Gly Thr Ala Gly Ser Ser Trp
                435                     440                     445
    Val Lys Arg Trp Asp Gln Ile Tyr Lys Arg Tyr Ser Lys His Ile Glu
                450                     455                     460
    Asp Ala Lys Arg Asn Arg Lys Ala Gly Thr Lys Ser Cys Gly Pro Ser
    465                     470                     475                     480
    Ser Ile Thr Asn Ala Ser Val Ser Thr Asp Glu Asn Lys Cys Val Gln
                            485                     490                     495
    Ser Asp Ile Asp Ser Phe Phe Lys His Leu Ile Asp Ile Gly Leu Thr
                500                     505                     510
    Thr Pro Ser Ser Tyr Leu Ser Ile Val Leu Asp Glu Asn Asn Cys Gly
                515                     520                     525
    Glu Asp Asn Ala Pro Trp Thr Thr Tyr Thr Thr Tyr Thr Thr Thr Glu
    530                     535                     540
```

-continued

```
Lys Cys Asn Lys Asp Lys Lys Ser Lys Ser Gln Ser Cys Asn Thr
545                 550                 555                 560

Ala Val Val Val Asn Val Pro Ser Pro Leu Gly Asn Thr Pro His Glu
                565                 570                 575

Tyr Lys Tyr Ala Cys Gln Cys Lys Ile Pro Thr Thr Glu Glu Thr Cys
            580                 585                 590

Asp Asp Arg Lys Glu Tyr Met Asn Gln Trp Ile Ser Asp Thr Ser Lys
        595                 600                 605

Lys Gln Lys Gly Ser Gly Ser Thr Asn Asn Asp Tyr Glu Leu Tyr Thr
610                 615                 620

Tyr Thr Gly Val Lys Glu Thr Lys Leu Pro Lys Lys Leu Asn Ser Pro
625                 630                 635                 640

Lys Leu Asp

<210> SEQ ID NO 5
<211> LENGTH: 640
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 1248 745 amino acids

<400> SEQUENCE: 5

Ser Tyr Val Lys Asn Asp Pro Tyr Ser Lys Glu Tyr Val Thr Lys Leu
1               5                   10                  15

Ser Phe Ile Leu Asn Pro Ser Asp Ala Asn Asn Pro Ser Gly Glu Thr
                20                  25                  30

Ala Asn His Asn Asp Glu Ala Cys Asn Pro Asn Glu Ser Glu Ile Ala
            35                  40                  45

Ser Val Gly Gln Ala Gln Thr Ser Asp Arg Leu Ser Gln Lys Ala Cys
        50                  55                  60

Ile Thr His Ser Phe Ile Gly Ala Asn Lys Lys Ile Val Cys Lys Asp
65                  70                  75                  80

Val Lys Leu Gly Val Arg Glu Lys Asp Lys Asp Leu Lys Ile Cys Val
                85                  90                  95

Ile Glu Asp Asp Ser Leu Arg Gly Val Glu Asn Cys Cys Phe Lys Asp
            100                 105                 110

Leu Leu Gly Ile Leu Gln Glu Asn Cys Ser Asp Asn Lys Ser Gly Ser
        115                 120                 125

Ser Ser Asn Gly Ser Cys Asn Asn Lys Asn Gln Asp Glu Cys Gln Lys
130                 135                 140

Lys Leu Asp Glu Ala Leu Ala Ser Leu His Asn Gly Tyr Lys Cys Asp
145                 150                 155                 160

Lys Cys Lys Ser Gly Thr Ser Arg Ser Lys Lys Ile Trp Thr Trp Arg
                165                 170                 175

Lys Phe Pro Gly Asn Gly Glu Gly Leu Gln Lys Glu Tyr Ala Asn Thr
            180                 185                 190

Ile Gly Leu Pro Pro Arg Thr Gln Ser Leu Tyr Leu Gly Asn Leu Arg
        195                 200                 205

Lys Leu Glu Asn Val Cys Lys Gly Val Thr Asp Ile Asn Phe Asp Thr
210                 215                 220

Lys Glu Lys Phe Leu Ala Gly Cys Leu Ile Ala Ala Phe His Glu Gly
225                 230                 235                 240
```

```
Lys Asn Leu Lys Ile Ser Asn Lys Lys Lys Asn Asp Asp Asn Gly Lys
            245                 250                 255

Lys Leu Cys Lys Asp Leu Lys Tyr Ser Phe Ala Asp Tyr Gly Asp Leu
        260                 265                 270

Ile Lys Gly Thr Ser Ile Trp Asp Asn Glu Tyr Thr Lys Asp Leu Glu
        275                 280                 285

Leu Asn Leu Gln Lys Ile Phe Gly Lys Leu Phe Arg Lys Tyr Ile Lys
        290                 295                 300

Lys Asn Ile Ala Ser Asp Glu Asn Thr Leu Tyr Ser Ser Leu Asp Glu
305                 310                 315                 320

Leu Arg Glu Ser Trp Trp Asn Thr Asn Lys Lys Tyr Ile Trp Leu Ala
                325                 330                 335

Met Lys His Gly Thr Thr Cys Ser Ser Gly Ser Gly Asp Asn Gly Asp
                340                 345                 350

Gly Ser Val Thr Gly Ser Gly Ser Ser Cys Asp Asp Met Ser Thr Ile
            355                 360                 365

Asp Leu Ile Pro Gln Tyr Leu Arg Phe Leu Gln Glu Trp Val Glu His
        370                 375                 380

Phe Cys Lys Gln Arg Gln Glu Lys Val Lys Asp Val Ile Glu Asn Cys
385                 390                 395                 400

Lys Ser Cys Lys Asn Thr Ser Gly Glu Arg Ile Ile Gly Gly Thr Cys
                405                 410                 415

Gly Ser Asp Cys Lys Thr Lys Cys Lys Gly Glu Cys Asp Ala Tyr Lys
            420                 425                 430

Asn Phe Ile Glu Glu Cys Lys Arg Gly Asp Gly Thr Ala Gly Ser Pro
        435                 440                 445

Trp Ser Lys Arg Trp Asp Gln Ile Tyr Met Arg Tyr Ser Lys Tyr Ile
        450                 455                 460

Glu Asp Ala Lys Arg Asn Arg Lys Ala Gly Thr Lys Asn Cys Gly Thr
465                 470                 475                 480

Ser Ser Thr Thr Asn Ala Ala Glu Asn Lys Cys Val Gln Ser Asp Ile
                485                 490                 495

Asp Ser Phe Phe Lys His Leu Ile Asp Ile Gly Leu Thr Thr Pro Ser
            500                 505                 510

Ser Tyr Leu Ser Ile Val Leu Asp Glu Asn Ile Cys Gly Asp Asp Lys
        515                 520                 525

Ala Pro Trp Thr Thr Tyr Thr Tyr Thr Thr Glu Lys Cys Asn
        530                 535                 540

Lys Glu Thr Asp Lys Ser Lys Ser Gln Ser Cys Asn Thr Ala Val Val
545                 550                 555                 560

Val Asn Val Pro Ser Pro Leu Gly Asn Thr Pro His Gly Tyr Lys Tyr
                565                 570                 575

Ala Cys Glu Cys Lys Ile Pro Thr Thr Glu Glu Thr Cys Asp Asp Arg
            580                 585                 590

Lys Glu Tyr Met Asn Gln Trp Ile Ser Asp Thr Ser Lys Lys Pro Lys
        595                 600                 605

Gly Gly Arg Ser Thr Asn Asn Asp Tyr Glu Leu Tyr Thr Tyr Asn Gly
        610                 615                 620

Val Lys Glu Thr Lys Leu Pro Lys Lys Ser Ser Ser Lys Leu Asp
625                 630                 635                 640

<210> SEQ ID NO 6
<211> LENGTH: 358
<212> TYPE: PRT
```

<213> ORGANISM: Plasmodium falciparum

<400> SEQUENCE: 6

Lys Cys Glu Lys Cys Lys Ser Glu Gln Ser L

<400> SEQUENCE: 7

Lys Cys Asp Lys Cys Lys Ser Glu Gln Ser Lys Lys Asn Asn Lys Asn
1               5                   10                  15

Trp Ile Trp Lys Gln Phe Pro Gly Asn Gly Glu Gly Leu Gln Lys Glu
            20                  25                  30

Tyr Ala Asn Thr Ile Gly Leu Pro Pro Arg Thr His Ser Leu Tyr Leu
        35                  40                  45

Gly Asn Leu Pro Lys Leu Glu Asn Val Cys Lys Gly Val Thr Asp Ile
    50                  55                  60

Asn Phe Asp Thr Lys Glu Lys Phe Leu Ala Gly Cys Leu Ile Ala Ala
65                  70                  75                  80

Phe His Glu Gly Lys Asn Leu Lys Thr Ser His Glu Lys Lys Lys Gly
                85                  90                  95

Asp Asn Gly Lys Lys Leu Cys Lys Asp Leu Lys Tyr Ser Phe Ala Asp
            100                 105                 110

Tyr Gly Asp Leu Ile Lys Gly Thr Ser Ile Trp Asp Asn Asp Phe Thr
        115                 120                 125

Lys Asp Leu Glu Leu Asn Leu Gln Gln Ile Phe Gly Lys Leu Phe Arg
    130                 135                 140

Lys Tyr Ile Lys Lys Asn Ile Ser Ala Glu Gln Asp Thr Ser Tyr Ser
145                 150                 155                 160

Ser Leu Asp Glu Leu Arg Glu Ser Trp Trp Asn Thr Asn Lys Lys Tyr
                165                 170                 175

Ile Trp Leu Ala Met Lys His Gly Thr Thr Cys Ser Ser Gly Ser Gly
            180                 185                 190

Asp Asn Gly Asp Gly Ser Val Thr Gly Ser Gly Ser Cys Asp Asp
        195                 200                 205

Met Pro Thr Thr Asp Phe Ile Pro Gln Tyr Leu Arg Phe Leu Gln Glu
    210                 215                 220

Trp Val Glu His Phe Cys Lys Gln Arg Gln Glu Lys Val Asn Ala Val
225                 230                 235                 240

Ile Thr Asn Cys Lys Ser Cys Lys Glu Ser Gly Gly Thr Cys Asn Ser
                245                 250                 255

Asp Cys Glu Lys Lys Cys Lys Asp Glu Cys Glu Lys Tyr Lys Lys Phe
            260                 265                 270

Ile Glu Glu Cys Arg Thr Ala Ala Asp Gly Thr Ala Gly Ser Ser Trp
        275                 280                 285

Ser Lys Arg Trp Asp Gln Ile Tyr Lys Met Tyr Ser Lys His Ile Glu
    290                 295                 300

Asp Ala Lys Arg Asn Arg Lys Ala Gly Thr Lys Asn Cys Gly Thr Ser
305                 310                 315                 320

Ser Thr Thr Asn Ala Ala Glu Asn Lys Cys Val Gln Ser
                325                 330

<210> SEQ ID NO 8
<211> LENGTH: 269
<212> TYPE: PRT
<213> ORGANISM: Plasmodium falciparum

<400> SEQUENCE: 8

Asp Tyr Ile Lys Asp Asp Pro Tyr Ser Lys Glu Tyr Thr Thr Lys Leu
1               5                   10                  15

Ser Phe Ile Leu Asn Ser Ser Asp Ala Asn Thr Ser Ser Gly Glu Thr
            20                  25                  30

Ala Asn His Asn Asp Glu Ala Cys Asn Cys Asn Glu Ser Glu Ile Ala
         35                  40                  45

Ser Val Glu Gln Ala Ser Ile Ser Asp Arg Ser Ser Gln Lys Ala Tyr
 50                  55                  60

Ile Thr His Ser Ser Ile Lys Thr Asn Lys Lys Val Cys Lys Tyr
 65                  70                  75                  80

Val Lys Leu Gly Ile Asn Asn Asn Asp Lys Val Leu Arg Val Cys Val
                 85                  90                  95

Ile Glu Asp Thr Ser Leu Ser Gly Val Glu Asn Cys Cys Phe Lys Asp
             100                 105                 110

Leu Leu Gly Ile Leu Gln Glu Asn Cys Ser Asp Asn Lys Arg Gly Ser
             115                 120                 125

Ser Phe Asn Asp Ser Cys Asn Asn Asn Glu Glu Ala Cys Gln Lys
 130                 135                 140

Lys Leu Glu Lys Val Leu Ala Ser Leu Thr Asn Gly Tyr Lys Cys Glu
145                 150                 155                 160

Lys Cys Lys Ser Gly Thr Ser Arg Ser Lys Lys Trp Ile Trp Lys
                 165                 170                 175

Lys Ser Ser Gly Lys Glu Gly Gly Leu Gln Lys Glu Tyr Ala Asn Thr
             180                 185                 190

Ile Gly Leu Pro Pro Arg Thr Gln Ser Leu Tyr Leu Gly Asn Leu Pro
     195                 200                 205

Lys Leu Glu Asn Val Cys Lys Gly Val Thr Asp Ile Asn Phe Asp Thr
210                 215                 220

Lys Glu Lys Phe Leu Ala Gly Cys Leu Ile Ala Ala Phe His Glu Gly
225                 230                 235                 240

Lys Asn Leu Lys Pro Ser His Gln Asn Lys Asn Asp Asp Asn Asn Ser
                 245                 250                 255

Lys Leu Cys Lys Asp Leu Lys Tyr Ser Phe Ala Asp Tyr
                 260                 265

<210> SEQ ID NO 9
<211> LENGTH: 333
<212> TYPE: PRT
<213> ORGANISM: Plasmodium falciparum

<400> SEQUENCE: 9

Lys Cys Asp Lys Cys Lys Ser Gly Thr Ser Arg Ser Lys Lys Lys Trp
 1               5                  10                  15

Thr Trp Arg Lys Ser Ser Gly Asn Lys Glu Gly Leu Gln Lys Glu Tyr
                 20                  25                  30

Ala Asn Thr Ile Gly Leu Pro Pro Arg Thr His Ser Leu Tyr Leu Gly
             35                  40                  45

Asn Leu Arg Lys Leu Glu Asn Val Cys Glu Asp Val Thr Asp Ile Asn
         50                  55                  60

Phe Asp Thr Lys Glu Lys Phe Leu Ala Gly Cys Leu Ile Ala Ala Phe
 65                  70                  75                  80

His Glu Gly Lys Asn Leu Lys Thr Thr Tyr Pro Gln Asn Lys Asn Asp
                 85                  90                  95

Asp Asn Asn Ser Lys Leu Cys Lys Ala Leu Lys Tyr Ser Phe Ala Asp
             100                 105                 110

Tyr Gly Asp Leu Ile Lys Gly Thr Ser Ile Trp Asp Asn Asp Phe Thr
         115                 120                 125

Lys Asp Leu Glu Leu Asn Leu Gln Lys Ile Phe Gly Lys Leu Phe Arg
130                 135                 140

Lys Tyr Ile Lys Lys Asn Ile Ser Thr Glu Gln His Thr Ser Tyr Ser
145                 150                 155                 160

Ser Leu Asp Glu Leu Arg Glu Ser Trp Trp Asn Thr Asn Lys Lys Tyr
                165                 170                 175

Ile Trp Leu Ala Met Lys His Gly Ala Glu Met Asn Gly Thr Thr Cys
            180                 185                 190

Ser Cys Ser Gly Asp Ser Ser Asp Ile Pro Thr Ile Asp Leu Ile
        195                 200                 205

Pro Gln Tyr Leu Arg Phe Leu Gln Glu Trp Val Glu His Phe Cys Lys
    210                 215                 220

Gln Arg Gln Ala Lys Val Asn Ala Val Ile Asn Ser Cys Asn Ser Cys
225                 230                 235                 240

Lys Asn Thr Ser Gly Glu Arg Lys Leu Gly Gly Thr Cys Gly Ser Glu
                245                 250                 255

Cys Lys Thr Glu Cys Lys Asn Lys Cys Asp Ala Tyr Lys Glu Phe Ile
                260                 265                 270

Asp Gly Thr Gly Ser Gly Gly Gly Thr Gly Thr Ala Gly Ser Ser Trp
            275                 280                 285

Val Lys Arg Trp Asp Gln Ile Tyr Lys Arg Tyr Ser Lys Tyr Ile Glu
    290                 295                 300

Asp Ala Lys Arg Asn Arg Lys Ala Gly Ser Lys Asn Cys Gly Thr Ser
305                 310                 315                 320

Ser Thr Thr Asn Ala Ala Glu Ser Lys Cys Val Gln Ser
                325                 330

<210> SEQ ID NO 10
<211> LENGTH: 650
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: hb31 745 amino acids

<400> SEQUENCE: 10

Ser Tyr Val Lys Asn Asn Pro Tyr Ser Ala Glu Tyr Val Thr Lys Leu
1               5                   10                  15

Ser Phe Ile Leu Asn Ser Ser Asp Ala Asn Thr Ser Ser Glu Thr Pro
            20                  25                  30

Ser Lys Tyr Tyr Asp Glu Val Cys Asn Cys Asn Glu Ser Glu Ile Ser
        35                  40                  45

Ser Val Gly Gln Ala Gln Thr Ser Gly Pro Ser Ser Asn Lys Thr Cys
    50                  55                  60

Ile Thr His Ser Ser Ile Lys Thr Asn Lys Lys Val Cys Lys Asp
65                  70                  75                  80

Val Lys Leu Gly Ile Asn Asn Asn Asp Lys Val Leu Arg Val Cys Val
                85                  90                  95

Ile Glu Asp Thr Ser Leu Ser Gly Val Asp Asn Cys Cys Cys Gln Asp
                100                 105                 110

Leu Leu Gly Ile Leu Gln Glu Asn Cys Ser Asp Lys Asn Gln Ser Gly
            115                 120                 125

Ser Ser Ser Asn Gly Ser Cys Asn Asn Lys Asn Gln Asp Glu Cys Gln
        130                 135                 140

Lys Lys Leu Glu Lys Val Phe Ala Ser Leu Thr Asn Gly Tyr Lys Cys
145                 150                 155                 160

-continued

```
Asp Lys Cys Lys Ser Gly Thr Ser Arg Ser Lys Lys Trp Ile Trp
                165                 170                 175

Arg Lys Ser Ser Gly Asn Glu Glu Gly Leu Gln Lys Glu Tyr Ala Asn
            180                 185                 190

Thr Ile Gly Leu Pro Pro Arg Thr Gln Ser Leu Tyr Leu Gly Asn Leu
        195                 200                 205

Arg Lys Leu Glu Asn Val Cys Lys Gly Val Thr Asp Ile Asn Phe Asp
    210                 215                 220

Thr Lys Glu Lys Phe Leu Ala Gly Cys Leu Ile Ala Ala Phe His Glu
225                 230                 235                 240

Gly Lys Asn Leu Lys Thr Thr Tyr Pro Gln Asn Lys Lys Lys Leu Cys
                245                 250                 255

Lys Asp Leu Lys Tyr Ser Phe Ala Asp Tyr Gly Asp Leu Ile Lys Gly
            260                 265                 270

Thr Ser Ile Trp Asp Asn Glu Tyr Thr Lys Asp Leu Glu Leu Asn Leu
        275                 280                 285

Gln Lys Ala Phe Gly Lys Leu Phe Arg Lys Tyr Ile Lys Lys Asn Ile
    290                 295                 300

Ser Thr Glu Gln His Thr Leu Tyr Ser Ser Leu Asp Glu Leu Arg Glu
305                 310                 315                 320

Ser Trp Trp Asn Thr Asn Lys Lys Tyr Ile Trp Leu Ala Met Lys His
                325                 330                 335

Gly Ala Gly Met Asn Ser Thr Cys Cys Gly Asp Gly Ser Val Thr
            340                 345                 350

Gly Ser Gly Ser Ser Cys Asp Asp Ile Pro Thr Ile Asp Leu Ile Pro
        355                 360                 365

Gln Tyr Leu Arg Phe Leu Gln Glu Trp Val Glu His Phe Cys Lys Gln
    370                 375                 380

Arg Gln Glu Lys Val Asn Ala Val Ile Glu Asn Cys Asn Ser Cys Lys
385                 390                 395                 400

Glu Cys Gly Asp Thr Cys Asn Gly Glu Cys Lys Thr Glu Cys Glu Lys
                405                 410                 415

Lys Cys Lys Ile Glu Cys Glu Lys Tyr Lys Thr Phe Ile Glu Glu Cys
            420                 425                 430

Val Thr Ala Val Gly Gly Thr Ser Gly Ser Pro Trp Ser Lys Arg Trp
        435                 440                 445

Asp Gln Ile Tyr Lys Arg Tyr Ser Lys Tyr Ile Glu Asp Ala Lys Arg
    450                 455                 460

Asn Arg Lys Ala Gly Thr Lys Asn Cys Gly Ile Thr Thr Gly Thr Ile
465                 470                 475                 480

Ser Gly Glu Ser Ser Gly Ala Asn Ser Gly Val Thr Thr Thr Glu Asn
                485                 490                 495

Lys Cys Val Gln Ser Asp Ile Asp Ser Phe Phe Lys His Leu Ile Asp
            500                 505                 510

Ile Gly Leu Thr Thr Pro Ser Ser Tyr Leu Ser Ile Val Leu Asp Asp
        515                 520                 525

Asn Ile Cys Gly Ala Asp Asn Ala Pro Trp Thr Thr Tyr Thr Thr Tyr
    530                 535                 540

Thr Thr Tyr Thr Thr Thr Lys Asn Cys Asp Ile Lys Lys Lys Thr Pro
545                 550                 555                 560

Lys Ser Gln Pro Ile Asn Thr Ser Val Val Val Asn Val Pro Ser Pro
                565                 570                 575
```

```
Leu Gly Asn Thr Pro His Gly Tyr Lys Tyr Ala Cys Gln Cys Lys Ile
                580                 585                 590

Pro Thr Thr Glu Glu Ser Cys Asp Asp Arg Lys Glu Tyr Met Asn Gln
            595                 600                 605

Trp Ile Ile Asp Thr Ser Lys Lys Gln Lys Gly Ser Gly Ser Thr Asn
    610                 615                 620

Asn Asp Tyr Glu Leu Tyr Thr Tyr Asn Gly Val Lys Glu Thr Lys Leu
625                 630                 635                 640

Pro Lys Lys Ser Ser Ser Lys Leu Asp
                645                 650

<210> SEQ ID NO 11
<211> LENGTH: 643
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: hb32 745 amino acids

<400> SEQUENCE: 11

Ser Tyr Val Lys Asp Asp Pro Tyr Ser Ala Glu Tyr Val Thr Lys Leu
1               5                   10                  15

Ser Phe Ile Leu Asn Ser Ser Asp Ala Asn Thr Ser Ser Glu Thr Pro
            20                  25                  30

Ser Lys Tyr Tyr Asp Glu Val Cys Asn Cys Asn Glu Ser Glu Ile Ser
        35                  40                  45

Ser Val Gly Gln Ala Gln Thr Ser Gly Pro Ser Ser Asn Lys Thr Cys
    50                  55                  60

Ile Thr His Ser Ser Ile Lys Thr Asn Lys Lys Val Cys Lys Asp
65                  70                  75                  80

Val Lys Leu Gly Ile Asn Asn Asn Asp Lys Val Leu Arg Val Cys Val
                85                  90                  95

Ile Glu Asp Thr Ser Leu Ser Gly Val Asp Asn Cys Cys Cys Gln Asp
            100                 105                 110

Leu Leu Gly Ile Leu Gln Glu Asn Cys Ser Asp Lys Asn Gln Ser Gly
        115                 120                 125

Ser Ser Ser Asn Gly Ser Cys Asn Asn Lys Asn Gln Asp Glu Cys Gln
    130                 135                 140

Lys Lys Leu Glu Lys Val Phe Ala Ser Leu Thr Asn Gly Tyr Lys Cys
145                 150                 155                 160

Asp Lys Cys Lys Ser Gly Thr Ser Arg Ser Lys Lys Lys Trp Ile Trp
                165                 170                 175

Arg Lys Ser Gly Asn Glu Glu Gly Leu Gln Lys Gly Tyr Ala Asn
            180                 185                 190

Thr Ile Gly Leu Pro Pro Arg Thr Gln Ser Leu Tyr Leu Gly Asn Leu
        195                 200                 205

Pro Lys Leu Glu Asn Val Cys Lys Gly Val Thr Asp Ile Ile Tyr Asp
    210                 215                 220

Thr Lys Glu Lys Phe Leu Ser Gly Cys Leu Ile Ala Ala Phe His Glu
225                 230                 235                 240

Gly Lys Asn Leu Lys Thr Ser His Glu Lys Asn Asp Asp Asn Gly
                245                 250                 255

Lys Lys Leu Cys Lys Ala Leu Glu Tyr Ser Phe Ala Asp Tyr Gly Asp
            260                 265                 270
```

```
Leu Ile Lys Gly Thr Ser Ile Trp Asp Asn Asp Phe Thr Lys Asp Leu
            275                 280                 285

Glu Leu Asn Leu Gln Lys Ile Phe Gly Lys Leu Phe Arg Lys Tyr Ile
            290                 295                 300

Lys Lys Asn Asn Thr Ala Glu Gln Asp Thr Ser Tyr Ser Ser Leu Asp
305                 310                 315                 320

Glu Leu Arg Glu Ser Trp Trp Asn Thr Asn Lys Lys Tyr Ile Trp Thr
            325                 330                 335

Ala Met Lys His Gly Ala Gly Met Asn Ser Thr Thr Cys Ser Gly Asp
            340                 345                 350

Gly Ser Val Thr Gly Ser Gly Ser Ser Cys Asp Asp Met Pro Thr Ile
            355                 360                 365

Asp Leu Ile Pro Gln Tyr Leu Arg Phe Leu Gln Glu Trp Val Glu His
            370                 375                 380

Phe Cys Lys Gln Arg Gln Glu Lys Val Lys Asp Val Ile Thr Asn Cys
385                 390                 395                 400

Asn Ser Cys Lys Glu Cys Gly Asp Thr Cys Asn Gly Glu Cys Lys Thr
            405                 410                 415

Glu Cys Lys Thr Lys Cys Lys Gly Glu Cys Glu Lys Tyr Lys Asn Phe
            420                 425                 430

Ile Glu Glu Cys Asn Gly Thr Ala Asp Gly Gly Thr Ser Gly Ser Ser
            435                 440                 445

Trp Ser Lys Arg Trp Asp Gln Ile Tyr Lys Arg Tyr Ser Lys Tyr Ile
            450                 455                 460

Glu Asp Ala Lys Arg Asn Arg Lys Ala Gly Thr Lys Asn Cys Gly Thr
465                 470                 475                 480

Ser Ser Thr Thr Asn Ala Ala Ala Ser Thr Thr Glu Asn Lys Cys Val
            485                 490                 495

Gln Ser Asp Ile Asp Ser Phe Phe Lys His Leu Ile Asp Ile Gly Leu
            500                 505                 510

Thr Thr Pro Ser Ser Tyr Leu Ser Asn Val Leu Asp Asp Asn Ile Cys
            515                 520                 525

Gly Glu Asp Lys Ala Pro Trp Thr Thr Tyr Thr Thr Tyr Thr Thr Lys
530                 535                 540

Asn Cys Asp Ile Gln Lys Lys Thr Pro Lys Pro Gln Ser Cys Asp Thr
545                 550                 555                 560

Leu Val Val Val Asn Val Pro Ser Pro Leu Gly Asn Thr Pro His Gly
            565                 570                 575

Tyr Lys Tyr Val Cys Glu Cys Lys Ile Pro Thr Thr Glu Glu Thr Cys
            580                 585                 590

Asp Asp Arg Lys Glu Tyr Met Asn Gln Trp Ile Ile Asp Thr Ser Lys
            595                 600                 605

Lys Gln Lys Gly Ser Gly Ser Thr Asn Asn Asp Tyr Glu Leu Tyr Thr
            610                 615                 620

Tyr Asn Gly Val Gln Ile Lys Gln Ala Ala Gly Thr Leu Lys Asn Ser
625                 630                 635                 640

Lys Leu Asp
```

<210> SEQ ID NO 12
<211> LENGTH: 269
<212> TYPE: PRT
<213> ORGANISM: Plasmodium falciparum

<400> SEQUENCE: 12

```
Asn Tyr Ile Lys Gly Asp Pro Tyr Ser Ala Glu Tyr Ala Thr Lys Leu
1               5                   10                  15

Ser Phe Ile Leu Asn Ser Ser Asp Thr Glu Asn Ala Ser Glu Lys Ile
            20                  25                  30

Gln Lys Asn Asn Asp Glu Val Cys Asn Cys Asn Glu Ser Glu Ile Ala
        35                  40                  45

Ser Val Glu Gln Ala Pro Ile Ser Asp Arg Ser Ser Gln Lys Ala Cys
50                  55                  60

Ile Thr His Ser Ser Ile Lys Ala Asn Lys Lys Val Cys Lys His
65                  70                  75                  80

Val Lys Leu Gly Val Arg Glu Asn Asp Lys Asp Leu Lys Ile Cys Val
                85                  90                  95

Ile Glu Asp Thr Ser Leu Ser Gly Val Asp Asn Cys Cys Gln Asp
            100                 105                 110

Leu Leu Gly Ile Leu Gln Glu Asn Cys Ser Asp Asn Lys Ser Gly Ser
            115                 120                 125

Ser Ser Asn Gly Ser Cys Asn Asn Asn Glu Glu Ile Cys Gln Lys
        130                 135                 140

Lys Leu Glu Lys Val Leu Ala Ser Leu Thr Asn Gly Tyr Lys Cys Asp
145                 150                 155                 160

Lys Cys Lys Ser Gly Thr Ser Thr Val Asn Lys Asn Trp Ile Trp Lys
                165                 170                 175

Lys Tyr Ser Gly Lys Glu Gly Gly Leu Gln Glu Glu Tyr Ala Asn Thr
            180                 185                 190

Ile Gly Leu Pro Pro Arg Thr Gln Ser Leu Tyr Leu Gly Asn Leu Pro
        195                 200                 205

Lys Leu Glu Asn Val Cys Glu Asp Val Lys Asp Ile Asn Phe Asp Thr
210                 215                 220

Lys Glu Lys Phe Leu Ala Gly Cys Leu Ile Ala Ala Phe His Glu Gly
225                 230                 235                 240

Lys Asn Leu Lys Thr Ser Asn Lys Lys Asn Asp Asp Asn Asn Ser
            245                 250                 255

Lys Leu Cys Lys Ala Leu Lys Tyr Ser Phe Ala Asp Tyr
        260                 265

<210> SEQ ID NO 13
<211> LENGTH: 344
<212> TYPE: PRT
<213> ORGANISM: Plasmodium falciparum

<400> SEQUENCE: 13

Lys Cys Asp Lys Cys Lys Ser Gly Thr Ser Thr Val Asn Lys Lys Trp
1               5                   10                  15

Ile Trp Lys Lys Tyr Ser Gly Thr Glu Gly Gly Leu Gln Glu Glu Tyr
            20                  25                  30

Ala Asn Thr Ile Ala Leu Pro Pro Arg Thr Gln Ser Leu Tyr Leu Gly
        35                  40                  45

Asn Leu Pro Lys Leu Glu Asn Val Cys Lys Asp Val Thr Asp Ile Asn
50                  55                  60

Phe Asp Thr Lys Glu Lys Phe Leu Ala Gly Cys Leu Ile Ala Ala Phe
65                  70                  75                  80

His Glu Gly Lys Asn Leu Lys Thr Thr Tyr Leu Glu Lys Lys Gly
            85                  90                  95

Asp Asn Gly Lys Lys Asn Asp Asp Asn Asn Ser Lys Leu Cys Lys Ala
            100                 105                 110
```

Leu Lys Tyr Ser Phe Ala Asp Tyr Gly Asp Leu Ile Lys Gly Thr Ser
            115                 120                 125

Ile Trp Asp Asn Asp Phe Thr Lys Asp Leu Glu Leu Asn Leu Gln Gln
130                 135                 140

Ile Phe Gly Lys Leu Phe Arg Lys Tyr Ile Lys Lys Asn Ile Ala Ser
145                 150                 155                 160

Asp Glu Asn Thr Leu Tyr Ser Ser Leu Asp Glu Leu Arg Glu Ser Trp
                165                 170                 175

Trp Asn Thr Asn Lys Lys Tyr Ile Trp Leu Ala Met Lys His Gly Ala
            180                 185                 190

Gly Met Asn Ser Thr Met Cys Asn Ala Asp Gly Ser Val Thr Gly Ser
        195                 200                 205

Gly Ser Ser Cys Asp Asp Ile Pro Thr Ile Asp Leu Ile Pro Gln Tyr
    210                 215                 220

Leu Arg Phe Leu Gln Glu Trp Val Glu His Phe Cys Lys Gln Arg Gln
225                 230                 235                 240

Ala Lys Val Lys Asp Val Ile Thr Asn Cys Asn Ser Cys Lys Glu Cys
                245                 250                 255

Gly Gly Thr Cys Asn Gly Glu Cys Lys Thr Glu Cys Glu Lys Lys Cys
            260                 265                 270

Lys Gly Glu Cys Asp Ala Tyr Lys Lys Phe Ile Glu Glu Cys Lys Gly
        275                 280                 285

Lys Ala Asp Glu Gly Thr Ser Gly Ser Ser Trp Ser Lys Arg Trp Asp
    290                 295                 300

Gln Ile Tyr Lys Arg Tyr Ser Lys Tyr Ile Glu Asp Ala Lys Arg Asn
305                 310                 315                 320

Arg Lys Ala Gly Thr Lys Asn Cys Gly Pro Ser Ser Thr Thr Ser Thr
                325                 330                 335

Ala Glu Ser Lys Cys Val Gln Ser
            340

<210> SEQ ID NO 14
<211> LENGTH: 334
<212> TYPE: PRT
<213> ORGANISM: Plasmodium falciparum

<400> SEQUENCE: 14

Lys Cys Asp Lys Cys Lys Ser Glu Gln Ser Lys Lys Asn Asn Asn Ile
1               5                   10                  15

Trp Ile Trp Lys Lys Ser Ser Gly Thr Glu Gly Gly Leu Gln Lys Glu
            20                  25                  30

Tyr Ala Asn Thr Ile Ala Leu Pro Pro Arg Thr Gln Ser Leu Tyr Leu
        35                  40                  45

Gly Asn Leu Arg Lys Leu Glu Asn Val Cys Glu Asp Val Lys Asp Ile
    50                  55                  60

Asn Phe Asp Thr Lys Glu Lys Phe Leu Ala Gly Cys Leu Ile Ala Ala
65                  70                  75                  80

Phe His Glu Gly Lys Asn Leu Lys Lys Arg Tyr Leu Glu Lys Lys Asn
                85                  90                  95

Gly Asp Asn Asn Ser Lys Leu Cys Lys Ala Leu Lys Tyr Ser Phe Ala
            100                 105                 110

Asp Tyr Gly Asp Leu Ile Lys Gly Thr Ser Ile Trp Asp Asn Glu Tyr
        115                 120                 125

Thr Lys Asp Leu Glu Leu Asn Leu Gln Lys Ile Phe Gly Lys Leu Phe

```
            130                 135                 140
Arg Lys Tyr Ile Lys Lys Asn Asn Thr Ala Glu Gln His Thr Ser Tyr
145                 150                 155                 160

Ser Ser Leu Asp Glu Leu Arg Glu Ser Trp Trp Asn Thr Asn Lys Lys
                165                 170                 175

Tyr Ile Trp Leu Ala Met Lys His Gly Thr Thr Cys Ser Ser Gly Ser
                    180                 185                 190

Gly Asp Asn Gly Ser Ile Ser Cys Asp Asp Ile Pro Thr Ile Asp Leu
                195                 200                 205

Ile Pro Gln Tyr Leu Arg Phe Leu Gln Glu Trp Val Glu His Phe Cys
        210                 215                 220

Glu Gln Arg Gln Gly Lys Val Asn Ala Val Ile Glu Asn Cys Asn Ser
225                 230                 235                 240

Cys Lys Asn Thr Ser Ser Lys Thr Lys Leu Gly Gly Thr Cys Asn Gly
                245                 250                 255

Glu Cys Lys Thr Glu Cys Lys Gly Glu Cys Asp Ala Tyr Lys Glu Phe
                    260                 265                 270

Ile Glu Lys Cys Lys Gly Thr Ala Ala Glu Gly Thr Ser Gly Ser Ser
                275                 280                 285

Trp Val Lys Arg Trp Tyr Gln Ile Tyr Met Arg Tyr Ser Lys Tyr Ile
        290                 295                 300

Glu Asp Ala Lys Arg Asn Arg Lys Ala Gly Thr Lys Asn Cys Gly Thr
305                 310                 315                 320

Ser Ser Thr Thr Ser Thr Ala Glu Ser Lys Cys Val Gln Ser
                325                 330

<210> SEQ ID NO 15
<211> LENGTH: 332
<212> TYPE: PRT
<213> ORGANISM: Plasmodium falciparum

<400> SEQUENCE: 15

Lys Cys Asp Lys Cys Lys Ser Glu Gln Ser Lys Lys Asn Asn Asn Ile
1               5                   10                  15

Trp Ile Trp Lys Lys Ser Ser Gly Thr Glu Gly Gly Leu Gln Lys Glu
                20                  25                  30

Tyr Ala Asn Thr Ile Ala Leu Pro Pro Arg Thr Gln Ser Leu Tyr Leu
                    35                  40                  45

Gly Asn Leu Arg Lys Leu Glu Asn Val Cys Glu Asp Val Lys Asp Ile
        50                  55                  60

Asn Phe Asp Thr Lys Glu Lys Phe Leu Ala Gly Cys Leu Ile Ala Ala
65                  70                  75                  80

Phe His Glu Gly Lys Asn Leu Lys Lys Arg Tyr Leu Glu Lys Lys Asn
                85                  90                  95

Gly Asp Asn Asn Ser Lys Leu Cys Lys Ala Leu Lys Tyr Ser Phe Ala
                    100                 105                 110

Asp Tyr Gly Asp Leu Ile Lys Gly Thr Ser Ile Trp Asp Asn Glu Tyr
            115                 120                 125

Thr Lys Asp Leu Glu Leu Asn Leu Gln Lys Ile Phe Gly Lys Leu Phe
        130                 135                 140

Arg Lys Tyr Ile Lys Lys Asn Asn Thr Ala Glu Gln Asp Thr Ser Tyr
145                 150                 155                 160

Ser Ser Leu Asp Glu Leu Arg Glu Ser Trp Trp Asn Thr Asn Lys Lys
                165                 170                 175
```

```
Tyr Ile Trp Thr Ala Met Lys His Gly Thr Thr Cys Ser Ser Gly Ser
            180                 185                 190

Gly Asp Asn Gly Ser Ile Ser Cys Asp Ile Pro Thr Ile Asp Leu
        195                 200                 205

Ile Pro Gln Tyr Leu Arg Phe Leu Gln Glu Trp Val Glu His Phe Cys
    210                 215                 220

Glu Gln Arg Gln Glu Lys Val Lys Asp Val Ile Lys Asn Cys Asn Ser
225                 230                 235                 240

Cys Lys Glu Cys Gly Gly Thr Cys Asn Gly Cys Lys Thr Glu Cys
            245                 250                 255

Lys Asn Lys Cys Lys Asp Glu Cys Asp Ala Tyr Lys Lys Phe Ile Glu
            260                 265                 270

Glu Cys Glu Gly Lys Ala Ala Glu Gly Thr Ser Gly Ser Ser Trp Ser
            275                 280                 285

Lys Arg Trp Asp Gln Ile Tyr Lys Arg Tyr Ser Lys Tyr Ile Glu Asp
            290                 295                 300

Ala Lys Arg Asn Arg Lys Ala Gly Thr Lys Asn Cys Gly Thr Ser Ser
305                 310                 315                 320

Thr Thr Ser Thr Ala Glu Asn Lys Cys Val Gln Ser
                325                 330

<210> SEQ ID NO 16
<211> LENGTH: 267
<212> TYPE: PRT
<213> ORGANISM: Plasmodium falciparum

<400> SEQUENCE: 16

Asn Tyr Ile Lys Asp Asp Pro Tyr Ser Ala Glu Tyr Thr Thr Lys Leu
1               5                   10                  15

Ser Phe Ile Leu Asn Ser Ser Asp Thr Glu Asn Ala Ser Glu Lys Ile
            20                  25                  30

Gln Lys Asn Asn Asp Glu Val Cys Asn Pro Asn Glu Ser Gly Ile Ala
        35                  40                  45

Cys Val Glu Leu Ala Gln Thr Ser Gly Ser Ser Asn Lys Thr Cys
    50                  55                  60

Asn Thr His Ser Phe Ile Lys Ala Asn Lys Lys Val Cys Lys Asp
65                  70                  75                  80

Val Lys Leu Gly Ile Asn Lys Lys Asp Lys Asp Leu Lys Ile Cys Val
            85                  90                  95

Ile Glu Asp Asp Ser Leu Arg Gly Val Asp Asn Cys Cys Cys Gln Asp
        100                 105                 110

Leu Leu Gly Ile Leu Gln Glu Asn Cys Ser Asp Lys Asn Gln Ser Gly
    115                 120                 125

Ser Ser Ser Asn Gly Ser Cys Asn Asn Lys Asn Gln Glu Ala Cys Gln
130                 135                 140

Lys Lys Leu Glu Asn Val Phe Ala Ser Leu Thr Asn Gly Tyr Lys Cys
145                 150                 155                 160

Glu Lys Cys Lys Ser Glu Gln Ser Lys Lys Asn Asn Lys Asn Trp Ile
            165                 170                 175

Trp Lys Lys Tyr Ser Val Lys Glu Glu Gly Leu Gln Lys Glu Tyr Ala
        180                 185                 190

Asn Thr Ile Ala Leu Pro Pro Arg Thr Gln Ser Leu Tyr Leu Gly Asn
    195                 200                 205

Leu Pro Lys Leu Gly Asn Val Cys Lys Gly Val Thr Asp Ile Asn Phe
210                 215                 220
```

Asp Thr Lys Glu Lys Phe Leu Ala Gly Cys Leu Ile Ala Ala Phe His
225                 230                 235                 240

Glu Gly Lys Asn Leu Lys Thr Thr Tyr Leu Gln Asn Lys Lys Lys Leu
            245                 250                 255

Cys Lys Ala Leu Lys Tyr Ser Phe Ala Asp Tyr
            260                 265

<210> SEQ ID NO 17
<211> LENGTH: 263
<212> TYPE: PRT
<213> ORGANISM: Plasmodium falciparum

<400> SEQUENCE: 17

Asp Tyr Ile Lys Gly Asp Pro Tyr Phe Ala Glu Tyr Ala Thr Lys Leu
1               5                   10                  15

Ser Phe Ile Leu Asn Ser Ser Asp Ala Asn Thr Ser Ser Gly Glu Thr
            20                  25                  30

Ala Asn His Asn Asp Glu Ala Cys Asn Pro Asn Glu Ser Glu Ile Ala
        35                  40                  45

Ser Val Glu Gln Ala Ser Ile Ser Asp Arg Ser Ser Gln Lys Ala Cys
50                  55                  60

Asn Thr His Ser Ser Ile Lys Ala Asn Lys Lys Glu Cys Lys His
65                  70                  75                  80

Val Lys Leu Gly Val Arg Glu Asn Asp Lys Asp Leu Lys Ile Cys Val
                85                  90                  95

Ile Glu Asp Thr Ser Leu Ser Gly Val Asp Asn Cys Cys Cys Gln Asp
            100                 105                 110

Leu Leu Gly Ile Leu Gln Glu Asn Cys Ser Asp Asn Lys Arg Gly Ser
        115                 120                 125

Ser Ser Asn Gly Ser Cys Asp Lys Asn Ser Glu Glu Ile Cys Gln Lys
130                 135                 140

Lys Leu Asp Glu Ala Leu Ala Ser Leu His Asn Gly Tyr Lys Asn Gln
145                 150                 155                 160

Lys Cys Lys Ser Glu Gln Ser Lys Lys Asn Lys Asn Lys Trp Ile Trp
                165                 170                 175

Lys Lys Ser Ser Gly Asn Glu Lys Gly Leu Gln Lys Glu Tyr Ala Asn
            180                 185                 190

Thr Ile Gly Leu Pro Pro Arg Thr Gln Ser Leu Tyr Leu Gly Asn Leu
        195                 200                 205

Pro Lys Leu Glu Asn Val Cys Glu Asp Val Thr Asp Ile Asn Phe Asp
210                 215                 220

Thr Lys Glu Lys Phe Leu Ala Gly Cys Leu Ile Ala Ala Phe His Glu
225                 230                 235                 240

Gly Lys Asn Leu Lys Thr Thr Tyr Pro Gln Asn Lys Asn Asp Asn
                245                 250                 255

Gly Lys Lys Leu Cys Lys Asp
            260

<210> SEQ ID NO 18
<211> LENGTH: 338
<212> TYPE: PRT
<213> ORGANISM: Plasmodium falciparum

<400> SEQUENCE: 18

Lys Cys Asp Lys Cys Lys Ser Glu Gln Ser Lys Lys Asn Asn Asn Ile
1               5                   10                  15

```
Trp Ile Trp Lys Lys Ser Ser Gly Asn Lys Gly Leu Gln Lys Glu
            20                  25                  30

Tyr Ala Asn Thr Ile Gly Leu Pro Pro Arg Thr Gln Ser Leu Tyr Leu
            35                  40                  45

Gly Asn Leu Pro Lys Leu Glu Asn Val Cys Lys Asp Val Thr Asp Ile
 50                  55                  60

Asn Phe Asp Thr Lys Glu Lys Phe Leu Ala Gly Cys Leu Ile Ala Ala
 65                  70                  75                  80

Phe His Glu Gly Lys Asn Leu Lys Ile Ser Asn Glu Lys Lys Asn Asp
                85                  90                  95

Asp Asn Gly Lys Lys Leu Cys Lys Asp Leu Lys Tyr Ser Phe Ala Asp
            100                 105                 110

Tyr Gly Asp Leu Ile Lys Gly Thr Ser Ile Trp Asp Asn Glu Tyr Thr
            115                 120                 125

Lys Asp Leu Glu Leu Asn Leu Gln Asn Asn Phe Gly Lys Leu Phe Arg
130                 135                 140

Lys Tyr Ile Lys Lys Asn Asn Thr Ala Glu Gln His Thr Leu Tyr Ser
145                 150                 155                 160

Ser Leu Asp Glu Leu Arg Glu Ser Trp Trp Asn Thr Asn Lys Lys Tyr
                165                 170                 175

Ile Trp Leu Ala Met Lys His Gly Thr Thr Cys Ser Ser Gly Ser Gly
            180                 185                 190

Asp Asn Gly Asp Gly Ser Val Thr Gly Ser Gly Ser Ser Cys Asp Asp
            195                 200                 205

Met Ser Thr Ile Asp Leu Ile Pro Gln Tyr Leu Arg Phe Leu Gln Glu
210                 215                 220

Trp Val Glu His Phe Cys Lys Gln Arg Gln Glu Lys Val Asn Ala Val
225                 230                 235                 240

Ile Glu Asn Cys Asn Ser Cys Lys Asn Thr Ser Ser Lys Thr Lys Leu
                245                 250                 255

Gly Gly Thr Cys Asn Gly Glu Cys Lys Thr Glu Cys Glu Lys Lys Cys
            260                 265                 270

Lys Asp Glu Cys Glu Lys Tyr Lys Glu Phe Ile Glu Glu Cys Lys Arg
            275                 280                 285

Gly Asp Gly Thr Ala Gly Ser Pro Trp Val Lys Arg Trp Asp Gln Ile
            290                 295                 300

Tyr Met Arg Tyr Ser Lys Tyr Ile Glu Asp Ala Lys Arg Asn Arg Lys
305                 310                 315                 320

Ala Gly Thr Lys Ser Cys Gly Thr Ser Ala Ala Glu Asn Lys Cys Val
                325                 330                 335

Gln Ser

<210> SEQ ID NO 19
<211> LENGTH: 341
<212> TYPE: PRT
<213> ORGANISM: Plasamodium falciparum

<400> SEQUENCE: 19

Lys Cys Asp Lys Cys Lys Ser Glu Gln Ser Lys Asn Asn Asn Ile
1               5                   10                  15

Trp Ile Trp Lys Lys Ser Ser Gly Asp Glu Lys Gly Leu Gln Lys Glu
            20                  25                  30

Tyr Ala Asn Thr Ile Ala Leu Pro Pro Arg Thr Gln Ser Leu Tyr Leu
            35                  40                  45
```

Gly Asn Leu Pro Lys Leu Glu Asn Val Cys Lys Asp Val Thr Asp Ile
 50                  55                  60

Asn Phe Asp Thr Lys Glu Lys Phe Leu Ala Gly Cys Leu Ile Ala Ala
 65                  70                  75                  80

Phe His Glu Gly Lys Asn Leu Lys Thr Ser His Gln Asn Lys Asn Ala
                 85                  90                  95

Asp Asn Gly Lys Lys Asn Asp Asp Asn Gly Lys Lys Leu Cys Lys Ala
            100                 105                 110

Leu Lys Tyr Ser Phe Ala Asp Tyr Gly Asp Leu Ile Lys Gly Thr Ser
            115                 120                 125

Ile Trp Asp Asn Glu Tyr Thr Lys Asp Leu Glu Leu Asn Leu Gln Gln
130                 135                 140

Ile Phe Gly Lys Leu Phe Arg Lys Tyr Ile Lys Arg Asn Asn Thr Ala
145                 150                 155                 160

Glu Gln His Thr Leu Tyr Ser Ser Leu Asp Glu Leu Arg Glu Ser Trp
                165                 170                 175

Trp Asn Thr Asn Lys Lys Tyr Ile Trp Leu Ala Met Lys His Gly Thr
                180                 185                 190

Thr Cys Ser Ser Gly Ser Gly Asp Asn Gly Asp Gly Ser Val Thr Gly
            195                 200                 205

Ser Gly Ser Ser Cys Asp Asp Met Ser Thr Ile Asp Leu Ile Pro Gln
210                 215                 220

Tyr Leu Arg Phe Leu Gln Glu Trp Val Glu His Phe Cys Lys Gln Arg
225                 230                 235                 240

Gln Glu Lys Val Lys Asp Val Ile Thr Asn Cys Asn Ser Cys Lys Glu
                245                 250                 255

Cys Gly Gly Thr Cys Gly Ser Asp Cys Lys Thr Lys Cys Glu Ala Tyr
            260                 265                 270

Lys Lys Phe Ile Glu Glu Cys Asn Gly Thr Ala Asp Gly Gly Thr Ser
            275                 280                 285

Gly Ser Ser Trp Ser Lys Arg Trp Asp Gln Ile Tyr Lys Arg Tyr Ser
290                 295                 300

Lys Tyr Ile Glu Asp Ala Lys Arg Asn Arg Lys Ala Gly Thr Lys Asn
305                 310                 315                 320

Cys Gly Pro Ser Ser Gly Ala Asn Ser Gly Val Thr Thr Thr Glu Asn
                325                 330                 335

Lys Cys Val Gln Ser
            340

<210> SEQ ID NO 20
<211> LENGTH: 352
<212> TYPE: PRT
<213> ORGANISM: Plasmodium falciparum

<400> SEQUENCE: 20

Lys Cys Glu Lys Cys Glu Ser Glu Gln Ser Lys Lys Asn Asn Lys Tyr
 1               5                  10                  15

Trp Ile Trp Lys Lys Ser Ser Gly Asn Gly Glu Gly Leu Gln Glu Glu
                 20                  25                  30

Tyr Ala Asn Thr Ile Ala Leu Pro Pro Arg Thr His Ser Leu Cys Leu
             35                  40                  45

Val Cys Leu His Glu Lys Glu Gly Lys Lys Thr Gln Glu Leu Lys Asn
 50                  55                  60

Ile Arg Thr Asn Ser Glu Leu Leu Lys Glu Arg Ile Ile Ala Ala Phe

```
                65                  70                  75                  80
His Glu Gly Lys Asn Leu Lys Thr Ser Pro Gln Asn Lys Asn Asp Asn
                    85                  90                  95

Gly Lys Lys Leu Cys Lys Asp Leu Lys Tyr Ser Phe Ala Asp Tyr Gly
                    100                 105                 110

Asp Leu Ile Lys Gly Thr Ser Ile Trp Asp Asn Glu Tyr Thr Lys Asp
                    115                 120                 125

Leu Glu Leu Asn Leu Gln Lys Ile Phe Gly Lys Leu Phe Arg Lys Tyr
            130                 135                 140

Ile Lys Lys Asn Thr Ala Glu Gln His Thr Leu Tyr Ser Ser Leu
145                 150                 155                 160

Asp Glu Leu Arg Glu Ser Trp Trp Asn Thr Asn Lys Lys Tyr Ile Trp
                    165                 170                 175

Leu Ala Met Lys His Gly Ala Gly Met Asn Ser Thr Met Cys Asn Ala
                    180                 185                 190

Asp Gly Ser Val Thr Gly Ser Ser Asp Ser Gly Ser Thr Thr Cys Cys
                    195                 200                 205

Gly Asp Asn Gly Ser Ile Ser Cys Asp Asp Met Pro Thr Ile Asp Leu
                210                 215                 220

Ile Pro Gln Tyr Leu Arg Phe Leu Gln Glu Trp Val Glu His Phe Cys
225                 230                 235                 240

Glu Gln Arg Gln Glu Lys Val Asn Ala Val Ile Thr Asn Cys Lys Ser
                    245                 250                 255

Cys Lys Glu Cys Gly Gly Thr Cys Asn Ser Asp Cys Glu Lys Lys Cys
                    260                 265                 270

Lys Ala Tyr Lys Glu Phe Ile Glu Lys Cys Lys Gly Gly Gly Thr Glu
                    275                 280                 285

Gly Thr Ser Gly Ser Ser Trp Ser Lys Arg Trp Asp Gln Ile Tyr Lys
                290                 295                 300

Arg His Ser Lys His Ile Glu Asp Ala Lys Arg Asn Arg Lys Ala Gly
305                 310                 315                 320

Thr Lys Asn Cys Gly Ile Thr Thr Gly Thr Ile Ser Gly Glu Ser Ser
                    325                 330                 335

Gly Ala Asn Ser Gly Val Thr Thr Glu Asn Lys Cys Val Gln Ser
                    340                 345                 350

<210> SEQ ID NO 21
<211> LENGTH: 344
<212> TYPE: PRT
<213> ORGANISM: Plasmodium falciparum

<400> SEQUENCE: 21

Lys Cys Asp Lys Cys Lys Ser Gly Thr Ser Arg Ser Arg Lys Ile Trp
1               5                   10                  15

Thr Trp Arg Lys Phe Arg Gly Asn Gly Glu Gly Leu Gln Lys Glu Tyr
                    20                  25                  30

Ala Asn Thr Ile Gly Leu Ser Pro Arg Thr Gln Leu Leu Tyr Leu Val
                35                  40                  45

Cys Leu His Glu Lys Gly Lys Lys Thr Gln Glu Leu Lys Asn Ile Ser
            50                  55                  60

Thr Asn Ser Glu Leu Leu Lys Glu Trp Ile Ile Ala Ala Phe His Glu
65                  70                  75                  80

Gly Lys Asn Leu Lys Thr Thr Tyr Pro Gln Lys Lys Asn Asp Asp Asn
                    85                  90                  95
```

```
Gly Lys Lys Leu Cys Lys Ala Leu Lys Tyr Ser Phe Ala Asp Tyr Gly
            100                 105                 110

Asp Leu Ile Lys Gly Thr Ser Ile Trp Asp Asn Asp Phe Thr Lys Asp
        115                 120                 125

Leu Glu Leu Asn Leu Gln Lys Ile Phe Gly Lys Leu Phe Arg Lys Tyr
    130                 135                 140

Ile Lys Lys Asn Ile Ala Ser Asp Glu Asn Thr Ser Tyr Ser Ser Leu
145                 150                 155                 160

Asp Glu Leu Arg Glu Ser Trp Trp Asn Thr Asn Lys Lys Tyr Ile Trp
                165                 170                 175

Thr Ala Met Lys His Gly Ala Met Asn Gly Thr Thr Cys Cys Gly
            180                 185                 190

Asp Gly Ser Val Thr Gly Ser Ser Asp Ser Gly Ser Thr Thr Cys Cys
        195                 200                 205

Gly Asp Gly Ser Val Thr Gly Ser Gly Ser Ser Cys Asp Asp Ile Pro
    210                 215                 220

Thr Ile Asp Leu Ile Pro Gln Tyr Leu Arg Phe Leu Gln Glu Trp Val
225                 230                 235                 240

Glu His Phe Cys Glu Gln Arg Gln Glu Lys Val Lys Asp Val Ile Thr
                245                 250                 255

Asn Cys Lys Ser Cys Lys Glu Ser Glu Lys Lys Cys Lys Asn Lys Cys
            260                 265                 270

Asp Ala Tyr Lys Glu Phe Ile Asp Gly Thr Gly Ser Gly Gly Gly Thr
        275                 280                 285

Gly Thr Ala Gly Ser Ser Trp Ser Lys Arg Trp Asp Gln Ile Tyr Met
    290                 295                 300

Arg Tyr Ser Lys Tyr Ile Glu Asp Ala Lys Arg Asn Arg Lys Ala Gly
305                 310                 315                 320

Thr Lys Asn Cys Gly Thr Ser Ser Gly Ala Asn Ser Gly Val Thr Thr
                325                 330                 335

Thr Glu Asn Lys Cys Val Gln Ser
            340

<210> SEQ ID NO 22
<211> LENGTH: 350
<212> TYPE: PRT
<213> ORGANISM: Plasmodium falciparum

<400> SEQUENCE: 22

Lys Cys Glu Lys Cys Lys Ser Glu Gln Ser Lys Lys Asn Asn Lys Ile
1               5                   10                  15

Trp Thr Trp Arg Lys Phe Pro Gly Asn Gly Glu Gly Leu Gln Lys Glu
                20                  25                  30

Tyr Ala Asn Thr Ile Gly Leu Ser Pro Arg Thr Gln Leu Leu Tyr Leu
            35                  40                  45

Val Cys Leu His Glu Lys Gly Lys Lys Thr Gln His Lys Thr Ile Ser
        50                  55                  60

Thr Asn Ser Glu Leu Leu Lys Glu Trp Ile Ile Ala Ala Phe His Glu
65                  70                  75                  80

Gly Lys Asn Leu Lys Lys Arg Tyr Leu Glu Lys Lys Gly Asp Asn
                85                  90                  95

Asn Ser Lys Leu Cys Lys Asp Leu Lys Tyr Ser Phe Ala Asp Tyr Gly
            100                 105                 110

Asp Leu Ile Lys Gly Thr Ser Ile Trp Asp Asn Asp Phe Thr Lys Asp
        115                 120                 125
```

Leu Glu Leu Asn Leu Gln Gln Ile Phe Gly Lys Leu Phe Arg Lys Tyr
                130                 135                 140

Ile Lys Lys Asn Ile Ala Ser Asp Glu Asn Thr Ser Tyr Ser Ser Leu
145                 150                 155                 160

Asp Glu Leu Arg Glu Ser Trp Trp Asn Thr Asn Lys Lys Tyr Ile Trp
                165                 170                 175

Thr Ala Met Lys His Gly Ala Gly Met Asn Ser Thr Met Cys Asn Gly
                180                 185                 190

Asp Gly Ser Val Thr Gly Ser Ser Asp Ser Gly Ser Thr Thr Cys Ser
                195                 200                 205

Gly Asp Asn Gly Ser Ile Ser Cys Asp Ile Pro Thr Ile Asp Leu
210                 215                 220

Ile Pro Gln Tyr Leu Arg Phe Leu Gln Glu Trp Val Glu His Phe Cys
225                 230                 235                 240

Glu Gln Arg Gln Glu Lys Val Lys Asp Val Ile Lys Asn Cys Asn Ser
                245                 250                 255

Cys Lys Glu Cys Gly Gly Thr Cys Asn Gly Glu Cys Lys Thr Glu Cys
                260                 265                 270

Lys Asn Lys Cys Lys Asp Glu Cys Glu Lys Tyr Lys Asn Phe Ile Glu
                275                 280                 285

Val Cys Thr Gly Gly Asp Gly Thr Ala Gly Ser Pro Trp Ser Lys Arg
                290                 295                 300

Trp Tyr Gln Ile Tyr Met Arg Tyr Ser Lys Tyr Ile Glu Asp Ala Lys
305                 310                 315                 320

Arg Asn Arg Lys Ala Gly Thr Lys Ser Cys Gly Thr Ser Ser Gly Ala
                325                 330                 335

Asn Ser Gly Val Thr Thr Thr Glu Ser Lys Cys Val Gln Ser
                340                 345                 350

<210> SEQ ID NO 23
<211> LENGTH: 359
<212> TYPE: PRT
<213> ORGANISM: Plasmodium falciparum

<400> SEQUENCE: 23

Lys Cys Glu Lys Cys Lys Ser Glu Gln Ser Lys Lys Asn Asn Lys Asn
1               5                   10                  15

Trp Ile Trp Arg Lys Phe Pro Gly Asn Gly Glu Gly Leu Gln Lys Glu
                20                  25                  30

Tyr Ala Asn Thr Ile Gly Leu Pro Pro Arg Thr His Ser Leu Tyr Leu
                35                  40                  45

Val Cys Leu His Glu Lys Gly Lys Lys Thr Gln Glu Leu Lys Asn Ile
50                  55                  60

Arg Thr Asn Ser Glu Leu Leu Lys Glu Trp Ile Ile Ala Ala Phe His
65                  70                  75                  80

Glu Gly Lys Asn Leu Lys Lys Arg Tyr His Gln Asn Asn Ser Gly
                85                  90                  95

Asn Lys Lys Lys Leu Cys Lys Ala Leu Glu Tyr Ser Phe Ala Asp Tyr
                100                 105                 110

Gly Asp Leu Ile Lys Gly Thr Ser Ile Trp Asp Asn Glu Tyr Thr Lys
                115                 120                 125

Asp Leu Glu Leu Asn Leu Gln Gln Ile Phe Gly Lys Leu Phe Arg Lys
                130                 135                 140

Tyr Ile Lys Lys Asn Ile Ser Thr Glu Gln Asp Thr Leu Tyr Ser Ser

```
                145                 150                 155                 160
Leu Asp Glu Leu Arg Glu Ser Trp Trp Asn Thr Asn Lys Lys Tyr Ile
                    165                 170                 175

Trp Leu Ala Met Lys His Gly Ala Gly Met Asn Ser Thr Thr Cys Cys
                180                 185                 190

Gly Asp Gly Ser Val Thr Gly Ser Asp Ser Gly Ser Thr Thr Cys
            195                 200                 205

Ser Gly Asp Asn Gly Ser Ile Ser Cys Asp Asp Met Pro Thr Ile Asp
        210                 215                 220

Leu Ile Pro Gln Tyr Leu Arg Phe Leu Gln Glu Trp Val Glu His Phe
225                 230                 235                 240

Cys Glu Gln Arg Gln Glu Lys Val Lys Asp Val Ile Glu Asn Cys Lys
                245                 250                 255

Ser Cys Lys Asn Thr Ser Gly Glu Arg Ile Ile Gly Gly Thr Cys Asn
                260                 265                 270

Gly Glu Cys Lys Thr Glu Cys Glu Lys Cys Lys Ala Ala Cys Glu
            275                 280                 285

Ala Tyr Lys Thr Phe Ile Glu Glu Cys Glu Gly Lys Ala Ala Glu Gly
        290                 295                 300

Thr Ser Gly Ser Ser Trp Ser Lys Arg Trp Tyr Gln Ile Tyr Met Arg
305                 310                 315                 320

Tyr Ser Lys Tyr Ile Glu Asp Ala Lys Arg Asn Arg Lys Ala Gly Thr
                325                 330                 335

Lys Asn Cys Gly Lys Ser Ser Gly Ala Asn Ser Gly Val Thr Thr Thr
                340                 345                 350

Glu Asn Lys Cys Val Gln Ser
            355

<210> SEQ ID NO 24
<211> LENGTH: 270
<212> TYPE: PRT
<213> ORGANISM: Plasmodium falciparum

<400> SEQUENCE: 24

Asn Tyr Ile Lys Asp Asp Pro Tyr Ser Lys Glu Tyr Val Thr Lys Leu
1               5                   10                  15

Ser Phe Ile Pro Asn Ser Ser Asp Ala Asn Asn Pro Ser Gly Glu Thr
                20                  25                  30

Ala Asn His Asn Asp Glu Val Cys Asn Pro Asn Glu Ser Glu Ile Ser
            35                  40                  45

Ser Val Glu His Ala Gln Thr Ser Val Leu Leu Ser Gln Lys Ala Tyr
        50                  55                  60

Ile Thr His Ser Ser Ile Lys Ala Asn Lys Lys Lys Val Cys Lys Tyr
65                  70                  75                  80

Val Lys Leu Gly Val Arg Glu Asn Asp Lys Asp Leu Lys Ile Cys Val
                85                  90                  95

Ile Glu Asp Asp Ser Leu Arg Gly Val Glu Asn Cys Cys Phe Lys Asp
                100                 105                 110

Phe Leu Arg Ile Leu Gln Glu Asn Cys Ser Asp Asn Lys Arg Glu Ser
            115                 120                 125

Ser Ser Asn Gly Ser Cys Asn Asn Asn Glu Glu Ala Cys Glu Lys
        130                 135                 140

Asn Leu Asp Glu Ala Leu Ala Ser Leu Thr Asn Cys Tyr Lys Asn Gln
145                 150                 155                 160
```

```
Lys Cys Lys Ser Gly Thr Ser Thr Val Asn Asn Lys Trp Ile Trp
            165                 170                 175

Lys Lys Ser Ser Gly Lys Glu Gly Leu Gln Lys Glu Tyr Ala Asn
        180                 185                 190

Thr Ile Gly Leu Pro Pro Arg Thr Gln Ser Leu Cys Leu Val Val Cys
            195                 200                 205

Leu Asp Glu Lys Glu Gly Lys Thr Gln Glu Leu Lys Asn Ile Arg Thr
210                 215                 220

Asn Ser Glu Leu Leu Lys Glu Trp Ile Ile Ala Ala Phe His Glu Gly
225                 230                 235                 240

Lys Asn Leu Lys Lys Arg Tyr His Gln Asn Lys Asn Asp Asp Asn Asn
            245                 250                 255

Ser Lys Leu Cys Lys Ala Leu Lys Tyr Ser Phe Ala Asp Tyr
            260                 265                 270

<210> SEQ ID NO 25
<211> LENGTH: 334
<212> TYPE: PRT
<213> ORGANISM: Plasmodium falciparum

<400> SEQUENCE: 25

Lys Cys Asp Lys Cys Lys Ser Glu Gln Ser Lys Lys Asn Asn Lys Tyr
1               5                   10                  15

Trp Ile Trp Lys Lys Tyr Ser Val Lys Glu Gly Gly Leu Gln Lys Glu
            20                  25                  30

Tyr Ala Asn Thr Ile Ala Leu Pro Pro Arg Thr Gln Ser Leu Cys Leu
            35                  40                  45

Val Val Cys Leu Asp Glu Lys Glu Gly Lys Thr Gln Glu Leu Lys Asn
50                  55                  60

Ile Arg Thr Asn Ser Glu Leu Leu Lys Glu Arg Ile Ile Ala Ala Phe
65                  70                  75                  80

His Glu Gly Lys Asn Leu Lys Thr Tyr His Glu Lys Lys Lys Gly Asp
            85                  90                  95

Asp Gly Lys Lys Leu Cys Lys Asp Leu Lys Tyr Ser Phe Ala Asp Tyr
            100                 105                 110

Gly Asp Leu Ile Lys Gly Thr Ser Ile Trp Asp Asn Asp Phe Thr Lys
            115                 120                 125

Asp Leu Glu Leu Asn Leu Gln Lys Ile Phe Gly Lys Leu Phe Arg Lys
            130                 135                 140

Tyr Ile Lys Lys Asn Asn Thr Ala Glu Gln His Thr Ser Tyr Ser Ser
145                 150                 155                 160

Leu Asp Glu Leu Arg Glu Ser Trp Trp Asn Thr Asn Lys Lys Tyr Ile
            165                 170                 175

Trp Thr Ala Met Lys His Gly Ala Glu Met Asn Gly Thr Thr Cys Ser
            180                 185                 190

Cys Ser Gly Asp Ser Ser Asn Asp Ile Pro Thr Ile Asp Leu Ile Pro
            195                 200                 205

Gln Tyr Leu Arg Phe Leu Gln Glu Trp Val Glu His Phe Cys Glu Gln
            210                 215                 220

Arg Gln Ala Lys Val Asn Ala Val Ile Lys Asn Cys Lys Ser Cys Lys
225                 230                 235                 240

Glu Cys Gly Gly Thr Cys Asn Gly Glu Cys Lys Thr Glu Cys Lys Thr
            245                 250                 255

Lys Cys Lys Gly Glu Cys Glu Lys Tyr Lys Glu Phe Ile Glu Lys Cys
            260                 265                 270
```

Glu Gly Gln Ala Ala Glu Gly Thr Ser Gly Ser Ser Trp Ser Lys Arg
        275                 280                 285

Trp Tyr Gln Ile Tyr Met Arg Tyr Ser Lys Tyr Ile Glu Asp Ala Lys
290                 295                 300

Arg Asn Arg Lys Ala Gly Thr Lys Asn Cys Gly Thr Ser Ser Gly Ala
305                 310                 315                 320

Asn Ser Gly Val Thr Thr Thr Glu Asn Lys Cys Val Gln Ser
                325                 330

<210> SEQ ID NO 26
<211> LENGTH: 351
<212> TYPE: PRT
<213> ORGANISM: Plasmodium falciparum

<400> SEQUENCE: 26

Lys Cys Asp Lys Cys Lys Ser Glu Gln Ser Lys Lys Asn Asn Lys Asn
1               5                   10                  15

Trp Ile Trp Lys Lys Tyr Ser Gly Thr Glu Gly Gly Leu Gln Lys Glu
            20                  25                  30

Tyr Ala Asn Thr Ile Ala Leu Pro Pro Arg Thr Gln Ser Leu Tyr Leu
        35                  40                  45

Val Cys Leu His Glu Lys Glu Lys Thr Gln Glu Leu Lys Asn Ile
    50                  55                  60

Ser Thr Asn Ser Glu Leu Leu Lys Glu Trp Ile Ala Ala Phe His
65                  70                  75                  80

Glu Gly Lys Asn Leu Lys Ile Ser Pro Gln Asn Lys Asn Asp Asn Gly
                85                  90                  95

Lys Asn Leu Cys Lys Asp Leu Lys Tyr Ser Phe Ala Asp Tyr Gly Asp
            100                 105                 110

Leu Ile Lys Gly Thr Ser Ile Trp Asp Asn Asp Phe Thr Lys Asp Leu
        115                 120                 125

Glu Leu Asn Leu Gln Gln Ile Phe Gly Lys Leu Phe Arg Lys Tyr Ile
    130                 135                 140

Lys Lys Asn Asn Thr Ala Glu Gln Asp Thr Leu Tyr Ser Ser Leu Asp
145                 150                 155                 160

Glu Leu Arg Glu Ser Trp Trp Asn Thr Asn Lys Lys Tyr Ile Trp Thr
                165                 170                 175

Ala Met Lys His Gly Ala Gly Met Asn Gly Thr Thr Cys Cys Gly Asp
            180                 185                 190

Gly Ser Val Thr Gly Ser Ser Asp Ser Gly Ser Thr Thr Cys Cys Gly
        195                 200                 205

Asp Gly Ser Val Thr Gly Ser Gly Ser Ser Cys Asp Asp Ile Pro Thr
    210                 215                 220

Ile Asp Leu Ile Pro Gln Tyr Leu Arg Phe Leu Gln Glu Trp Val Glu
225                 230                 235                 240

His Phe Cys Glu Gln Arg Gln Ala Lys Val Lys Asp Val Ile Lys Asn
                245                 250                 255

Cys Asn Ser Cys Lys Glu Cys Gly Gly Thr Cys Asn Gly Glu Cys Lys
            260                 265                 270

Thr Glu Cys Glu Lys Lys Cys Lys Gly Glu Cys Glu Ala Tyr Lys Lys
        275                 280                 285

Phe Ile Glu Lys Cys Asn Gly Gly Gly Glu Gly Thr Ser Gly Ser
    290                 295                 300

Ser Trp Ser Lys Arg Trp Asp Gln Ile Tyr Met Arg Tyr Ser Lys Tyr

```
        305                 310                 315                 320
Ile Glu Asp Ala Lys Arg Asn Arg Lys Ala Gly Thr Lys Asn Cys Gly
                    325                 330                 335

Thr Ser Ser Thr Thr Asn Ala Ala Glu Asn Lys Cys Val Gln Ser
                340                 345                 350

<210> SEQ ID NO 27
<211> LENGTH: 353
<212> TYPE: PRT
<213> ORGANISM: Plasmodium falciparum

<400> SEQUENCE: 27

Lys Cys Asp Lys Cys Lys Ser Gly Thr Ser Thr Val Asn Lys Lys Trp
1               5                   10                  15

Ile Trp Lys Lys Phe Pro Gly Lys Glu Gly Gly Leu Gln Glu Glu Tyr
                20                  25                  30

Ala Asn Thr Ile Ala Leu Pro Pro Arg Thr Gln Ser Leu Cys Leu Val
            35                  40                  45

Val Cys Leu Asp Glu Lys Glu Gly Lys Thr Gln His Lys Thr Ile Ser
        50                  55                  60

Thr Asn Ser Glu Leu Leu Lys Glu Trp Ile Ile Ala Ala Phe His Glu
65                  70                  75                  80

Gly Lys Asn Leu Lys Ile Ser Asn Lys Lys Asn Asp Glu Asn Asn
                85                  90                  95

Ser Lys Leu Cys Lys Asp Leu Lys Tyr Ser Phe Ala Asp Tyr Gly Asp
                100                 105                 110

Leu Ile Lys Gly Thr Ser Ile Trp Asp Asn Asp Phe Thr Lys Asp Leu
            115                 120                 125

Glu Leu Asn Leu Gln Lys Ile Phe Gly Lys Leu Phe Arg Lys Tyr Ile
        130                 135                 140

Lys Lys Asn Asn Thr Ala Glu Gln Asp Thr Ser Tyr Ser Ser Leu Asp
145                 150                 155                 160

Glu Leu Arg Glu Ser Trp Trp Asn Thr Asn Lys Lys Tyr Ile Trp Leu
                165                 170                 175

Ala Met Lys His Gly Thr Thr Cys Ser Ser Gly Ser Gly Asp Asn Gly
            180                 185                 190

Asp Gly Ser Val Thr Gly Ser Ser Asp Ser Gly Ser Thr Thr Cys Cys
        195                 200                 205

Gly Asp Gly Ser Val Thr Gly Ser Gly Ser Ser Cys Asp Asp Ile Pro
    210                 215                 220

Thr Ile Asp Leu Ile Pro Gln Tyr Leu Arg Phe Leu Gln Glu Trp Val
225                 230                 235                 240

Glu His Phe Cys Lys Gln Arg Gln Ala Lys Val Lys Asp Val Ile Glu
                245                 250                 255

Asn Cys Lys Ser Cys Lys Asn Thr Ser Ser Lys Thr Lys Leu Gly Asp
            260                 265                 270

Thr Cys Asn Ser Asp Cys Lys Thr Cys Lys Val Ala Cys Glu Lys
        275                 280                 285

Tyr Lys Glu Phe Ile Glu Lys Cys Val Ser Ala Ala Gly Gly Thr Ser
    290                 295                 300

Gly Ser Ser Trp Val Lys Arg Trp Asp Gln Ile Tyr Met Arg Tyr Ser
305                 310                 315                 320

Lys Tyr Ile Glu Asp Ala Lys Arg Asn Arg Lys Ala Gly Thr Lys Asn
                325                 330                 335
```

```
Cys Gly Pro Ser Ser Thr Thr Ser Thr Ala Glu Ser Lys Cys Val Gln
            340                 345                 350
Ser
```

<210> SEQ ID NO 28
<211> LENGTH: 327
<212> TYPE: PRT
<213> ORGANISM: Plasmodium falciparum

<400> SEQUENCE: 28

```
Lys Cys Asp Lys Cys Lys Ser Gly Thr Ser Thr Val Asn Lys Lys Trp
1               5                   10                  15

Ile Trp Lys Lys Tyr Ser Gly Lys Glu Gly Gly Leu Gln Lys Glu Tyr
            20                  25                  30

Ala Asn Thr Ile Gly Leu Pro Pro Arg Thr Gln Ser Leu Cys Leu Val
        35                  40                  45

Cys Leu His Glu Lys Glu Gly Lys Thr Gln Glu Leu Lys Asn Ile Ser
    50                  55                  60

Thr Asn Ser Glu Leu Leu Lys Glu Trp Ile Ile Ala Ala Phe His Glu
65                  70                  75                  80

Gly Lys Asn Leu Lys Ile Ser Asn Lys Lys Asn Asp Asp Asn Gly
                85                  90                  95

Lys Lys Leu Cys Lys Asp Leu Lys Tyr Ser Phe Ala Asp Tyr Gly Asp
                100                 105                 110

Leu Ile Lys Gly Thr Ser Ile Trp Asp Asn Asp Phe Thr Lys Asp Leu
            115                 120                 125

Glu Leu Asn Leu Gln Lys Ile Phe Gly Lys Leu Phe Arg Lys Tyr Ile
        130                 135                 140

Lys Lys Asn Asn Thr Ala Glu Gln Asp Thr Leu Tyr Ser Ser Leu Asp
145                 150                 155                 160

Glu Leu Arg Glu Ser Trp Trp Asn Thr Asn Lys Lys Tyr Ile Trp Thr
                165                 170                 175

Ala Met Lys His Gly Ala Gly Met Asn Ser Thr Thr Cys Ser Cys Ser
            180                 185                 190

Gly Asp Ser Ser Asn Asp Ile Pro Thr Ile Asp Leu Ile Pro Gln Tyr
        195                 200                 205

Leu Arg Phe Leu Gln Glu Trp Val Glu His Phe Cys Lys Gln Arg Gln
    210                 215                 220

Glu Lys Val Asn Ala Val Ile Thr Asn Cys Lys Ser Cys Lys Glu Ser
225                 230                 235                 240

Gly Gly Thr Cys Asn Ser Asp Cys Glu Lys Cys Lys Ile Glu Cys
                245                 250                 255

Glu Lys Tyr Lys Asn Phe Ile Glu Lys Cys Val Thr Ala Ala Gly Gly
            260                 265                 270

Thr Ser Gly Ser Ser Trp Ser Lys Arg Trp Asp Gln Ile Tyr Lys Met
        275                 280                 285

Tyr Ser Lys Tyr Ile Glu Asp Ala Lys Arg Asn Arg Lys Ala Gly Thr
    290                 295                 300

Lys Asn Cys Gly Pro Ser Ser Thr Thr Asn Ala Ala Ser Thr Asp
305                 310                 315                 320

Glu Asn Lys Cys Val Gln Ser
                325
```

<210> SEQ ID NO 29
<211> LENGTH: 628

<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: dd2full 745 amino acids

<400> SEQUENCE: 29

```
Asn Tyr Ile Lys Gly Asp Pro Tyr Phe Ala Glu Tyr Ala Thr Lys Leu
1               5                   10                  15

Ser Phe Ile Leu Asn Ser Ser Asp Thr Glu Asn Ala Ser Glu Thr Pro
            20                  25                  30

Ser Lys Tyr Tyr Asp Glu Ala Cys Asn Cys Asn Glu Ser Glu Ile Ala
        35                  40                  45

Ser Val Gly Gln Ala Gln Thr Ser Gly Pro Ser Ser Asn Lys Thr Cys
50                  55                  60

Ile Thr His Ser Ser Ile Lys Thr Asn Lys Lys Glu Cys Lys Asp
65                  70                  75                  80

Val Lys Leu Gly Ile Asn Asn Asn Asp Lys Val Leu Arg Val Cys Val
                85                  90                  95

Ile Glu Asp Thr Ser Leu Ser Gly Val Asp Asn Cys Cys Cys Gln Asp
            100                 105                 110

Leu Leu Gly Ile Leu Gln Glu Asn Cys Ser Asp Asn Lys Arg Gly Ser
        115                 120                 125

Ser Ser Asn Gly Ser Cys Asp Lys Asn Ser Glu Glu Ile Cys Gln Lys
130                 135                 140

Lys Leu Glu Lys Val Phe Ala Ser Leu Thr Asn Gly Tyr Lys Cys Asp
145                 150                 155                 160

Lys Cys Lys Ser Gly Thr Ser Arg Ser Lys Lys Trp Ile Trp Lys
                165                 170                 175

Lys Ser Ser Gly Asn Glu Glu Gly Leu Gln Lys Glu Tyr Ala Asn Thr
            180                 185                 190

Ile Gly Leu Pro Pro Arg Thr Gln Ser Leu Cys Leu Val Cys Leu His
        195                 200                 205

Glu Lys Glu Gly Lys Thr Gln His Lys Thr Ile Ser Thr Asn Ser Glu
210                 215                 220

Leu Leu Lys Glu Trp Ile Ile Ala Ala Phe His Glu Gly Lys Asn Leu
225                 230                 235                 240

Lys Thr Ser His Glu Lys Lys Asn Asp Asp Asn Gly Lys Lys Leu Cys
                245                 250                 255

Lys Ala Leu Glu Tyr Ser Phe Ala Asp Tyr Gly Asp Leu Ile Lys Gly
            260                 265                 270

Thr Ser Ile Trp Asp Asn Glu Tyr Thr Lys Asp Leu Glu Leu Asn Leu
        275                 280                 285

Gln Lys Ile Phe Gly Lys Leu Phe Arg Lys Tyr Ile Lys Lys Asn Asn
290                 295                 300

Thr Ala Glu Gln His Thr Ser Tyr Ser Ser Leu Asp Glu Leu Arg Glu
305                 310                 315                 320

Ser Trp Trp Asn Thr Asn Lys Lys Tyr Ile Trp Thr Ala Met Lys His
                325                 330                 335

Gly Ala Gly Met Asn Gly Thr Thr Cys Ser Cys Ser Gly Asp Ser Ser
            340                 345                 350

Asn Asp Met Pro Thr Ile Asp Leu Ile Pro Gln Tyr Leu Arg Phe Leu
        355                 360                 365
```

```
Gln Glu Trp Val Glu His Phe Cys Lys Gln Arg Gln Glu Lys Val Asn
    370                 375                 380

Ala Val Ile Glu Asn Cys Asn Ser Cys Lys Glu Ser Gly Gly Thr Cys
385                 390                 395                 400

Asn Ser Asp Cys Lys Thr Glu Cys Lys Asn Lys Cys Glu Ala Tyr Lys
                405                 410                 415

Glu Phe Ile Glu Asp Cys Lys Gly Gly Thr Gly Thr Ala Gly Ser
            420                 425                 430

Pro Trp Ser Lys Arg Trp Asp Gln Ile Tyr Lys Arg Tyr Ser Lys His
        435                 440                 445

Ile Glu Asp Ala Lys Arg Asn Arg Lys Ala Gly Thr Lys Asn Cys Gly
    450                 455                 460

Thr Ser Thr Thr Asn Ala Ala Ala Ser Thr Asp Glu Asn Lys Cys
465                 470                 475                 480

Val Gln Ser Asp Val Asp Ser Phe Phe Lys His Leu Ile Asp Ile Gly
                485                 490                 495

Leu Thr Thr Pro Ser Ser Tyr Leu Ser Asn Val Leu Asp Asp Asn Ile
            500                 505                 510

Cys Gly Ala Asp Lys Ala Pro Trp Thr Thr Tyr Thr Thr Tyr Thr Thr
    515                 520                 525

Thr Lys Asn Cys Asp Ile Gln Lys Lys Thr Pro Lys Ser Gln Ser Cys
    530                 535                 540

Asp Thr Leu Val Val Val Asn Val Pro Ser Pro Leu Gly Asn Thr Pro
545                 550                 555                 560

His Glu Tyr Lys Tyr Ala Cys Glu Cys Lys Ile Pro Thr Thr Glu Glu
                565                 570                 575

Thr Cys Asp Asp Arg Lys Glu Tyr Met Asn Gln Trp Ser Cys Gly Ser
            580                 585                 590

Ala Gln Thr Val Arg Gly Arg Ser Gly Lys Asp Asp Tyr Glu Leu Tyr
        595                 600                 605

Thr Tyr Asn Gly Val Lys Glu Thr Lys Pro Leu Gly Thr Leu Lys Asn
    610                 615                 620

Ser Lys Leu Asp
625

<210> SEQ ID NO 30
<211> LENGTH: 350
<212> TYPE: PRT
<213> ORGANISM: Plasmodium falciparum

<400> SEQUENCE: 30

Lys Cys Glu Lys Cys Lys Ser Glu Gln Ser Lys Lys Asn Asn Lys Asn
1               5                   10                  15

Trp Ile Trp Arg Lys Phe Arg Gly Thr Glu Gly Gly Leu Gln Glu Glu
            20                  25                  30

Tyr Ala Asn Thr Ile Gly Leu Pro Pro Arg Thr Gln Ser Leu Cys Leu
        35                  40                  45

Val Val Cys Leu Asp Glu Lys Gly Lys Thr Gln Glu Leu Lys Asn
    50                  55                  60

Ile Arg Thr Asn Ser Glu Leu Leu Lys Glu Trp Ile Ile Ala Ala Phe
65                  70                  75                  80

His Glu Gly Lys Asn Leu Lys Pro Ser His Gln Asn Lys Asn Ser Gly
                85                  90                  95

Asn Lys Glu Asn Leu Cys Lys Ala Leu Lys Tyr Ser Phe Ala Asp Tyr
            100                 105                 110
```

Gly Asp Leu Ile Lys Gly Thr Ser Ile Trp Asp Asn Asp Phe Thr Lys
            115                 120                 125

Asp Leu Glu Leu Asn Leu Gln Lys Ile Phe Gly Lys Leu Phe Arg Lys
    130                 135                 140

Tyr Ile Lys Lys Asn Asn Thr Ala Glu Gln His Thr Ser Tyr Ser Ser
145                 150                 155                 160

Leu Asp Glu Leu Arg Glu Ser Trp Trp Asn Thr Asn Lys Lys Tyr Ile
                165                 170                 175

Trp Thr Ala Met Lys His Gly Ala Glu Met Asn Gly Thr Thr Cys Asn
            180                 185                 190

Ala Asp Gly Ser Val Thr Gly Ser Ser Asp Ser Gly Ser Thr Thr Cys
            195                 200                 205

Ser Gly Asp Asn Gly Ser Ile Ser Cys Asp Asp Ile Pro Thr Ile Asp
    210                 215                 220

Leu Ile Pro Gln Tyr Leu Arg Phe Leu Gln Glu Trp Val Glu His Phe
225                 230                 235                 240

Cys Lys Gln Arg Gln Glu Lys Val Asn Ala Val Ile Asn Ser Cys Asn
                245                 250                 255

Ser Cys Lys Asn Thr Ser Ser Lys Thr Lys Leu Gly Asp Thr Cys Asn
            260                 265                 270

Ser Asp Cys Lys Thr Lys Cys Lys Ile Glu Cys Glu Lys Tyr Lys Thr
    275                 280                 285

Phe Ile Glu Lys Cys Val Thr Ala Ala Gly Gly Thr Ser Gly Ser Pro
290                 295                 300

Trp Ser Lys Arg Trp Asp Gln Ile Tyr Lys Arg Tyr Ser Lys Tyr Ile
305                 310                 315                 320

Glu Asp Ala Lys Arg Asn Arg Lys Ala Gly Thr Lys Asn Cys Gly Pro
                325                 330                 335

Ser Ser Thr Thr Ser Thr Ala Glu Ser Lys Cys Val Gln Ser
            340                 345                 350

<210> SEQ ID NO 31
<211> LENGTH: 330
<212> TYPE: PRT
<213> ORGANISM: Plasmodium falciparum

<400> SEQUENCE: 31

Lys Cys Asp Lys Cys Lys Ser Glu Gln Ser Lys Lys Asn Asn Lys Asn
1               5                   10                  15

Trp Ile Trp Arg Lys Tyr Ser Gly Asn Gly Glu Gly Leu Gln Lys Glu
            20                  25                  30

Tyr Ala Asn Thr Ile Gly Leu Pro Pro Arg Thr His Ser Leu Tyr Leu
            35                  40                  45

Val Cys Leu His Glu Lys Glu Gly Lys Thr Gln Glu Leu Lys Asn Ile
    50                  55                  60

Arg Thr Asn Ser Glu Leu Leu Lys Glu Trp Ile Ile Ala Ala Phe His
65                  70                  75                  80

Glu Gly Lys Asn Leu Lys Thr Thr Tyr Leu Glu Asn Lys Asn Asp Glu
                85                  90                  95

Asn Lys Lys Lys Leu Cys Lys Ala Leu Lys Tyr Ser Phe Ala Asp Tyr
            100                 105                 110

Gly Asp Leu Ile Lys Gly Thr Ser Ile Trp Asp Asn Asp Phe Thr Lys
            115                 120                 125

Asp Leu Glu Leu Asn Leu Gln Lys Ile Phe Gly Lys Leu Phe Arg Lys
    130                 135                 140

```
            130                 135                 140
Tyr Ile Lys Lys Asn Ile Ala Ser Asp Glu Asn Thr Leu Tyr Ser Ser
145                 150                 155                 160

Leu Asp Glu Leu Arg Glu Ser Trp Trp Asn Thr Asn Lys Lys Tyr Ile
                165                 170                 175

Trp Thr Ala Met Lys His Gly Ala Glu Met Asn Gly Thr Thr Cys Ser
                180                 185                 190

Ser Gly Ser Gly Asp Asn Gly Ser Ile Ser Cys Asp Asp Ile Pro Thr
            195                 200                 205

Ile Asp Leu Ile Pro Gln Tyr Leu Arg Phe Leu Gln Glu Trp Val Gly
        210                 215                 220

His Phe Cys Lys Gln Arg Gln Glu Lys Val Asn Ala Val Ile Thr Asn
225                 230                 235                 240

Cys Asn Ser Cys Lys Glu Ser Gly Gly Thr Cys Asn Ser Asp Cys Glu
                245                 250                 255

Lys Lys Cys Lys Ile Glu Cys Glu Lys Tyr Lys Lys Phe Ile Glu Glu
                260                 265                 270

Cys Arg Thr Ala Ala Gly Gly Thr Gly Ser Pro Trp Ser Lys Arg
        275                 280                 285

Trp Asp Gln Ile Tyr Lys Met Tyr Ser Lys Tyr Ile Glu Asp Ala Lys
        290                 295                 300

Arg Asn Arg Lys Ala Gly Thr Lys Asn Cys Gly Pro Ser Ser Thr Thr
305                 310                 315                 320

Ser Thr Ala Glu Ser Lys Cys Val Gln Ser
                325                 330

<210> SEQ ID NO 32
<211> LENGTH: 334
<212> TYPE: PRT
<213> ORGANISM: Plasmodium falciparum

<400> SEQUENCE: 32

Lys Cys Asp Lys Cys Lys Ser Glu Gln Ser Lys Lys Asn Asn Lys Asn
1               5                   10                  15

Trp Ile Trp Arg Lys Tyr Ser Gly Asn Gly Glu Gly Leu Gln Lys Glu
                20                  25                  30

Tyr Ala Asn Thr Ile Gly Leu Pro Pro Arg Thr His Ser Leu Tyr Leu
            35                  40                  45

Val Cys Leu His Glu Lys Glu Gly Lys Thr Gln His Lys Thr Ile Ser
    50                  55                  60

Thr Asn Ser Glu Leu Leu Lys Glu Trp Ile Ile Ala Ala Phe His Glu
65                  70                  75                  80

Gly Lys Asn Leu Lys Lys Arg Tyr Pro Gln Asn Asn Ser Gly Asn
                85                  90                  95

Lys Lys Lys Leu Cys Lys Asp Leu Lys Tyr Ser Phe Ala Asp Tyr Gly
                100                 105                 110

Asp Leu Ile Lys Gly Thr Ser Ile Trp Asp Asn Glu Tyr Thr Lys Asp
            115                 120                 125

Leu Glu Leu Asn Leu Gln Lys Ala Phe Gly Lys Leu Phe Arg Lys Tyr
        130                 135                 140

Ile Lys Lys Asn Ile Ala Ser Asp Glu Asn Thr Leu Tyr Ser Ser Leu
145                 150                 155                 160

Asp Glu Leu Arg Glu Ser Trp Trp Asn Thr Asn Lys Lys Tyr Ile Trp
                165                 170                 175
```

```
Leu Ala Met Lys His Gly Ala Glu Met Asn Gly Thr Met Cys Asn Ala
            180                 185                 190

Asp Gly Ser Val Thr Gly Ser Gly Ser Ser Cys Asp Asp Met Ser Thr
            195                 200                 205

Ile Asp Leu Ile Pro Gln Tyr Leu Arg Phe Leu Gln Glu Trp Val Glu
            210                 215                 220

His Phe Cys Glu Gln Arg Gln Ala Lys Val Lys Asp Val Ile Asn Ser
225                 230                 235                 240

Cys Lys Ser Cys Lys Glu Ser Gly Asp Thr Cys Asn Ser Asp Cys Glu
                245                 250                 255

Lys Lys Cys Lys Asn Lys Cys Asp Ala Tyr Lys Thr Phe Ile Glu Glu
            260                 265                 270

Phe Cys Thr Ala Asp Gly Gly Thr Ala Gly Ser Pro Trp Ser Lys Arg
            275                 280                 285

Trp Asp Gln Ile Tyr Lys Arg Tyr Ser Lys Tyr Ile Glu Asp Ala Lys
            290                 295                 300

Arg Asn Arg Lys Ala Gly Thr Lys Asn Cys Gly Thr Ser Ser Gly Ala
305                 310                 315                 320

Asn Ser Gly Val Thr Thr Thr Glu Asn Lys Cys Val Gln Ser
                325                 330

<210> SEQ ID NO 33
<211> LENGTH: 350
<212> TYPE: PRT
<213> ORGANISM: Plasmodium falciparum

<400> SEQUENCE: 33

Lys Cys Asp Lys Cys Lys Ser Gly Thr Ser Thr Val Asn Lys Asn Trp
1               5                   10                  15

Ile Trp Lys Lys Tyr Ser Gly Lys Glu Gly Leu Gln Lys Glu Tyr
            20                  25                  30

Ala Asn Thr Ile Ala Leu Pro Pro Arg Thr His Ser Leu Tyr Leu Val
            35                  40                  45

Cys Leu His Glu Lys Gly Lys Lys Thr Gln Glu Leu Lys Asn Ile Arg
    50                  55                  60

Thr Asn Ser Glu Leu Leu Lys Glu Trp Ile Ile Ala Ala Phe His Glu
65                  70                  75                  80

Gly Lys Asn Leu Lys Thr Ser Pro Gln Asn Asn Asn Ser Gly Asn Lys
                85                  90                  95

Lys Lys Leu Cys Lys Ala Leu Lys Tyr Ser Phe Ala Asp Tyr Gly Asp
            100                 105                 110

Leu Ile Lys Gly Thr Ser Ile Trp Asp Asn Asp Phe Thr Lys Asp Leu
            115                 120                 125

Glu Leu Asn Leu Gln Lys Ile Phe Gly Lys Leu Phe Arg Lys Tyr Ile
            130                 135                 140

Lys Lys Asn Asn Thr Ala Glu Gln His Thr Ser Tyr Ser Ser Leu Asp
145                 150                 155                 160

Glu Leu Arg Glu Ser Trp Trp Asn Thr Asn Lys Lys Tyr Ile Trp Leu
                165                 170                 175

Ala Met Lys His Gly Ala Glu Met Asn Gly Thr Thr Cys Cys Gly Asp
            180                 185                 190

Gly Ser Val Thr Gly Ser Ser Asp Ser Gly Thr Thr Cys Ser Gly
            195                 200                 205

Asp Asn Gly Ser Ile Ser Cys Asp Asp Met Pro Thr Thr Asp Phe Ile
            210                 215                 220
```

```
Pro Gln Tyr Leu Arg Phe Leu Gln Glu Trp Val Glu His Phe Cys Lys
225                 230                 235                 240

Gln Arg Gln Glu Lys Val Lys His Val Met Glu Ser Cys Lys Ser Cys
            245                 250                 255

Lys Glu Cys Gly Asp Thr Cys Asn Gly Glu Cys Lys Thr Glu Cys Glu
        260                 265                 270

Lys Lys Cys Lys Asn Lys Cys Glu Ala Tyr Lys Thr Phe Ile Glu Lys
        275                 280                 285

Cys Val Ser Ala Asp Gly Gly Thr Gly Ser Ser Trp Ser Lys Arg
    290                 295                 300

Trp Asp Gln Ile Tyr Met Arg Tyr Ser Lys Tyr Ile Glu Asp Ala Lys
305                 310                 315                 320

Arg Asn Arg Lys Ala Gly Thr Lys Asn Cys Gly Thr Ser Ser Thr Thr
            325                 330                 335

Asn Ala Ala Ala Ser Thr Ala Glu Asn Lys Cys Val Gln Ser
            340                 345                 350

<210> SEQ ID NO 34
<211> LENGTH: 647
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: P13 745 amino acids

<400> SEQUENCE: 34

Asp Tyr Ile Lys Asp Asp Pro Tyr Ser Ala Glu Tyr Ala Thr Lys Leu
1               5                   10                  15

Ser Phe Ile Leu Asn Pro Ser Asp Ala Asn Thr Ser Ser Gly Glu Thr
            20                  25                  30

Ala Asn His Asn Asp Glu Val Cys Asn Cys Asn Glu Ser Glu Ile Ala
        35                  40                  45

Ser Val Glu Leu Ala Pro Ile Ser Asp Ser Ser Asn Lys Thr Cys
    50                  55                  60

Ile Thr His Ser Phe Ile Gly Ala Asn Lys Lys Glu Cys Lys Asp
65                  70                  75                  80

Val Lys Leu Gly Val Arg Glu Lys Asp Lys Asp Leu Lys Ile Cys Val
                85                  90                  95

Ile Glu Asp Asp Ser Leu Arg Gly Val Glu Asn Cys Cys Cys Gln Asp
            100                 105                 110

Leu Leu Gly Ile Leu Gln Glu Asn Cys Ser Asp Asn Lys Ser Gly Ser
        115                 120                 125

Ser Ser Asn Gly Ser Cys Asp Lys Asn Ser Glu Asp Glu Cys Gln Lys
    130                 135                 140

Lys Leu Glu Asn Val Phe Ala Ser Leu Lys Asn Gly Tyr Lys Cys Asp
145                 150                 155                 160

Lys Cys Lys Ser Gly Thr Ser Thr Val Asn Lys Lys Trp Ile Trp Arg
                165                 170                 175

Lys Tyr Ser Gly Asn Gly Glu Gly Leu Gln Lys Glu Tyr Ala Asn Thr
            180                 185                 190

Ile Gly Leu Pro Pro Arg Thr His Ser Leu Tyr Leu Val Cys Leu His
        195                 200                 205

Glu Lys Glu Gly Lys Thr Gln His Lys Thr Ile Ser Thr Asn Ser Glu
    210                 215                 220
```

```
Leu Leu Lys Glu Trp Ile Ile Ala Ala Phe His Glu Gly Lys Asn Leu
225                 230                 235                 240

Lys Thr Ser His Gln Asn Asn Ser Gly Asn Lys Lys Lys Leu Cys
            245                 250                 255

Lys Ala Leu Lys Tyr Ser Phe Ala Asp Tyr Gly Asp Leu Ile Lys Gly
                260                 265                 270

Thr Ser Ile Trp Asp Asn Asp Phe Thr Lys Asp Leu Glu Leu Asn Leu
            275                 280                 285

Gln Lys Ile Phe Gly Lys Leu Phe Arg Lys Tyr Ile Lys Lys Asn Ile
290                 295                 300

Ala Ser Asp Glu Asn Thr Ser Tyr Ser Ser Leu Asp Glu Leu Arg Glu
305                 310                 315                 320

Ser Trp Trp Asn Thr Asn Lys Lys Tyr Ile Trp Leu Ala Met Lys His
                325                 330                 335

Gly Ala Glu Met Asn Ser Thr Met Cys Asn Gly Asp Gly Ser Val Thr
                340                 345                 350

Gly Ser Ser Asp Ser Gly Ser Thr Thr Cys Ser Gly Asp Asn Gly Ser
            355                 360                 365

Ile Ser Cys Asp Asp Ile Pro Thr Ile Asp Leu Ile Pro Gln Tyr Leu
370                 375                 380

Arg Phe Leu Gln Glu Trp Val Glu His Phe Cys Lys Gln Arg Gln Glu
385                 390                 395                 400

Lys Val Lys Asp Val Ile Thr Asn Cys Lys Ser Cys Lys Glu Ser Gly
                405                 410                 415

Asp Thr Cys Asn Ser Asp Cys Glu Lys Cys Lys Asn Lys Cys Glu
                420                 425                 430

Ala Tyr Lys Lys Phe Ile Glu Glu Arg Arg Thr Ala Ala Gln Gly Thr
                435                 440                 445

Ala Glu Ser Ser Trp Val Lys Arg Trp Asp Gln Ile Tyr Met Arg Tyr
450                 455                 460

Ser Lys Tyr Ile Glu Asp Ala Lys Arg Asn Arg Lys Ala Gly Thr Lys
465                 470                 475                 480

Ser Cys Gly Pro Ser Ser Thr Thr Asn Ala Ala Ser Thr Ala Glu
                485                 490                 495

Asn Lys Cys Val Gln Ser Asp Ile Asp Ser Phe Phe Lys His Leu Ile
                500                 505                 510

Asp Ile Gly Leu Thr Thr Pro Ser Ser Tyr Leu Ser Ile Val Leu Asp
            515                 520                 525

Asp Asn Ile Cys Gly Ala Asp Asn Ala Pro Trp Thr Thr Tyr Thr Thr
            530                 535                 540

Tyr Thr Thr Thr Lys Asn Cys Asp Ile Lys Lys Lys Thr Pro Lys Pro
545                 550                 555                 560

Gln Ser Cys Asp Thr Leu Val Val Val Asn Val Pro Ser Pro Leu Gly
                565                 570                 575

Asn Thr Pro His Glu Tyr Lys Tyr Ala Cys Gln Cys Arg Thr Pro Asn
            580                 585                 590

Lys Gln Glu Ser Cys Asp Asp Arg Lys Glu Tyr Met Asn Gln Trp Ser
                595                 600                 605

Ser Gly Ser Ala Gln Thr Val Arg Gly Arg Ser Thr Asn Asn Asp Tyr
            610                 615                 620

Glu Leu Tyr Thr Tyr Asn Gly Val Lys Glu Thr Lys Pro Leu Gly Thr
625                 630                 635                 640
```

```
Leu Lys Asn Ser Lys Leu Asp
            645

<210> SEQ ID NO 35
<211> LENGTH: 341
<212> TYPE: PRT
<213> ORGANISM: Plasmodium falciparum

<400> SEQUENCE: 35

Lys Cys Asp Lys Cys Lys Ser Gly Thr Ser Thr Val Asn Lys Lys Trp
1               5                   10                  15

Ile Trp Arg Lys Ser Ser Gly Asn Lys Glu Gly Leu Gln Lys Glu Tyr
            20                  25                  30

Ala Asn Thr Ile Gly Leu Pro Pro Arg Thr Gln Ser Leu Tyr Leu Gly
        35                  40                  45

Asn Leu Pro Lys Leu Glu Asn Val Cys Glu Asp Val Lys Asp Ile Asn
    50                  55                  60

Phe Asp Thr Lys Glu Lys Phe Leu Ala Gly Cys Leu Ile Val Ser Phe
65                  70                  75                  80

His Glu Gly Lys Asn Leu Lys Thr Ser His Glu Lys Lys Asn Asp Asp
                85                  90                  95

Asn Gly Lys Lys Leu Cys Lys Ala Leu Glu Tyr Ser Phe Ala Asp Tyr
            100                 105                 110

Gly Asp Leu Ile Lys Gly Thr Ser Ile Trp Asp Asn Glu Tyr Thr Lys
        115                 120                 125

Asp Leu Glu Leu Asn Leu Gln Lys Ile Phe Gly Lys Leu Phe Arg Lys
    130                 135                 140

Tyr Ile Lys Lys Asn Asn Thr Ala Glu Gln Asp Thr Ser Tyr Ser Ser
145                 150                 155                 160

Leu Asp Glu Leu Arg Glu Ser Trp Trp Asn Thr Asn Lys Lys Tyr Ile
                165                 170                 175

Trp Thr Ala Met Lys His Gly Ala Gly Met Asn Ile Thr Thr Cys Cys
            180                 185                 190

Gly Asp Gly Ser Ser Gly Glu Asn Gln Thr Asn Ser Cys Asp Asp Ile
        195                 200                 205

Pro Thr Ile Asp Leu Ile Pro Gln Tyr Leu Arg Phe Leu Gln Glu Trp
    210                 215                 220

Val Glu His Phe Cys Lys Gln Arg Gln Glu Lys Val Asn Ala Val Val
225                 230                 235                 240

Thr Asn Cys Lys Ser Cys Lys Glu Ser Gly Thr Cys Asn Gly Glu
                245                 250                 255

Cys Lys Thr Lys Cys Lys Asn Lys Cys Glu Val Tyr Lys Thr Phe Ile
            260                 265                 270

Asp Asn Val Gly Asp Gly Thr Ala Gly Ser Pro Trp Val Lys Arg Trp
        275                 280                 285

Asp Gln Ile Tyr Lys Arg Tyr Ser Lys His Ile Glu Asp Ala Lys Arg
    290                 295                 300

Asn Arg Lys Ala Gly Thr Lys Asn Cys Gly Ile Thr Gly Thr Ile
305                 310                 315                 320

Ser Gly Glu Ser Ser Gly Ala Thr Ser Gly Val Thr Thr Glu Asn
                325                 330                 335

Lys Cys Val Gln Ser
            340

<210> SEQ ID NO 36
```

<211> LENGTH: 632
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: 7g8 745 amino acids

<400> SEQUENCE: 36

```
Asn Tyr Ile Lys Asp Asp Pro Tyr Ser Lys Glu Tyr Val Thr Lys Leu
1               5                   10                  15

Ser Phe Ile Pro Asn Ser Ser Asp Ala Asn Thr Ser Ser Glu Lys Ile
            20                  25                  30

Gln Lys Asn Asn Asp Glu Val Cys Asn Pro Asn Glu Ser Gly Ile Ser
        35                  40                  45

Ser Val Glu Gln Ala Gln Thr Ser Gly Pro Ser Ser Asn Lys Thr Cys
    50                  55                  60

Ile Thr His Ser Ser Ile Lys Ala Asn Lys Lys Glu Cys Lys Asp
65                  70                  75                  80

Val Lys Leu Gly Val Arg Glu Asn Asp Lys Asp Leu Lys Ile Cys Val
                85                  90                  95

Ile Glu Asp Thr Ser Leu Ser Gly Val Asp Asn Cys Cys Gln Asp
            100                 105                 110

Leu Leu Gly Ile Leu Gln Glu Asn Cys Ser Asp Asn Lys Arg Gly Ser
        115                 120                 125

Ser Ser Asn Asp Ser Cys Asp Asn Lys Asn Gln Asp Glu Cys Gln Lys
    130                 135                 140

Lys Leu Asp Glu Ala Leu Glu Ser Leu His Asn Gly Tyr Lys Asn Gln
145                 150                 155                 160

Lys Cys Lys Ser Gly Thr Ser Thr Val Asn Lys Trp Ile Trp Lys
                165                 170                 175

Lys Ser Ser Gly Asn Lys Glu Gly Leu Gln Lys Glu Tyr Ala Asn Thr
            180                 185                 190

Ile Gly Leu Pro Pro Arg Thr Gln Ser Leu Tyr Leu Gly Asn Leu Pro
        195                 200                 205

Lys Leu Glu Asn Val Ser Lys Gly Val Thr Asp Ile Ile Tyr Asp Thr
    210                 215                 220

Lys Glu Lys Phe Leu Ala Gly Cys Leu Ile Val Ser Phe His Glu Gly
225                 230                 235                 240

Lys Asn Leu Lys Thr Ser His Glu Lys Lys Asn Asp Asp Asn Gly Lys
                245                 250                 255

Lys Leu Cys Lys Ala Leu Glu Tyr Ser Phe Ala Asp Tyr Gly Asp Leu
            260                 265                 270

Ile Lys Gly Thr Ser Ile Trp Asp Asn Glu Tyr Thr Lys Asp Leu Glu
        275                 280                 285

Leu Asn Leu Gln Lys Ala Phe Gly Lys Leu Phe Arg Lys Tyr Ile Lys
    290                 295                 300

Lys Asn Ile Ser Ala Glu Gln Asp Thr Ser Tyr Ser Ser Leu Asp Glu
305                 310                 315                 320

Leu Arg Glu Ser Trp Trp Asn Thr Asn Lys Lys Tyr Ile Trp Ile Ala
                325                 330                 335

Met Lys His Gly Ala Gly Met Asn Gly Thr Thr Cys Cys Gly Asp Gly
            340                 345                 350

Ser Ser Gly Glu Asn Gln Thr Asn Ser Cys Asp Asp Ile Pro Thr Ile
        355                 360                 365
```

```
Asp Leu Ile Pro Gln Tyr Leu Arg Phe Leu Gln Glu Trp Val Glu His
    370                 375                 380
Phe Cys Glu Gln Arg Gln Ala Lys Val Lys Asp Val Ile Thr Asn Cys
385                 390                 395                 400
Lys Ser Cys Lys Asn Thr Ser Gly Glu Arg Lys Ile Gly Gly Thr Cys
            405                 410                 415
Asn Gly Glu Cys Lys Thr Lys Cys Lys Asn Lys Cys Glu Ala Tyr Lys
            420                 425                 430
Thr Phe Ile Glu His Cys Lys Gly Gly Asp Gly Thr Ala Gly Ser Ser
            435                 440                 445
Trp Val Lys Arg Trp Asp Gln Ile Tyr Lys Arg Tyr Ser Lys His Ile
    450                 455                 460
Glu Asp Ala Lys Arg Asn Arg Lys Ala Gly Thr Lys Ser Cys Gly Thr
465                 470                 475                 480
Ser Thr Ala Glu Asn Lys Cys Val Gln Ser Asp Ile Asp Ser Phe Phe
            485                 490                 495
Lys His Leu Ile Asp Ile Gly Leu Thr Thr Pro Ser Ser Tyr Leu Ser
            500                 505                 510
Ile Val Leu Asp Glu Asn Asn Cys Gly Glu Asp Lys Ala Pro Trp Thr
            515                 520                 525
Thr Tyr Thr Thr Thr Lys Asn Cys Asp Ile Gln Lys Asp Lys Ser Lys
    530                 535                 540
Ser Gln Ser Ser Asp Thr Leu Val Val Val Asn Val Pro Ser Pro Leu
545                 550                 555                 560
Gly Asn Thr Pro His Gly Tyr Lys Tyr Ala Cys Gln Cys Lys Ile Pro
            565                 570                 575
Thr Thr Glu Glu Thr Cys Asp Asp Arg Lys Glu Tyr Met Asn Gln Trp
            580                 585                 590
Ser Cys Gly Ser Ala Arg Thr Met Lys Arg Gly Tyr Lys Asn Asp Asn
            595                 600                 605
Tyr Glu Leu Cys Lys Tyr Asn Gly Val Asp Val Lys Pro Thr Thr Val
    610                 615                 620
Arg Ser Ser Ser Thr Lys Leu Asp
625                 630

<210> SEQ ID NO 37
<211> LENGTH: 639
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Indo 745 amino acids

<400> SEQUENCE: 37

Asp Tyr Ile Lys Gly Asp Pro Tyr Ser Ala Glu Tyr Val Thr Lys Leu
1               5                   10                  15
Ser Phe Ile Pro Asn Ser Ser Asp Ala Asn Asn Pro Ser Glu Lys Ile
            20                  25                  30
Gln Lys Asn Asn Asp Glu Val Cys Asn Cys Asn Glu Ser Glu Ile Ser
        35                  40                  45
Ser Val Gly Gln Ala Ser Ile Ser Asp Pro Ser Ser Asn Lys Thr Cys
    50                  55                  60
Asn Thr His Ser Ser Ile Lys Ala Asn Lys Lys Val Cys Lys Asp
65                  70                  75                  80
```

```
Val Lys Leu Gly Val Arg Glu Asn Asp Lys Val Leu Lys Ile Cys Val
                85                  90                  95

Ile Glu His Thr Ser Leu Arg Gly Val Asp Asn Cys Cys Phe Lys Asp
                100                 105                 110

Leu Leu Gly Ile Leu Gln Glu Pro Arg Ile Asp Lys Asn Gln Ser Gly
                115                 120                 125

Ser Ser Ser Asn Gly Ser Cys Asp Lys Asn Ser Glu Glu Ala Cys Glu
            130                 135                 140

Lys Asn Leu Glu Lys Val Leu Ala Ser Leu Thr Asn Gly Tyr Lys Cys
145                 150                 155                 160

Asp Lys Cys Lys Ser Gly Thr Ser Arg Ser Lys Lys Trp Ile Trp
                165                 170                 175

Lys Lys Tyr Ser Gly Lys Glu Gly Leu Gln Glu Glu Tyr Ala Asn
                180                 185                 190

Thr Ile Gly Leu Pro Pro Arg Thr Gln Ser Leu Cys Leu Val Val Cys
                195                 200                 205

Leu Asp Glu Lys Glu Gly Lys Thr Gln Glu Leu Lys Asn Ile Ser Thr
    210                 215                 220

Asn Ser Glu Leu Leu Lys Glu Trp Ile Ile Ala Ala Phe Pro Glu Gly
225                 230                 235                 240

Lys Asn Leu Lys Pro Ser Pro Glu Lys Lys Gly Asp Asn Gly Lys
                245                 250                 255

Lys Leu Cys Lys Asp Leu Lys Tyr Ser Phe Ala Asp Tyr Gly Asp Leu
                260                 265                 270

Ile Lys Gly Thr Ser Ile Trp Asp Asn Glu Tyr Thr Lys Asp Leu Glu
                275                 280                 285

Leu Asn Leu Gln Lys Ile Phe Gly Lys Leu Phe Arg Lys Tyr Ile Lys
    290                 295                 300

Lys Asn Ile Ala Ser Asp Glu Asn Thr Leu Tyr Ser Ser Leu Asp Glu
305                 310                 315                 320

Leu Arg Glu Ser Trp Trp Asn Thr Asn Lys Lys Tyr Ile Trp Leu Ala
                325                 330                 335

Met Lys His Gly Ala Gly Met Asn Ser Thr Met Cys Asn Ala Asp Gly
                340                 345                 350

Ser Val Thr Gly Ser Gly Ser Ser Cys Asp Asp Met Pro Thr Ile Asp
                355                 360                 365

Leu Ile Pro Gln Tyr Leu Arg Phe Leu Gln Glu Trp Val Glu His Phe
    370                 375                 380

Cys Lys Gln Arg Gln Glu Lys Val Lys Pro Val Ile Glu Asn Cys Asn
385                 390                 395                 400

Ser Cys Lys Asn Thr Ser Ser Glu Arg Lys Ile Gly Gly Thr Cys Asn
                405                 410                 415

Ser Asp Cys Lys Thr Glu Cys Lys Asn Lys Cys Glu Val Tyr Lys Lys
                420                 425                 430

Phe Ile Glu Asp Cys Lys Gly Gly Asp Gly Thr Ala Gly Ser Ser Trp
                435                 440                 445

Ser Lys Arg Trp Asp Gln Ile Tyr Lys Arg Tyr Ser Lys Tyr Ile Glu
    450                 455                 460

Asp Ala Lys Arg Asn Arg Lys Ala Gly Thr Lys Asn Cys Gly Pro Ser
465                 470                 475                 480

Ser Thr Thr Asn Ala Ala Glu Asn Lys Cys Val Gln Ser Asp Ile Asp
                485                 490                 495
```

-continued

```
Ser Phe Phe Lys His Leu Ile Asp Ile Gly Leu Thr Thr Pro Ser Ser
                500                 505                 510

Tyr Leu Ser Thr Val Leu Asp Asp Asn Ile Cys Gly Glu Asp Asn Ala
            515                 520                 525

Pro Trp Thr Thr Tyr Thr Thr Tyr Thr Thr Lys Asn Cys Asp Lys
        530                 535                 540

Asp Lys Lys Lys Ser Lys Ser Gln Ser Cys Asp Thr Leu Val Val Val
545                 550                 555                 560

Asn Val Pro Ser Pro Leu Gly Asn Thr Pro His Glu Tyr Lys Tyr Ala
                565                 570                 575

Cys Glu Cys Arg Thr Pro Asn Lys Gln Glu Ser Cys Asp Asp Arg Lys
            580                 585                 590

Glu Tyr Met Asn Gln Trp Ile Ser Asp Asn Thr Lys Asn Pro Lys Gly
        595                 600                 605

Ser Gly Ser Gly Lys Asp Tyr Tyr Glu Leu Tyr Thr Tyr Asn Gly Val
    610                 615                 620

Asp Val Lys Pro Thr Thr Val Arg Ser Ser Ser Thr Lys Leu Asp
625                 630                 635

<210> SEQ ID NO 38
<211> LENGTH: 655
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: MC 745 amino acids

<400> SEQUENCE: 38

Asp Tyr Ile Lys Gly Asp Pro Tyr Phe Ala Glu Tyr Ala Thr Lys Leu
1               5                   10                  15

Ser Phe Ile Leu Asn Ser Ser Asp Ala Asn Thr Ser Ser Gly Glu Thr
            20                  25                  30

Ala Asn His Asn Asp Glu Ala Cys Asn Cys Asn Glu Ser Glu Ile Ser
        35                  40                  45

Ser Val Glu His Ala Ser Ile Ser Asp Pro Ser Ser Asn Lys Thr Cys
    50                  55                  60

Asn Thr His Ser Ser Ile Lys Ala Asn Lys Lys Val Cys Lys His
65                  70                  75                  80

Val Lys Leu Gly Val Arg Glu Asn Asp Lys Asp Leu Arg Val Cys Val
                85                  90                  95

Ile Glu His Thr Ser Leu Ser Gly Val Glu Asn Cys Cys Phe Lys Asp
            100                 105                 110

Phe Leu Arg Ile Leu Gln Glu Asn Cys Ser Asp Asn Lys Ser Gly Ser
        115                 120                 125

Ser Ser Asn Gly Ser Cys Asp Lys Asn Asn Glu Glu Ala Cys Glu Lys
    130                 135                 140

Asn Leu Glu Lys Val Phe Ala Ser Leu Thr Asn Cys Tyr Lys Cys Glu
145                 150                 155                 160

Lys Cys Lys Ser Glu Gln Ser Lys Lys Asn Lys Lys Trp Thr Trp
                165                 170                 175

Arg Lys Ser Ser Gly Asn Lys Gly Gly Leu Gln Glu Glu Tyr Ala Asn
            180                 185                 190

Thr Ile Gly Leu Pro Pro Arg Thr Gln Ser Leu Cys Leu Val Val Cys
        195                 200                 205
```

-continued

```
Leu Asp Glu Lys Glu Gly Lys Lys Thr Gln Glu Leu Lys Asn Ile Arg
210                 215                 220
Thr Asn Ser Glu Leu Leu Lys Glu Trp Ile Ile Ala Ala Phe His Glu
225                 230                 235                 240
Gly Lys Asn Leu Lys Pro Ser His Glu Lys Lys Asn Asp Asp Asn Gly
                245                 250                 255
Lys Lys Asn Asp Asp Asn Ser Lys Leu Cys Lys Asp Leu Lys Tyr
            260                 265                 270
Ser Phe Ala Asp Tyr Gly Asp Leu Ile Lys Gly Thr Ser Ile Trp Asp
                275                 280                 285
Asn Glu Tyr Thr Lys Asp Leu Glu Leu Asn Leu Gln Lys Ile Phe Gly
290                 295                 300
Lys Leu Phe Arg Lys Tyr Ile Lys Asn Ile Ala Ser Asp Glu Asn
305                 310                 315                 320
Thr Leu Tyr Ser Ser Leu Asp Glu Leu Arg Glu Ser Trp Trp Asn Thr
                325                 330                 335
Asn Lys Lys Tyr Ile Trp Leu Ala Met Lys His Gly Ala Glu Met Asn
                340                 345                 350
Gly Thr Thr Cys Asn Ala Asp Gly Ser Val Thr Gly Ser Gly Ser Ser
                355                 360                 365
Cys Asp Asp Ile Pro Thr Ile Asp Leu Ile Pro Gln Tyr Leu Arg Phe
370                 375                 380
Leu Gln Glu Trp Val Glu His Phe Cys Lys Gln Arg Gln Ala Lys Val
385                 390                 395                 400
Lys Asp Val Ile Glu Asn Cys Lys Ser Cys Lys Glu Ser Gly Asn Lys
                405                 410                 415
Cys Lys Thr Glu Cys Lys Asn Lys Cys Glu Ala Tyr Lys Lys Phe Ile
                420                 425                 430
Glu Asn Cys Lys Gly Gly Asp Gly Thr Ala Gly Ser Ser Trp Val Lys
                435                 440                 445
Arg Trp Asp Gln Ile Tyr Met Arg Tyr Ser Lys Tyr Ile Glu Asp Ala
            450                 455                 460
Lys Arg Asn Arg Lys Ala Gly Thr Lys Asn Cys Gly Pro Ser Ser Ile
465                 470                 475                 480
Thr Asn Val Ser Ala Ser Thr Asp Glu Asn Lys Cys Val Gln Ser Asp
                485                 490                 495
Ile Asp Ser Phe Phe Lys His Leu Ile Asp Ile Gly Leu Thr Thr Pro
                500                 505                 510
Ser Ser Tyr Leu Ser Ile Val Leu Asp Asp Asn Ile Cys Gly Asp Asp
            515                 520                 525
Lys Ala Pro Trp Thr Thr Tyr Thr Thr Tyr Thr Thr Tyr Thr Thr Tyr
530                 535                 540
Thr Thr Tyr Thr Thr Tyr Thr Thr Tyr Thr Thr Lys Asn Cys Asp
545                 550                 555                 560
Lys Glu Arg Asp Lys Ser Lys Ser Gln Ser Cys Asn Thr Ala Val Val
                565                 570                 575
Val Asn Val Pro Ser Pro Leu Gly Asn Thr Pro His Glu Tyr Lys Tyr
                580                 585                 590
Ala Cys Glu Cys Arg Thr Pro Ser Asn Lys Glu Leu Cys Asp Asp Arg
                595                 600                 605
Lys Glu Tyr Met Asn Gln Trp Ser Ser Gly Ser Ala Gln Thr Val Arg
                610                 615                 620
Asp Arg Ser Gly Lys Asp Tyr Tyr Glu Leu Tyr Thr Tyr Asn Gly Val
```

Lys Glu Thr Lys Leu Pro Lys Lys Leu Asn Ser Ser Lys Leu Asp
            645             650             655

<210> SEQ ID NO 39
<211> LENGTH: 347
<212> TYPE: PRT
<213> ORGANISM: Plasmodium falciparum

<400> SEQUENCE: 39

Lys Cys Asp Lys Cys Lys Ser Glu Gln Ser Lys Lys Asn Asn Lys Tyr
1               5                   10                  15

Trp Ile Trp Lys Lys Ser Ser Val Lys Glu Glu Gly Leu Gln Lys Glu
            20                  25                  30

Tyr Ala Asn Thr Ile Ala Leu Pro Pro Arg Thr His Ser Leu Cys Leu
        35                  40                  45

Val Val Cys Leu Asp Glu Lys Gly Lys Thr Gln Glu Leu Lys Asn
    50                  55                  60

Ile Ser Thr Asn Ser Glu Leu Leu Lys Glu Arg Ile Ile Ala Ala Phe
65                  70                  75                  80

His Glu Gly Lys Asn Leu Lys Thr Thr Tyr Leu Glu Lys Lys Asn Ala
                85                  90                  95

Asp Asn Asn Ser Lys Leu Cys Lys Ala Leu Lys Tyr Ser Phe Ala Asp
            100                 105                 110

Tyr Gly Asp Leu Ile Lys Gly Thr Ser Ile Trp Asp Asn Glu Tyr Thr
        115                 120                 125

Lys Asp Leu Glu Leu Asn Leu Gln Gln Ile Phe Gly Lys Leu Phe Arg
    130                 135                 140

Lys Tyr Ile Lys Lys Asn Asn Thr Ala Glu Gln His Thr Leu Tyr Ser
145                 150                 155                 160

Ser Leu Asp Glu Leu Arg Glu Ser Trp Trp Asn Thr Asn Lys Lys Tyr
                165                 170                 175

Ile Trp Leu Ala Met Lys His Gly Ala Gly Met Asn Gly Thr Thr Cys
            180                 185                 190

Cys Gly Asp Gly Ser Val Thr Gly Ser Ser Asp Ser Gly Ser Thr Thr
        195                 200                 205

Cys Ser Gly Asp Asn Gly Ser Ile Ser Cys Asp Asp Met Pro Thr Thr
    210                 215                 220

Asp Phe Ile Pro Gln Tyr Leu Arg Phe Leu Gln Glu Trp Val Glu His
225                 230                 235                 240

Phe Cys Lys Gln Arg Gln Glu Lys Val Lys Asp Val Ile Glu Asn Cys
                245                 250                 255

Asn Ser Cys Lys Asn Asn Leu Gly Lys Thr Glu Ile Asn Glu Lys Cys
            260                 265                 270

Lys Thr Glu Cys Lys Asn Lys Cys Glu Ala Tyr Lys Asn Phe Ile Glu
        275                 280                 285

Lys Phe Cys Thr Ala Asp Gly Gly Thr Ser Gly Ser Pro Trp Ser Lys
    290                 295                 300

Arg Trp Asp Gln Ile Tyr Lys Arg Tyr Ser Lys Tyr Ile Glu Asp Ala
305                 310                 315                 320

Lys Arg Asn Arg Lys Ala Gly Thr Lys Asn Cys Gly Thr Ser Ser Thr
                325                 330                 335

Thr Ser Thr Ala Glu Asn Lys Cys Val Gln Ser
            340                 345

```
<210> SEQ ID NO 40
<211> LENGTH: 335
<212> TYPE: PRT
<213> ORGANISM: Plasmodium falciparum

<400> SEQUENCE: 40

Lys Cys Glu Lys Cys Lys Ser Gly Thr Ser Thr Val Asn Lys Tyr Trp
1               5                   10                  15

Ile Trp Arg Lys Ser Ser Gly Asn Lys Glu Gly Leu Gln Lys Glu Tyr
            20                  25                  30

Ala Asn Thr Ile Ala Leu Pro Pro Arg Thr His Ser Leu Cys Leu Val
        35                  40                  45

Val Cys Leu Asp Glu Lys Glu Gly Lys Thr Gln Glu Leu Lys Asn Ile
50                  55                  60

Ser Thr Asn Ser Glu Leu Leu Lys Glu Arg Ile Ile Ala Ala Phe His
65                  70                  75                  80

Glu Gly Glu Asn Leu Lys Thr Ser His Glu Lys Lys Gly Asp Asp
                85                  90                  95

Gly Lys Lys Asn Ala Asp Asn Ser Lys Leu Cys Lys Ala Leu Lys
                100                 105                 110

Tyr Ser Phe Ala Asp Tyr Gly Asp Leu Ile Lys Gly Thr Ser Ile Trp
            115                 120                 125

Asp Asn Glu Tyr Thr Lys Asp Leu Glu Leu Asn Leu Gln Lys Ile Phe
130                 135                 140

Gly Lys Leu Phe Arg Lys Tyr Ile Lys Lys Asn Ile Ala Ser Asp Glu
145                 150                 155                 160

Asn Thr Ser Tyr Ser Ser Leu Asp Glu Leu Arg Glu Ser Trp Trp Asn
                165                 170                 175

Thr Asn Lys Lys Tyr Ile Trp Leu Ala Met Lys His Gly Ala Gly Met
            180                 185                 190

Asn Gly Thr Thr Cys Ser Cys Ser Gly Asp Ser Ser Asp Asp Met Pro
        195                 200                 205

Thr Thr Asp Phe Ile Pro Gln Tyr Leu Arg Phe Leu Gln Glu Trp Val
210                 215                 220

Glu His Phe Cys Lys Gln Arg Gln Glu Asn Val Asn Ala Val Ile Glu
225                 230                 235                 240

Asn Cys Asn Ser Cys Lys Glu Cys Gly Gly Thr Cys Asn Ser Asp Cys
                245                 250                 255

Glu Lys Lys Cys Lys Thr Glu Cys Lys Asn Lys Cys Glu Ala Tyr Lys
            260                 265                 270

Asn Phe Ile Glu Lys Phe Cys Thr Ala Asp Gly Gly Thr Ser Gly Tyr
        275                 280                 285

Ser Trp Ser Lys Arg Trp Asp Gln Ile Tyr Lys Arg Tyr Ser Lys Tyr
290                 295                 300

Ile Glu Asp Ala Lys Arg Asn Arg Lys Ala Gly Thr Lys Ser Cys Gly
305                 310                 315                 320

Thr Ser Ser Thr Thr Ser Thr Ala Glu Ser Lys Cys Val Gln Ser
                325                 330                 335

<210> SEQ ID NO 41
<211> LENGTH: 667
<212> TYPE: PRT
<213> ORGANISM: Artificial Sequence
<220> FEATURE:
<223> OTHER INFORMATION: Description of Artificial Sequence: Synthetic
      polypeptide
```

<220> FEATURE:
<223> OTHER INFORMATION: ghana2 745 amino acids

<400> SEQUENCE: 41

```
Ser Tyr Val Lys Asn Asn Pro Tyr Ser Lys Glu Tyr Val Thr Lys Leu
1               5                   10                  15

Ser Phe Ile Leu Asn Pro Ser Asp Ala Asn Asn Pro Ser Glu Thr Pro
            20                  25                  30

Ser Lys Tyr Tyr Asp Glu Val Cys Asn Cys Asn Glu Ser Gly Ile Ala
        35                  40                  45

Cys Val Gly Gln Ala Gln Thr Ser Gly Pro Ser Ser Asn Lys Thr Cys
    50                  55                  60

Ile Thr His Ser Phe Ile Gly Ala Asn Lys Lys Val Cys Lys Asp
65                  70                  75                  80

Val Lys Leu Gly Val Arg Glu Lys Asp Lys Asp Leu Lys Ile Cys Val
                85                  90                  95

Ile Glu Asp Thr Tyr Leu Ser Gly Val Asp Asn Cys Cys Phe Lys Asp
            100                 105                 110

Phe Leu Gly Met Leu Gln Glu Asn Cys Ser Asp Asn Lys Ser Gly Ser
        115                 120                 125

Ser Ser Asn Gly Ser Cys Asn Asn Lys Asn Gln Asp Glu Cys Glu Lys
    130                 135                 140

Asn Leu Asp Glu Ala Leu Ala Ser Leu Thr Asn Gly Tyr Lys Cys Glu
145                 150                 155                 160

Lys Cys Lys Ser Gly Thr Ser Thr Val Asn Lys Tyr Trp Ile Trp Arg
                165                 170                 175

Lys Ser Ser Gly Asn Lys Glu Gly Leu Gln Lys Glu Tyr Ala Asn Thr
            180                 185                 190

Ile Ala Leu Pro Pro Arg Thr His Ser Leu Cys Leu Val Val Cys Leu
        195                 200                 205

Asp Glu Lys Glu Gly Lys Thr Gln His Lys Thr Ile Ser Thr Asn Ser
    210                 215                 220

Glu Leu Leu Lys Glu Trp Ile Ile Ala Ala Phe His Glu Gly Lys Asn
225                 230                 235                 240

Leu Lys Thr Ser His Glu Lys Lys Lys Gly Asp Asp Gly Lys Lys Asn
                245                 250                 255

Ala Asp Asn Asn Ser Lys Leu Cys Lys Ala Leu Lys Tyr Ser Phe Ala
            260                 265                 270

Asp Tyr Gly Asp Leu Ile Lys Gly Thr Ser Ile Trp Asp Asn Asp Phe
        275                 280                 285

Thr Lys Asp Leu Glu Leu Asn Leu Gln Lys Ile Phe Gly Lys Leu Phe
    290                 295                 300

Arg Lys Tyr Ile Lys Lys Asn Ile Ala Ser Asp Glu Asn Thr Ser Tyr
305                 310                 315                 320

Ser Ser Leu Asp Glu Leu Arg Glu Ser Trp Trp Asn Thr Asn Lys Lys
                325                 330                 335

Tyr Ile Trp Leu Ala Met Lys His Gly Ala Gly Met Asn Ser Thr Thr
            340                 345                 350

Cys Cys Gly Asp Gly Ser Val Thr Gly Ser Ser Asp Ser Gly Ser Thr
        355                 360                 365

Thr Cys Cys Gly Asp Gly Ser Val Thr Gly Ser Gly Ser Ser Cys Asp
    370                 375                 380

Asp Met Pro Thr Thr Asp Phe Ile Pro Gln Tyr Leu Arg Phe Leu Gln
385                 390                 395                 400
```

```
Glu Trp Val Glu His Phe Cys Lys Gln Arg Gln Asn Val Asn Ala
            405                 410                 415

Val Ile Glu Asn Cys Asn Ser Cys Lys Glu Cys Gly Gly Thr Cys Asn
            420                 425                 430

Ser Asp Cys Glu Lys Lys Cys Lys Thr Glu Cys Lys Gly Glu Cys Asp
            435                 440                 445

Ala Tyr Lys Glu Phe Ile Glu Lys Cys Asn Gly Gly Ala Ala Glu Gly
            450                 455                 460

Thr Ser Gly Ser Ser Trp Ser Lys Arg Trp Asp Gln Ile Tyr Lys Arg
465                 470                 475                 480

Tyr Ser Lys Tyr Ile Glu Asp Ala Lys Arg Asn Arg Lys Ala Gly Thr
                485                 490                 495

Lys Asn Cys Gly Thr Ser Ser Thr Ser Thr Ala Glu Ser Lys Cys
            500                 505                 510

Val Gln Ser Asp Ile Asp Ser Phe Phe Lys His Leu Ile Asp Ile Gly
            515                 520                 525

Leu Thr Thr Pro Ser Ser Tyr Leu Ser Ile Val Leu Asp Glu Asn Ile
530                 535                 540

Cys Gly Ala Asp Asn Ala Pro Trp Thr Thr Tyr Thr Thr Tyr Thr Thr
545                 550                 555                 560

Tyr Thr Thr Tyr Thr Thr Thr Glu Lys Cys Asn Lys Glu Thr Asp Lys
                565                 570                 575

Ser Lys Leu Gln Gln Cys Asn Thr Ser Val Val Asn Val Pro Ser
            580                 585                 590

Pro Leu Gly Asn Thr Pro His Gly Tyr Lys Tyr Val Cys Glu Cys Arg
            595                 600                 605

Thr Pro Asn Lys Gln Glu Thr Cys Asp Asp Arg Lys Glu Tyr Met Asn
            610                 615                 620

Gln Trp Ile Ser Asp Asn Thr Lys Asn Pro Lys Gly Ser Arg Ser Thr
625                 630                 635                 640

Asn Asn Asp Tyr Glu Leu Tyr Thr Tyr Asn Gly Val Gln Ile Lys Pro
                645                 650                 655

Thr Thr Val Arg Ser Asn Ser Thr Lys Leu Asp
            660                 665

<210> SEQ ID NO 42
<211> LENGTH: 348
<212> TYPE: PRT
<213> ORGANISM: Plasmodium falciparum

<400> SEQUENCE: 42

Lys Cys Asp Lys Cys Lys Ser Glu Gln Ser Lys Lys Asn Asn Lys Asn
1               5                   10                  15

Trp Ile Trp Lys Lys Ser Ser Gly Asn Glu Lys Gly Leu Gln Lys Glu
            20                  25                  30

Tyr Ala Asn Thr Ile Gly Leu Pro Pro Arg Thr Gln Ser Leu Cys Leu
        35                  40                  45

Val Val Cys Leu Asp Glu Lys Glu Gly Lys Thr Gln Glu Leu Lys Asn
    50                  55                  60

Ile Arg Thr Asn Ser Glu Leu Leu Lys Glu Trp Ile Ile Ala Ala Phe
65                  70                  75                  80

His Glu Gly Lys Asn Leu Lys Thr Ser His Glu Lys Lys Lys Gly Asp
                85                  90                  95

Asn Asn Ser Lys Leu Cys Lys Asp Leu Lys Tyr Ser Phe Ala Asp Tyr
```

```
                100                 105                 110
Gly Asp Leu Ile Lys Gly Thr Ser Ile Trp Asp Asn Glu Tyr Thr Lys
            115                 120                 125

Asp Leu Glu Leu Asn Leu Gln Asn Asn Phe Gly Lys Leu Phe Arg Lys
        130                 135                 140

Tyr Ile Lys Lys Asn Ile Ala Ser Asp Glu Asn Thr Ser Tyr Ser Ser
145                 150                 155                 160

Leu Asp Glu Leu Arg Glu Ser Trp Trp Asn Thr Asn Lys Lys Tyr Ile
                165                 170                 175

Trp Leu Ala Met Lys His Gly Ala Gly Met Asn Ser Thr Thr Cys Ser
            180                 185                 190

Ser Gly Ser Gly Ser Thr Thr Cys Ser Ser Gly Ser Gly Ser Thr Thr
        195                 200                 205

Cys Ser Ser Gly Ser Gly Asp Ser Cys Asp Asp Met Pro Thr Ile Asp
    210                 215                 220

Leu Ile Pro Gln Tyr Leu Arg Phe Leu Gln Glu Trp Val Glu His Phe
225                 230                 235                 240

Cys Lys Gln Arg Gln Glu Lys Val Asn Ala Val Ile Lys Asn Cys Asn
                245                 250                 255

Ser Cys Lys Glu Ser Gly Gly Thr Cys Asn Gly Glu Cys Lys Thr Glu
            260                 265                 270

Cys Lys Asn Lys Cys Glu Ala Tyr Lys Thr Phe Ile Glu Glu Phe Cys
        275                 280                 285

Thr Ala Asp Gly Gly Thr Ser Gly Ser Pro Trp Ser Lys Arg Trp Asp
    290                 295                 300

Gln Ile Tyr Lys Met Tyr Ser Lys His Ile Glu Asp Ala Lys Arg Asn
305                 310                 315                 320

Arg Lys Ala Gly Thr Lys Asn Cys Gly Pro Ser Ser Thr Thr Asn Val
                325                 330                 335

Ser Val Ser Thr Asp Glu Asn Lys Cys Val Gln Ser
            340                 345

<210> SEQ ID NO 43
<211> LENGTH: 652
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ghana1 745 amino acids

<400> SEQUENCE: 43

Asp Tyr Ile Lys Asp Asp Pro Tyr Phe Ala Glu Tyr Val Thr Lys Leu
1               5                   10                  15

Ser Phe Ile Leu Asn Ser Ser Asp Ala Asn Asn Pro Ser Gly Glu Thr
            20                  25                  30

Ala Asn His Asn Asp Glu Val Cys Asn Pro Asn Glu Ser Gly Ile Ala
        35                  40                  45

Ser Val Glu Gln Ala Gln Thr Ser Asp Pro Ser Ser Asn Lys Thr Cys
    50                  55                  60

Asn Thr His Ser Ser Ile Lys Ala Asn Lys Lys Val Cys Lys His
65                  70                  75                  80

Val Lys Leu Gly Val Arg Glu Asn Asp Lys Asp Leu Lys Ile Cys Val
                85                  90                  95

Ile Glu His Thr Ser Leu Ser Gly Val Glu Asn Cys Cys Cys Gln Asp
```

-continued

```
            100                 105                 110
Phe Leu Arg Ile Leu Gln Glu Asn Cys Ser Asp Asn Lys Ser Gly Ser
        115                 120                 125
Ser Ser Asn Gly Ser Cys Asn Lys Asn Gln Glu Ala Cys Glu Lys
    130                 135                 140
Asn Leu Glu Lys Val Leu Ala Ser Leu Thr Asn Cys Tyr Lys Cys Asp
145                 150                 155                 160
Lys Cys Lys Ser Glu Gln Ser Lys Lys Asn Asn Lys Asn Trp Ile Trp
                165                 170                 175
Lys Lys Ser Ser Gly Asn Glu Lys Gly Leu Gln Lys Glu Tyr Ala Asn
            180                 185                 190
Thr Ile Gly Leu Pro Pro Arg Thr Gln Ser Leu Cys Leu Val Val Cys
        195                 200                 205
Leu Asp Glu Lys Glu Gly Lys Thr Gln Glu Leu Lys Asn Ile Arg Thr
210                 215                 220
Asn Ser Glu Leu Leu Lys Glu Trp Ile Ile Ala Ala Phe His Glu Gly
225                 230                 235                 240
Lys Asn Leu Lys Lys Arg Tyr Pro Gln Asn Lys Asn Asp Asn Asn
                245                 250                 255
Ser Lys Leu Cys Lys Asp Leu Lys Tyr Ser Phe Ala Asp Tyr Gly Asp
            260                 265                 270
Leu Ile Lys Gly Thr Ser Ile Trp Asp Asn Glu Tyr Thr Lys Asp Leu
        275                 280                 285
Glu Leu Asn Leu Gln Asn Asn Phe Gly Lys Leu Phe Arg Lys Tyr Ile
    290                 295                 300
Lys Lys Asn Ile Ser Thr Glu Gln Asp Thr Leu Tyr Ser Ser Leu Asp
305                 310                 315                 320
Glu Leu Arg Glu Ser Trp Trp Asn Thr Asn Lys Lys Tyr Ile Trp Leu
                325                 330                 335
Ala Met Lys His Gly Ala Gly Met Asn Ser Thr Thr Cys Ser Ser Gly
            340                 345                 350
Ser Gly Ser Thr Thr Cys Ser Ser Gly Ser Gly Ser Thr Thr Cys Ser
        355                 360                 365
Ser Gly Ser Gly Asp Ser Cys Asp Asp Met Pro Thr Thr Asp Phe Ile
    370                 375                 380
Pro Gln Tyr Leu Arg Phe Leu Gln Glu Trp Val Glu His Phe Cys Lys
385                 390                 395                 400
Gln Arg Gln Glu Lys Val Asn Ala Val Ile Lys Asn Cys Asn Ser Cys
                405                 410                 415
Lys Glu Ser Gly Gly Thr Cys Asn Gly Glu Cys Lys Thr Glu Cys Lys
            420                 425                 430
Asn Lys Cys Glu Ala Tyr Lys Thr Phe Ile Glu Glu Phe Cys Thr Ala
        435                 440                 445
Asp Gly Gly Thr Ser Gly Ser Pro Trp Ser Lys Arg Trp Asp Gln Ile
    450                 455                 460
Tyr Lys Met Tyr Ser Lys His Ile Glu Asp Ala Lys Arg Asn Arg Lys
465                 470                 475                 480
Ala Gly Thr Lys Asn Cys Gly Pro Ser Ser Thr Thr Asn Val Ser Val
                485                 490                 495
Ser Thr Asp Glu Asn Lys Cys Val Gln Ser Asp Ile Asp Ser Phe Phe
            500                 505                 510
Lys His Leu Ile Asp Ile Gly Leu Thr Thr Pro Ser Ser Tyr Leu Ser
        515                 520                 525
```

-continued

```
Ile Val Leu Asp Asp Asn Ile Cys Gly Glu Asp Lys Ala Pro Trp Thr
            530                 535                 540
Thr Tyr Thr Thr Tyr Thr Thr Lys Lys Cys Asn Lys Glu Thr Asp
545                 550                 555                 560
Lys Ser Lys Ser Gln Ser Cys Asn Thr Ala Val Val Val Asn Val Pro
                565                 570                 575
Ser Pro Leu Gly Asn Thr Pro His Gly Tyr Lys Tyr Ala Cys Glu Cys
            580                 585                 590
Lys Ile Pro Thr Thr Glu Glu Thr Cys Asp Asp Arg Lys Glu Tyr Met
        595                 600                 605
Asn Gln Trp Ile Ile Asp Thr Ser Lys Lys Gln Lys Gly Ser Gly Ser
610                 615                 620
Gly Lys Asp Asp Tyr Glu Leu Tyr Thr Tyr Asn Gly Val Asp Val Lys
625                 630                 635                 640
Pro Thr Thr Val Arg Ser Asn Ser Thr Lys Leu Asp
                645                 650
```

<210> SEQ ID NO 44
<211> LENGTH: 628
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: V1S1 745 amino acids

<400> SEQUENCE: 44

```
Asp Tyr Ile Lys Asp Asp Pro Tyr Ser Ala Gln Tyr Thr Thr Lys Leu
1               5                   10                  15
Ser Phe Ile Leu Asn Pro Ser Asp Ala Asn Thr Ser Ser Glu Lys Ile
            20                  25                  30
Gln Lys Asn Asn Asp Glu Ala Cys Asn Cys Asn Glu Ser Gly Ile Ser
        35                  40                  45
Ser Val Gly Gln Ala Gln Thr Ser Gly Pro Ser Ser Asn Lys Thr Cys
50                  55                  60
Ile Thr His Ser Ser Ile Lys Ala Asn Lys Lys Val Cys Lys Asp
65                  70                  75                  80
Val Lys Leu Gly Ile Asn Asn Asn Asp Lys Val Leu Arg Val Cys Val
                85                  90                  95
Ile Glu Asp Thr Ser Leu Ser Gly Val Asp Asn Cys Cys Gln Asp
            100                 105                 110
Leu Leu Gly Ile Leu Gln Glu Asn Cys Ser Asp Asn Lys Arg Gly Ser
        115                 120                 125
Ser Ser Asn Gly Ser Cys Asn Asn Asn Glu Glu Ala Cys Glu Lys
130                 135                 140
Asn Leu Asp Glu Ala Pro Ala Ser Leu His Asn Gly Tyr Lys Asn Gln
145                 150                 155                 160
Lys Cys Lys Ser Gly Thr Ser Arg Ser Lys Lys Lys Trp Ile Trp Lys
                165                 170                 175
Lys Ser Ser Gly Asn Glu Lys Gly Leu Gln Glu Glu Tyr Ala Asn Thr
            180                 185                 190
Ile Gly Leu Pro Pro Arg Thr Gln Ser Leu Cys Leu Val Cys Leu His
        195                 200                 205
Glu Lys Glu Gly Lys Thr Gln His Lys Thr Ile Ser Thr Asn Ser Glu
210                 215                 220
```

-continued

Leu Leu Lys Glu Trp Ile Ile Ala Ala Phe His Glu Gly Lys Asn Leu
225                 230                 235                 240

Lys Thr Ser His Glu Lys Lys Asn Asp Asp Asn Gly Lys Lys Leu Cys
            245                 250                 255

Lys Ala Leu Glu Tyr Ser Phe Ala Asp Tyr Gly Asp Leu Ile Lys Gly
                260                 265                 270

Thr Ser Ile Trp Asp Asn Glu Tyr Thr Lys Asp Leu Glu Leu Asn Leu
            275                 280                 285

Gln Lys Ala Phe Gly Lys Leu Phe Arg Lys Tyr Ile Lys Lys Asn Asn
290                 295                 300

Thr Ala Glu Gln Asp Thr Ser Tyr Ser Ser Leu Asp Glu Leu Arg Glu
305                 310                 315                 320

Ser Trp Trp Asn Thr Asn Lys Lys Tyr Ile Trp Ile Ala Met Lys His
                325                 330                 335

Gly Ala Gly Met Asn Gly Thr Thr Cys Ser Cys Ser Gly Asp Ser Ser
                340                 345                 350

Asn Asp Met Pro Thr Ile Asp Leu Ile Pro Gln Tyr Leu Arg Phe Leu
            355                 360                 365

Gln Glu Trp Val Glu His Phe Cys Glu Gln Arg Gln Ala Lys Val Lys
370                 375                 380

Asp Val Ile Thr Asn Cys Lys Ser Cys Lys Glu Ser Gly Asn Lys Cys
385                 390                 395                 400

Lys Thr Glu Cys Lys Thr Lys Cys Lys Asp Glu Cys Glu Lys Tyr Lys
                405                 410                 415

Thr Phe Ile Glu Asp Cys Asn Gly Gly Thr Gly Thr Ala Gly Ser
                420                 425                 430

Ser Trp Val Lys Arg Trp Asp Gln Ile Tyr Lys Arg Tyr Ser Lys His
            435                 440                 445

Ile Glu Asp Ala Lys Arg Asn Arg Lys Ala Gly Thr Lys Asn Cys Gly
450                 455                 460

Pro Ser Ser Ile Thr Asn Ala Ala Ser Thr Asp Glu Asn Lys Cys
465                 470                 475                 480

Val Gln Ser Asp Ile Asp Ser Phe Phe Lys His Leu Ile Asp Ile Gly
                485                 490                 495

Leu Thr Thr Pro Ser Ser Tyr Leu Ser Asn Val Leu Asp Glu Asn Ser
                500                 505                 510

Cys Gly Asp Asp Lys Ala Pro Trp Thr Thr Tyr Thr Thr Tyr Thr Thr
            515                 520                 525

Thr Lys Asn Cys Asp Ile Gln Lys Asp Lys Ser Lys Ser Gln Pro Ile
            530                 535                 540

Asn Thr Ser Val Val Val Asn Val Pro Ser Pro Leu Gly Asn Thr Pro
545                 550                 555                 560

Tyr Arg Tyr Lys Tyr Ala Cys Glu Cys Lys Ile Pro Thr Thr Glu Glu
                565                 570                 575

Ser Cys Asp Asp Arg Lys Glu Tyr Met Asn Gln Trp Ser Cys Gly Ser
            580                 585                 590

Ala Arg Thr Met Lys Arg Gly Tyr Lys Asn Asp Asn Tyr Glu Leu Cys
            595                 600                 605

Lys Tyr Asn Gly Val Asp Val Lys Pro Thr Thr Val Arg Ser Asn Ser
            610                 615                 620

Ser Lys Leu Asp
625

<210> SEQ ID NO 45
<211> LENGTH: 653
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: raj116_var25 745 amino acids

<400> SEQUENCE: 45

```
Asp Tyr Ile Lys Gly Asp Pro Tyr Phe Ala Glu Tyr Ala Thr Lys Leu
1               5                   10                  15

Ser Phe Ile Leu Asn Pro Ser Asp Thr Glu Asn Ala Ser Glu Thr Pro
            20                  25                  30

Ser Lys Tyr Tyr Asp Glu Ala Cys Asn Pro Asn Glu Ser Glu Ile Ala
        35                  40                  45

Ser Val Glu Gln Ala Gln Thr Ser Gly Pro Ser Ser Asn Lys Thr Cys
    50                  55                  60

Ile Thr His Ser Ser Ile Lys Thr Asn Lys Lys Glu Cys Lys Asp
65                  70                  75                  80

Val Lys Leu Gly Val Arg Glu Asn Asp Lys Asp Leu Lys Ile Cys Val
                85                  90                  95

Ile Glu Asp Thr Ser Leu Ser Gly Val Asp Asn Cys Cys Phe Lys Asp
            100                 105                 110

Leu Leu Gly Ile Leu Gln Glu Asn Cys Ser Asp Asn Lys Arg Gly Ser
        115                 120                 125

Ser Ser Asn Asp Ser Cys Asn Asn Asn Glu Glu Ala Cys Glu Lys
    130                 135                 140

Asn Leu Asp Glu Ala Leu Ala Ser Leu Thr Asn Gly Tyr Lys Cys Asp
145                 150                 155                 160

Lys Cys Lys Ser Gly Thr Ser Thr Val Asn Lys Lys Trp Thr Trp Arg
                165                 170                 175

Lys Ser Ser Gly Asn Glu Glu Gly Leu Gln Lys Glu Tyr Ala Asn Thr
            180                 185                 190

Ile Gly Leu Pro Pro Arg Thr Gln Ser Leu Cys Leu Val Cys Leu His
        195                 200                 205

Glu Lys Glu Gly Lys Thr Lys His Lys Thr Ile Ser Thr Asn Ser Glu
    210                 215                 220

Leu Leu Lys Glu Trp Ile Ile Ala Ala Phe His Glu Gly Lys Asn Leu
225                 230                 235                 240

Lys Thr Ser His Glu Lys Lys Asn Asp Asp Asn Gly Lys Lys Leu Cys
                245                 250                 255

Lys Ala Leu Glu Tyr Ser Phe Ala Asp Tyr Gly Asp Leu Ile Lys Gly
            260                 265                 270

Thr Ser Ile Trp Asp Asn Glu Tyr Thr Lys Asp Leu Glu Leu Asn Leu
        275                 280                 285

Gln Lys Ala Phe Gly Lys Leu Phe Arg Lys Tyr Ile Lys Lys Asn Asn
    290                 295                 300

Thr Ala Glu Gln Asp Thr Ser Tyr Ser Ser Leu Asp Glu Leu Arg Glu
305                 310                 315                 320

Ser Trp Trp Asn Thr Asn Lys Lys Tyr Ile Trp Thr Ala Met Lys His
                325                 330                 335

Gly Ala Glu Met Asn Gly Thr Thr Cys Ser Ser Gly Ser Gly Asp Asn
            340                 345                 350
```

Gly Asp Ser Ser Ile Thr Gly Ser Ser Asp Ser Gly Ser Thr Thr Cys
355                 360                 365

Ser Gly Asp Asn Gly Ser Ile Ser Cys Asp Asp Ile Pro Thr Thr Asp
370                 375                 380

Phe Ile Pro Gln Tyr Leu Arg Phe Leu Gln Glu Trp Val Glu His Phe
385                 390                 395                 400

Cys Glu Gln Arg Gln Ala Lys Val Lys Asp Val Ile Asn Ser Cys Asn
                405                 410                 415

Ser Cys Asn Glu Ser Gly Gly Thr Cys Asn Gly Glu Cys Lys Thr Lys
            420                 425                 430

Cys Lys Asp Glu Cys Glu Lys Tyr Lys Lys Phe Ile Glu Asp Cys Asn
        435                 440                 445

Gly Gly Asp Gly Thr Ala Gly Ser Ser Trp Val Lys Arg Trp Asp Gln
450                 455                 460

Ile Tyr Lys Arg Tyr Ser Lys His Ile Glu Asp Ala Lys Arg Asn Arg
465                 470                 475                 480

Lys Ala Gly Thr Lys Asn Cys Gly Pro Ser Ser Ile Thr Asn Ala Ala
                485                 490                 495

Ala Ser Thr Asp Glu Asn Lys Cys Val Gln Ser Asp Val Asp Ser Phe
            500                 505                 510

Phe Lys His Leu Ile Asp Ile Gly Leu Thr Thr Pro Ser Ser Tyr Leu
        515                 520                 525

Ser Ile Val Leu Asp Glu Asn Ser Cys Gly Asp Asp Lys Ala Pro Trp
530                 535                 540

Thr Thr Tyr Thr Thr Tyr Thr Thr Thr Glu Lys Cys Asn Lys Glu Arg
545                 550                 555                 560

Asp Lys Ser Lys Ser Gln Ser Ser Asp Thr Leu Val Val Val Asn Val
                565                 570                 575

Pro Ser Pro Leu Gly Asn Thr Pro His Glu Tyr Lys Tyr Ala Cys Glu
            580                 585                 590

Cys Lys Ile Pro Thr Asn Glu Glu Thr Cys Asp Asp Arg Lys Asp Tyr
        595                 600                 605

Met Asn Gln Trp Ile Ser Asp Thr Ser Lys Lys Gln Lys Gly Ser Gly
610                 615                 620

Ser Gly Lys Asp Tyr Tyr Glu Leu Tyr Thr Tyr Asn Gly Val Gln Ile
625                 630                 635                 640

Lys Gln Ala Ala Gly Arg Ser Ser Ser Thr Lys Leu Asp
                645                 650

<210> SEQ ID NO 46
<211> LENGTH: 490
<212> TYPE: PRT
<213> ORGANISM: Plasmodium falciparum

<400> SEQUENCE: 46

Lys Cys Asp Lys Cys Lys Ser Glu Gln Ser Lys Lys Asn Asn Asn Lys
1               5                   10                  15

Trp Ile Trp Lys Lys Tyr Ser Gly Asn Gly Glu Gly Leu Gln Lys Glu
                20                  25                  30

Tyr Ala Asn Thr Ile Gly Leu Pro Pro Arg Thr Gln Ser Leu Cys Leu
            35                  40                  45

Val Cys Leu His Glu Lys Glu Gly Lys Thr Gln His Lys Thr Ile Ser
        50                  55                  60

Thr Asn Ser Glu Leu Leu Lys Glu Trp Ile Ile Ala Ala Phe His Glu
65                  70                  75                  80

```
Gly Lys Asn Leu Lys Lys Arg Tyr Pro Gln Asn Lys Asn Asp Asp Asn
                85                  90                  95

Asn Ser Lys Leu Cys Lys Ala Leu Glu Tyr Ser Phe Ala Asp Tyr Gly
               100                 105                 110

Asp Leu Ile Lys Gly Thr Ser Ile Trp Asp Asn Glu Tyr Thr Lys Asp
           115                 120                 125

Leu Glu Leu Asn Leu Gln Lys Ala Phe Gly Lys Leu Phe Arg Lys Tyr
       130                 135                 140

Ile Lys Lys Asn Asn Thr Ala Glu Gln Asp Thr Ser Tyr Ser Ser Leu
145                 150                 155                 160

Asp Glu Leu Arg Glu Ser Trp Trp Asn Thr Asn Lys Lys Tyr Ile Trp
               165                 170                 175

Thr Ala Met Lys His Gly Ala Glu Met Asn Gly Thr Thr Cys Ser Ser
               180                 185                 190

Gly Ser Gly Asp Asn Gly Asp Ser Ser Cys Asp Asp Ile Pro Thr Ile
           195                 200                 205

Asp Leu Ile Pro Gln Tyr Leu Arg Phe Leu Gln Glu Trp Val Glu His
       210                 215                 220

Phe Cys Lys Gln Arg Gln Ala Lys Val Lys Asp Val Ile Asn Ser Cys
225                 230                 235                 240

Asn Ser Cys Lys Asn Thr Ser Gly Glu Arg Lys Ile Gly Gly Thr Cys
               245                 250                 255

Asn Ser Asp Cys Glu Lys Lys Cys Lys Val Ala Cys Asp Ala Tyr Lys
               260                 265                 270

Thr Phe Ile Glu Glu Cys Arg Thr Ala Val Gly Gly Thr Ala Gly Ser
           275                 280                 285

Ser Trp Val Lys Arg Trp Asp Gln Ile Tyr Lys Arg Tyr Ser Lys His
       290                 295                 300

Ile Glu Asp Ala Lys Arg Asn Arg Lys Ala Gly Thr Lys Asn Cys Gly
305                 310                 315                 320

Pro Ser Ser Thr Thr Asn Ala Ala Glu Asn Lys Cys Val Gln Ser Asp
               325                 330                 335

Ile Asp Ser Phe Phe Lys His Leu Ile Asp Ile Gly Leu Thr Thr Pro
           340                 345                 350

Ser Ser Tyr Leu Ser Asn Val Leu Asp Glu Asn Ser Cys Gly Ala Asp
       355                 360                 365

Lys Ala Pro Trp Thr Thr Tyr Thr Thr Tyr Thr Thr Tyr Thr Thr Tyr
       370                 375                 380

Thr Thr Tyr Thr Thr Thr Glu Lys Cys Asn Lys Glu Arg Asp Lys Ser
385                 390                 395                 400

Lys Ser Gln Gln Ser Asn Thr Ser Val Val Val Asn Val Pro Ser Pro
               405                 410                 415

Leu Gly Asn Thr Pro His Glu Tyr Lys Tyr Ala Cys Glu Cys Lys Ile
           420                 425                 430

Pro Thr Thr Glu Glu Thr Cys Asp Asp Arg Lys Glu Tyr Met Asn Gln
               435                 440                 445

Trp Ile Ile Asp Asn Thr Lys Asn Pro Lys Gly Ser Gly Ser Thr Asp
           450                 455                 460

Asn Asp Tyr Glu Leu Tyr Thr Tyr Asn Gly Val Gln Ile Lys Gln Ala
465                 470                 475                 480

Ala Gly Arg Ser Ser Ser Thr Lys Leu Asp
               485                 490
```

<210> SEQ ID NO 47
<211> LENGTH: 335
<212> TYPE: PRT
<213> ORGANISM: Plasmodium falciparum

<400> SEQUENCE: 47

Lys Cys Glu Lys Cys Lys Ser Gly Thr Ser Thr Val Asn Asn Lys Trp
1               5                   10                  15

Ile Trp Arg Lys Ser Ser Gly Lys Glu Gly Gly Leu Gln Lys Glu Tyr
            20                  25                  30

Ala Asn Thr Ile Gly Leu Pro Pro Arg Thr Gln Ser Leu Tyr Leu Gly
        35                  40                  45

Asn Leu Pro Lys Leu Glu Asn Val Cys Lys Gly Val Thr Asp Ile Ile
    50                  55                  60

Tyr Asp Thr Lys Glu Lys Phe Leu Ser Gly Cys Leu Ile Ala Ala Phe
65                  70                  75                  80

His Glu Gly Lys Asn Leu Lys Thr Thr Tyr Leu Glu Lys Lys Asn Asp
                85                  90                  95

Asp Asn Gly Lys Lys Leu Cys Lys Ala Leu Glu Tyr Ser Phe Ala Asp
            100                 105                 110

Tyr Gly Asp Leu Ile Lys Gly Thr Ser Ile Trp Asp Asn Glu Tyr Thr
        115                 120                 125

Lys Asp Leu Glu Leu Asn Leu Gln Lys Ile Phe Gly Lys Leu Phe Arg
    130                 135                 140

Lys Tyr Ile Lys Lys Asn Asn Thr Ala Glu Gln Asp Thr Ser Tyr Ser
145                 150                 155                 160

Ser Leu Asp Glu Leu Arg Glu Ser Trp Trp Asn Thr Asn Lys Lys Tyr
                165                 170                 175

Ile Trp Ile Ala Met Lys His Gly Ala Gly Met Asn Gly Thr Thr Cys
            180                 185                 190

Ser Ser Gly Ser Gly Asp Ser Ser Asn Asp Ile Pro Thr Thr Asp Phe
        195                 200                 205

Ile Pro Gln Tyr Leu Arg Phe Leu Gln Glu Trp Val Glu Asn Phe Cys
    210                 215                 220

Glu Gln Arg Gln Ala Lys Val Lys Pro Val Ile Glu Asn Cys Asn Ser
225                 230                 235                 240

Cys Lys Glu Ser Gly Gly Thr Cys Asn Gly Glu Cys Lys Thr Lys Cys
                245                 250                 255

Lys Val Ala Cys Asp Ala Tyr Lys Lys Phe Ile Asp Gly Thr Gly Ser
            260                 265                 270

Gly Gly Gly Ser Arg Pro Thr Gly Ile Ala Gly Ser Ser Trp Ser Lys
        275                 280                 285

Arg Trp Asp Gln Ile Tyr Lys Arg Tyr Ser Lys His Ile Glu Asp Ala
    290                 295                 300

Lys Arg Asn Arg Lys Ala Gly Thr Lys Asn Cys Gly Pro Ser Ser Ile
305                 310                 315                 320

Thr Asn Val Ser Val Ser Thr Asp Glu Asn Lys Cys Val Gln Ser
                325                 330                 335

<210> SEQ ID NO 48
<211> LENGTH: 637
<212> TYPE: PRT
<213> ORGANISM: Artificial Sequence
<220> FEATURE:
<223> OTHER INFORMATION: Description of Artificial Sequence: Synthetic
      polypeptide <220> FEATURE:
<223> OTHER INFORMATION: T2C6 745 amino acids

<400> SEQUENCE: 48

```
Asn Tyr Ile Lys Asp Asp Pro Tyr Ser Lys Glu Tyr Val Thr Lys Leu
1               5                   10                  15

Ser Phe Ile Pro Asn Ser Ser Asp Ala Asn Thr Ser Ser Glu Lys Ile
            20                  25                  30

Gln Lys Asn Asn Asp Glu Val Cys Asn Pro Asn Glu Ser Gly Ile Ser
        35                  40                  45

Ser Val Glu Gln Ala Gln Thr Ser Asp Pro Ser Ser Asn Lys Thr Cys
    50                  55                  60

Ile Thr His Ser Ser Ile Lys Ala Asn Lys Lys Glu Cys Lys Asp
65                  70                  75                  80

Val Lys Leu Gly Val Arg Glu Asn Asp Lys Asp Leu Lys Ile Cys Val
                85                  90                  95

Ile Glu His Thr Ser Leu Ser Gly Val Asp Asn Cys Cys Phe Lys Asp
            100                 105                 110

Phe Leu Arg Met Leu Gln Glu Pro Arg Ile Asp Lys Asn Gln Arg Gly
        115                 120                 125

Ser Ser Ser Asn Gly Ser Cys Asp Lys Asn Ser Glu Glu Ala Cys Glu
    130                 135                 140

Lys Asn Leu Asp Glu Ala Leu Ala Ser Leu Thr Asn Gly Tyr Lys Cys
145                 150                 155                 160

Asp Lys Cys Lys Ser Glu Gln Ser Lys Lys Asn Asn Asn Lys Trp Ile
                165                 170                 175

Trp Lys Lys Phe Pro Gly Lys Glu Gly Leu Gln Glu Glu Tyr Ala
            180                 185                 190

Asn Thr Ile Gly Leu Pro Pro Arg Thr Gln Tyr Leu Cys Leu Val Val
        195                 200                 205

Cys Leu Asp Glu Lys Glu Gly Lys Thr Gln Glu Leu Lys Asn Ile Arg
    210                 215                 220

Thr Asn Ser Glu Leu Leu Lys Glu Trp Ile Ile Ala Ala Phe His Glu
225                 230                 235                 240

Gly Lys Asn Leu Lys Thr Thr Tyr Pro Gln Lys Lys Asn Asp Asp Asn
                245                 250                 255

Gly Lys Lys Leu Cys Lys Asp Leu Lys Tyr Ser Phe Ala Asp Tyr Gly
            260                 265                 270

Asp Leu Ile Lys Gly Thr Ser Ile Trp Asp Asn Glu Tyr Thr Lys Asn
        275                 280                 285

Val Glu Leu Asn Leu Gln Asn Asn Phe Gly Lys Leu Phe Arg Lys Tyr
    290                 295                 300

Ile Lys Lys Asn Asn Thr Ala Glu Gln Asp Thr Ser Tyr Ser Ser Leu
305                 310                 315                 320

Asp Glu Leu Arg Glu Ser Trp Trp Asn Thr Asn Lys Lys Tyr Ile Trp
                325                 330                 335

Leu Ala Met Lys His Gly Ala Glu Met Asn Ser Thr Thr Cys Cys Gly
            340                 345                 350

Asp Gly Ser Val Thr Gly Ser Gly Ser Ser Cys Asp Asp Ile Pro Thr
        355                 360                 365

Ile Asp Leu Ile Pro Gln Tyr Leu Arg Phe Leu Gln Glu Trp Val Glu
    370                 375                 380

His Phe Cys Lys Gln Arg Gln Ala Lys Val Lys Asp Val Ile Thr Asn
385                 390                 395                 400
```

```
Cys Asn Ser Cys Lys Glu Ser Gly Asn Lys Cys Lys Thr Glu Cys Lys
                405                 410                 415

Asn Lys Cys Lys Asp Glu Cys Glu Lys Tyr Lys Lys Phe Ile Glu Ala
            420                 425                 430

Cys Gly Thr Ala Val Gly Gly Thr Gly Thr Ala Gly Ser Pro Trp Ser
        435                 440                 445

Lys Arg Trp Asp Gln Ile Tyr Lys Arg Tyr Ser Lys His Ile Glu Asp
    450                 455                 460

Ala Lys Arg Asn Arg Lys Ala Gly Thr Lys Asn Cys Gly Pro Ser Ser
465                 470                 475                 480

Thr Thr Asn Ala Ala Glu Asn Lys Cys Val Gln Ser Asp Ile Asp Ser
                485                 490                 495

Phe Phe Lys His Leu Ile Asp Ile Gly Leu Thr Thr Pro Ser Ser Tyr
            500                 505                 510

Leu Ser Ile Val Leu Asp Asp Asn Ile Cys Gly Ala Asp Lys Ala Pro
        515                 520                 525

Trp Thr Thr Tyr Thr Thr Tyr Thr Thr Glu Asn Cys Asp Ile Gln Lys
    530                 535                 540

Lys Thr Pro Lys Ser Gln Ser Cys Asp Thr Leu Val Val Val Asn Val
545                 550                 555                 560

Pro Ser Pro Leu Gly Asn Thr Pro His Gly Tyr Lys Tyr Ala Cys Gln
                565                 570                 575

Cys Arg Thr Pro Asn Lys Gln Glu Ser Cys Asp Asp Arg Lys Glu Tyr
            580                 585                 590

Met Asn Gln Trp Ile Ile Asp Asn Thr Lys Asn Pro Lys Gly Ser Gly
        595                 600                 605

Ser Gly Lys Asp Tyr Tyr Glu Leu Cys Lys Tyr Asn Gly Val Lys Glu
    610                 615                 620

Thr Lys Pro Leu Gly Thr Leu Lys Asn Ser Lys Leu Asp
625                 630                 635

<210> SEQ ID NO 49
<211> LENGTH: 330
<212> TYPE: PRT
<213> ORGANISM: Plasmodium falciparum

<400> SEQUENCE: 49

Lys Cys Asp Lys Cys Lys Ser Glu Gln Ser Lys Lys Asn Asn Asn Lys
1               5                   10                  15

Trp Ile Trp Arg Lys Phe Pro Gly Lys Glu Gly Gly Leu Gln Lys Glu
            20                  25                  30

Tyr Ala Asn Thr Ile Gly Leu Pro Pro Arg Thr Gln Ser Leu Cys Leu
        35                  40                  45

Val Cys Leu His Glu Lys Glu Gly Lys Thr Gln His Lys Thr Ile Ser
    50                  55                  60

Thr Asn Ser Glu Leu Leu Lys Glu Trp Ile Ile Ala Ala Phe His Glu
65                  70                  75                  80

Gly Lys Asn Leu Lys Thr Thr Tyr Leu Glu Lys Asn Ala Glu Asn
                85                  90                  95

Lys Lys Lys Leu Cys Lys Ala Leu Lys Tyr Ser Phe Ala Asp Tyr Gly
            100                 105                 110

Asp Leu Ile Lys Gly Thr Ser Ile Trp Asp Asn Glu Tyr Thr Lys Asp
        115                 120                 125

Leu Glu Leu Asn Leu Gln Lys Ile Phe Gly Lys Leu Phe Arg Lys Tyr
```

```
                130              135              140
Ile Lys Lys Asn Asn Thr Ala Glu Gln Asp Thr Ser Tyr Ser Ser Leu
145              150              155              160

Asp Glu Leu Arg Glu Ser Trp Trp Asn Thr Asn Lys Lys Tyr Ile Trp
            165              170              175

Thr Ala Met Lys His Gly Ala Gly Met Asn Gly Thr Met Cys Asn Ala
        180              185              190

Asp Gly Ser Val Thr Gly Ser Gly Ser Ser Cys Asp Asp Met Pro Thr
        195              200              205

Thr Asp Phe Ile Pro Gln Tyr Leu Arg Phe Leu Gln Glu Trp Val Glu
    210              215              220

His Phe Cys Lys Gln Arg Gln Ala Lys Val Lys Asp Val Ile Glu Asn
225              230              235              240

Cys Lys Ser Cys Lys Glu Ser Gly Asn Lys Cys Lys Thr Glu Cys Lys
            245              250              255

Asn Lys Cys Asp Ala Tyr Lys Thr Phe Ile Glu Glu Cys Gly Thr Ala
            260              265              270

Val Gly Gly Thr Ala Gly Ser Ser Trp Val Lys Arg Trp Asp Gln Ile
        275              280              285

Tyr Lys Arg Tyr Ser Lys His Ile Glu Asp Ala Lys Arg Asn Arg Lys
        290              295              300

Ala Gly Thr Lys Asn Cys Gly Thr Ser Ser Thr Thr Asn Ala Ala Ala
305              310              315              320

Ser Thr Ala Glu Asn Lys Cys Val Gln Ser
                325              330

<210> SEQ ID NO 50
<211> LENGTH: 269
<212> TYPE: PRT
<213> ORGANISM: Plasmodium falciparum

<400> SEQUENCE: 50

Asn Tyr Ile Lys Asp Asp Pro Tyr Ser Lys Glu Tyr Val Thr Lys Leu
1               5               10              15

Ser Phe Ile Leu Asn Ser Ser Asp Ala Glu Asn Ala Ser Glu Thr Pro
            20              25              30

Ser Lys Tyr Tyr Asp Glu Ala Cys Asn Cys Asn Glu Ser Gly Ile Ser
        35              40              45

Ser Val Glu Gln Ala Ser Ile Ser Asp Arg Ser Ser Gln Lys Ala Cys
    50              55              60

Asn Thr His Ser Phe Ile Gly Ala Asn Lys Lys Val Cys Lys His
65              70              75              80

Val Lys Leu Gly Val Arg Glu Asn Asp Lys Asp Leu Lys Ile Cys Val
            85              90              95

Ile Glu Asp Asp Ser Leu Arg Gly Val Glu Asn Cys Cys Phe Lys Asp
            100             105             110

Phe Leu Arg Met Leu Gln Glu Pro Arg Ile Asp Lys Asn Gln Arg Gly
        115             120             125

Ser Ser Ser Asn Asp Ser Cys Asn Asn Asn Glu Glu Ala Cys Glu
    130             135             140

Lys Asn Leu Asp Glu Ala Leu Ala Ser Leu His Asn Gly Tyr Lys Asn
145             150             155             160

Gln Lys Cys Lys Ser Glu Gln Ser Lys Lys Asn Asn Asn Lys Trp Ile
            165             170             175
```

```
Trp Lys Lys Ser Ser Gly Lys Glu Gly Gly Leu Gln Lys Glu Tyr Ala
            180                 185                 190

Asn Thr Ile Gly Leu Pro Pro Arg Thr Gln Ser Leu Cys Leu Val Cys
            195                 200                 205

Leu His Glu Lys Glu Gly Lys Thr Gln His Lys Thr Ile Ser Thr Asn
            210                 215                 220

Ser Glu Leu Leu Lys Glu Trp Ile Ile Asp Ala Phe His Glu Gly Lys
225                 230                 235                 240

Asn Leu Lys Thr Thr Tyr Leu Glu Lys Lys Gly Asp Asn Gly Lys
            245                 250                 255

Lys Leu Cys Lys Ala Leu Lys Tyr Ser Phe Ala Asp Tyr
            260                 265

<210> SEQ ID NO 51
<211> LENGTH: 347
<212> TYPE: PRT
<213> ORGANISM: Plasmodium falciparum

<400> SEQUENCE: 51

Lys Cys Asp Lys Cys Lys Ser Glu Gln Ser Lys Asn Asn Lys Asn
1               5                   10                  15

Trp Ile Trp Lys Lys Ser Ser Gly Lys Glu Gly Gly Leu Gln Lys Glu
            20                  25                  30

Tyr Ala Asn Thr Ile Ala Leu Pro Pro Arg Thr Gln Ser Leu Cys Leu
            35                  40                  45

Val Val Cys Leu His Glu Lys Glu Gly Lys Thr Gln His Lys Thr Ile
            50                  55                  60

Ser Thr Asn Ser Glu Leu Leu Lys Glu Trp Ile Ile Asp Ala Phe His
65                  70                  75                  80

Glu Gly Lys Asn Leu Lys Thr Thr Tyr Leu Glu Lys Gln Asn Ala Asp
            85                  90                  95

Asn Gly Lys Lys Asn Ala Asp Asn Ser Lys Leu Cys Lys Asp Leu
            100                 105                 110

Lys Tyr Ser Phe Ala Asp Tyr Gly Asp Leu Ile Lys Gly Thr Ser Ile
            115                 120                 125

Trp Asp Asn Glu Tyr Thr Lys Asp Leu Glu Leu Asn Leu Gln Gln Ile
            130                 135                 140

Phe Gly Lys Leu Phe Arg Lys Tyr Ile Lys Lys Asn Ile Ala Ser Asp
145                 150                 155                 160

Glu Asn Thr Leu Tyr Ser Ser Leu Asp Glu Leu Arg Glu Ser Trp Trp
            165                 170                 175

Asn Thr Asn Lys Lys Tyr Ile Trp Thr Ala Met Lys His Gly Ala Glu
            180                 185                 190

Met Asn Gly Thr Thr Cys Ser Ser Gly Ser Gly Asp Ser Ser Ser Gly
            195                 200                 205

Glu Asn Gln Thr Asn Ser Cys Asp Asp Ile Pro Thr Ile Asp Leu Ile
            210                 215                 220

Pro Gln Tyr Leu Arg Phe Leu Gln Glu Trp Val Glu His Phe Cys Glu
225                 230                 235                 240

Gln Arg Gln Ala Lys Val Lys Asp Val Ile Thr Asn Cys Lys Ser Cys
            245                 250                 255

Lys Glu Ser Gly Gly Thr Cys Asn Ser Asp Cys Lys Thr Lys Cys Lys
            260                 265                 270

Gly Glu Cys Glu Lys Tyr Lys Lys Phe Ile Glu Lys Cys Lys Gly Gly
            275                 280                 285
```

-continued

Gly Thr Glu Gly Thr Ser Gly Ser Ser Trp Val Lys Arg Trp Tyr Gln
        290                 295                 300

Ile Tyr Met Arg Tyr Ser Lys Tyr Ile Glu Asp Ala Lys Arg Asn Arg
305                 310                 315                 320

Lys Ala Gly Thr Lys Ser Cys Gly Thr Ser Ser Gly Ala Asn Ser Gly
                325                 330                 335

Val Thr Thr Thr Glu Ser Lys Cys Val Gln Ser
            340                 345

<210> SEQ ID NO 52
<211> LENGTH: 269
<212> TYPE: PRT
<213> ORGANISM: Plasmodium falciparum

<400> SEQUENCE: 52

Asp Tyr Ile Lys Asp Asp Pro Tyr Ser Lys Glu Tyr Thr Thr Lys Leu
1               5                   10                  15

Ser Phe Ile Leu Asn Ser Ser Asp Ala Asn Thr Ser Ser Glu Lys Ile
            20                  25                  30

Gln Lys Asn Asn Asp Glu Val Cys Asn Pro Asn Glu Ser Glu Ile Ser
        35                  40                  45

Ser Val Glu Gln Ala Gln Thr Ser Arg Pro Ser Ser Asn Lys Thr Cys
    50                  55                  60

Ile Thr His Ser Ser Ile Lys Ala Asn Lys Lys Val Cys Lys Asp
65                  70                  75                  80

Val Lys Leu Gly Val Arg Glu Asn Asp Lys Val Leu Arg Val Cys Val
                85                  90                  95

Ile Glu His Thr Ser Leu Ser Gly Val Glu Asn Cys Cys Cys Gln Asp
            100                 105                 110

Leu Leu Gly Ile Leu Gln Glu Asn Cys Ser Asp Asn Lys Arg Gly Ser
        115                 120                 125

Ser Ser Asn Gly Ser Cys Asp Lys Asn Ser Glu Ala Cys Glu Lys
    130                 135                 140

Asn Leu Asp Glu Ala Leu Ala Ser Leu Thr Asn Cys Tyr Lys Asn Gln
145                 150                 155                 160

Lys Cys Lys Ser Glu Gln Ser Lys Lys Asn Asn Lys Trp Ile Trp
                165                 170                 175

Lys Lys Ser Ser Gly Asn Glu Lys Gly Leu Gln Lys Glu Tyr Ala Asn
            180                 185                 190

Thr Ile Gly Leu Pro Pro Arg Thr Gln Ser Leu Cys Leu Val Cys Leu
        195                 200                 205

His Glu Lys Glu Gly Lys Thr Gln Glu Leu Lys Asn Ile Ser Thr Asn
    210                 215                 220

Ser Glu Leu Leu Lys Glu Trp Ile Ile Ala Ala Phe His Glu Gly Lys
225                 230                 235                 240

Asn Leu Lys Thr Thr Tyr Pro Gln Asn Lys Asn Asp Asp Asn Gly Lys
                245                 250                 255

Lys Leu Phe Lys Asp Leu Lys Tyr Ser Phe Ala Asp Tyr
            260                 265

<210> SEQ ID NO 53
<211> LENGTH: 646
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: MTS1 745 amino acids

<400> SEQUENCE: 53

```
Asp Tyr Ile Lys Asp Asp Pro Tyr Ser Lys Glu Tyr Thr Thr Lys Leu
1               5                  10                  15

Ser Phe Ile Leu Asn Ser Ser Asp Ala Asn Thr Ser Ser Glu Lys Ile
            20                  25                  30

Gln Lys Asn Asn Asp Glu Val Cys Asn Pro Asn Glu Ser Glu Ile Ser
        35                  40                  45

Ser Val Glu Gln Ala Gln Thr Ser Arg Pro Ser Ser Asn Lys Thr Cys
    50                  55                  60

Ile Thr His Ser Ser Ile Lys Ala Asn Lys Lys Val Cys Lys Asp
65                  70                  75                  80

Val Lys Leu Gly Val Arg Glu Asn Asp Lys Val Leu Arg Val Cys Val
                85                  90                  95

Ile Glu His Thr Ser Leu Ser Gly Val Glu Asn Cys Cys Cys Gln Asp
            100                 105                 110

Leu Leu Gly Ile Leu Gln Glu Asn Cys Ser Asp Asn Lys Arg Gly Ser
        115                 120                 125

Ser Ser Asn Gly Ser Cys Asp Lys Asn Ser Glu Glu Ala Cys Glu Lys
    130                 135                 140

Asn Leu Asp Glu Ala Leu Ala Ser Leu Thr Asn Cys Tyr Lys Asn Gln
145                 150                 155                 160

Lys Cys Lys Ser Glu Gln Ser Lys Lys Asn Asn Asn Lys Trp Ile Trp
                165                 170                 175

Lys Lys Ser Ser Gly Lys Glu Gly Leu Gln Lys Glu Tyr Ala Asn
            180                 185                 190

Thr Ile Gly Leu Pro Pro Arg Thr Gln Ser Leu Tyr Leu Gly Asn Leu
        195                 200                 205

Pro Lys Leu Glu Asn Val Cys Lys Gly Val Thr Asp Ile Asn Phe Asp
    210                 215                 220

Thr Lys Glu Lys Phe Leu Ala Gly Cys Leu Ile Ala Ala Phe His Glu
225                 230                 235                 240

Gly Lys Asn Leu Lys Thr Thr Tyr Leu Glu Lys Lys Asn Asp Asp Asn
                245                 250                 255

Gly Lys Lys Leu Cys Lys Ala Leu Glu Tyr Ser Phe Ala Asp Tyr Gly
            260                 265                 270

Asp Leu Ile Lys Gly Thr Ser Ile Trp Asp Asn Glu Tyr Thr Lys Asp
        275                 280                 285

Leu Glu Leu Asn Leu Gln Lys Ala Phe Gly Lys Leu Phe Arg Lys Tyr
    290                 295                 300

Ile Lys Lys Asn Asn Thr Ala Glu Gln Asp Thr Ser Tyr Ser Ser Leu
305                 310                 315                 320

Asp Glu Leu Arg Glu Ser Trp Trp Asn Thr Asn Lys Lys Tyr Ile Trp
                325                 330                 335

Thr Ala Met Lys His Gly Ala Gly Met Asn Gly Thr Thr Cys Ser Ser
            340                 345                 350

Gly Ser Gly Asp Ser Ser Asn Asp Ile Pro Thr Thr Asp Phe Ile Pro
        355                 360                 365

Gln Tyr Leu Arg Phe Leu Gln Glu Trp Val Glu Asn Phe Cys Glu Gln
    370                 375                 380

Arg Gln Ala Lys Val Lys Asp Val Ile Glu Asn Cys Asn Ser Cys Lys
```

```
            385                 390                 395                 400
Asn Thr Ser Gly Glu Arg Lys Ile Gly Asp Thr Cys Asn Ser Asp Cys
                    405                 410                 415
Glu Lys Lys Cys Lys Asp Glu Cys Glu Lys Tyr Lys Lys Phe Ile Glu
                420                 425                 430
Asp Cys Lys Gly Gly Asp Gly Thr Ala Gly Ser Ser Trp Val Lys Arg
            435                 440                 445
Trp Asp Gln Ile Tyr Lys Arg Tyr Ser Lys His Ile Glu Asp Ala Lys
        450                 455                 460
Arg Asn Arg Lys Ala Gly Thr Lys Asn Cys Gly Ile Thr Thr Gly Thr
465                 470                 475                 480
Ile Ser Gly Glu Ser Gly Ala Thr Ser Gly Val Thr Thr Thr Glu
                485                 490                 495
Asn Lys Cys Val Gln Ser Asp Ile Asp Ser Phe Phe Lys His Leu Ile
                500                 505                 510
Asp Ile Gly Leu Thr Thr Pro Ser Ser Tyr Leu Ser Asn Val Leu Asp
            515                 520                 525
Asp Asn Ile Cys Gly Glu Asp Asn Ala Pro Trp Thr Thr Tyr Thr Thr
        530                 535                 540
Tyr Thr Thr Glu Lys Cys Asn Lys Glu Thr Asp Lys Ser Lys Ser Gln
545                 550                 555                 560
Gln Ser Asn Thr Ala Val Val Asn Val Pro Ser Pro Leu Gly Asn
                565                 570                 575
Thr Pro His Gly Tyr Lys Tyr Ala Cys Glu Cys Lys Ile Pro Thr Thr
                580                 585                 590
Glu Glu Thr Cys Asp Asp Arg Lys Glu Tyr Met Asn Gln Trp Ser Cys
            595                 600                 605
Gly Ser Ala Gln Thr Val Arg Asp Arg Ser Gly Lys Asp Asp Tyr Glu
        610                 615                 620
Leu Cys Lys Tyr Asn Gly Val Gln Ile Lys Gln Ala Ala Gly Thr Leu
625                 630                 635                 640
Lys Asn Ser Lys Leu Asp
                645

<210> SEQ ID NO 54
<211> LENGTH: 632
<212> TYPE: PRT
<213> ORGANISM: Plasmodium falciparum

<400> SEQUENCE: 54

Asn Tyr Ile Lys Gly Asp Pro Tyr Phe Ala Glu Tyr Ala Thr Lys Leu
1               5                   10                  15
Ser Phe Ile Leu Asn Ser Ser Asp Ala Asn Asn Pro Ser Glu Lys Ile
                20                  25                  30
Gln Lys Asn Asn Asp Glu Val Cys Asn Cys Asn Glu Ser Gly Ile Ala
            35                  40                  45
Ser Val Glu Gln Glu Gln Ile Ser Asp Pro Ser Ser Asn Lys Thr Cys
        50                  55                  60
Ile Thr His Ser Ser Ile Lys Ala Asn Lys Lys Val Cys Lys His
65                  70                  75                  80
Val Lys Leu Gly Val Arg Glu Asn Asp Lys Asp Leu Arg Val Cys Val
                85                  90                  95
Ile Glu His Thr Ser Leu Ser Gly Val Glu Asn Cys Cys Cys Gln Asp
                100                 105                 110
```

-continued

```
Phe Leu Arg Ile Leu Gln Glu Asn Cys Ser Asp Asn Lys Ser Gly Ser
            115                 120                 125

Ser Ser Asn Gly Ser Cys Asn Lys Asn Gln Glu Ala Cys Glu Lys
    130                 135                 140

Asn Leu Glu Lys Val Leu Ala Ser Leu Thr Asn Cys Tyr Lys Cys Asp
145                 150                 155                 160

Lys Cys Lys Ser Glu Gln Ser Lys Lys Asn Asn Lys Asn Trp Ile Trp
                165                 170                 175

Lys Lys Ser Ser Gly Lys Glu Gly Gly Leu Gln Lys Glu Tyr Ala Asn
            180                 185                 190

Thr Ile Gly Leu Pro Pro Arg Thr Gln Ser Leu Cys Leu Val Val Cys
        195                 200                 205

Leu Asp Glu Lys Gly Lys Lys Thr Gln Glu Leu Lys Asn Ile Arg Thr
    210                 215                 220

Asn Ser Glu Leu Leu Lys Glu Trp Ile Ile Ala Ala Phe His Glu Gly
225                 230                 235                 240

Lys Asn Leu Lys Pro Ser His Glu Lys Lys Asn Asp Asp Asn Gly Lys
                245                 250                 255

Lys Leu Cys Lys Ala Leu Glu Tyr Ser Phe Ala Asp Tyr Gly Asp Leu
            260                 265                 270

Ile Lys Gly Thr Ser Ile Trp Asp Asn Glu Tyr Thr Lys Asp Leu Glu
        275                 280                 285

Leu Asn Leu Gln Lys Ile Phe Gly Lys Leu Phe Arg Lys Tyr Ile Lys
    290                 295                 300

Lys Asn Asn Thr Ala Glu Gln Asp Thr Ser Tyr Ser Ser Leu Asp Glu
305                 310                 315                 320

Leu Arg Glu Ser Trp Trp Asn Thr Asn Lys Lys Tyr Ile Trp Leu Ala
                325                 330                 335

Met Lys His Gly Ala Gly Met Asn Ser Thr Thr Cys Cys Gly Asp Gly
            340                 345                 350

Ser Val Thr Gly Ser Gly Ser Cys Asp Asp Ile Pro Thr Ile Asp
        355                 360                 365

Leu Ile Pro Gln Tyr Leu Arg Phe Leu Gln Glu Trp Val Glu His Phe
    370                 375                 380

Cys Lys Gln Arg Gln Glu Lys Val Lys Pro Val Ile Glu Asn Cys Lys
385                 390                 395                 400

Ser Cys Lys Glu Ser Gly Gly Thr Cys Asn Gly Glu Cys Lys Thr Glu
                405                 410                 415

Cys Lys Asn Lys Cys Glu Val Tyr Lys Lys Phe Ile Glu Asp Cys Lys
            420                 425                 430

Gly Gly Asp Gly Thr Ala Gly Ser Ser Trp Val Lys Arg Trp Asp Gln
        435                 440                 445

Ile Tyr Lys Arg Tyr Ser Lys Tyr Ile Glu Asp Ala Lys Arg Asn Arg
    450                 455                 460

Lys Ala Gly Thr Lys Asn Cys Gly Pro Ser Ser Thr Thr Asn Ala Ala
465                 470                 475                 480

Glu Asn Lys Cys Val Gln Ser Asp Ile Asp Ser Phe Phe Lys His Leu
                485                 490                 495

Ile Asp Ile Gly Leu Thr Thr Pro Ser Ser Tyr Leu Ser Ile Val Leu
            500                 505                 510

Asp Asp Asn Ile Cys Gly Ala Asp Lys Ala Pro Trp Thr Thr Tyr Thr
        515                 520                 525

Thr Tyr Thr Thr Thr Glu Lys Cys Asn Lys Glu Thr Asp Lys Ser Lys
```

```
                        530                 535                 540
Leu Gln Gln Cys Asn Thr Ala Val Val Asn Val Pro Ser Pro Leu
545                 550                 555                 560

Gly Asn Thr Pro His Gly Tyr Lys Tyr Ala Cys Gln Cys Lys Ile Pro
                565                 570                 575

Thr Asn Glu Glu Thr Cys Asp Asp Arg Lys Glu Tyr Met Asn Gln Trp
                580                 585                 590

Ser Cys Gly Ser Ala Arg Thr Met Lys Arg Gly Tyr Lys Asn Asp Asn
                595                 600                 605

Tyr Glu Leu Cys Lys Tyr Asn Gly Val Asp Val Lys Pro Thr Thr Val
                610                 615                 620

Arg Ser Asn Ser Ser Lys Leu Asp
625                 630

<210> SEQ ID NO 55
<211> LENGTH: 2730
<212> TYPE: PRT
<213> ORGANISM: Plasmodium falciparum

<400> SEQUENCE: 55

Met Asp Lys Ser Ser Ile Ala Asn Lys Ile Glu Ala Tyr Leu Gly Ala
1               5                   10                  15

Lys Ser Asp Asp Ser Lys Ile Asp Gln Ser Leu Lys Ala Asp Pro Ser
                20                  25                  30

Glu Val Gln Tyr Tyr Gly Ser Gly Asp Gly Tyr Tyr Leu Arg Lys
                35                  40                  45

Asn Ile Cys Lys Ile Thr Val Asn His Ser Asp Ser Gly Thr Asn Asp
            50                  55                  60

Pro Cys Asp Arg Ile Pro Pro Tyr Gly Asp Asn Asp Gln Trp Lys
65                  70                  75                  80

Cys Ala Ile Ile Leu Ser Lys Val Ser Glu Lys Pro Glu Asn Val Phe
                85                  90                  95

Val Pro Pro Arg Arg Gln Arg Met Cys Ile Asn Asn Leu Glu Lys Leu
                100                 105                 110

Asn Val Asp Lys Ile Arg Asp Lys His Ala Phe Leu Ala Asp Val Leu
                115                 120                 125

Leu Thr Ala Arg Asn Glu Gly Glu Arg Ile Val Gln Asn His Pro Asp
            130                 135                 140

Thr Asn Ser Ser Asn Val Cys Asn Ala Leu Glu Arg Ser Phe Ala Asp
145                 150                 155                 160

Ile Ala Asp Ile Ile Arg Gly Thr Asp Leu Trp Lys Gly Thr Asn Ser
                165                 170                 175

Asn Leu Glu Gln Asn Leu Lys Gln Met Phe Ala Lys Ile Arg Glu Asn
                180                 185                 190

Asp Lys Val Leu Gln Asp Lys Tyr Pro Lys Asp Gln Asn Tyr Arg Lys
                195                 200                 205

Leu Arg Glu Asp Trp Trp Asn Ala Asn Arg Gln Lys Val Trp Glu Val
            210                 215                 220

Ile Thr Cys Gly Ala Arg Ser Asn Asp Leu Leu Ile Lys Arg Gly Trp
225                 230                 235                 240

Arg Thr Ser Gly Lys Ser Asn Gly Asp Asn Lys Leu Glu Leu Cys Arg
                245                 250                 255

Lys Cys Gly His Tyr Glu Glu Lys Val Pro Thr Lys Leu Asp Tyr Val
                260                 265                 270
```

```
Pro Gln Phe Leu Arg Trp Leu Thr Glu Trp Ile Asp Phe Tyr Arg
        275                 280                 285
Glu Lys Gln Asn Leu Ile Asp Asp Met Glu Arg His Arg Glu Cys
    290                 295                 300
Thr Ser Glu Asp His Lys Ser Lys Glu Gly Thr Ser Tyr Cys Ser Thr
305                 310                 315                 320
Cys Lys Asp Lys Cys Lys Lys Tyr Cys Glu Cys Val Lys Lys Trp Lys
                325                 330                 335
Ser Glu Trp Glu Asn Gln Lys Asn Lys Tyr Thr Glu Leu Tyr Gln Gln
            340                 345                 350
Asn Lys Asn Glu Thr Ser Gln Lys Asn Thr Ser Arg Tyr Asp Asp Tyr
        355                 360                 365
Val Lys Asp Phe Phe Lys Lys Leu Glu Ala Asn Tyr Ser Ser Leu Glu
    370                 375                 380
Asn Tyr Ile Lys Gly Asp Pro Tyr Phe Ala Glu Tyr Ala Thr Lys Leu
385                 390                 395                 400
Ser Phe Ile Leu Asn Ser Ser Asp Ala Asn Asn Pro Ser Glu Lys Ile
                405                 410                 415
Gln Lys Asn Asn Asp Glu Val Cys Asn Cys Asn Glu Ser Gly Ile Ala
            420                 425                 430
Ser Val Glu Gln Glu Gln Ile Ser Asp Pro Ser Ser Asn Lys Thr Cys
        435                 440                 445
Ile Thr His Ser Ser Ile Lys Ala Asn Lys Lys Val Cys Lys His
    450                 455                 460
Val Lys Leu Gly Val Arg Glu Asn Asp Lys Asp Leu Arg Val Cys Val
465                 470                 475                 480
Ile Glu His Thr Ser Leu Ser Gly Val Glu Asn Cys Cys Gln Asp
                485                 490                 495
Phe Leu Arg Ile Leu Gln Glu Asn Cys Ser Asp Asn Lys Ser Gly Ser
            500                 505                 510
Ser Ser Asn Gly Ser Cys Asn Asn Lys Asn Gln Glu Ala Cys Glu Lys
        515                 520                 525
Asn Leu Glu Lys Val Leu Ala Ser Leu Thr Asn Cys Tyr Lys Cys Asp
    530                 535                 540
Lys Cys Lys Ser Glu Gln Ser Lys Lys Asn Asn Lys Asn Trp Ile Trp
545                 550                 555                 560
Lys Lys Ser Ser Gly Lys Gly Gly Leu Gln Lys Glu Tyr Ala Asn
                565                 570                 575
Thr Ile Gly Leu Pro Pro Arg Thr Gln Ser Leu Cys Leu Val Val Cys
            580                 585                 590
Leu Asp Glu Lys Gly Lys Lys Thr Gln Glu Leu Lys Asn Ile Arg Thr
        595                 600                 605
Asn Ser Glu Leu Leu Lys Glu Trp Ile Ile Ala Ala Phe His Glu Gly
    610                 615                 620
Lys Asn Leu Lys Pro Ser His Glu Lys Lys Asn Asp Asp Asn Gly Lys
625                 630                 635                 640
Lys Leu Cys Lys Ala Leu Glu Tyr Ser Phe Ala Asp Tyr Gly Asp Leu
                645                 650                 655
Ile Lys Gly Thr Ser Ile Trp Asp Asn Glu Tyr Thr Lys Asp Leu Glu
            660                 665                 670
Leu Asn Leu Gln Lys Ile Phe Gly Lys Leu Phe Arg Lys Tyr Ile Lys
        675                 680                 685
Lys Asn Asn Thr Ala Glu Gln Asp Thr Ser Tyr Ser Ser Leu Asp Glu
```

```
                690             695             700
Leu Arg Glu Ser Trp Trp Asn Thr Asn Lys Lys Tyr Ile Trp Leu Ala
705                 710                 715                 720

Met Lys His Gly Ala Gly Met Asn Ser Thr Thr Cys Cys Gly Asp Gly
                725                 730                 735

Ser Val Thr Gly Ser Gly Ser Ser Cys Asp Asp Ile Pro Thr Ile Asp
                740                 745                 750

Leu Ile Pro Gln Tyr Leu Arg Phe Leu Gln Glu Trp Val Glu His Phe
            755                 760                 765

Cys Lys Gln Arg Gln Glu Lys Val Lys Pro Val Ile Glu Asn Cys Lys
        770                 775                 780

Ser Cys Lys Glu Ser Gly Gly Thr Cys Asn Gly Cys Lys Thr Glu
785                 790                 795                 800

Cys Lys Asn Lys Cys Glu Val Tyr Lys Lys Phe Ile Glu Asp Cys Lys
                805                 810                 815

Gly Gly Asp Gly Thr Ala Gly Ser Ser Trp Val Lys Arg Trp Asp Gln
                820                 825                 830

Ile Tyr Lys Arg Tyr Ser Lys Tyr Ile Glu Asp Ala Lys Arg Asn Arg
            835                 840                 845

Lys Ala Gly Thr Lys Asn Cys Gly Pro Ser Ser Thr Thr Asn Ala Ala
850                 855                 860

Glu Asn Lys Cys Val Gln Ser Asp Ile Asp Ser Phe Phe Lys His Leu
865                 870                 875                 880

Ile Asp Ile Gly Leu Thr Thr Pro Ser Ser Tyr Leu Ser Ile Val Leu
                885                 890                 895

Asp Asp Asn Ile Cys Gly Ala Asp Lys Ala Pro Trp Thr Thr Tyr Thr
                900                 905                 910

Thr Tyr Thr Thr Thr Glu Lys Cys Asn Lys Glu Thr Asp Lys Ser Lys
            915                 920                 925

Leu Gln Gln Cys Asn Thr Ala Val Val Asn Val Pro Ser Pro Leu
930                 935                 940

Gly Asn Thr Pro His Gly Tyr Lys Tyr Ala Cys Gln Cys Lys Ile Pro
945                 950                 955                 960

Thr Asn Glu Glu Thr Cys Asp Asp Arg Lys Glu Tyr Met Asn Gln Trp
                965                 970                 975

Ser Cys Gly Ser Ala Arg Thr Met Lys Arg Gly Tyr Lys Asn Asp Asn
                980                 985                 990

Tyr Glu Leu Cys Lys Tyr Asn Gly Val Asp Val Lys Pro Thr Thr Val
            995                 1000                1005

Arg Ser Asn Ser Ser Lys Leu Asp Asp Lys Asp Val Thr Phe Phe
1010                1015                1020

Asn Leu Phe Glu Gln Trp Asn Lys Glu Ile Gln Tyr Gln Ile Glu
    1025                1030                1035

Gln Tyr Met Thr Asn Thr Lys Ile Ser Cys Asn Asn Glu Lys Asn
    1040                1045                1050

Val Leu Ser Arg Val Ser Asp Glu Ala Ala Gln Pro Lys Phe Ser
    1055                1060                1065

Asp Asn Glu Arg Asp Arg Asn Ser Ile Thr His Glu Asp Lys Asn
    1070                1075                1080

Cys Lys Glu Lys Cys Lys Cys Tyr Ser Leu Trp Ile Glu Lys Ile
    1085                1090                1095

Asn Asp Gln Trp Asp Lys Gln Lys Asp Asn Tyr Asn Lys Phe Gln
    1100                1105                1110
```

```
Arg Lys Gln Ile Tyr Asp Ala Asn Lys Gly Ser Gln Asn Lys Lys
1115                1120                1125

Val Val Ser Leu Ser Asn Phe Leu Phe Phe Ser Cys Trp Glu Glu
1130                1135                1140

Tyr Ile Gln Lys Tyr Phe Asn Gly Asp Trp Ser Lys Ile Lys Asn
1145                1150                1155

Ile Gly Ser Asp Thr Phe Glu Phe Leu Ile Lys Lys Cys Gly Asn
1160                1165                1170

Asp Ser Gly Asp Gly Glu Thr Ile Phe Ser Glu Lys Leu Asn Asn
1175                1180                1185

Ala Glu Lys Lys Cys Lys Glu Asn Glu Ser Thr Asn Asn Lys Met
1190                1195                1200

Lys Ser Ser Glu Thr Ser Cys Asp Cys Ser Glu Pro Ile Tyr Ile
1205                1210                1215

Arg Gly Cys Gln Pro Lys Ile Tyr Asp Gly Lys Ile Phe Pro Gly
1220                1225                1230

Lys Gly Gly Glu Lys Gln Trp Ile Cys Lys Asp Thr Ile Ile His
1235                1240                1245

Gly Asp Thr Asn Gly Ala Cys Ile Pro Pro Arg Thr Gln Asn Leu
1250                1255                1260

Cys Val Gly Glu Leu Trp Asp Lys Arg Tyr Gly Gly Arg Ser Asn
1265                1270                1275

Ile Lys Asn Asp Thr Lys Glu Ser Leu Lys Gln Lys Ile Lys Asn
1280                1285                1290

Ala Ile Gln Lys Glu Thr Glu Leu Leu Tyr Glu Tyr His Asp Lys
1295                1300                1305

Gly Thr Ala Ile Ile Ser Arg Asn Pro Met Lys Gly Gln Lys Glu
1310                1315                1320

Lys Glu Glu Lys Asn Asn Asp Ser Asn Gly Leu Pro Lys Gly Phe
1325                1330                1335

Cys His Ala Val Gln Arg Ser Phe Ile Asp Tyr Lys Asn Met Ile
1340                1345                1350

Leu Gly Thr Ser Val Asn Ile Tyr Glu Tyr Ile Gly Lys Leu Gln
1355                1360                1365

Glu Asp Ile Lys Lys Ile Ile Glu Lys Gly Thr Thr Lys Gln Asn
1370                1375                1380

Gly Lys Thr Val Gly Ser Gly Ala Glu Asn Val Asn Ala Trp Trp
1385                1390                1395

Lys Gly Ile Glu Gly Glu Met Trp Asp Ala Val Arg Cys Ala Ile
1400                1405                1410

Thr Lys Ile Asn Lys Lys Gln Lys Lys Asn Gly Thr Phe Ser Ile
1415                1420                1425

Asp Glu Cys Gly Ile Phe Pro Pro Thr Gly Asn Asp Glu Asp Gln
1430                1435                1440

Ser Val Ser Trp Phe Lys Glu Trp Ser Glu Gln Phe Cys Ile Glu
1445                1450                1455

Arg Leu Gln Tyr Glu Lys Asn Ile Arg Asp Ala Cys Thr Asn Asn
1460                1465                1470

Gly Gln Gly Asp Lys Ile Gln Gly Asp Cys Lys Arg Lys Cys Glu
1475                1480                1485

Glu Tyr Lys Lys Tyr Ile Ser Glu Lys Lys Gln Glu Trp Asp Lys
1490                1495                1500
```

Gln Lys Thr Lys Tyr Glu Asn Lys Tyr Val Gly Lys Ser Ala Ser
1505                1510                1515

Asp Leu Leu Lys Glu Asn Tyr Pro Glu Cys Ile Ser Ala Asn Phe
1520                1525                1530

Asp Phe Ile Phe Asn Asp Asn Ile Glu Tyr Lys Thr Tyr Tyr Pro
1535                1540                1545

Tyr Gly Asp Tyr Ser Ser Ile Cys Ser Cys Glu Gln Val Lys Tyr
1550                1555                1560

Tyr Glu Tyr Asn Asn Ala Glu Lys Lys Asn Asn Lys Ser Leu Cys
1565                1570                1575

His Glu Lys Gly Asn Asp Arg Thr Trp Ser Lys Lys Tyr Ile Lys
1580                1585                1590

Lys Leu Glu Asn Gly Arg Thr Leu Glu Gly Val Tyr Val Pro Pro
1595                1600                1605

Arg Arg Gln Gln Leu Cys Leu Tyr Glu Leu Phe Pro Ile Ile Ile
1610                1615                1620

Lys Asn Lys Asn Asp Ile Thr Asn Ala Lys Lys Glu Leu Leu Glu
1625                1630                1635

Thr Leu Gln Ile Val Ala Glu Arg Glu Ala Tyr Tyr Leu Trp Lys
1640                1645                1650

Gln Tyr His Ala His Asn Asp Thr Thr Tyr Leu Ala His Lys Lys
1655                1660                1665

Ala Cys Cys Ala Ile Arg Gly Ser Phe Tyr Asp Leu Glu Asp Ile
1670                1675                1680

Ile Lys Gly Asn Asp Leu Val His Asp Glu Tyr Thr Lys Tyr Ile
1685                1690                1695

Asp Ser Lys Leu Asn Glu Ile Phe Asp Ser Ser Asn Lys Asn Asp
1700                1705                1710

Ile Glu Thr Lys Arg Ala Arg Thr Asp Trp Trp Glu Asn Glu Ala
1715                1720                1725

Ile Ala Val Pro Asn Ile Thr Gly Ala Asn Lys Ser Asp Pro Lys
1730                1735                1740

Thr Ile Arg Gln Leu Val Trp Asp Ala Met Gln Ser Gly Val Arg
1745                1750                1755

Lys Ala Ile Asp Glu Glu Lys Glu Lys Lys Pro Asn Glu Asn
1760                1765                1770

Phe Pro Pro Cys Met Gly Val Gln His Ile Gly Ile Ala Lys Pro
1775                1780                1785

Gln Phe Ile Arg Trp Leu Glu Glu Trp Thr Asn Glu Phe Cys Glu
1790                1795                1800

Lys Tyr Thr Lys Tyr Phe Glu Asp Met Lys Ser Asn Cys Asn Leu
1805                1810                1815

Arg Lys Gly Ala Asp Asp Cys Asp Asp Asn Ser Asn Ile Glu Cys
1820                1825                1830

Lys Lys Ala Cys Ala Asn Tyr Thr Asn Trp Leu Asn Pro Lys Arg
1835                1840                1845

Ile Glu Trp Asn Gly Met Ser Asn Tyr Tyr Asn Lys Ile Tyr Arg
1850                1855                1860

Lys Ser Asn Lys Glu Ser Glu Asp Gly Lys Asp Tyr Ser Met Ile
1865                1870                1875

Met Glu Pro Thr Val Ile Asp Tyr Leu Asn Lys Arg Cys Asn Gly
1880                1885                1890

Glu Ile Asn Gly Asn Tyr Ile Cys Cys Ser Cys Lys Asn Ile Gly

```
            1895                1900                1905
Glu Asn Ser Thr Ser Gly Thr Val Asn Lys Lys Leu Gln Lys Lys
    1910                1915                1920
Glu Thr Gln Cys Glu Asp Asn Lys Gly Pro Leu Asp Leu Met Asn
    1925                1930                1935
Lys Val Leu Asn Lys Met Asp Pro Lys Tyr Ser Glu His Lys Met
    1940                1945                1950
Lys Cys Thr Glu Val Tyr Leu Glu His Val Glu Gln Leu Lys
    1955                1960                1965
Glu Ile Asp Asn Ala Ile Lys Asp Tyr Lys Leu Tyr Pro Leu Asp
    1970                1975                1980
Arg Cys Phe Asp Asp Lys Ser Lys Met Lys Val Cys Asp Leu Ile
    1985                1990                1995
Gly Asp Ala Ile Gly Cys Lys His Lys Thr Lys Leu Asp Glu Leu
    2000                2005                2010
Asp Glu Trp Asn Asp Val Asp Met Arg Asp Pro Tyr Asn Lys Tyr
    2015                2020                2025
Lys Gly Val Leu Ile Pro Pro Arg Arg Arg Gln Leu Cys Phe Ser
    2030                2035                2040
Arg Ile Val Arg Gly Pro Ala Asn Leu Arg Asn Leu Lys Glu Phe
    2045                2050                2055
Lys Glu Glu Ile Leu Lys Gly Ala Gln Ser Glu Gly Lys Phe Leu
    2060                2065                2070
Gly Asn Tyr Tyr Asn Glu Asp Lys Asp Lys Glu Lys Ala Leu Glu
    2075                2080                2085
Ala Met Lys Asn Ser Phe Tyr Asp Tyr Glu Tyr Ile Ile Lys Gly
    2090                2095                2100
Ser Asp Met Leu Thr Asn Ile Gln Phe Lys Asp Ile Lys Arg Lys
    2105                2110                2115
Leu Asp Arg Leu Leu Glu Lys Glu Thr Asn Asn Thr Glu Lys Val
    2120                2125                2130
Asp Asp Trp Trp Glu Thr Asn Lys Lys Ser Ile Trp Asn Ala Met
    2135                2140                2145
Leu Cys Gly Tyr Lys Lys Ser Gly Asn Lys Ile Ile Asp Pro Ser
    2150                2155                2160
Trp Cys Thr Ile Pro Thr Thr Glu Thr Pro Pro Gln Phe Leu Arg
    2165                2170                2175
Trp Ile Lys Glu Trp Gly Thr Asn Val Cys Ile Gln Lys Glu Glu
    2180                2185                2190
His Lys Glu Tyr Val Lys Ser Lys Cys Ser Asn Val Thr Asn Leu
    2195                2200                2205
Gly Ala Gln Glu Ser Glu Ser Lys Asn Cys Thr Ser Glu Ile Lys
    2210                2215                2220
Lys Tyr Gln Glu Trp Ser Arg Lys Arg Ser Ile Gln Trp Glu Ala
    2225                2230                2235
Ile Ser Glu Gly Tyr Lys Lys Tyr Lys Gly Met Asp Glu Phe Lys
    2240                2245                2250
Asn Thr Phe Lys Asn Ile Lys Glu Pro Asp Ala Asn Glu Pro Asn
    2255                2260                2265
Ala Asn Glu Tyr Leu Lys Lys His Cys Ser Lys Cys Pro Cys Gly
    2270                2275                2280
Phe Asn Asp Met Gln Glu Ile Thr Lys Tyr Thr Asn Ile Gly Asn
    2285                2290                2295
```

-continued

```
Glu Ala Phe Lys Gln Ile Lys Glu Gln Val Asp Ile Pro Ala Glu
        2300                2305                2310

Leu Glu Asp Val Ile Tyr Arg Leu Lys His His Glu Tyr Asp Lys
        2315                2320                2325

Gly Asn Asp Tyr Ile Cys Asn Lys Tyr Lys Asn Ile Asn Val Asn
        2330                2335                2340

Met Lys Lys Asn Asn Asp Asp Thr Trp Thr Asp Leu Val Lys Asn
        2345                2350                2355

Ser Ser Asp Ile Asn Lys Gly Val Leu Leu Pro Pro Arg Arg Lys
        2360                2365                2370

Asn Leu Phe Leu Lys Ile Asp Glu Ser Asp Ile Cys Lys Tyr Lys
        2375                2380                2385

Arg Asp Pro Lys Leu Phe Lys Asp Phe Ile Tyr Ser Ser Ala Ile
        2390                2395                2400

Ser Glu Val Glu Arg Leu Lys Lys Val Tyr Gly Glu Ala Lys Thr
        2405                2410                2415

Lys Val Val His Ala Met Lys Tyr Ser Phe Ala Asp Ile Gly Ser
        2420                2425                2430

Ile Ile Lys Gly Asp Asp Met Met Glu Asn Asn Ser Ser Asp Lys
        2435                2440                2445

Ile Gly Lys Ile Leu Gly Asp Gly Val Gly Gln Asn Glu Lys Arg
        2450                2455                2460

Lys Lys Trp Trp Asp Met Asn Lys Tyr His Ile Trp Glu Ser Met
        2465                2470                2475

Leu Cys Gly Tyr Lys His Ala Tyr Gly Asn Ile Ser Glu Asn Asp
        2480                2485                2490

Arg Lys Met Leu Asp Ile Pro Asn Asn Asp Asp Glu His Gln Phe
        2495                2500                2505

Leu Arg Trp Phe Gln Glu Trp Thr Glu Asn Phe Cys Thr Lys Arg
        2510                2515                2520

Asn Glu Leu Tyr Glu Asn Met Val Thr Ala Cys Asn Ser Ala Lys
        2525                2530                2535

Cys Asn Thr Ser Asn Gly Ser Val Asp Lys Lys Glu Cys Thr Glu
        2540                2545                2550

Ala Cys Lys Asn Tyr Ser Asn Phe Ile Leu Ile Lys Lys Lys Glu
        2555                2560                2565

Tyr Gln Ser Leu Asn Ser Gln Tyr Asp Met Asn Tyr Lys Glu Thr
        2570                2575                2580

Lys Ala Glu Lys Lys Glu Ser Pro Glu Tyr Phe Lys Asp Lys Cys
        2585                2590                2595

Asn Gly Glu Cys Ser Cys Leu Ser Glu Tyr Phe Lys Asp Glu Thr
        2600                2605                2610

Arg Trp Lys Asn Pro Tyr Glu Thr Leu Asp Asp Thr Glu Val Lys
        2615                2620                2625

Asn Asn Cys Met Cys Lys Pro Pro Pro Ala Ser Asn Asn Thr
        2630                2635                2640

Ser Asp Ile Leu Gln Lys Thr Ile Pro Phe Gly Ile Ala Leu Ala
        2645                2650                2655

Leu Gly Ser Ile Ala Phe Leu Phe Met Lys Lys Lys Pro Lys Thr
        2660                2665                2670

Pro Val Asp Leu Leu Arg Val Leu Asp Ile Pro Lys Gly Asp Tyr
        2675                2680                2685
```

-continued

```
Gly Ile Pro Thr Pro Lys Ser Ser Asn Arg Tyr Ile Pro Tyr Ala
2690                2695                2700

Ser Asp Arg Tyr Lys Gly Lys Thr Tyr Ile Tyr Met Glu Gly Asp
2705                2710                2715

Thr Ser Gly Asp Asp Lys Tyr Ile Trp Asp Leu
2720                2725                2730
```

<210> SEQ ID NO 56
<211> LENGTH: 2734
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: FCR3, ID1-DBL2b

<400> SEQUENCE: 56

```
Met Asp Ser Thr Ser Thr Ile Ala Asn Lys Ile Glu Glu Tyr Leu Gly
1               5                   10                  15

Ala Lys Ser Asp Asp Ser Lys Ile Asp Glu Leu Leu Lys Ala Asp Pro
            20                  25                  30

Ser Glu Val Glu Tyr Tyr Arg Ser Gly Gly Asp Gly Asp Tyr Leu Lys
        35                  40                  45

Asn Asn Ile Cys Lys Ile Thr Val Asn His Ser Asp Ser Gly Lys Tyr
    50                  55                  60

Asp Pro Cys Glu Lys Lys Leu Pro Pro Tyr Asp Asp Asn Asp Gln Trp
65                  70                  75                  80

Lys Cys Gln Gln Asn Ser Ser Asp Gly Ser Gly Lys Pro Glu Asn Ile
                85                  90                  95

Cys Val Pro Pro Arg Arg Glu Arg Leu Cys Thr Tyr Asn Leu Glu Asn
            100                 105                 110

Leu Lys Phe Asp Lys Ile Arg Asp Asn Asn Ala Phe Leu Ala Asp Val
        115                 120                 125

Leu Leu Thr Ala Arg Asn Glu Gly Glu Lys Ile Val Gln Asn His Pro
    130                 135                 140

Asp Thr Asn Ser Ser Asn Val Cys Asn Ala Leu Glu Arg Ser Phe Ala
145                 150                 155                 160

Asp Leu Ala Asp Ile Ile Arg Gly Thr Asp Gln Trp Lys Gly Thr Asn
                165                 170                 175

Ser Asn Leu Glu Lys Asn Leu Lys Gln Met Phe Ala Lys Ile Arg Glu
            180                 185                 190

Asn Asp Lys Val Leu Gln Asp Lys Tyr Pro Lys Asp Gln Lys Tyr Thr
        195                 200                 205

Lys Leu Arg Glu Ala Trp Trp Asn Ala Asn Arg Gln Lys Val Trp Glu
    210                 215                 220

Val Ile Thr Cys Gly Ala Arg Ser Asn Asp Leu Leu Ile Lys Arg Gly
225                 230                 235                 240

Trp Arg Thr Ser Gly Lys Ser Asp Arg Lys Asn Phe Glu Leu Cys
                245                 250                 255

Arg Lys Cys Gly His Tyr Glu Lys Glu Val Pro Thr Lys Leu Asp Tyr
            260                 265                 270

Val Pro Gln Phe Leu Arg Trp Leu Thr Glu Trp Ile Glu Asp Phe Tyr
        275                 280                 285

Arg Glu Lys Gln Asn Leu Ile Asp Asp Met Glu Arg His Arg Glu Glu
    290                 295                 300
```

```
Cys Thr Arg Glu Asp His Lys Ser Lys Glu Gly Thr Ser Tyr Cys Ser
305                 310                 315                 320

Thr Cys Lys Asp Lys Cys Lys Lys Tyr Cys Glu Cys Val Lys Lys Trp
            325                 330                 335

Lys Thr Glu Trp Glu Asn Gln Glu Asn Lys Tyr Lys Asp Leu Tyr Glu
        340                 345                 350

Gln Asn Lys Asn Lys Thr Ser Gln Lys Asn Thr Ser Arg Tyr Asp Asp
            355                 360                 365

Tyr Val Lys Asp Phe Phe Glu Lys Leu Glu Ala Asn Tyr Ser Ser Leu
    370                 375                 380

Glu Asn Tyr Ile Lys Gly Asp Pro Tyr Phe Ala Glu Tyr Ala Thr Lys
385                 390                 395                 400

Leu Ser Phe Ile Leu Asn Pro Ser Asp Ala Asn Asn Pro Ser Gly Glu
                405                 410                 415

Thr Ala Asn His Asn Asp Glu Ala Cys Asn Cys Asn Glu Ser Gly Ile
            420                 425                 430

Ser Ser Val Gly Gln Ala Gln Thr Ser Gly Pro Ser Ser Asn Lys Thr
        435                 440                 445

Cys Ile Thr His Ser Ser Ile Lys Thr Asn Lys Lys Glu Cys Lys
    450                 455                 460

Asp Val Lys Leu Gly Val Arg Glu Asn Asp Lys Asp Leu Lys Ile Cys
465                 470                 475                 480

Val Ile Glu Asp Thr Ser Leu Ser Gly Val Asp Asn Cys Cys Cys Gln
                485                 490                 495

Asp Leu Leu Gly Ile Leu Gln Glu Asn Cys Ser Asp Asn Lys Arg Gly
            500                 505                 510

Ser Ser Ser Asn Asp Ser Cys Asp Asn Lys Asn Gln Asp Glu Cys Gln
            515                 520                 525

Lys Lys Leu Glu Lys Val Phe Ala Ser Leu Thr Asn Gly Tyr Lys Cys
    530                 535                 540

Asp Lys Cys Lys Ser Gly Thr Ser Arg Ser Lys Lys Trp Ile Trp
545                 550                 555                 560

Lys Lys Ser Ser Gly Asn Glu Glu Gly Leu Gln Glu Glu Tyr Ala Asn
            565                 570                 575

Thr Ile Gly Leu Pro Pro Arg Thr Gln Ser Leu Tyr Leu Gly Asn Leu
        580                 585                 590

Pro Lys Leu Glu Asn Val Cys Glu Asp Val Lys Asp Ile Asn Phe Asp
    595                 600                 605

Thr Lys Glu Lys Phe Leu Ala Gly Cys Leu Ile Val Ser Phe His Glu
610                 615                 620

Gly Lys Asn Leu Lys Lys Arg Tyr Pro Gln Asn Lys Asn Ser Gly Asn
625                 630                 635                 640

Lys Glu Asn Leu Cys Lys Ala Leu Glu Tyr Ser Phe Ala Asp Tyr Gly
            645                 650                 655

Asp Leu Ile Lys Gly Thr Ser Ile Trp Asp Asn Glu Tyr Thr Lys Asp
            660                 665                 670

Leu Glu Leu Asn Leu Gln Asn Asn Phe Gly Lys Leu Phe Gly Lys Tyr
            675                 680                 685

Ile Lys Lys Asn Asn Thr Ala Glu Gln Asp Thr Ser Tyr Ser Ser Leu
            690                 695                 700

Asp Glu Leu Arg Glu Ser Trp Trp Asn Thr Asn Lys Lys Tyr Ile Trp
705                 710                 715                 720

Thr Ala Met Lys His Gly Ala Glu Met Asn Ile Thr Thr Cys Asn Ala
```

```
                    725                 730                 735
Asp Gly Ser Val Thr Gly Ser Ser Cys Asp Ile Pro Thr
                740                 745                 750

Ile Asp Leu Ile Pro Gln Tyr Leu Arg Phe Leu Gln Glu Trp Val Glu
                755                 760                 765

Asn Phe Cys Glu Gln Arg Gln Ala Lys Val Lys Asp Val Ile Thr Asn
            770                 775                 780

Cys Lys Ser Cys Lys Glu Ser Gly Asn Lys Cys Lys Thr Glu Cys Lys
785                 790                 795                 800

Thr Lys Cys Lys Asp Glu Cys Glu Lys Tyr Lys Lys Phe Ile Glu Ala
                805                 810                 815

Cys Gly Thr Ala Gly Gly Ile Gly Thr Ala Gly Ser Pro Trp Ser
                820                 825                 830

Lys Arg Trp Asp Gln Ile Tyr Lys Arg Tyr Ser Lys His Ile Glu Asp
                835                 840                 845

Ala Lys Arg Asn Arg Lys Ala Gly Thr Lys Asn Cys Gly Thr Ser Ser
            850                 855                 860

Thr Thr Asn Ala Ala Ala Ser Thr Asp Glu Asn Lys Cys Val Gln Ser
865                 870                 875                 880

Asp Ile Asp Ser Phe Phe Lys His Leu Ile Asp Ile Gly Leu Thr Thr
                    885                 890                 895

Pro Ser Ser Tyr Leu Ser Asn Val Leu Asp Asp Asn Ile Cys Gly Ala
                900                 905                 910

Asp Lys Ala Pro Trp Thr Thr Tyr Thr Thr Tyr Thr Thr Thr Glu Lys
                915                 920                 925

Cys Asn Lys Glu Arg Asp Lys Ser Lys Ser Gln Ser Ser Asp Thr Leu
930                 935                 940

Val Val Val Asn Val Pro Ser Pro Leu Gly Asn Thr Pro Tyr Arg Tyr
945                 950                 955                 960

Lys Tyr Ala Cys Gln Cys Lys Ile Pro Thr Asn Glu Glu Thr Cys Asp
                965                 970                 975

Asp Arg Lys Glu Tyr Met Asn Gln Trp Ser Cys Gly Ser Ala Arg Thr
                980                 985                 990

Met Lys Arg Gly Tyr Lys Asn Asp  Asn Tyr Glu Leu Cys  Lys Tyr Asn
                995                 1000                1005

Gly Val  Asp Val Lys Pro Thr  Thr Val Arg Ser Asn  Ser Ser Lys
    1010                1015                1020

Leu Asp  Gly Asn Asp Val Thr  Phe Phe Asn Leu Phe  Glu Gln Trp
    1025                1030                1035

Asn Lys  Glu Ile Gln Tyr Gln  Ile Glu Gln Tyr Met  Thr Asn Ala
    1040                1045                1050

Asn Ile  Ser Cys Ile Asp Glu  Lys Glu Val Leu Asp  Ser Val Ser
    1055                1060                1065

Asp Glu  Gly Thr Pro Lys Val  Arg Gly Gly Tyr Glu  Asp Gly Arg
    1070                1075                1080

Asn Asn  Asn Thr Asp Gln Gly  Thr Asn Cys Lys Glu  Lys Cys Lys
    1085                1090                1095

Cys Tyr  Lys Leu Trp Ile Glu  Lys Ile Asn Asp Gln  Trp Gly Lys
    1100                1105                1110

Gln Lys  Asp Asn Tyr Asn Lys  Phe Arg Ser Lys Gln  Ile Tyr Asp
    1115                1120                1125

Ala Asn  Lys Gly Ser Gln Asn  Lys Lys Val Val Ser  Leu Ser Asn
    1130                1135                1140
```

```
Phe Leu Phe Phe Ser Cys Trp Glu Glu Tyr Ile Gln Lys Tyr Phe
    1145            1150                1155

Asn Gly Asp Trp Ser Lys Ile Lys Asn Ile Gly Ser Asp Thr Phe
    1160            1165                1170

Glu Phe Leu Ile Lys Lys Cys Gly Asn Asn Ser Ala His Gly Glu
    1175            1180                1185

Glu Ile Phe Asn Glu Lys Leu Lys Asn Ala Glu Lys Lys Cys Lys
    1190            1195                1200

Glu Asn Glu Ser Thr Asp Thr Asn Ile Asn Lys Ser Glu Thr Ser
    1205            1210                1215

Cys Asp Leu Asn Ala Thr Asn Tyr Ile Arg Gly Cys Gln Ser Lys
    1220            1225                1230

Thr Tyr Asp Gly Lys Ile Phe Pro Gly Lys Gly Glu Lys Gln
    1235            1240                1245

Trp Ile Cys Lys Asp Thr Ile Ile His Gly Asp Thr Asn Gly Ala
    1250            1255                1260

Cys Ile Pro Pro Arg Thr Gln Asn Leu Cys Val Gly Glu Leu Trp
    1265            1270                1275

Asp Lys Ser Tyr Gly Gly Arg Ser Asn Ile Lys Asn Asp Thr Lys
    1280            1285                1290

Glu Leu Leu Lys Glu Lys Ile Lys Asn Ala Ile His Lys Glu Thr
    1295            1300                1305

Glu Leu Leu Tyr Glu Tyr His Asp Thr Gly Thr Ala Ile Ile Ser
    1310            1315                1320

Lys Asn Asp Lys Lys Gly Gln Lys Gly Lys Asn Asp Pro Asn Gly
    1325            1330                1335

Leu Pro Lys Gly Phe Cys His Ala Val Gln Arg Ser Phe Ile Asp
    1340            1345                1350

Tyr Lys Asn Met Ile Leu Gly Thr Ser Val Asn Ile Tyr Glu His
    1355            1360                1365

Ile Gly Lys Leu Gln Glu Asp Ile Lys Lys Ile Ile Glu Lys Gly
    1370            1375                1380

Thr Pro Gln Gln Lys Asp Lys Ile Gly Gly Val Gly Ser Ser Thr
    1385            1390                1395

Glu Asn Val Asn Ala Trp Trp Lys Gly Ile Glu Arg Glu Met Trp
    1400            1405                1410

Asp Ala Val Arg Cys Ala Ile Thr Lys Ile Asn Lys Lys Asn Asn
    1415            1420                1425

Asn Ser Ile Phe Asn Gly Asp Glu Cys Gly Val Ser Pro Pro Thr
    1430            1435                1440

Gly Asn Asp Glu Asp Gln Ser Val Ser Trp Phe Lys Glu Trp Gly
    1445            1450                1455

Glu Gln Phe Cys Ile Glu Arg Leu Arg Tyr Glu Gln Asn Ile Arg
    1460            1465                1470

Glu Ala Cys Thr Ile Asn Gly Lys Asn Glu Lys Lys Cys Ile Asn
    1475            1480                1485

Ser Lys Ser Gly Gln Gly Asp Lys Ile Gln Gly Ala Cys Lys Arg
    1490            1495                1500

Lys Cys Glu Lys Tyr Lys Lys Tyr Ile Ser Glu Lys Lys Gln Glu
    1505            1510                1515

Trp Asp Lys Gln Lys Thr Lys Tyr Glu Asn Lys Tyr Val Gly Lys
    1520            1525                1530
```

```
Ser Ala Ser Asp Leu Leu Lys Glu Asn Tyr Pro Glu Cys Ile Ser
1535                1540                1545

Ala Asn Phe Asp Phe Ile Phe Asn Asp Asn Ile Glu Tyr Lys Thr
1550                1555                1560

Tyr Tyr Pro Tyr Gly Asp Tyr Ser Ser Ile Cys Ser Cys Glu Gln
1565                1570                1575

Val Lys Tyr Tyr Lys Tyr Asn Asn Ala Glu Lys Lys Asn Asn Lys
1580                1585                1590

Ser Leu Cys Tyr Glu Lys Asp Asn Asp Met Thr Trp Ser Lys Lys
1595                1600                1605

Tyr Ile Lys Lys Leu Glu Asn Gly Arg Ser Leu Glu Gly Val Tyr
1610                1615                1620

Val Pro Pro Arg Arg Gln Gln Leu Cys Leu Tyr Glu Leu Phe Pro
1625                1630                1635

Ile Ile Ile Lys Asn Glu Glu Gly Met Glu Lys Ala Lys Glu Glu
1640                1645                1650

Leu Leu Glu Thr Leu Gln Ile Val Ala Glu Arg Glu Ala Tyr Tyr
1655                1660                1665

Leu Trp Lys Gln Tyr Asn Pro Thr Gly Lys Gly Ile Asp Asp Ala
1670                1675                1680

Asn Lys Lys Ala Cys Cys Ala Ile Arg Gly Ser Phe Tyr Asp Leu
1685                1690                1695

Glu Asp Ile Ile Lys Gly Asn Asp Leu Val His Asp Glu Tyr Thr
1700                1705                1710

Lys Tyr Ile Asp Ser Lys Leu Asn Glu Ile Phe Gly Ser Ser Asp
1715                1720                1725

Thr Asn Asp Ile Asp Thr Lys Arg Ala Arg Thr Asp Trp Trp Glu
1730                1735                1740

Asn Glu Thr Ile Thr Asn Gly Thr Asp Arg Lys Thr Ile Arg Gln
1745                1750                1755

Leu Val Trp Asp Ala Met Gln Ser Gly Val Arg Tyr Ala Val Glu
1760                1765                1770

Glu Lys Asn Glu Asn Phe Pro Leu Cys Met Gly Val Glu His Ile
1775                1780                1785

Gly Ile Ala Lys Pro Gln Phe Ile Arg Trp Leu Glu Glu Trp Thr
1790                1795                1800

Asn Glu Phe Cys Glu Lys Tyr Thr Lys Tyr Phe Glu Asp Met Lys
1805                1810                1815

Ser Lys Cys Asp Pro Pro Lys Arg Ala Asp Thr Cys Gly Asp Asn
1820                1825                1830

Ser Asn Ile Glu Cys Lys Lys Ala Cys Ala Asn Tyr Thr Asn Trp
1835                1840                1845

Leu Asn Pro Lys Arg Ile Glu Trp Asn Gly Met Ser Asn Tyr Tyr
1850                1855                1860

Asn Lys Ile Tyr Arg Lys Ser Asn Lys Glu Ser Glu Gly Gly Lys
1865                1870                1875

Asp Tyr Ser Met Ile Met Ala Pro Thr Val Ile Asp Tyr Leu Asn
1880                1885                1890

Lys Arg Cys His Gly Glu Ile Asn Gly Asn Tyr Ile Cys Cys Ser
1895                1900                1905

Cys Lys Asn Ile Gly Ala Tyr Asn Thr Thr Ser Gly Thr Val Asn
1910                1915                1920

Lys Lys Leu Gln Lys Lys Glu Thr Glu Cys Glu Glu Glu Lys Gly
```

-continued

```
            1925                1930                1935

Pro Leu Asp Leu Met Asn Glu Val Leu Asn Lys Met Asp Lys Lys
        1940                1945                1950

Tyr Ser Ala His Lys Met Lys Cys Thr Glu Val Tyr Leu Glu His
        1955                1960                1965

Val Glu Glu Gln Leu Asn Glu Ile Asp Asn Ala Ile Lys Asp Tyr
        1970                1975                1980

Lys Leu Tyr Pro Leu Asp Arg Cys Phe Asp Asp Gln Thr Lys Met
        1985                1990                1995

Lys Val Cys Asp Leu Ile Ala Asp Ala Ile Gly Cys Lys Asp Lys
        2000                2005                2010

Thr Lys Leu Asp Glu Leu Asp Glu Trp Asn Asp Met Asp Leu Arg
        2015                2020                2025

Gly Thr Tyr Asn Lys His Lys Gly Val Leu Ile Pro Pro Arg Arg
        2030                2035                2040

Arg Gln Leu Cys Phe Ser Arg Ile Val Arg Gly Pro Ala Asn Leu
        2045                2050                2055

Arg Ser Leu Asn Glu Phe Lys Glu Glu Ile Leu Lys Gly Ala Gln
        2060                2065                2070

Ser Glu Gly Lys Phe Leu Gly Asn Tyr Tyr Lys Glu His Lys Asp
        2075                2080                2085

Lys Glu Lys Ala Leu Glu Ala Met Lys Asn Ser Phe Tyr Asp Tyr
        2090                2095                2100

Glu Asp Ile Ile Lys Gly Thr Asp Met Leu Thr Asn Ile Glu Phe
        2105                2110                2115

Lys Asp Ile Lys Ile Lys Leu Asp Arg Leu Leu Glu Lys Glu Thr
        2120                2125                2130

Asn Asn Thr Lys Lys Ala Glu Asp Trp Trp Lys Thr Asn Lys Lys
        2135                2140                2145

Ser Ile Trp Asn Ala Met Leu Cys Gly Tyr Lys Lys Ser Gly Asn
        2150                2155                2160

Lys Ile Ile Asp Pro Ser Trp Cys Thr Ile Pro Thr Thr Glu Thr
        2165                2170                2175

Pro Pro Gln Phe Leu Arg Trp Ile Lys Glu Trp Gly Thr Asn Val
        2180                2185                2190

Cys Ile Gln Lys Gln Glu His Lys Glu Tyr Val Lys Ser Lys Cys
        2195                2200                2205

Ser Asn Val Thr Asn Leu Gly Ala Gln Ala Ser Glu Ser Asn Asn
        2210                2215                2220

Cys Thr Ser Glu Ile Lys Lys Tyr Gln Glu Trp Ser Arg Lys Arg
        2225                2230                2235

Ser Ile Arg Trp Glu Thr Ile Ser Lys Arg Tyr Lys Lys Tyr Lys
        2240                2245                2250

Arg Met Asp Ile Leu Lys Asp Val Lys Glu Pro Asp Ala Asn Thr
        2255                2260                2265

Tyr Leu Arg Glu His Cys Ser Lys Cys Pro Cys Gly Phe Asn Asp
        2270                2275                2280

Met Glu Glu Met Asn Asn Asn Glu Asp Asn Glu Lys Glu Ala Phe
        2285                2290                2295

Lys Gln Ile Lys Glu Gln Val Lys Ile Pro Ala Glu Leu Glu Asp
        2300                2305                2310

Val Ile Tyr Arg Ile Lys His His Glu Tyr Asp Lys Gly Asn Asp
        2315                2320                2325
```

```
Tyr Ile Cys Asn Lys Tyr Lys Asn Ile His Asp Arg Met Lys Lys
    2330            2335            2340

Asn Asn Gly Asn Phe Val Thr Asp Asn Phe Val Lys Lys Ser Trp
    2345            2350            2355

Glu Ile Ser Asn Gly Val Leu Ile Pro Pro Arg Arg Lys Asn Leu
    2360            2365            2370

Phe Leu Tyr Ile Asp Pro Ser Lys Ile Cys Glu Tyr Lys Lys Asp
    2375            2380            2385

Pro Lys Leu Phe Lys Asp Phe Ile Tyr Trp Ser Ala Phe Thr Glu
    2390            2395            2400

Val Glu Arg Leu Lys Lys Ala Tyr Gly Gly Ala Arg Ala Lys Val
    2405            2410            2415

Val His Ala Met Lys Tyr Ser Phe Thr Asp Ile Gly Ser Ile Ile
    2420            2425            2430

Lys Gly Asp Asp Met Met Glu Lys Asn Ser Ser Asp Lys Ile Gly
    2435            2440            2445

Lys Ile Leu Gly Asp Thr Asp Gly Gln Asn Glu Lys Arg Lys Lys
    2450            2455            2460

Trp Trp Asp Met Asn Lys Tyr His Ile Trp Glu Ser Met Leu Cys
    2465            2470            2475

Gly Tyr Arg Glu Ala Glu Gly Asp Thr Glu Thr Asn Glu Asn Cys
    2480            2485            2490

Arg Phe Pro Asp Ile Glu Ser Val Pro Gln Phe Leu Arg Trp Phe
    2495            2500            2505

Gln Glu Trp Ser Glu Asn Phe Cys Asp Arg Arg Gln Lys Leu Tyr
    2510            2515            2520

Asp Lys Leu Asn Ser Glu Cys Ile Ser Ala Glu Cys Thr Asn Gly
    2525            2530            2535

Ser Val Asp Asn Ser Lys Cys Thr His Ala Cys Val Asn Tyr Lys
    2540            2545            2550

Asn Tyr Ile Leu Thr Lys Lys Thr Glu Tyr Glu Ile Gln Thr Asn
    2555            2560            2565

Lys Tyr Asp Asn Glu Phe Lys Asn Lys Asn Ser Asn Asp Lys Asp
    2570            2575            2580

Ala Pro Asp Tyr Leu Lys Glu Lys Cys Asn Asp Asn Lys Cys Glu
    2585            2590            2595

Cys Leu Asn Lys His Ile Asp Asp Lys Asn Lys Thr Trp Lys Asn
    2600            2605            2610

Pro Tyr Glu Thr Leu Glu Asp Thr Phe Lys Ser Lys Cys Asp Cys
    2615            2620            2625

Pro Lys Pro Leu Pro Ser Pro Ile Lys Pro Asp Asp Leu Pro Pro
    2630            2635            2640

Gln Ala Asp Glu Pro Phe Asp Pro Thr Ile Leu Gln Thr Thr Ile
    2645            2650            2655

Pro Phe Gly Ile Ala Leu Ala Leu Gly Ser Ile Ala Phe Leu Phe
    2660            2665            2670

Met Lys Val Ile Tyr Ile Tyr Ile Tyr Val Cys Cys Ile Cys Met
    2675            2680            2685

Tyr Val Cys Met Tyr Val Cys Met Tyr Val Cys Met Tyr Val Cys
    2690            2695            2700

Met Tyr Val Cys Met His Val Cys Met Leu Cys Val Tyr Val Ile
    2705            2710            2715
```

Tyr Val Phe Lys Ile Cys Ile Tyr Ile Glu Lys Glu Lys Arg Lys
2720                2725                2730

Lys

<210> SEQ ID NO 57
<211> LENGTH: 577
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ID1 and DBL2Xb domains of FCR3

<400> SEQUENCE: 57

Asn Tyr Ile Lys Gly Asp Pro Tyr Phe Ala Glu Tyr Ala Thr Lys Leu
1               5                   10                  15

Ser Phe Ile Leu Asn Pro Ser Asp Ala Asn Asn Pro Ser Gly Glu Thr
            20                  25                  30

Ala Asn His Asn Asp Glu Ala Cys Asn Cys Asn Glu Ser Gly Ile Ser
        35                  40                  45

Ser Val Gly Gln Ala Gln Thr Ser Gly Pro Ser Ser Asn Lys Thr Cys
50                  55                  60

Ile Thr His Ser Ser Ile Lys Thr Asn Lys Lys Glu Cys Lys Asp
65                  70                  75                  80

Val Lys Leu Gly Val Arg Glu Asn Asp Lys Asp Leu Lys Ile Cys Val
                85                  90                  95

Ile Glu Asp Thr Ser Leu Ser Gly Val Asp Asn Cys Cys Cys Gln Asp
            100                 105                 110

Leu Leu Gly Ile Leu Gln Glu Asn Cys Ser Asp Asn Lys Arg Gly Ser
        115                 120                 125

Ser Ser Asn Asp Ser Cys Asp Asn Lys Asn Gln Asp Glu Cys Gln Lys
130                 135                 140

Lys Leu Glu Lys Val Phe Ala Ser Leu Thr Asn Gly Tyr Lys Cys Asp
145                 150                 155                 160

Lys Cys Lys Ser Gly Thr Ser Arg Ser Lys Lys Trp Ile Trp Lys
                165                 170                 175

Lys Ser Ser Gly Asn Glu Glu Gly Leu Gln Glu Glu Tyr Ala Asn Thr
            180                 185                 190

Ile Gly Leu Pro Pro Arg Thr Gln Ser Leu Tyr Leu Gly Asn Leu Pro
        195                 200                 205

Lys Leu Glu Asn Val Cys Glu Asp Val Lys Asp Ile Asn Phe Asp Thr
210                 215                 220

Lys Glu Lys Phe Leu Ala Gly Cys Leu Ile Val Ser Phe His Glu Gly
225                 230                 235                 240

Lys Asn Leu Lys Lys Arg Tyr Pro Gln Asn Lys Asn Ser Gly Asn Lys
                245                 250                 255

Glu Asn Leu Cys Lys Ala Leu Glu Tyr Ser Phe Ala Asp Tyr Gly Asp
            260                 265                 270

Leu Ile Lys Gly Thr Ser Ile Trp Asp Asn Glu Tyr Thr Lys Asp Leu
        275                 280                 285

Glu Leu Asn Leu Gln Asn Phe Gly Lys Leu Phe Gly Lys Tyr Ile
290                 295                 300

Lys Lys Asn Asn Thr Ala Glu Gln Asp Thr Ser Tyr Ser Ser Leu Asp
305                 310                 315                 320

Glu Leu Arg Glu Ser Trp Trp Asn Thr Asn Lys Lys Tyr Ile Trp Thr

```
            325                 330                 335
Ala Met Lys His Gly Ala Glu Met Asn Ile Thr Thr Cys Asn Ala Asp
            340                 345                 350
Gly Ser Val Thr Gly Ser Gly Ser Cys Asp Asp Ile Pro Thr Ile
            355                 360             365
Asp Leu Ile Pro Gln Tyr Leu Arg Phe Leu Gln Glu Trp Val Glu Asn
    370                 375                 380
Phe Cys Glu Gln Arg Gln Ala Lys Val Lys Asp Val Ile Thr Asn Cys
385                 390                 395                 400
Lys Ser Cys Lys Glu Ser Gly Asn Lys Cys Lys Thr Glu Cys Lys Thr
                405                 410                 415
Lys Cys Lys Asp Glu Cys Glu Lys Tyr Lys Lys Phe Ile Glu Ala Cys
            420                 425                 430
Gly Thr Ala Gly Gly Ile Gly Thr Ala Gly Ser Pro Trp Ser Lys
            435                 440                 445
Arg Trp Asp Gln Ile Tyr Lys Arg Tyr Ser Lys His Ile Glu Asp Ala
    450                 455                 460
Lys Arg Asn Arg Lys Ala Gly Thr Lys Asn Cys Gly Thr Ser Ser Thr
465                 470                 475                 480
Thr Asn Ala Ala Ala Ser Thr Asp Glu Asn Lys Cys Val Gln Ser Asp
                485                 490                 495
Ile Asp Ser Phe Phe Lys His Leu Ile Asp Ile Gly Leu Thr Thr Pro
            500                 505                 510
Ser Ser Tyr Leu Ser Asn Val Leu Asp Asp Asn Ile Cys Gly Ala Asp
            515                 520                 525
Lys Ala Pro Trp Thr Thr Tyr Thr Thr Tyr Thr Thr Thr Glu Lys Cys
    530                 535                 540
Asn Lys Glu Arg Asp Lys Ser Lys Ser Gln Ser Ser Asp Thr Leu Val
545                 550                 555                 560
Val Val Asn Val Pro Ser Pro Leu Gly Asn Thr Pro Tyr Arg Tyr Lys
                565                 570                 575
Tyr

<210> SEQ ID NO 58
<211> LENGTH: 999
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: DBL1X-ID2a region of VAR2CSA including V5 tag
      and histidine tag

<400> SEQUENCE: 58

Gly His Ser Asp Ser Gly Lys Tyr Asp Pro Cys Glu Lys Lys Leu Pro
1               5                   10                  15
Pro Tyr Asp Asp Asn Asp Gln Trp Lys Cys Gln Gln Asn Ser Ser Asp
            20                  25                  30
Gly Ser Gly Lys Pro Glu Asn Ile Cys Val Pro Pro Arg Arg Glu Arg
        35                  40                  45
Leu Cys Thr Tyr Asn Leu Glu Asn Leu Lys Phe Asp Lys Ile Arg Asp
    50                  55                  60
Asn Asn Ala Phe Leu Ala Asp Val Leu Leu Thr Ala Arg Asn Glu Gly
65                  70                  75                  80
Glu Lys Ile Val Gln Asn His Pro Asp Thr Asn Ser Ser Asn Val Cys
```

```
                        85                  90                  95
Asn Ala Leu Glu Arg Ser Phe Ala Asp Leu Ala Asp Ile Ile Arg Gly
                100                 105                 110

Thr Asp Gln Trp Lys Gly Thr Asn Ser Asn Leu Glu Lys Asn Leu Lys
            115                 120                 125

Gln Met Phe Ala Lys Ile Arg Glu Asn Asp Lys Val Leu Gln Asp Lys
        130                 135                 140

Tyr Pro Lys Asp Gln Lys Tyr Thr Lys Leu Arg Glu Ala Trp Trp Asn
145                 150                 155                 160

Ala Asn Arg Gln Lys Val Trp Glu Val Ile Thr Cys Gly Ala Arg Ser
                165                 170                 175

Asn Asp Leu Leu Ile Lys Arg Gly Trp Arg Thr Ser Gly Lys Ser Asp
            180                 185                 190

Arg Lys Lys Asn Phe Glu Leu Cys Arg Lys Cys Gly His Tyr Glu Lys
        195                 200                 205

Glu Val Pro Thr Lys Leu Asp Tyr Val Pro Gln Phe Leu Arg Trp Leu
210                 215                 220

Thr Glu Trp Ile Glu Asp Phe Tyr Arg Glu Lys Gln Asn Leu Ile Asp
225                 230                 235                 240

Asp Met Glu Arg His Arg Glu Glu Cys Thr Arg Glu Asp His Lys Ser
                245                 250                 255

Lys Glu Gly Thr Ser Tyr Cys Ser Thr Cys Lys Asp Lys Cys Lys Lys
            260                 265                 270

Tyr Cys Glu Cys Val Lys Lys Trp Lys Thr Glu Trp Glu Asn Gln Glu
        275                 280                 285

Asn Lys Tyr Lys Asp Leu Tyr Glu Gln Asn Lys Asn Lys Thr Ser Gln
            290                 295                 300

Lys Asn Thr Ser Arg Tyr Asp Asp Tyr Val Lys Asp Phe Phe Glu Lys
305                 310                 315                 320

Leu Glu Ala Asn Tyr Ser Ser Leu Glu Asn Tyr Ile Lys Gly Asp Pro
                325                 330                 335

Tyr Phe Ala Glu Tyr Ala Thr Lys Leu Ser Phe Ile Leu Asn Pro Ser
            340                 345                 350

Asp Ala Asn Asn Pro Ser Gly Glu Thr Ala Asn His Asn Asp Glu Ala
        355                 360                 365

Cys Asn Cys Asn Glu Ser Gly Ile Ser Ser Val Gly Gln Ala Gln Thr
            370                 375                 380

Ser Gly Pro Ser Ser Asn Lys Thr Cys Ile Thr His Ser Ser Ile Lys
385                 390                 395                 400

Thr Asn Lys Lys Lys Glu Cys Lys Asp Val Lys Leu Gly Val Arg Glu
                405                 410                 415

Asn Asp Lys Asp Leu Lys Ile Cys Val Ile Glu Asp Thr Ser Leu Ser
            420                 425                 430

Gly Val Asp Asn Cys Cys Cys Gln Asp Leu Leu Gly Ile Leu Gln Glu
        435                 440                 445

Asn Cys Ser Asp Asn Lys Arg Gly Ser Ser Ser Asn Asp Ser Cys Asp
            450                 455                 460

Asn Lys Asn Gln Asp Glu Cys Gln Lys Lys Leu Glu Lys Val Phe Ala
465                 470                 475                 480

Ser Leu Thr Asn Gly Tyr Lys Cys Asp Lys Cys Lys Ser Gly Thr Ser
                485                 490                 495

Arg Ser Lys Lys Lys Trp Ile Trp Lys Lys Ser Ser Gly Asn Glu Glu
            500                 505                 510
```

-continued

```
Gly Leu Gln Glu Glu Tyr Ala Asn Thr Ile Gly Leu Pro Pro Arg Thr
            515                 520                 525

Gln Ser Leu Tyr Leu Gly Asn Leu Pro Lys Leu Glu Asn Val Cys Glu
        530                 535                 540

Asp Val Lys Asp Ile Asn Phe Asp Thr Lys Glu Lys Phe Leu Ala Gly
545                 550                 555                 560

Cys Leu Ile Val Ser Phe His Glu Gly Lys Asn Leu Lys Lys Arg Tyr
                565                 570                 575

Pro Gln Asn Lys Asn Ser Gly Asn Lys Glu Asn Leu Cys Lys Ala Leu
            580                 585                 590

Glu Tyr Ser Phe Ala Asp Tyr Gly Asp Leu Ile Lys Gly Thr Ser Ile
        595                 600                 605

Trp Asp Asn Glu Tyr Thr Lys Asp Leu Glu Leu Asn Leu Gln Asn Asn
    610                 615                 620

Phe Gly Lys Leu Phe Gly Lys Tyr Ile Lys Lys Asn Asn Thr Ala Glu
625                 630                 635                 640

Gln Asp Thr Ser Tyr Ser Ser Leu Asp Glu Leu Arg Glu Ser Trp Trp
                645                 650                 655

Asn Thr Asn Lys Lys Tyr Ile Trp Thr Ala Met Lys His Gly Ala Glu
            660                 665                 670

Met Asn Ile Thr Thr Cys Asn Ala Asp Gly Ser Val Thr Gly Ser Gly
        675                 680                 685

Ser Ser Cys Asp Asp Ile Pro Thr Ile Asp Leu Ile Pro Gln Tyr Leu
    690                 695                 700

Arg Phe Leu Gln Glu Trp Val Glu Asn Phe Cys Glu Gln Arg Gln Ala
705                 710                 715                 720

Lys Val Lys Asp Val Ile Thr Asn Cys Lys Ser Cys Lys Glu Ser Gly
                725                 730                 735

Asn Lys Cys Lys Thr Glu Cys Lys Thr Lys Cys Lys Asp Glu Cys Glu
            740                 745                 750

Lys Tyr Lys Lys Phe Ile Glu Ala Cys Gly Thr Ala Gly Gly Gly Ile
        755                 760                 765

Gly Thr Ala Gly Ser Pro Trp Ser Lys Arg Trp Asp Gln Ile Tyr Lys
    770                 775                 780

Arg Tyr Ser Lys His Ile Glu Asp Ala Lys Arg Asn Arg Lys Ala Gly
785                 790                 795                 800

Thr Lys Asn Cys Gly Thr Ser Ser Thr Thr Asn Ala Ala Ala Ser Thr
                805                 810                 815

Asp Glu Asn Lys Cys Val Gln Ser Asp Ile Asp Ser Phe Phe Lys His
            820                 825                 830

Leu Ile Asp Ile Gly Leu Thr Thr Pro Ser Ser Tyr Leu Ser Asn Val
        835                 840                 845

Leu Asp Asp Asn Ile Cys Gly Ala Asp Lys Ala Pro Trp Thr Thr Tyr
    850                 855                 860

Thr Thr Tyr Thr Thr Thr Glu Lys Cys Asn Lys Glu Arg Asp Lys Ser
865                 870                 875                 880

Lys Ser Gln Ser Ser Asp Thr Leu Val Val Asn Val Pro Ser Pro
                885                 890                 895

Leu Gly Asn Thr Pro Tyr Arg Tyr Lys Tyr Ala Cys Gln Cys Lys Ile
            900                 905                 910

Pro Thr Asn Glu Glu Thr Cys Asp Asp Arg Lys Glu Tyr Met Asn Gln
        915                 920                 925
```

```
Trp Ser Cys Gly Ser Ala Arg Thr Met Lys Arg Gly Tyr Lys Asn Asp
    930             935             940

Asn Tyr Glu Leu Cys Lys Tyr Asn Gly Val Asp Val Lys Pro Thr Thr
945             950             955             960

Val Arg Ser Asn Ser Ser Lys Leu Asp Ser Gly Arg Gly Glu Leu Glu
            965             970             975

Gly Lys Pro Ile Pro Asn Pro Leu Leu Gly Leu Asp Ser Thr Arg Thr
            980             985             990

Gly His His His His His His
        995
```